(12) United States Patent
Pierce et al.

(10) Patent No.: US 9,856,472 B2
(45) Date of Patent: Jan. 2, 2018

(54) SMALL CONDITIONAL RNAS

(71) Applicant: California Institute of Technology, Pasadena, CA (US)

(72) Inventors: Niles A. Pierce, Pasadena, CA (US); Lisa Hochrein, Pasadena, CA (US)

(73) Assignee: CALIFORNIA INSTITUTE OF TECHNOLOGY, Pasadena, CA (US)

( * ) Notice: Subject to any disclaimer, the term of this patent is extended or adjusted under 35 U.S.C. 154(b) by 245 days.

(21) Appl. No.: 14/320,479

(22) Filed: Jun. 30, 2014

(65) Prior Publication Data

US 2015/0004615 A1    Jan. 1, 2015

Related U.S. Application Data

(60) Provisional application No. 61/841,692, filed on Jul. 1, 2013.

(51) Int. Cl.
  *C12Q 1/68* (2006.01)
  *C12N 15/11* (2006.01)

(52) U.S. Cl.
  CPC ...... *C12N 15/111* (2013.01); *C12N 2310/531* (2013.01); *C12N 2320/50* (2013.01); *C12N 2330/00* (2013.01)

(58) Field of Classification Search
  None
  See application file for complete search history.

(56) References Cited

U.S. PATENT DOCUMENTS

| | | |
|---|---|---|
| 4,714,680 A | 12/1987 | Civin et al. |
| 4,897,355 A | 1/1990 | Eppstein et al. |
| 4,965,204 A | 10/1990 | Civin et al. |
| 5,057,410 A | 10/1991 | Kawasaki et al. |
| 5,061,620 A | 10/1991 | Tsukamoto et al. |
| 5,118,801 A | 6/1992 | Lizardi et al. |
| 5,270,163 A | 12/1993 | Gold et al. |
| 5,312,728 A | 5/1994 | Lizardi et al. |
| 5,424,413 A | 6/1995 | Hogan et al. |
| 5,459,127 A | 10/1995 | Felgner et al. |
| 5,563,256 A | 10/1996 | Chakraborty et al. |
| 5,579,793 A | 12/1996 | Gajewski et al. |
| 5,643,741 A | 7/1997 | Tsukamoto et al. |
| 5,677,136 A | 10/1997 | Simmons et al. |
| 5,691,145 A | 11/1997 | Pitner et al. |
| 5,716,827 A | 2/1998 | Tsukamoto et al. |
| 5,750,397 A | 5/1998 | Tsukamoto et al. |

(Continued)

FOREIGN PATENT DOCUMENTS

| | | |
|---|---|---|
| EP | 0 273 085 | 7/1988 |
| EP | 1 479 766 | 11/2004 |

(Continued)

OTHER PUBLICATIONS

Ha et al., Regulation of microRNA biogenesis, Nature Reviews Molecular Cell Biology 15, 509-524. Jul. 16, 2014.

(Continued)

*Primary Examiner* — Robert T Crow
(74) *Attorney, Agent, or Firm* — Knobbe, Martens, Olson & Bear, LLP

(57) ABSTRACT

The present subject matter relates to the use conditional hairpins, such as, but not limited to shRNAs. The conditional formation of these structures can allow for further events, such as gene silencing (in some embodiments).

40 Claims, 63 Drawing Sheets
(46 of 63 Drawing Sheet(s) Filed in Color)

(56) References Cited

U.S. PATENT DOCUMENTS

| | | |
|---|---|---|
| 5,928,913 A | 7/1999 | Efstathiou et al. |
| 5,989,823 A | 11/1999 | Jayasena et al. |
| 6,130,047 A | 10/2000 | Nadeau et al. |
| 6,242,246 B1 | 6/2001 | Gold et al. |
| 6,255,469 B1 | 7/2001 | Seeman et al. |
| 6,261,783 B1 | 7/2001 | Jayasena et al. |
| 6,264,825 B1 | 7/2001 | Blackburn et al. |
| 6,361,944 B1 | 3/2002 | Mirkin et al. |
| 6,361,945 B1 | 3/2002 | Becker et al. |
| 6,485,965 B1 | 11/2002 | Klatzmann et al. |
| 6,506,559 B1 | 1/2003 | Fire et al. |
| 6,555,367 B1 | 4/2003 | Spence et al. |
| 6,696,285 B1 | 2/2004 | Mills, Jr. |
| 6,899,871 B2 | 5/2005 | Kasahara et al. |
| 7,033,834 B2 | 4/2006 | Valerio et al. |
| 7,632,641 B2 | 12/2009 | Dirks et al. |
| 7,727,721 B2 | 6/2010 | Pierce et al. |
| 7,960,357 B2 | 6/2011 | Dirks et al. |
| 8,105,778 B2 | 1/2012 | Dirks et al. |
| 8,124,751 B2 | 2/2012 | Pierce et al. |
| 8,241,854 B2 | 8/2012 | Yin et al. |
| 8,318,921 B2 | 11/2012 | Pierce et al. |
| 8,478,543 B2 | 7/2013 | Pierce et al. |
| 8,497,364 B2 | 7/2013 | Pierce et al. |
| 8,507,204 B2 | 8/2013 | Pierce et al. |
| 8,658,780 B2 | 2/2014 | Pierce et al. |
| 8,877,438 B2 | 11/2014 | Yin et al. |
| 8,962,241 B2 | 2/2015 | Yin et al. |
| 8,962,582 B2 | 2/2015 | Dirks et al. |
| 9,217,151 B2 | 12/2015 | Yin et al. |
| 2001/0014445 A1 | 8/2001 | Urnovitz et al. |
| 2002/0051769 A1 | 5/2002 | Zhang et al. |
| 2002/0172950 A1 | 11/2002 | Kenny et al. |
| 2003/0092162 A1 | 5/2003 | Shankara et al. |
| 2003/0129611 A1 | 7/2003 | Bao et al. |
| 2004/0009510 A1 | 1/2004 | Seiwert et al. |
| 2004/0043386 A1 | 3/2004 | Pray et al. |
| 2004/0126773 A1 | 7/2004 | Beske et al. |
| 2004/0223953 A1 | 11/2004 | Kung et al. |
| 2005/0089864 A1 | 4/2005 | Li et al. |
| 2005/0112614 A1 | 5/2005 | Cook et al. |
| 2005/0233332 A1 | 10/2005 | Collis |
| 2005/0239061 A1 | 10/2005 | Marshall et al. |
| 2005/0260635 A1 | 11/2005 | Dirks et al. |
| 2006/0035375 A1 | 2/2006 | Head et al. |
| 2006/0088864 A1 | 4/2006 | Smolke et al. |
| 2006/0228733 A1 | 10/2006 | Pierce et al. |
| 2006/0234261 A1 | 10/2006 | Pierce et al. |
| 2007/0072215 A1 | 3/2007 | Seelig |
| 2007/0087334 A1 | 4/2007 | Dirks et al. |
| 2007/0117109 A1 | 5/2007 | Rothemund |
| 2008/0214488 A1 | 9/2008 | Pierce et al. |
| 2009/0011956 A1 | 1/2009 | Yin et al. |
| 2009/0123914 A1 | 5/2009 | Erikson et al. |
| 2009/0197271 A1 | 8/2009 | Kotlikoff et al. |
| 2009/0227774 A1 | 9/2009 | Turberfield et al. |
| 2009/0247615 A1 | 10/2009 | Pierce et al. |
| 2009/0311799 A1 | 12/2009 | Sotzing et al. |
| 2010/0021901 A1 | 1/2010 | Yin et al. |
| 2010/0021904 A1 | 1/2010 | Pierce et al. |
| 2010/0035233 A1 | 2/2010 | Yin et al. |
| 2010/0047926 A1 | 2/2010 | Dirks et al. |
| 2011/0059064 A1 | 3/2011 | Possani-Postay et al. |
| 2011/0104676 A1 | 5/2011 | Pierce et al. |
| 2011/0287557 A1 | 11/2011 | Zhang et al. |
| 2011/0288148 A1 | 11/2011 | Pierce et al. |
| 2011/0288832 A1 | 11/2011 | Pierce et al. |
| 2011/0313030 A1 | 12/2011 | Dirks et al. |
| 2012/0021410 A1 | 1/2012 | Yin et al. |
| 2012/0022243 A1 | 1/2012 | Yin et al. |
| 2012/0022244 A1 | 1/2012 | Yin |
| 2012/0190835 A1 | 7/2012 | Pierce et al. |
| 2012/0251583 A1 | 10/2012 | Rothemund et al. |
| 2014/0107983 A1 | 4/2014 | Wolfe et al. |
| 2015/0004615 A1 | 1/2015 | Pierce et al. |
| 2015/0154347 A1 | 6/2015 | Wolfe et al. |

FOREIGN PATENT DOCUMENTS

| | | |
|---|---|---|
| EP | 1 634 890 | 3/2006 |
| EP | 2155770 | 5/2008 |
| EP | 2 055 781 | 5/2009 |
| EP | 1730161 | 9/2010 |
| EP | 1931806 | 10/2011 |
| WO | WO 92/03464 | 3/1992 |
| WO | WO 94/01550 | 1/1994 |
| WO | WO 99/31276 | 6/1999 |
| WO | WO 01/40516 | 6/2001 |
| WO | WO 2005/098049 | 10/2005 |
| WO | WO 2006/002167 A2 | 1/2006 |
| WO | WO 2006/048025 | 5/2006 |
| WO | WO 2007/008276 | 1/2007 |
| WO | WO 2007/044727 | 4/2007 |
| WO | WO 2008/106658 | 2/2008 |
| WO | WO 2008/144562 | 5/2008 |
| WO | WO 2011/126996 | 4/2011 |

OTHER PUBLICATIONS

Johnston et al. Psoralen-DNA Photoreaction: Controlled Prodiction of Mono- and Diadducts with Nanosecond Ultraviolet Laser Pulses, Science, New Series, vol. 197, pp. 906-908, 1997.

Lin et al., "DNA Tile Based Self-Assembly: Building Complex Nanoarchitectures", ChemPhysChem, vol. 7, pp. 1641-1647, 2006.

Liu et al., "A colorimetric lead blosensor using DNAzyme-directed assembly of gold nanoparticles," J. Am. Chem. Soc., 125(22), pp. 6642-6643, 2003.

Liu et al., "Approaching the Limit: Can One DNA Oligonucleotide Assemble into Large Nanostructures?", Angew. Chem. Int. Ed., vol. 45, pp. 1942-1945, 2006.

Liu et al., "DNA nanotubes self-assembled from triple-crossover tiles as templates for conductive nanowires", PNAS, vol. 101, No. 3, pp. 717-722, Jan. 20, 2004.

Macechko et al., "Comparison of Immunologic Amplification vs Enzymatic Deposition of Fluorochrome-conjugated Tyramide as Detection Systems for FISH," J Histochem Cytochem, 45(3), pp. 359-363, 1997.

Mahato et al., "Modulation of gene expression by antisense and antigene oligodeoxynucleotides and small interfering RNA", Expert Opin. Drug Deliv., vol. 2, No. 1, pp. 3-28. 2005.

Manche et al., "Interactions between Double-Stranded RNA Regulators and the Protein Kinase DAI", Molecular and Cellular Biology, vol. 12, No. 11, pp. 5238-5248, Nov. 1992.

Shah et al., "The Fries Isomerization of Acetyl and Benzoyl Esters of Umbelliferones." *J. Org. Chem.* 19: 1681-1685, 1954.

Shaner et al., "A guide to choosing fluorescent proteins", Nature Methods, vol. 2, No. 12, pp. 905-909, Dec. 2005.

Shlyakhtenko et al., "Structure of Three-Way DNA Junctions 1. Non-Planar DNA Geometry" Journal of Biomolecular Structure and Dynamics, vol. 11: pp. 1175-1189, Nov. 6, 1994.

Vieregg et al., "Selective Nucleic Acid Capture with Shielded Covalent Probes", J. Am. Chem. Soc., vol. 135, 9691-9699, 2013.

Vieregg et al., "Selective Nucleic Acid Capture with Shielded Covalent Probes—Supplemental Materials", J. Am. Chem. Soc., vol. 135, pp. S1-S52, 2013.

File History of U.S. Appl. No. 14/033,081.

File History of U.S. Appl. No. 14/320,479.

File History of U.S. Appl. No. 14/497,070.

Office Action dated Jun. 25, 2014 for U.S. Appl. No. 13/136,315.

Office Action dated Jul. 2, 2014 for U.S. Appl. No. 13/154,989.

Office Action dated Aug. 1, 2014 for U.S. Appl. No. 12/454,799.

Office Action dated Aug. 29, 2014 for U.S. Appl. No. 12/467,755.

Office Action dated Oct. 29, 2014 for U.S. Appl. No. 13/186,228.

Office Action dated Oct. 14, 2014 for U.S. Appl. No. 12/152,893.

Office Action dated Oct. 30, 2014 for U.S. Appl. No. 13/896,235.

Office Action dated Jan. 13, 2015 for U.S. Appl. No. 12/467,755.

(56) References Cited

OTHER PUBLICATIONS

Final Office Action dated May 8, 2015 for U.S. Appl. No. 12/467,755.
Office Action dated May 5, 2015 for U.S. Appl. No. 12/454,799.
Office Action dated Jul. 2, 2015 for U.S. Appl. No. 13/186,228.
Office Action dated Aug. 27, 2015 in U.S. Appl. No. 12/467,755.
Office Action dated Jul. 8, 2016 for U.S. Appl. No. 13/186,228.
Notice of Allowance dated Jun. 26, 2015 for U.S. Appl. No. 12/152,893.
Supplemental Notice of Allowance dated Sep. 17, 2015 for U.S. Appl. No. 12/152,893.
Aagaard et al., "RNAi Therapeutics: Principles, Prospects and Challenges." Advanced Drug Delivery Reviews 59 (2007): 75-86.
Allan et al., "A Concise Total Synthesis of (−)-Quinocarcin via Aryne Annulation." Journal of American Chemical Society 130 (2008) 17270-17271.
Amarzguioui et al., "Rational design and in vitro and in vitro delivery of Dicer substrate siRNA,", Nature Protocols, vol. 1, No. 2, pp. 508-517, 2006.
An, C. I.; Trinh, V. B.; Yokobayashi, Y. "Artificial control of gene expression in mammalian cells by modulating RNA interference through aptamer-small molecule interaction" RNA 2006, 12, 710-716.
Andronescu et al., "A New Algorithm for RNA Secondary Structure Design", J. Mol. Biol., vol. 336, pp. 607-624, 2004.
Asbury, C.L., "Kinesin: world's tiniest biped", Current Opinion in Cell Biology, vol. 17, pp. 89-97, 2005.
Barish, R.D.; Schulman, R.; Rothemund, P.W.K.; Winfree, E., "An Information-Bearing seed for nucleating algorithmic self assembly." Proceedings of the National Academy of Sciences 2009, 106, 6054-6059.
Bates, M.; Huang, B.; Dempsey, G.T.; and Zhuang, X. "Multicolor super-resolution imaging with photo-switchable fluorescent probes." Science, 317: 1749-1753, 2007.
Bath et al., "DNA nanomachines", Nature Nanotechnology, vol. 2, pp. 275-284, May 2007.
Behenna et al., "The Enantioselective Tsuji Allylation." Journal of American Chemical Society 126.46 (2004): 15044-15045.
Beisel, C. L.; Bayer, T. S.; Hoff, K. G.; Smolke, C. D. "Model-guided design of ligand-regulated RNAi for programmable control of gene expression" Mol. Syst. Biol. 2008, 4, 224.
Beisel, C. L.; Chen, Y. Y.; Culler, S. J.; Hoff, K. G.; Smolke, C. D. "Design of small molecule-responsive microRNAs based on structural requirements for Drosha processing" Nucleic Acids Res. 2011, 39, 2981-2994.
Bloomfield et al., "Nucleic Acids: Structures, Properties, and Functions." University Science Books (2000).
Bois et al., "Topological constraints in nucleic acid hybridization kinetics", Nucleic Acids Research, vol. 33, No. 13, pp. 4090-4095, 2005.
Bois J.S., "Analysis of interacting nucleic acids in dilute solutions" Ph.D. Thesis. California Institute of Technology. (2007).
Bolt et al., Differential Reactivities of the mono- and di-epoxide of 1,3-butadiene. Toxicology 113 (1996): 294-296.
Bonnet et al. Thermodynamic basis of the enhanced specificity of structured DNA probes, Proc. Natl. Acad. Sci. USA vol. 96 (May 1999), pp. 6171-6176.
Brummelkamp, T. R.; Bernards, R.; Agami, R. "A system for stable expression of short interfering RNAs in mammalian cells" Science 2002, 296, 550-553.
Bumcrot et al., "RNAi Therapeutics: A Potential New Class of Pharmaceutical Drugs." Nature Chemical Biology 2.12 (Dec. 2006): 711-719.
Bushnell et al., "ProbeDesigner: for the design of probesets for branched DNA (bDNA) signal amplification assays," Bioinformatics, 15(5), pp. 348-355, 1999.
Butterfoss et al., Computer-Based Design of Novel Protein Structures, Annu. Rev. Biophys. Biomol. Struct., vol. 35, pp. 49-65, 2006.
Caltech News Release, "Caltech Scientists Create New Process to Program", Sep. 6, 2010.
Caplen, "RNAi as a gene therapy approach", Expert Opin. Biol. Ther., vol. 3, No. 4, pp. 575-586, 2003.
Castanotto et al., "The Promises and Pitfalls of RNA-Interface-Based Therapeutics." Nature 457 (Jan. 22, 2009):426-433.
Cerutti et al., "On the Origin and Functions of RNA-Mediated Silencing: From Protists to Man." Current Genetics 50 (2006) 81-99.
Check et al, "RNA to the rescue?", Nature, vol. 425, pp. 10-12, Sep. 4, 2003.
Chen, H.L.; Cheng, Q.; Goel, A.; Huang, M.D. Espanes, P.M.d. "Invadable self-assembly: Combining robustness with efficiency." In Proceedings of the 15$^{th}$ annual ACM-SIAM Symposium on Discrete Algorithms (SODA); 2004.
Chen, Y.; Liu, H.P.; Ye, T.; Kim, J.; Mao, C.D. "DNA-Directed Assembly of Single-Wall Carbon Nanotubes." J.Am. Chem. Soc. 2007,129.
Choi et al., Nature Biotechnology 28(11): 1208-1214, 2010.
Coburn et al., "siRNAs: a new wave of RNA-based therapeutics", Journal of Antimicrobial Chemotherapy, vol. 51, pp. 753-756, 2003.
Coleman et al., "Template-Directed Cross-Linking of Oligonucleotides: Site-Specific Covalent Modification of dG-N7 Within Duplex DNA." J. Org. Chem. 60 (1995): 6252-6253.
Coleman, R.S. and Pires, R.M. Covalent cross-linking of duplex DNA using 4-thio-2'-deoxyuridine as a readily modifiable platform for introduction of reactive functionality into oligonucleotides. Nucleic Acids Research, 1997. 25: p. 4771-4777.
Collins et al., "A branched DNA signal amplification assay for quantification of nucleic acid targets below 100 molecules/ml," Nucleic Acids Res, 25(15), pp. 2979-2984, 1997.
Coppelli et al., "Oligonucleotides as Anticancer Agents: From the Benchside to the Clinic and Beyond", Current Pharmaceutical Design, vol. 11, pp. 2825-2840, 2005.
Cullen et al., "Genome-wide Screening for Gene Function Using RNAi in Mammalian Cells." Immunology and Cell Biology 83 (2005) 217-223.
Czauderna et al., "Structural Variations and Stabilising Modifications of Synthetic siRNAs in Mammalian Cells." Nucleic Acids Research 31.11 (2003): 2705-2716.
Dabby NL, Chen HL, Schaeffer JM, Winfree E. "The kinetics of toehold-mediated four-way branch migration." California Institute of Technology Thesis, Chapter 5 (2013), pp. 75-105.
Definition for "substantial" from Merriam-Webster Online Dictionary. Downloaded from merriam-webster.com; downloaded on Mar. 5, 2008.
Dias et al., "Antisense Oligonucleotides: Basic Concepts and Mechanisms." Molecular Cancer Therapeutics 1 (Mar. 2002) 347-355.
Dietz et al., "Folding DNA into Twisted and Curved Nanoscale Shapes." Science 2009, 325, 725-730.
Dirks et al., "A Partition Function Algorithm for Nucleic Acid Secondary Structure Including Pseudoknots." Journal of Computational Chemistry 24.13 (2003) 1664-1677.
Dirks et al., "An Algorithm for Computing Nucleic Acid Base-Pairing Probabilities Including Pseudoknots." Journal of Computational Chemistry 25.10 (2004): 1295-1304.
Dirks et al., "Paradigms for computational nucleic acid design," Nucleic Acids Research, vol. 32, No. 4, pp. 1392-1403, Oxford University Press, 2004.
Dirks et al., "Thermodynamic Analysis of Interacting Nucleic Acid Strands." SIAM Review 49.1 (2007): 65-88.
Dirks et al., "Triggered amplification by hybridization chain reaction," PNAS, vol. 101, No. 43, pp. 15275-15278, Oct. 26, 2004.
Dirks et al., Retraction for "Selective cell death mediated by small conditional RNAs" (which appeared in issue 39, Sep. 28, 2010 of Proc Natl Acad Sci USA), Proc Natl Acad Sci USA, Jan. 2, 2013 vol. 110, No. 1, p. 384.
Dohjima, T. et al., "Small Interfering RNAs Expressed from a Pol III Promoter Suppress the EWS/Fli-1 Transcript in an Ewing Sarcoma Cell Line", Molecular Therapy, vol. 7, No. 6, pp. 811-816, Jun. 2003.
Douglas et al., "DNA-nanotube-induced alignment of membrane proteins for NMR structure determination", PNAS, vol. 104, No. 16, pp. 6644-6648, Apr. 17, 2007.

(56) References Cited

OTHER PUBLICATIONS

Douglas et al., "Self-assembly of DNA into nanoscale three-dimensional shapes", Nature, vol. 459, pp. 414-418, May 21, 2009.
Du Qa, Thonberg H, Wang J, Wahlestedt C, Liang ZC (2005) A systematic analysis of the silencing effects of an active siRNA at all single-nucleotide mismatched target sites. Nucleic Acids Res 33:1671-1677.
Duckworth et al., "A Universal Method for the Preparation of Covalent Protein-DNA Conjugates for Use in Creating Protein Nanostructures", Agnew. Chem. Int. Ed., vol. 46, pp. 8819-8822, 2007.
Dunn JJ, Studier FW (1983) Complete nucleotide-sequence of bacteriophage-T7 DNA and the locations of T7 genetic elements. J Mol Biol 166:477-535.
Eckstein, F. "Phosphrothioate oligodeooxynucleotides: what is their origin and what is unique about them?" Antisense Nucleic Acid Drug Dev., 10:117-121, 2000.
Eddy, S.R. "Non-coding RNA genes and the modern RNA world." Nature Reviews, 2: 919-929, 2001.
Elbashir et al., "Functional anatomy of siRNAs for mediating efficient RNAi in *Drosophila melanogaster* embryo lysate", The EMBO Journal, vol. 20, No. 23, pp. 6877-6888, 2001.
Elghanian et al.,"Selective colorimetric detection of polynucleotides based on the distance-dependent optical properties of gold nanoparticles," Science, 277(5329), pp. 1078-1081, 1997.
Ellington et al., "In vitro selection of RNA molecules that bind specific ligands," Nature 346, pp. 818-822, 1990.
Elmén et al., "Locked Nucleic Acid (LNA) Mediated Improvements in siRNA Stability and Functionality." Nucleic Acids Research 33.1 (2005): 439-447.
Enquist et al., "The Total Synthesis of ( − )-Cyanthiwigin F by Means of Double Catalytic Enantioselective Alkylation." Nature 453.7199 (Jun. 26, 2008) 1228-1231.
Evanko, "Hybridization chain reaction", Nature Methods, vol. 1, No. 3, pp. 186-187, Dec. 2004.
Feldkamp U, Niemeyer CM (2006) Rational design of DNA nanoarchitectures. Angew Chem, Int Ed 45:1856-1876.
Felgner, et al., "Nomenclature for Synthetic Gene Delivery Systems", Human Gene Therapy, vol. 8, pp. 511-512, Mar. 20, 1997.
Femino et al., "Visualization of Single Molecules of mRNA in Situ." Methods of Enzymology 361 (2003): 245-304.
Ferkol et al., "Gene Transfer into the Airway Epithelium of Animals by Targeting the Polymeric Immunoglobulin Receptor", J. Clin. Invest., vol. 95, pp. 493-502, Feb. 1995.
Ferkol et al., "Regulation of the phosphoenolpyruvate carboxykinase/human factor IX gene introduced into the lives of adult rats by receptor-mediated gene transfer", The FASEB Journal, vol. 7, pp. 1081-1091, Aug. 1993.
Ferreira et al., "The Palladium-Catalyzed Oxidative Kinetic Resolution of Secondary Alcohols with Molecular Oxygen." Journal of American Chemical Society 123.31 (2001): 7725-7726.
Fire et al., "Potent and specific genetic interference by double-stranded RNA in *Caenorhabditis elegans*", Nature, vol. 391, pp. 806-811, Feb. 19, 1998.
Flamm et al., "RNA folding at elementary step resolution," RNA, vol. 6, pp. 325-338, 2000.
Friedrich et al., A Cellular Screening Assay to Test the Ability of PKR to Induce Cell Death in Mammalian Cells, Molecular Therapy, vol. 12, No. 5, pp. 969-975, Nov. 2005.
Friedrich et al., "RNA molecules as anti-cancer agents", Seminars in Cancer Biology, vol. 14, pp. 223-230, 2004.
Fu et al., "DNA Double-Crossover Molecules", Biochemistry, vol. 32, pp. 3211-3220, 1993.
Garcia et al., "Impact of Protein Kinase PKR in Cell Biology: from Antiviral to Antiproliferative Action." Microbiology and Molecular Biology Reviews vol. 70, No. 4 (Dec. 2006): pp. 1032-1060.
Garg et al., "A Ligand-free Solid-supported System for Sonogashira Couplings: Applications in Nucleoside Chemistry." Chem. Commun. (2005) 4551-4553.
Garg et al., "Development of an Enantiodivergent Strategy for the Total Synthesis of (+)- and (−)-Dragmacidin F from a Single Enantiomer of Quinic Acid." Journal of American Chemical Society 127 (2005) 5970-5978.
Gasparro et al., Site-specific targeting of psoralen photadducts with a triple helix-forming oligonuicleotide: characterization of psoralen monoadduct and crosslink formation. Nucleic Acids Research 22 (1994), pp. 2845-2852.
Gilman et al., "The Biological Actions and Therapeutic Applications of the B-Chloroethyl Amines and Sulfides." Science 103.2675 (Apr. 5, 1946): 409-415.
Goodman, R.P.; Schaap, I.A.T.; Tardin, C.F.; Erben, C.M.; Berry, R.M.; Schmidt, C.F.; and Turberfield, A.K. "Rapid chiral assembly of rigid DNA blocks for molecular nanofabrication." Science, 310, 2005.
Green et al., "DNA Hairpins: Fuel for Autonomous DNA Devices", Biophysical Journal, vol. 91, pp. 2966-2975, Oct. 2006.
Hansma et al., "DNA Binding to Mica Correlates with Cationic Radius: Assay by Atomic Force Microscopy", Biophysical Journal, vol. 70, pp. 1933-1939, Apr. 1996.
Hashimoto et al., "Recent Progress in Diazirine-Based Photoaffinity Labeling." Eur. J. Org. Chem. (2008): 2513-2523.
Haugland RP. The Handbook: A Guide to Fluorescent Probes and Labeling Technologies. 10th Ed. Molecular Probes/Invitrogen; 2005.
Hearst et al., "Psoralen Photochemistry." Ann.Rev. Biophys.Bioeng. 10 (1981): 69-86.
Heidel, J.D., "Targeted, systematic non-viral delivery of small interfering RNA in vivo", Doctoral thesis, California Institute of Technology, pp. 1-128, 2005.
Hell, S.W. "Far-field optical nanoscopy." Science, 316: 1153-1158, 2007.
Herath et al., "Synthesis of Acrimarins from 1,3,5-Trioxygenated-9-acridone Derivatives." Journal of Heterocyclic Chem. 41 (2004): 23-28.
Higuchi et al. Selective regulation of mutant K-ras mRNA expression by photo-cross-linking antisense oligonucleotide. Nucleic Acids Symposium Series (2007) vol. 51 (1) pp. 443-444.
Hochrein et al., "Conditional Dicer Substrate Formation via Shape and Sequence Transduction with Small Conditional RNAs," J. Am. Chem. Soc. 2013, 135, 17322-17330.
Hofacker et al., "Fast folding and comparison of RNA secondary structures," Monatshefte für Chemie, vol. 125, pp. 167-188, 1994.
Hokaiwado et al., "RNAi-based drug discovery and its application to therapeutics", IDrugs, vol. 11, No. 4, pp. 274-278, 2008.
Hughes et al., "Double Labeling wit Fluorescence in Situ Hybridization in *Drosophila* Whole-Mount Embryos," BioTechniques, 24(4), pp. 530-532, 1998.
Huizenga et al., "A DNA Aptamer That Binds Adenosine and ATP." Biochemistry 34, pp. 656-665, 1995.
Hu-Lieskovan et al., "Sequence-Specific Knockdown of EWS-FLI1 by Targeted, Nonviral Delivery of Small Interfering RNA Inhibits Tumor Growth in a Murine Model of Metastatic Ewing's Sarcoma." Cancer Research 65.19 (Oct. 1, 2005): 8984-8992.
Iqbal et al., "A review of molecular recognition technologies for detection of biological threat agents", Biosensors & Bioelectronics, vol. 15, pp. 549-578, 2000.
Jagus et al., "PKR, apoptosis and cancer", The International Journal of Biochemistry & Cell Biology, vol. 31, pp. 123-138, 1999.
Jayasena et al., "Aptamers: An Emerging Class of Molecules That Rival Antiodies in Diagnostics", Clinical Chemistry, vol. 45, No. 9, pp. 1628-1650, 1999.
Jhaveri et al., "In vitro selection of signaling aptamers", Nature Biotechnology, vol. 18, pp. 1293-1297, Dec. 2000.
Jinek M, Doudna JA (2009) A three-dimensional view of the molecular machinery of RNA interference. Nature 457:405-412.
Judge et al., "Design of Noninflammatory Synthetic siRNA Mediating Potent Gene Silencing in Vivo." Molecular Therapy 13.3 (Mar. 2006): 494-505.
Judge et al., "Overcoming the Innate Immune Response to Small Interfering RNA", Human Gene Therapy, vol. 19, pp. 111-124, Feb. 2008.

(56) References Cited

OTHER PUBLICATIONS

Julian et al., "Biomimetic Approaches to Gas Phase Peptide Chemistry: Combining Selective Binding Motifs with Reactive Carbene Precursors to Form Molecular Mousetraps." International Journal of Mass Spectrometry 228 (2003): 851-864.
Julian et al., "Molecular Mousetraps: Gas-Phase Studies of the Covalent Coupling of Noncovalent Complexes Initiated by Reactive Carbenes Formed by Controlled Activation of Diazo Precursors." Agnew. Chem.Int. Ed. 42.9 (2003) 1012-1015.
Kadnikov et al., "Synthesis of Coumarins via Palladium—Catalyzed Carbonylative Annulation of Internal Alkynes by o-Iodophenols." Organic Letters 2.23 (2000): 3643-3646.
Ke et al. "Scaffolded DNA Origami of a DNA Tetrahedron Molecular Container," Nanoletters, 2009. 9(6): 2445-2447.
Killops, K.L., Campos, L.M., Hawker, C.J. Robust, Efficient, and Orthogonal Synthesis of Dendrimers via Thiol-ene "Click" Chemistry. Journal of the American Chemical Society, 2008. 130: p. 5062-5064.
Kim DH, Behlke MA, Rose SD, Chang MS, Choi S, Rossi JJ (2005) Synthetic dsRNA Dicer substrates enhance RNAi potency and efficacy. Nat Biotechnol 23:222-226.
Kim DH, Rossi JJ (2007) Strategies for silencing human disease using RNA interference. Nat Rev Genet 8:173-184.
Kim J, White KS, Winfree E (2006) Construction of an in vitro bistable circuit from synthetic transcriptional switches. Mol Syst Biol 2:68.
Kislauskis et al. "Isoform-specific 3'-untranslated Sequences Sort $\alpha$-cardiac and $\beta$-cytoplasmic Actin Mesenger RNAs to Different ytoplasmic Compartments," The Journal of Cell Biology, 123(1), pp. 165-172, 1993.
Knorre et al., "Photoaffinity Labeling as an Approach to Study Supramolecular Nucleoprotein Complexes." FEBS Letters 433 (1998): 9-14.
Kobertz et al., "An Efficient Synthesis of a Furan-Side Furocoumarin Thymidine Monoadduct." J. Org. Chem. 62.8 (1997) 2630-2632.
Kobertz et al., "Solid-Phase Synthesis of Oligonucleotides Containing a Site-Specific Psoralen Derivative." Journal of American Chemical Society 119 (1997): 5960-5961.
Kobertz et al., "Total Synthesis of a Cis-Syn 2-Carbomethoxypsoralen Furan-Side Thymidine Monoadduct." Journal of American Chemical Society 118 (1996): 7101-7107.
Kosman, et al., "Multiplex Detection of RNA Expression in *Drosophila* Embryos," Science, 305, p. 846, 2004.
Kumar D, An CI, Yokobayashi Y (2009) Conditional RNA interference mediated by allosteric ribozyme. J Am Chem Soc 131:13906-13907.
Kumar D, Kim SH, Yokobayashi Y (2011) Combinatorially inducible RNA interference triggered by chemically modified oligonucleotides. J Am Chem Soc 133:2783-2788.
Kurreck, J. Angew. "RNA interference: from basic research to therapeutic applications" Chem., Int. Ed. 2009, 48, 1378-1398.
Kuzuya et al., "Six-Helix and Eight-Helix DNA Nanotubes Assembled from Half-Tubes", Nano Lett., vol. 7, No. 6, pp. 1757-1763, 2007.
Lacenere et al., "Effects of a Modified Dye-Labeled Nucleotide Spacer Arm on Incorporation by Thermophilic DNA Polymerases." Nucleosides, Nucleotides, and Nucleic Acids 25 (2006) 9-15.
Ladiges, et al., "Tissue specific expression of PKR protein kinase in aging B6D2F1 mice," Mechanisms of Ageing and Development, vol. 114, pp. 123-132, (2000).
Lawley et al., "DNA Adducts from Chemotherapeutic Agents." Mutation Research—Fundamental and Molecular mechanisms of Mutagenesis 355 (1996): 13-40.
Lawrence et al., "Highly Localized Tracks of Specific Transcripts within Interphase Nuclei Visualized by In Situ Hybridication," Cell, 57, pp. 493-502, 1989.
Layzer et al., "In Vivo Activity of Nuclease-Resistant siRNAs." RNA 10 (2004): 766-771.
Le et al., "DNA-Templated Self-Assembly of Metallic Nanocomponent Arrays on a Surface", Nano Lett., vol. 4, No. 12, pp. 2343-2347, 2004.
Lee et al., "A self-replicating peptide", Nature, vol. 382, pp. 525-528, Aug. 8, 1996.
Lee, J.F., Hesselberth, J.R.; Meyers, L.A.; and Ellington, A.D. "Aptamer database." Nucleic Acids Research, 32: D95-100, 2004.
Lee, S. K.; Kumar, P. "Conditional RNAi: towards a silent gene therapy" Adv. Drug Delivery Rev. 2009, 61, 650-664.
Levsky et al., "Single-Cell Gene Expression Profiling," Science 297, pp. 836-840, 2002.
Levy et al., "Exponential growth by cross-catalytic cleavage of deoxyribozymogens", PNAS, vol. 100, No. 11, pp. 6416-6421, May 27, 2003.
Li et al., A new class of homogenous nucleic acid probes based on specific displacement hybridization, Nucleic Acids Research, vol. 30, No. 2e5 (2002), pp. 1-9.
Li, H.; LaBean, T.H.; Kenan, D.J. "Single-chain antibodies against DNA aptamers for use as adapter molecules on DNA tile arrays in nanoscale materials organization." Organic and Biomolecular Chemistry 2006, 3420-3426. 2006.
Li, Z, Trimble, M.J.; Brun, Y.V.; Jensen, G.J. "The structure of FtsZ filaments in vivo suggests a force-generating role in cell division." EMBO J.,26, pp. 4694-4708. 2007.
Lima W.F., Wu H.J., Nichols J.G., Sun H., Murray H.M., Crooke S.T. "Binding and cleavage specificities of human Argonaute2" J Biol Chem 284:26017-26028 (2009).
Manoharan et al., "RNA Interference and Chemically Modified Small Interfering RNAs." Current Opinion in Chemical Biology 8 (2004): 570-579.
Masu, H.; Narita, A.; Tokunaga, T.; Ohashi, M.; Aoyama, Y.; Sando, S. Angew. "An activatable siRNA probe: trigger-RNA-dependent activation of RNAi function" Chem., Int. Ed. 2009, 48, 9481-9483.
Mathieu et al., "Six-Helix Bundles Designed from DNA", Nano Lett., vol. 5, No. 4, pp. 661-665, 2005.
Matsui, T. et al., "Expression of Unphosphorylated Form of Human Double-Stranded RNA-Activated Protein Kinase in *Escherichia coli*", Biochemical and Biophysical Research Communications, vol. 284, No. 3, pp. 798-807, 2001.
McIntyre, G. J.; Yu, Y. H.; Lomas, M.; Fanning, G. C. "The effects of stem length and core placement on shRNA activity" BMC Mol. Biol. 2011, 12, 34.
Meinhardt et al., "Wavelength-dependent Penetration Depths of Ultraviolet Radiation in Human Skin." Journal of Biomedical Optics 13.4 (Jul./Aug. 2008) 044030-1-044030-5.
Mitchell et al., "Self-Assembly of Chiral DNA Nanotubes", J. Am. Chem. Soc., vol. 126, pp. 16342-16343, 2004.
Mittelstadt, et al., "Interaction of human tRNA-dihydrouridine synthase-2 with interferon-induced protein kinase PKR," Nucleic Acids Research, vol. 36, No. 3, pp. 998-1008, (2008).
Mohr et al., "Catalytic Enantioselective Decarboxylative Protonation." Journal of American Chemical Society 128.35 (2006): 11348-11349.
Mohr et al., "Natural Products as Inspiration for the Development of Asymmetric Catalysis." Nature 455 (Sep. 18, 2008) 323-332.
Nakano et al., "Selection for thermodynamically stable DNA tetraloops using temperature gradient gel electrophoresis reveals four motifs: d(cGNNAg), d(cGNABg), d(cCNNGg), and d(gCNNGc)," Biochemistry, vol. 41, pp. 14281-14292,American Chemical Society, 2002.
Naked Scientists (The): Science Radio & Science Podcasts, "RNA-away cancer cells", Sep. 12, 2010, http://www.thenakedscientists.com/HTML/content/news/news/2051/.
National Science Foundation, "These Cells Will Self-Destruct in Five . . . Four . . . ", Press Release 10-160, p. 1-3. Sep. 6, 2010.
Noll et al., "Formation and Repair of Interstrand Cross-Links in DNA." Chemical Reviews 106.2 (2006) 277-301.
Noll et al., "Preparation of Interstrand Cross-Linked DNA Oligonucleotide Duplexes." Frontiers in Bioscience 9 (Jan. 1, 2004): 421-437.
Nutiu et al., "Structure-switching signaling aptamers," J. Am. Chem. Soc., vol. 125, pp. 4771-4778, American Chemical Society, 2003.

(56) References Cited

OTHER PUBLICATIONS

Opalinska et al., "Nucleic-Acid Therapeutics: Basic Principles and Recent Applications", Nature Reviews Drug Discovery, vol. 1, pp. 503-514, 2002.
Ouporov, Igor V., and Leontis, Necocles B., "Refinement of the Solution Structure of a Branched DNA Three-Way Junction," Biophysical Journal, vol. 68, ppg. 266-274. Jan. 1995.
Park et al., "Rapid Identification of Candida dubliniensis Using a Species-Specific Molecular Beacon", Journal of Clinical Microbiology, vol. 38, No. 8, pp. 2829-2836, 2000.
Park et al., "Three-Helix Bundle DNA Tiles Self-Assemble into 2D Lattice or 1D Templates for Silver Nanowires", Nano Lett., vol. 5, No. 4, pp. 693-696, 2005.
Park, S.H.; Yin, P.; Liu, Y.; Reif, J.H.; LaBean, T.H.; Yan, H. "Programmable DNA Self-Assemblies for Nanoscale Organization of Ligands and Proteins." Nano Letters 2005, 5, 729-733.
Patel et al., Cancer Biology & Therapy 14: 8, 693-696; Aug. 2013.
Paul et al., "A self-replicating ligase ribozyme", PNAS, vol. 99, No. 20, pp. 12733-12740, Oct. 1, 2002.
Peng et al., Facile SNP detection using bifunctional, cross-linking oligonucleotide probes, Nucleic Acids Research vol. 36 No. 5e31 (2008), pp. 1-7.
Perales et al., "Gene Transfer in vivo: Sustained Expression and Regulation of Genes Introduced into the Liver by Receptor-Targeted Uptake", Proceedings of the National Academy of Sciences of the United States of America, vol. 91, pp. 4086-4090, Apr. 1994.
Pieles, U. and Englisch, U. Psoralen covalently linked to oligodeoxyribonucleotides: synthesis, sequence specific recognition of DNA and photo-cross-linking to purimidine residues of DNA. Nucleic Acids Research, 1989. 17: p. 285-299.
Piston et al., "Fluorescent protein FRET: the good, the bad and the ugly", Trends Biochem Sci., Sep. 2007, vol. 32, No. 9, pp. 407-414.
Player et al., "Single-copy Gene Detection Using Branched Dna (bDNA)) in Situ Hybridization," J. Histochem & Cytochem, 49(5), pp. 603-611, 2001.
Pouton et al., "Key issues in non-viral gene delivery", Advanced Drug Delivery Reviews, vol. 46, pp. 187-203, 2001.
Provost, P.; Dishart, D.; Doucet, J.; Frendewey, D.; Samuelsson, B.; Radmark, O. "Ribonuclease activity and RNA binding of recombinant human Dicer" EMBO J. 2002, 21, 5864-5874.
Qi et al., "Surface Transfer Doping of Diamond (100) by Tetrafluoro-tetracyanoquinodimethane", J. Am. Chem. Soc., vol. 129, pp. 8084-8085, 2007.
Qian et al., "Recent Developments in Signal Amplification Methods for In Situ Hybridization," Diagnostic Molecular Pathology, 12(1), pp. 1-13, 2003.
Qian, X., L. Jin, and R.V. Lloyd, In situ hybridization: basic approaches and recent development. The Journal of Histotechnology, 2004. 27(1): p. 53-67.
Rachofsky et al., "Probing structure and dynamics of DNA with 2-aminopurine: Effects of local environment on fluorescence," Biochemistry, vol. 40, pp. 946-956, 2001.
Raj et al., "Imaging Individual mRNA Molecules Using Multiple Singly Labeled Probes." Nature Methods 5.10 (Oct. 2008): 877-879.
Read et al., "Barriers to Gene Delivery Using Synthetic Vectors", Advances in Genetics, vol. 53, pp. 19-46, 2005.
Reif, J.H.; Sahu, S.; Yin, P. "Compact Error-Resilient Computational DNA tiling Assemblies." In Proc. 10th International Meeting on DNA Computing; 2004.
Reif, J.H.; Sahu, S.; Yin, P. "Complexity of Graph Self-Assembly in Accretive Systems and Self-Destructible Systems." In Proc. 11th International Meeting on DNA Computing; 2005.
Reynolds et al., "Rational siRNA Design for RNA Interference." Nature Biotechnology 22.3 (Mar. 2004) 326-330.
Rothemund et al., "Design and Characterization of Programmable DNA Nanotubes", J. Am. Chem. Soc., vol. 126, pp. 16344-16352, 2004.
Rothemund, P.; Papadakis, J.; Winfree, E. "Algorithmic Self-Assembly of DNA Sierpinski Triangles." PLoS Biology 2004, 2, 2041-2053.
Rothemund, P.W.K., "Folding DNA to creat nanoscale shapes and patterns", Nature, vol. 440, pp. 297-302, 2006.
Rothemund, P.W.K.; Winfree, E. "The Program-size complexity of self-assembled squares (extended abstract)." In Proceedings of the thirty-second annual ACM symposium on Theory of computing; ACM Press: 2000.
Sahu et al., "A self-Assembly Model of Time-Dependent Glue Strength." In Proc. 11th International Meeting on DNA Computing; 2005.
Santalucia J. "A unified view of polymer, dumbbell, and oligonucleotide DNA nearest-neighbor thermodynamics" Proc Natl Acad Sci 95:1460-1465 (1998).
Saunders et al., "Introduction of DNA into Bacteria." Methods in Microbiology 29 (1999): 3-49.
Schärer et al., "DNA Interstrand Crosslinks: Natural and Drug-Induced DNA Adducts that Induce Unique Cellular Responses." ChemBioChem 6 (2005): 27-32.
Scherer et al., "Approaches for the sequence-specific knockdown of mRNA", Nature Biotechnology, vol., 21, No. 12, pp. 1457-1465, 2003.
Schipani, Vanessa, "A targeted cancer therapy?" The Scientist, Sep. 7, 2010 blog post, http://www.the-scientist.com/blog/display/57674/.
Schulman et al., "Synthesis of crystals with a programmable kinetic barrier to nucleation", PNAS, vol. 104, No. 39, pp. 15236-15241, Sep. 25, 2007.
Schulte-Merker et al., "no tail (ntl) is the zebrafish homologue of the mouse T (Brachyury) gene." Development 120 (1994): 1009-1015.
Schwartz et al., "Cloning and Functional Analysis of Multiply Spliced mRNA Species of Human Immunodeficiency Virus Type 1", Journal of Virology, vol. 64, No. 6, pp. 2519-2529, Jun. 1990.
Schweitzer et al., "Combining nucleic acid amplification and detection," Curr Opin Biotechnol, 12, pp. 21-27 2001.
Seelig et al., "Catalyzed Relaxation of a Metastable DNA Fuel", Journal American Chemical Society, vol. 128, No. 37, pp. 12211-12220, 2006.
Seeman, "De Novo Design of Sequences for Nucleic Acid Structural Engineering", Journal of Biomolecular Structure & Dynamics, pp. 573-581, vol. 8, No. 3, 1990.
Seeman, "DNA in a material world", Department of Chemistry, New York University, Nature, vol. 421, pp. 427-431 (Jan. 23, 2003).
Seeman, "Nucleic acid junctions and lattices," J. Theor. Biol., vol. 99, pp. 237-247, Academic Press Inc. (London) Ltd., 1982.
Seeman, "Nucleic acid nanstructures and topology", Angew. Chem. Int. Ed. Volume 37, pp. 3220-3238 (1998).
Seeman, et al., Nucleic Acid Nanostructures: Bottom Up Control of Geometry on the Nanoscale, Reports on Progress in Physics, 68 : 237 (2005).
Sekulic, A.; Hudson, C.C; Homme, J.L.; Yin, P.; Otterness, D.M.; Karnitz, L.M.; Abraham, R.T. A Direct Linkage between the Phosphoinositide 3-Kinase-AKT Signaling Pathway and the Mammalian Target of Rapamycin in Mitogen-stimulated and Transformed Cells. Cancer Research 2000, 60, 3504-3513.
Serra M.J., Turner D.H., "Predicting thermodynamic properties of RNA" Methods Enzymol 259: 242-261 (1995).
Sharma et al., "DNA-Tile-Directed Self-Assembly of Quantum Dots into Two-Dimensional Nanopatterns", Angew. Chem. Int. Ed., vol. 47, pp. 5157-5159, 2008.
Sharma, J.; Chhabra, R.; Cheng, a.; Brownell, J.; Liu, Y.; Yan, H. "Control of Self-Assembly of DNA Tubules through Integration of Gold Nanoparticles" Science 2009, 112-116.
Shih et al., "A 1.7-kilobase single-stranded DNA that folds into a nanoscale octahedron", Nature, vol. 427, pp. 618-621, Feb. 12, 2004.
Shir et al., "Inhibition of glioma growth by tumor-specific activation of double-stranded RNA-dependent protein kinase PKR", Nature Biotechnology, vol. 20, pp. 895-900, Sep. 2002.
Shlyakhtenko et al., "Structure and Dynamics of Three-Way DNA Junctions: Atomic Force Microscopy Studies." Nucleic Acids Research. 2000. 28(19): 3472-3477.

(56) References Cited

OTHER PUBLICATIONS

Silverman et al., "Oligonucleotide Probes for RNA-Targeted Fluorescence In Situ Hybridization." Advances in Clinical Chemistry 43 (2007): 79-115.
Silverman et al., "Quenched Autoligation Probes Allow Discrimination of Live Bacterial Species by Single Nucleotide Differences in rRNA." Nucleic Acids Research 33.15 (2005): 4978-4986.
Siolas, D.; Lerner, C.; Burchard, J.; Ge, W.; Linsley, P. S.; Paddison, P. J.; Hannon, G. J.; Cleary, M. A. "Synthetic shRNAs as potent RNAi triggers" Nat. Biotechnol. 2005, 23, 227-231.
Situma et al., "Immobilized molecular beacons: A new strategy using UV-activated poly(methyl methacrylate) surfaces to provide large fluorescence sensitivities for reporting on molecular association events." Analytical Biochemistry 363 (2007) 35-45.
Sokol et al., "Real time detection of DNA•RNA hybridization in living cells", Proc. Natl. Acad. Sci. USA, vol. 95, pp. 11538-11543, Sep. 1998.
Stemmer, et al, Single Step Assembly of a Gene and Entire Plasmid from Large Numbers of Oligodeoxyribonnucleotides. Gene, vol. 164, pp. 49-53 (1995).
Storhoff et al., "One-pot colorimetric differentiation of polynucleotides with single base imperfections using gold nanoparticles," J. Am. Chem. Soc., 120, pp. 1959-1964, 1998.
Stuheimer, et al. "Global Structure of Three-Way DNA Junctions with and without Additional Unpaired Bases: A Fluorescence Resonance Energy Transfer Analysis". Biochemistry 1997. 35: pp. 13530-13538.
Sun et al., "Side Chain Chemistry Mediates Backbone Fragmentation in Hydrogen Deficient Peptide Radicals." Journal of Proteome Research 8 (2009) 958-966.
Takei et al., "A Small Interfering RNA Targeting Vascular Endothelial Growth Factor as Cancer Therapeutics." Cancer Research 64. (May 15, 2004): 3365-3370.
Tani et al., "Synthesis and Structural Analysis of 2-Quinuclidonium Tetrafluoroborate." Nature 441 (Jun. 8, 2006) 731-734.
Thomas et al., "Photoaffinity Cross-Linking and RNA Structure Analysis." Methods in Enzymology 318 (2000) 136-147.
Thompson, N.L.; Lieto, A.M., and Allen, N.W. "Recent advances in fluorescence correlation spectroscopy." Curr. Opin.Struct. Biol., 12, 2002.
Tijsterman et al., "Dicers at RISC: The Mechanism of RNAi", Cell, vol. 117, pp. 1-3, 2004.
Tuerk et al., "Systematic Evolution of Ligands by Exponential Enrichment: RNA Ligands to Bacteriophage T4 DNA Polymerase," Science 249, pp. 505-510, 1990.
Tuleuova, N.; An, C. I.; Ramanculov, E.; Revzin, A.; Yokobayashi, Y. "Modulating endogenous gene expression of mammalian cells via RNA-small molecule interaction" Biochem. Biophys. Res. Commun. 2008, 376, 169-173.
Turberfield, et al., "DNA fuel for free-running nanomachines, "Physical Review Letters, vol. 90, No. 11, pp. 118102-1-118102-4, Mar. 21, 2003.
Turk, Greg and Levoy, Marc. "Zippered polygon meshes from range images." in SIGGRAPH, pp. 311-318, 1994.
Tyagi et al., "Molecular Beacons: Probes that Fluoresce upon Hybridization," Nature Biotechnology 14, pp. 303-308, 1996.
Tyagi et al., et al., Multicolor Molecular Beacons for Allele Discrimination, Nature Biotechnology vol. 16, pp. 49-53, Jan. 1998.
Van de Corput et al., "Sensitive mRNA Detection by Fluorescence In Situ Hybridization Using Horseradish Peroxidase-labeled Oligodeoxynucleotides and Tyramide Signal Amplification," J. Histochem Cytochem, 46(11), pp. 1249-1259, 1998.
Venkataraman et al. "Selective Cell Death Mediated by Small Conditional RNAs", Proc Natl Acad Sci USA, early edition, approved Jul. 21, 2010, p. 1-6.
Venkataraman et al. Abstract of "Selective Cell Death Mediated by Small Conditional RNAs", Proc Natl Acad Sci USA, early edition, http://www.pnas.org/content/early/2010/09/01/1006377107.abstract.
Venkataraman, S.; Dirks, R. M.; Rothemund, P. W. K.; Winfree, E.; Pierce, N. A. "An autonomous polymerization motor powered by DNA hybridization" Nat. Nanotechnol. 2007.
Vermeulen et al., "The contributions of dsRNA structure to Dicer specificity and efficiency", RNA, vol. 11, pp. 674-682, 2005.
Vodovozova et al., "Photoaffinity Labeling and Its Application in Structural Biology." Biochemistry (Moscow) 72.1 (2007): 1-20.
Volker, et al., "Conformational energetics of stable and metastable states formed by DNA triple repeat oligonucleotides: implications for triplet expansion diseases,"PNAS, vol. 99, No. 23, pp. 14700-14705, Nov. 12, 2002.
Von Kiedrowski, "A Self-Replicating Hexadeoxynucleotide", Agnew. Chem. Int. Ed. Engl., vol. 25, No. 10, pp. 932-935, 1986.
Voorhoeve et al., "Knockdown Stands Up.:" Trends in Biotechnology 21.1 (Jan. 2003) 2-4.
Wagner et al., "Transferrin-Polycation Conjugates as Carriers for DNA Uptake into Cells", Proceedings of the National Academy of Sciences of the United States of America, vol. 87, pp. 3410-3414, May 1990.
Wassarman et al., "Psoralen Crosslinking of Small RNAs in vitro." Molecular Biology Reports 17 (1993): 143-151.
White et al., "The Catalytic Asymmetric Total Synthesis of Elatol." Journal of American Chemical Society 130.3 (2008): 810-811.
Wijen et al., "The in vivo Genetic Activity Profile of the Monofunctional Nitrogen Mustard 2-Chloroethylamine Differs Drastically from its Bifunctional Counterpart Mechlorethamine." Carcinogenesis 21.10 (2000) 1859-1867.
Wilkie et al., "Transcribed genes are localized according to chromosomal position within polarized *Drosophila* embryonic nuclei," Current Biology, 9, pp. 1263-1266, 1999.
Williams, B.R.G., "PKR; a sentinel kinase for cellular stress", Oncogene, vol. 18, pp. 6112-6120, 1999.
Willis, M.C., et al. Photocross-linking of 5-Iodouracil-Substituted RNA and DNA to Proteins. Science, 1993. 262: p. 1255-1257.
Winfree et al., "Design and self-assembly of two-dimensional DNA crystals", Nature, vol. 394, pp. 539-544, Aug. 6, 1998.
Winfree, E. "On the computational power of DNA annealing and ligation." Computation and Neural Systems, California Institute of Technology, May 25, 1995.
Winfree, E. Algorithmic Self-Assembly of DNA, Ph.D. thesis. Thesis, California Institute of Technology, 1998.
Wiznerowicz, M.; Szulc, J.; Trono, D. "Tuning silence: conditional systems for RNA interference" Nat. Methods 2006, 3, 682-688.
Wu et al., "A Model for the Double-stranded RNA (dsRNA)-dependent Dimerization and Activation of the dsRNA-activated Protein Kinase PKR", The Journal of Biological Chemistry, vol. 272, No. 2, pp. 1291-1296, 1997.
Wu et al., "Receptor-mediated in Vitro Gene Transformation by a Soluble DNA Carrier System", The Journal of Biological Chemistry, vol. 262, No. 10, pp. 4429-4432, 1987.
Xie, Z.; Liu, S. J.; Bleris, L.; Benenson, Y. "Logic integration of mRNA signals by an RNAi-based molecular computer" Nucleic Acids Res. 2010, 38, 2692-2701.
Yan et al., "DNA-Templated Self-Assembly of Protein Arrays and Highly Conductive Nanowires", Science, vol. 301, pp. 1882-1884, Sep. 26, 2003.
Yin, P.; Choi, H. M. T.; Calvert, C. R.; Pierce, N. A. "Programming biomolecular self-assembly pathways" Nature 2008, 451, 318-322.
Yin, P.; Hariadi, R.; Sahu, S.; Choi, H.M.T.; Park, S.H.; :LaBean, T.H.; J.H. Reif, "Programming DNA Tube Circumferences." Science 2008, 321, 824-826.
Yin, P.; Hartemink, "Theoretical and practical advances in genome halving." A.K. Bioinformatics 2005, 21, 869-879.
Yin, P.; Turberfield, A.J.; Reif, J.H. "Designs of Autonomous Unidirectional Walking DNA Devices." In Proc. 10th International Meeting on DNA computing; 2004.
Yin, P.; Yan, H.; Daniell, X.; Turberfield, A.J.; Reif, J. "A Unidirectional DNA Walker that Moves Autonomously along a Track." Angewandte Chemie International Edition 2004, 43, 4906-4911.
Yoshimura et al., "Interstrand Photocrosslinking of DNA via p-carbamoylvinyl Phenol Nucleoside." Bioorganic & Medicinal Chemistry Letters 15 (2005): 1299-1301.

(56) References Cited

OTHER PUBLICATIONS

Yurke, B.; Turberfield, A. J.; Mills, A. P., Jr.; Simmel, F. C.; Neumann, J. L. "A DNA-fuelled molecular machine made of DNA" Nature 2000, 406, 605-608.
Zadeh et al., "Software News and Updates NUPACK: Analysis and Design of Nucleic Acid Systems", Journal of Computational Chemistry, vol. 32, No. 1, pp. 170-173, 2011.
Zadeh, J. N.; Wolfe, B. R.; Pierce, N. A. "Nucleic acid sequence design via efficient ensemble defect optimization" J. Comput. Chem. 2011, 32, 439-452.
Zhang et al., Targeted Gene Silencing by Small Interfering RNA-Based Knock-Down Technology, Current Pharmaceutical Biotechnology, vol. 5, pp. 1-7, 2004.
Zhang, D. Y.; Seelig, G. "Dynamic DNA nanotechnology using strand-displacement reactions" Nat. Chem. 2011, 3, 103-113.
Zhang, L., Zhou, W., Velculescu, V.E.; Kern, S.E., Hruban, R.H., Hamilton, S.R.; Vogelstein, B.; and Kinzler, K.W. "Gene expression profiles in normal and cancer cells." Science, 276:1268-1272, 1997.
Zheng et al., "Activation of the protein kinase PKR by short double-stranded RNAs with single-stranded tails", RNA, vol. 10, pp. 1934-1945, 2004.
Zhou et al., "RNA Interference and Potential Applications", Current Topics in Medicinal Chemistry, vol. 6, pp. 901-911, 2006.
Zuker et al., "Optimal computer folding of large RNA sequence using thermodynamics and auxiliary information," Nucleic Acids Research, vol. 9, No. 1, pp. 133-147, 1981.
International Search Report and Written Opinion from PCT/US2005/009471, dated Mar. 8, 2006.
International Search Report and Written Opinion from PCT/US2008/055559, dated Sep. 3, 2008.
Supplementary European Search Report from PCT/US2005/009471, dated May 6, 2008.
Extended European Search Report dated Apr. 22, 2010 in European Patent Application No. 06836249.0.
Extended European Search Report from Application No. 08755764.1, dated Nov. 7, 2011.
Communication Article 94(3) EPC from Application No. 08755764.1, dated Nov. 7, 2012.
U.S. File History for U.S. Appl. No. 11/087,937.
U.S. File History for U.S. Appl. No. 11/371,347.
U.S. File History for U.S. Appl. No. 11/371,346.
U.S. File History for U.S. Appl. No. 12/040,735.
U.S. File History for U.S. Appl. No. 12/152,893.
U.S. File History for U.S. Appl. No. 12/611,875.
U.S. File History for U.S. Appl. No. 12/790,379.
U.S. File History for U.S. Appl. No. 12/395,489.
U.S. File History for U.S. Appl. No. 12/454,799.
U.S. File History for U.S. Appl. No. 12/467,755.
U.S. File History for U.S. Appl. No. 12/454,743.
U.S. File History for U.S. Appl. No. 13/186,228.
File History of U.S. Appl. No. 13/186,331.
File History of U.S. Appl. No. 13/186,315.
File History of U.S. Appl. No. 11/544,306.
Final Office Action dated Jun. 28, 2013 for U.S. Appl. No. 13/186,228.
Final Office Action dated Jul. 15, 2011 for U.S. Appl. No. 12/040,735.
Final Office Action dated Jul. 25, 2011 for U.S. Appl. No. 12/395,489.
Final Office Action dated Oct. 15, 2010 for U.S. Appl. No. 12/152,893.
Final Office Action dated Sep. 17, 2010 for U.S. Appl. No. 12/467,755.
Final Office Action dated Sep. 20, 2010 for U.S. Appl. No. 12/454,799.
Final Office Action dated May 27, 2010 for U.S. Appl. No. 11/544,306.
Final Office Action dated Mar. 7, 2013 for U.S. Appl. No. 13/016,811.
Final Office Action dated Jan. 22, 2014 for U.S. Appl. No. 13/186,331.
Office Action dated Apr. 1, 2010 for U.S. Appl. No. 12/467,755.
Office Action dated Apr. 2, 2014 for U.S. Appl. No. 12/467,755.
Office Action dated Apr. 16, 2010 in U.S. Appl. No. 12/454,799.
Office Action dated Nov. 9, 2010 for U.S. Appl. No. 12/040,735.
Office Action dated Oct. 14, 2011 for U.S. Appl. No. 12/454,743.
Office Action dated Dec. 16, 2010 for U.S. Appl. No. 12/395,489.
Office Action dated Feb. 4, 2010 for U.S. Appl. No. 12/152,893.
Office Action dated Jan. 24, 2013 for U.S. Appl. No. 13/186,228.
Office Action dated Mar. 10, 2011 for U.S. Appl. No. 12/454,743.
Office Action dated Mar. 17, 2011 for U.S. Appl. No. 12/611,875.
Office Action dated Aug. 2, 2013 for U.S. Appl. No. 13/186,315.
Office Action dated Aug. 8, 2013 for U.S. Appl. No. 13/186,331.
Notice of Allowance dated Feb. 20, 2013 for U.S. Appl. No. 12/395,489.
Notice of Allowance dated Apr. 4, 2013 for U.S. Appl. No. 13/363,022.
Notice of Allowance dated May 24, 2013 for U.S. Appl. No. 13/016,811.
Office Action dated Jan. 27, 2014 for U.S. Appl. No. 13/186,315.
Office Action dated Feb. 27, 2014 for U.S. Appl. No. 12/454,799.
Office Action dated May 22, 2014 for U.S. Appl. No. 13/186,228.
Final Office Action dated Jun. 25, 2014 for U.S. Appl. No. 13/186,315.
Notice of Allowance dated Jul. 1, 2014 for U.S. Appl. No. 13/183,331.
Final Office Action dated Jul. 2, 2014 for U.S. Appl. No. 13/154,989.
Final Office Action dated Aug. 1, 2014 for U.S. Appl. No. 12/454,799.
Final Office Action dated Aug. 29, 2014 for U.S. Appl. No. 12/467,755.
Notice of Allowance dated Oct. 8, 2014 for U.S. Appl. No. 13/186,315.
Notice of Allowance dated Oct. 9, 2014 for U.S. Appl. No. 13/154,989.
Final Office Action dated Oct. 29, 2014 for U.S. Appl. No. 13/186,228.
Bhatia et al., Icosahedral DNA Nanocapsules by Modular Assembly, Angew. Chem. Int. Ed., vol. 48, pp. 4134-4137, 2009.
He et al., Hierarchical self-assembly of DNA into symmetric supramolecular polyhedral, Nature, vol. 452, pp. 198-202, 2008.
Jonoska et al., DNA cages with icosahedral symmetry bionanotechnology, Algorithmic Bioprocesses', 2008,.
Linuma et al., Polyhedra Self-Assembled from DNA Tripods and Characterized with 3D DNA-Paint, Science, vol. 344, No. 6179, pp. 65-69, 2014.
Mathews et al, "22 predicting rna secondary structure," Cold Spring Harbor Monograph Archive 43, pp. 631-657, 2006.
Zadeh. "Algorithms for nucleic acid sequence design." Doctoral Thesis [online[, orally defended Dec. 8, 2009 (Dec. 8, 2009), published May 25, 2010 (May 25, 2010), [Retrieved on Jul. 6, 2011], pp. 1-85, Retrieved from the Internet: <URL: http://resolver.caltech.edu/CaltechTHESIS:05112010-205335518>.
Zadeh. "Algorithms for nucleic acid sequence design." Doctoral Thesis, defended Dec. 8, 2009; Abstract only [online]; downloaded from URL: http://thesis.library.caltech.edu/5801/ on Jul. 6, 2011.
Zhang et al., Conformational flexibility facilitates self-assembly of complex DNA nanostructures, PNAS, vol. 105, No. 31, pp. 10665-10669, 2008.
International Search Report and Written Opinion of the International Searching Authority for PCT/US11/31127, dated Oct. 31, 2011.
Final Office Action dated Feb. 4, 2016 for U.S. Appl. No. 12/467,755.
Final Office Action dated Nov. 25, 2015 for U.S. Appl. No. 12/454,799.
Stratagene Catalog. gene characterization kits, Stratagene Catalog, p. 39, 1988.
Office Action dated Jun. 22, 2012 for U.S. Appl. No. 13/363,022.
Final Office Action dated Dec. 10, 2012 for U.S. Appl. No. 13/363,022.

(56) References Cited

OTHER PUBLICATIONS

Notice of Allowance dated Jan. 15, 2013 for U.S. Appl. No. 13/363,022.
Office Action dated Sep. 20, 2012 for U.S. Appl. No. 13/016,811.
Notice of Allowance dated Oct. 23, 2013 for U.S. Appl. No. 13/016,811.
Office Action dated Jan. 30, 2014 for U.S. Appl. No. 13/154,989.
Notice of Allowance dated Nov. 8, 2016 for U.S. Appl. No. 13/186,228.
Office Action dated Jan. 5, 2017 for U.S. Appl. No. 14/033,081.
Office Action dated Feb. 22, 2017 for U.S. Appl. No. 14/497,070.
Notice of Allowance dated Apr. 5, 2017 for U.S. Appl. No. 13/186,228.

SMALL CONDITIONAL RNAS

CROSS-REFERENCE TO RELATED APPLICATIONS

The present application claims priority to U.S. Provisional Application No. 61/841,692 filed Jul. 1, 2013, which is hereby incorporated by reference in its entirety.

STATEMENT REGARDING FEDERALLY SPONSORED R&D

This invention was made with government support under CA140759 awarded by National Institutes of Health. The government has certain rights in the invention.

REFERENCE TO SEQUENCE LISTING, TABLE, OR COMPUTER PROGRAM LISTING AND COLOR DRAWINGS

The present application is being filed along with a Sequence Listing in electronic format. The Sequence Listing is provided as a file entitled CALTE101A.txt, created Jun. 26, 2014, which is 7,706 bytes in size. The information is the electronic format of the Sequence Listing and is incorporated herein by reference in its entirety. The patent or application file contains at least one drawing executed in color. Copies of this patent or patent application publication with color drawing(s) will be provided by the Office upon request and payment of the necessary fee.

BACKGROUND

Field

The present invention relates to scRNA and methods of use thereof.

Description of the Related Art

RNAi can allow for knock down of specific gene expression in eukaryotes, and can be a powerful tool for probing gene function within endogenous biological circuits. RNAi can be activated by double-stranded RNAs that are cleaved by the enzyme Dicer to produce siRNAs. One strand of an siRNA duplex, referred to as the "guide strand," can be loaded into an RNA-induced silencing complex (RISC), where it can serve as a recognition domain for recruitment of target mRNAs containing the complementary sequence. RISC cleaves and releases the mRNA for subsequent degradation, enabling a single guide strand to mediate destruction of multiple copies of the mRNA silencing target.

SUMMARY

In some embodiments, the shRNA or Dicer substrate that is produced by the approaches and compositions provided herein can target a "silencing target" of choice. The sequence of the "detection target" that triggers shRNA formation places no constraint on the sequence of the "silencing target".

In some embodiments, a method of conditional Dicer substrate formation is provided. The method can comprise providing a duplex that comprises a first strand hybridized to a second strand and combining the duplex to a mixture for detection of a target strand. A presence of a target strand results in a displacement of the first strand from the second strand, and wherein the displacement of the first strand from the second strand allows for the second strand to form an shRNA, and wherein the shRNA is formed in a conditional manner.

In some embodiments, a method of conditional hairpin formation is provided. The method comprises providing a duplexed scRNA to a sample comprising a target sequence. The duplexed scRNA comprises a first strand and a second strand. The first strand hybridizes to the target sequence to at least partially dehybridize the second strand from the first strand, and upon partial dehybridization of the second strand from the first strand, the second strand self-hybridizes to form a hairpin. The hairpin is formed in a conditional manner that is dependent upon the presence of the target strand.

In some embodiments, a conditional Dicer substrate formation kit is provided. The kit comprises a duplexed scRNA. The duplexed scRNA comprises a first strand and a second strand. The first strand is configured to hybridize to a target sequence and expose an internal toehold in the second strand, and upon exposing the internal toehold in the second strand, the second strand self-hybridizes into an shRNA. The kit further includes at least one reagent for a qPCR assay.

In some embodiments, a method of forming a Dicer substrate is provided. The method comprises providing a duplex that comprises a first strand hybridized to a second strand and contacting the duplex with a sample that comprises a target strand. The presence of the target strand in the sample results in a partial displacement of the first strand from the second strand. The partial displacement of the first strand from the second strand allows for the second strand to form an shRNA. The shRNA is formed in a conditional manner and forms a Dicer substrate.

In some embodiments, a method of conditional Dicer substrate formation is provided. The method comprises providing a duplex that comprises a first strand hybridized to a second strand and combining the duplex with a mixture for detection of a target strand. A presence of a target strand results in a partial displacement of the first strand from the second strand, and the partial displacement of the first strand from the second strand allows for the second strand to form an shRNA. The shRNA is formed in a conditional manner based upon a presence or absence of the target strand.

In some embodiments, a method of conditional Dicer substrate formation is provided. The method comprises providing a complex that comprises: a first strand, a second strand, and a third strand. The first strand is hybridized to the second strand and the third strand is also hybridized to the second strand when the first strand is hybridized to the second strand. The method further comprises adding the complex to a mixture for detection of a target strand. A presence of the target strand results in a displacement of the first strand from the second strand. The displacement of the first strand from the second strand allows for the second strand to self-hybridize and displace the third strand from the second strand such that the second strand forms an shRNA.

In some embodiments, a method of conditional Dicer substrate formation is provided. The method comprises providing a first duplex comprising: a first strand and a second strand. The first strand is hybridized to the second strand. The method further comprises providing a second duplex comprising: a third strand and a fourth strand. The third strand is hybridized to the fourth strand. The method further comprises combining the first and second duplex with a sample. A presence of a target sequence in the sample results in the first duplex and the second duplex nucleating with the target strand via hybridization of the second strand with the target and hybridization of the fourth strand with the target, mediating hybridization of the first strand to the third strand to yield a duplex Dicer substrate.

In some embodiments, a method of conditional Dicer substrate formation is provided. The method comprises providing a duplexed scRNA to a sample that may or may not contain a target polynucleotide. The duplexed scRNA comprises a first strand and a second strand. The first strand is configured to hybridize to a target sequence and expose an internal toehold in the second strand upon the hybridization. Upon exposing the internal toehold in the second strand, the second strand self-hybridizes into an shRNA.

In some embodiments, a duplexed scRNA is provided that comprises a first strand and a second strand. The first strand is hybridized to the second strand. The first strand is configured to hybridize to a target sequence and upon hybridization expose an internal toehold in the second strand. Upon exposing the internal toehold in the second strand, the second strand self-hybridizes to form a hairpin.

In some embodiments, a method of conditional Dicer substrate formation is provided. The method comprises providing a duplex that comprises a first strand hybridized to a second strand and combining the duplex to a mixture for detection of a target strand. The presence of a target strand results in partial displacement of the first strand from the second strand, and the partial displacement of the first strand from the second strand allows for the second strand to form an shRNA. The shRNA is formed in a conditional manner.

In some embodiments, a method of forming a conditional shRNA is provided. The method comprises providing a duplexed scRNA to a sample comprising a target sequence. The duplexed scRNA comprises a first strand and a second strand. The first strand hybridizes to the target sequence, partially displacing the second strand, causing the second strand to self-hybridize into an shRNA.

In some embodiments, a Dicer substrate kit is provided. The kit can comprise a duplexed scRNA. The duplexed scRNA comprises a first strand and a second strand. The first strand is configured to hybridize to a target sequence and partially dehybridize from the second strand. Upon partial dehybridization of the first strand from the second strand, the second strand self-hybridizes into an shRNA. The kit can further include at least one reagent for a qPCR assay.

In some embodiments, a method of forming a Dicer substrate is provided. The method can comprise providing a duplex that comprises a first strand hybridized to a second strand; contacting the duplex to a sample. The presence of a target strand in the sample results in a partial displacement of the first strand from the second strand. The partial displacement of the first strand from the second strand allows for the second strand to form an shRNA, and the shRNA is formed in a conditional manner, forming a Dicer substrate.

In some embodiments, a method of conditional Dicer substrate formation is provided. The method comprises providing a duplex that comprises a first strand hybridized to a second strand. The method further comprises combining the duplex to a mixture for detection of a target strand. A presence of a target strand results in a full or partial displacement of the first strand from the second strand, and the full or partial displacement of the first strand from the second strand allows for the second strand to form an shRNA. The shRNA is formed in a conditional manner based upon the presence or absence of the target strand.

In some embodiments, a method of conditional Dicer substrate formation is provided. The method can comprise providing a complex that comprises: a first strand; a second strand; and a third strand. The first strand is hybridized to the second strand and the third strand is also hybridized to the second strand when the first strand is hybridized to the second strand. The method further includes combining the complex to a mixture for detection of a target strand. The presence of the target strand results in a displacement of the first strand from the second strand, and the displacement of the first strand from the second strand allows for the second strand to form an shRNA. The third strand is displaced from the first strand by the second strand self-hybridizing to form an shRNA.

In some embodiments, a method of conditional Dicer substrate formation is provided. The method can comprise providing a first duplex comprising: a first strand and a second strand, wherein the first strand is hybridized to the second strand. The method can further comprise providing a second duplex comprising: a third strand and a fourth strand. The third strand is hybridized to the fourth strand. The method can further include combining the first and second duplex with a sample. The presence of a target sequence in the sample causes the second and fourth strands to hybridize to the target, in turn causing the first and third strands to hybridize to each other and form a Dicer substrate. In some embodiments, the strands are configured for the above functions based upon their sequences and the resulting hybridizations. Thus, the strands can be configured for such activities by selection of the appropriate nucleic acid sequences.

BRIEF DESCRIPTION OF THE DRAWINGS

FIG. 5 illustrates a stepping gel for Mechanism 1, in which native PAGE demonstrates the assembly and disassembly operations in FIG. 3a.

FIG. 11 illustrates a stepping gel for Mechanism 2. As shown, native PAGE demonstrates the assembly and disassembly operations in FIG. 9a.

FIG. 16 illustrates a stepping gel for Mechanism 3. As shown, native PAGE demonstrates the assembly and disassembly operations in FIG. 14a.

FIG. 21 illustrates a stepping gel for Mechanism 4. As shown, native PAGE demonstrates the assembly and disassembly operations in FIG. 19a.

FIG. 26 illustrates a Stepping gel for Mechanism 5. As shown, native PAGE demonstrates the assembly operations in FIG. 24a.

DETAILED DESCRIPTION OF THE PREFERRED EMBODIMENT

Figure 1:
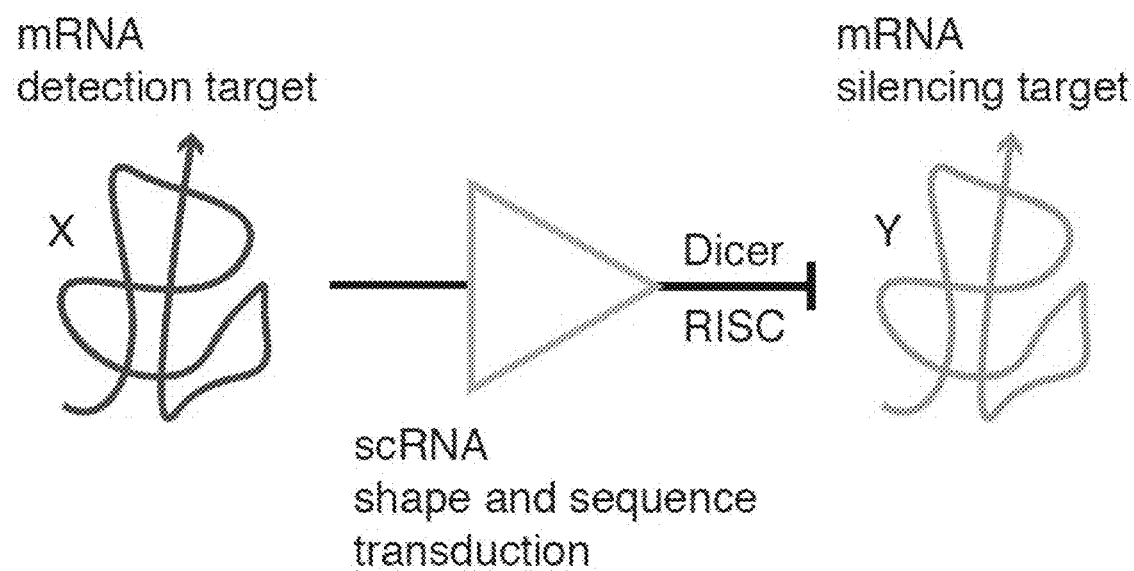
FIG. 1 illustrates the molecular logic of conditional RNA interference (RNAi) mediated by small conditional RNAs: if detection target mRNA X is present, scRNA shape and sequence transduction yield a Dicer substrate targeting independent silencing target mRNA Y for RISC-mediated destruction.

RNA interference (RNAi) mediated by small interfering RNAs (siRNAs) allows for the knockdown of a gene of choice, executing the logical operation of silencing gene Y. The fact that the siRNA is constitutively active is a significant limitation to its use, making it difficult to confine knockdown to a specific locus and time. To achieve spatiotemporal control over silencing, small conditional RNAs (scRNAs) that mediate 'conditional RNAi' can be configured such that if gene X is transcribed, independent gene Y is silenced. By appropriately selecting gene X as a target, knockdown of gene Y can then be restricted in a tissue- and time-specific manner.

To implement the conditional RNAi, one approach is to engineer scRNAs that upon binding to a target mRNA ('detection target' X), subsequent shape and sequence transduction is performed to form a Dicer substrate targeting an independent mRNA ('silencing target' Y), with subsequent Dicer processing yielding an siRNA targeting mRNA Y for destruction. Toward this end, diverse scRNA mechanisms for conditional Dicer substrate formation are provided herein and were experimentally validated. Studies provided herein demonstrated strong OFF/ON conditional response, with, in some embodiments, at least an order of magnitude increase in Dicer substrate production in the presence of the cognate mRNA detection target. By appropriately dimensioning and/or chemically modifying the scRNAs, only the product of signal transduction, and not the reactants or intermediates, are efficiently processed by Dicer. The systems described herein allow for scRNA signal transduction cascades with desired reactant stability vs metastability, catalytic vs non-catalytic transduction, pre- vs posttranscriptional transduction, reactant and product molecularity, and various modes of molecular self-assembly and disassembly. The description initially provides a brief outline of various terms used herein, followed by a detailed description Definitions As utilized in accordance with the embodiments provided herein, the following terms, unless otherwise indicated, shall be understood to have the following meanings:

A "self-assembly pathway" is a series of reactions autonomously executed by monomer, dimer, or trimer reactants. The self-assembly pathway comprises assembly of the reactants via a prescribed sequence of hybridization events. In some embodiments, the self-assembly pathway can also comprise one or more disassembly reactions. In some embodiments, nucleic acid self-assembly systems are provided that involve metastable reactants. In some embodiments, nucleic acid self-assembly systems are provided that involve stable reactants.

The term "nucleic acid" refers to natural nucleic acids, artificial nucleic acids, analogs thereof, or combinations thereof. Nucleic acids can also include analogs of DNA or RNA having modifications to either the bases or the backbone. For example, nucleic acid, as used herein, includes the use of peptide nucleic acids (PNA) and 2'OMe-RNA. The term "nucleic acids" also includes chimeric molecules. Nucleic acids include, but are not limited to, DNA, cDNA, genomic DNA, mitochondrial DNA, RNA, 2'OMe-RNA, mRNA, miRNA, siRNA, piwi-interacting RNA, lincRNA, rRNA, tRNA, snRNA, and viral RNA. In some embodiments nucleic acid duplexes are provided for conditional strand displacement.

As used herein, the terms "polynucleotide," "oligonucleotide," and "nucleic acid oligomers" are used interchangeably and mean single-stranded and double-stranded polymers of nucleic acids, including, but not limited to, 2'-deoxyribonucleotides (DNA) and ribonucleotides (RNA) linked by internucleotide phosphodiester bond linkages, e.g. 3'-5' and 2'-5', inverted linkages, e.g. 3'-3' and 5'-5', branched structures, or analog nucleic acids. Polynucleotides have associated counter ions, such as H+, $NH_4+$, trialkylammonium, $Mg^2+$, Na+ and the like. A polynucleotide can be composed entirely of deoxyribonucleotides, entirely of ribonucleotides, or chimeric mixtures thereof. Polynucleotides can be comprised of nucleobase and sugar analogs. Polynucleotides typically range in size from a few monomeric units, e.g. 5-40 when they are more commonly frequently referred to in the art as oligonucleotides, to several thousands of monomeric nucleotide units. Unless denoted otherwise, whenever a DNA sequence is represented, it will be understood that the nucleotides are in 5' to 3' order from left to right and that "A" denotes deoxyadenosine, "C" denotes deoxycytidine, "G" denotes deoxyguanosine, and "T" denotes thymidine. Similarly, whenever a RNA sequence is represented, it will be understood that the nucleotides are in 5' to 3' order from left to right and that "G" denotes guanine, "A" denotes adenine, "U" denotes uracil, and "C" denotes cytosine.

A "gene" (e.g., a marker gene) or "coding sequence" or a sequence, which "encodes" a particular protein, is a nucleic acid molecule which is transcribed (in the case of DNA) and translated (in the case of mRNA) into a polypeptide in vitro or in vivo when placed under the control of appropriate regulatory or control sequences. The boundaries of the gene are determined by a start codon at the 5' (amino) terminus and a translation stop codon at the 3' (carboxy) terminus. A gene can include, but is not limited to, cDNA from prokaryotic or eukaryotic mRNA, genomic DNA sequences from prokaryotic or eukaryotic DNA, and even synthetic DNA sequences. A transcription termination sequence will usually be located 3' to the gene sequence. In some embodiments, the Dicer substrate or shRNA is configured for silencing a target gene.

As used herein, the terms "complementary" or "complementarity" are used in reference to polynucleotides (e.g., a sequence of nucleotides) related by the base-pairing rules. For example, the sequence "5'-A-G-T-3" is complementary to the sequence "3'-T-C-A-5'." The nucleic acid sequences can comprise natural nucleotides (including their hydrogen bonding bases A, C, G, T, or U) and/or modified nucleotides or bases. Complementarity may be "partial," in which less than all of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. As used herein, a hybridizing nucleic acid sequence is "substantially complementary" when it is at least 80%, more preferably at least 85%, 90%, 91%, 92%, 93%, 94%, 95%, 96%, 97%, 98%, 99% or 100%, identical and/or includes no more than one non-Watson-Crick base pairing interaction to a reference sequence in the hybridizing portion of the sequences. In some embodiments, shRNA is configured by complementary binding.

The term "RNAi" as used herein refer to RNA interference (RNAi) which is a biological process in which pieces of RNA can inhibit gene expression by destruction of specific mRNA molecules. RNAi can include two types of RNA molecules, microRNA (miRNA) and small interfering RNA (siRNA) molecules. The small RNAs as described can bind to specific mRNA and either increase or decrease their activity which effects production of a specific protein. RNAi can be mediated by the enzyme Dicer.

The term "Dicer" as used herein, is an endoribonuclease that can cleave double stranded RNA (dsRNA) and pre-micro RNA (pre-miRNA) into short double stranded RNA fragments that are called small interfering RNA and microRNA respectively. While not limiting in all embodiments, the fragments can be 20-25 base pairs in length with a 2 base overhang at the 3' end. Dicer facilitates the activation of RNA induced silencing complex (RISC) which is relevant for RNA interference. The catalytic component of RISC is Argonaute which is an endonuclease that can degrade messenger RNA.

The term "displacement" encompasses both complete displacement and at least partial displacement. As will be appreciated by one of skill in the art, partial displacement may be sufficient for various embodiments herein, and/or could occur before complete displacement occurs. Complete or partial displacement will be adequate for the function to be achieved. Complete or partial displacement can each be specified as desired by the term "complete" or "partial".

The term "scRNA" refers to a small conditional RNA that can change conformation to perform signal transduction in response to binding its cognate input. The term "scDNA" refers to a small conditional DNA that can change conformation to perform signal transduction in response to binding its cognate input. For example, an scRNA can mediate conditional gene silencing, such that if the scRNA binds to cognate input mRNA X, the scRNA changes conformation to mediate silencing of independent gene Y The term "siRNA" small interfering RNA, short interfering RNA or silencing RNA is a class of double stranded RNA molecules that plays a role in the RNAi pathway. siRNA interferes with the expression of specific genes with complementary nucleotide sequences causing mRNA to be broken down after transcription leading to no translation and therefore no expression of a protein. One strand of the siRNA duplex, called the guide strand is loaded into the RNA-induced silencing complex (RISC) where it serves as a recognition domain for recruitment of target mRNAs containing the complementary sequence. "RISC," as described herein is a multi-protein complex that incorporates the one strand of the siRNA as a template for recognizing the complementary mRNA for cleavage by a protein called Argonaute, which is a catalytic component of the RISC complex.

The term "small hairpin RNA" or "short hairpin RNA" (shRNA) refers to a sequence of RNA that makes a hairpin. In some embodiments the shRNA can be configured such that it can be used to silence target gene expression via the RNA interference (RNAi) pathway. In some embodiments, expression of shRNA can be accomplished by delivery of plasmids through viral or bacterial vectors, or delivery of double stranded small conditional RNAs (scRNA). shRNAs can be 19-29 base pair stems with a 2-nucleotide 3' overhang and are Dicer substrates. Other substrates for Dicer also include Dicer-substrate RNAs (DsiRNAs) which are ~25 base pair duplexes with a 2-nucleotide 3' overhang at one end. Dicer can function to cleave ~21-23 nucleotide siRNA strands that form a duplex with 2-nucleotide 3' overhangs at both ends. Short hairpin RNA can be configured by complementary binding within its domain sequences. Dicer substrates are double stranded RNA molecules with a 2-nucleotide 3' overhang. In some embodiments, an shRNA is formed in a conditional manner. In some embodiments, the shRNA comprises a Dicer substrate sequence. In some embodiments, the shRNA comprises a stem region, wherein the stem region comprises a Dicer substrate and a loop region that is connected to the stem region. In some embodiments, the shRNA comprises a 2-nucleotide overhang at the 3' terminus.

The terms "hybridize," "hybridization," and their cognates are used herein to refer to the pairing of complementary nucleic acids or bases. Hybridization and the strength of hybridization (e.g., the strength of the association between the nucleic acids) is influenced by such factors as the degree of complementarity between the nucleic acids, stringency of the hybridization conditions involved, the melting temperature (Tm) of the formed hybrid, and the G:C ratio within the nucleic acids. A hybridizing sequence is typically at least 80%, 85%, 90%, 91%, 92%, 93%, 94%, 95%, 96%, 97%, 98%, 99% or 100% identical and is matched according to the base pairing rules. It may contain natural and/or modified nucleotides and bases. In some embodiments, shRNA is formed by hybridization of domains.

The term "hairpin" as used herein refers to a structure formed by intramolecular base pairing in a single-stranded polynucleotide ending in an unpaired loop (the "hairpin loop"). In various embodiments, hairpins comprise a hairpin loop protected by stems. For example, a hairpin can comprise a first stem region, a hairpin loop region, and a second stem region. The first and second stem regions can hybridize to each other and together form a duplex region. Thus, a stem region of a hairpin monomer is a region that hybridizes to a complementary portion of the same monomer to form the duplex stem of a hairpin. Unlike other looped structures, a hairpin loop will have only a single stem that forms the start and end of the looped section.

"Chemical modification" as described herein, refers to the chemical modification of a protein or nucleic acid. 2'O-methylation of RNA is an RNA analog that can offer stability against general bases hydrolysis and nucleases. In some embodiments, the chemical modification is selected or capable of preventing and/or reducing Dicer cleavage.

The term "hairpin loop" refers to a single stranded region that loops back on itself and is closed by complementary binding of domains.

The term "nucleate" as used herein means to begin a process of, for example, a physical and/or chemical change at a discrete point in a system. For example, consider two scRNAs that have exposed sequence domains that are complementary. Hybridization of these two complementary domains brings the two scRNAs together, nucleating further interactions between the two scRNAs. The term "nucleation" refers to the beginning of physical and/or chemical changes at discrete points in a system. In some embodiments, nucleation of a self-assembly reaction can occur by, for example, the hybridization of a portion of an initiator to an exposed toehold of a hairpin monomer. In some embodiments, toehold/toehold nucleation, loop/toehold nucleation, and template/toehold nucleation are used to nucleate interactions. In some embodiments, 3-way branch migration, 4-way branch migration, and spontaneous dissociation are used to achieve strand displacement following nucleation.

The term "toehold" refers to nucleation site of a domain comprising a nucleic acid sequence configured to initiate hybridization of the domain with a complementary nucleic acid sequence. The secondary structure of a monomer, dimer, or trimer reactant can be such that the toehold is exposed or sequestered. For example, in some embodiments, the secondary structure of the toehold is such that the toehold is available to hybridize to a complementary nucleic acid (the toehold is "exposed," or "accessible"), and in some embodiments, the secondary structure of the toehold is such that the toehold is not available to hybridize to a complementary nucleic acid (the toehold is "sequestered," or "inaccessible"). If the toehold is sequestered or otherwise unavailable, the toehold can be made available by some event such as, for example, the opening of the reactant of which it is a part of. When exposed, a toehold is configured such that a complementary nucleic acid sequence can nucleate at the toehold. In some embodiments, nucleation of a complementary nucleic acid sequence at an exposed toehold initiates branch migration to change the conformation of the reactant.

The term "target" as used herein, refers to a substance or moiety of interest which is to be detected or bound or silenced. Exemplary domains in the sense of the present disclosure comprise mRNA, mRNA silencing target, and mRNA detection target. Alternatively, the detection target could be a miRNA or any other type of nucleic acid detection target.

The term "domain" as used herein, refers to one or more sequences within a strand of nucleic acid. Various letters are used in reference to the figures and in the specification to denote the various domains on the various strands. Capital letters refer to entire strands, while lower case letters refer to domains within a strand. In some embodiments, the strand can consist of a single domain, although there are usually multiple domains in each strand.

Figure 14A:
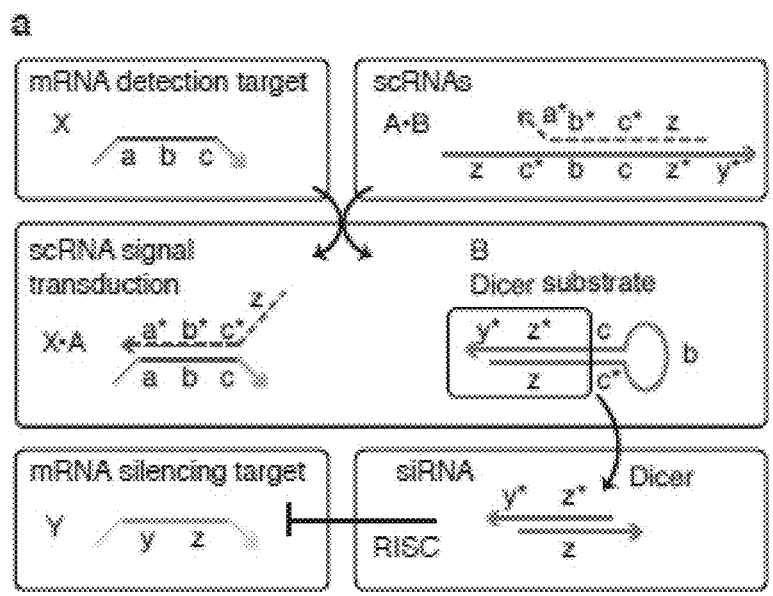
FIGS. 14a-d illustrate the conditional shRNA formation using a single stable scRNA for Mechanism 3. a) Mechanism 3. scRNA A·B detects mRNA detection target X (containing subsequence a-b-c), leading to production of shRNA Dicer substrate B targeting mRNA silencing target Y (containing independent subsequence y-z). b) Conditional Dicer substrate formation. c) Quantification of the Dicer substrate band (B) in panel (b). d) Conditional Dicer processing.
Figure 31A:
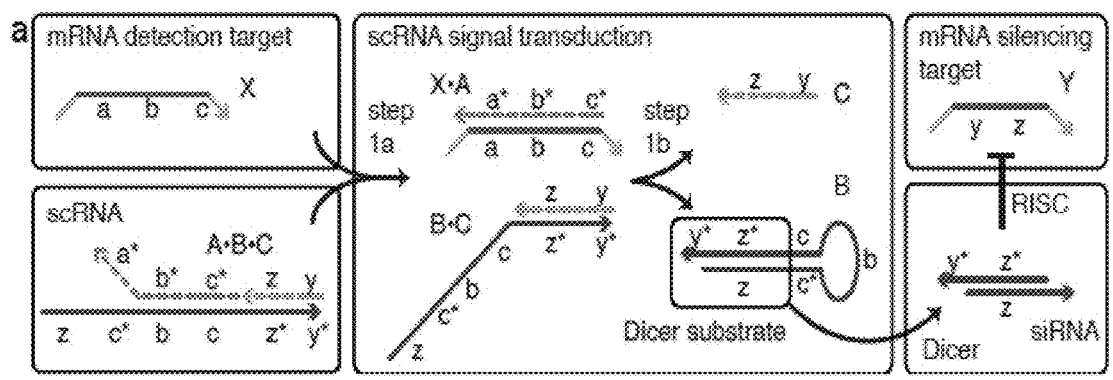
FIG. 31a illustrates a variation on Mechanism 3, in which the strand which binds to the target (c*-b*-a*) is separate from a y-z strand, but in which both can initially start out bound to the strand that comprises z-c*-b-c-z*-y* as shown.
Figure 31B:
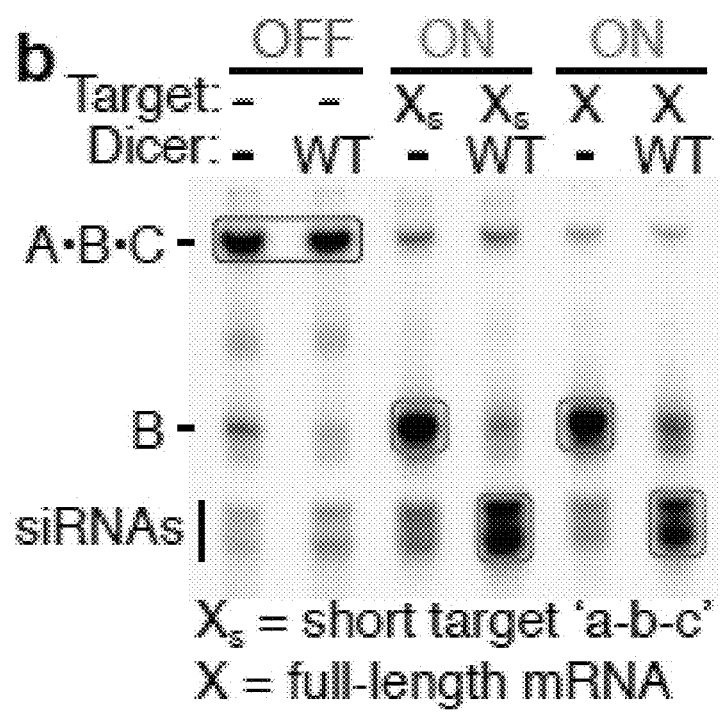
FIG. 31b illustrates scRNA-mediated conditional Dicer substrate formation and subsequent Dicer-mediated siRNA production in human cell lysate. By convention, the sequence domains are listed within a strand from 5' to 3' (the arrowhead denotes the 3' end).

In specific regard to mechanism 3 and the embodiments shown in FIGS. 14a and 31, the following additional optional descriptions and terms can be employed. The target strand is usually denoted as "X". The initial duplex is usually a Dicer substrate forming strand (or "Dicer strand"), which is usually denoted as "B" hybridized to at least one shielding strand (A or A and C). The shielding strand (A, in FIG. 14A) can bind to the target sequence. The shielding strand will include one or more domains (in FIG. 14a, they are domains a*, b*, and c*, which will allow for hybridization to the target to be detected (strand X, containing sequence a-b-c, for FIG. 14a). In some embodiments, the shielding strand can start as a duplex to a strand that does not self-hybridize (such as that in FIG. 9). Not all embodiments need a shielding strand (or the shielding strand can be separate or part of another structure or performed by other aspects). In some embodiments (such as in FIG. 14a), the B strand will include a loop domain "b" and one or more stem-forming domains (usually in pairs). The stem-forming domain (which can vary by embodiment, but in FIG. 14a is z-c* and c-z*) can form the stem of the hairpin. It can also include a sequestered toehold domain (domain c) which is exposed once the shielding strand (A) is partially displaced by the target. The B strand will further include an overhang (an "overhang domain", domain y in FIG. 14a) so as to serve as a Dicer substrate with a 2-nucleotide 3' overhang when the B strand is in its shRNA configuration. After being processed by Dicer, the B strand will be in its processed form, and can be referred to as a "processed strand". This processed stand can result in silencing the target. As shown in the figures (for example, FIG. 14A), the gene to be silenced will be determined based upon the sequence(s) in domains y and z (using FIG. 14A for exemplary purposes only). Thus, these domains can also be referred to as silencing target sequences or domains (for example, y can be a first silencing targeting sequence or domain and z can be a second silencing targeting sequence or domain). Thus, y can have multiple names (and be the same sequence) such as overhang domain and first silencing target sequence and z can have multiple names (stem forming domain and/or second silencing target sequence). Throughout the specification, the above domains are usually referred to in terms of their single letter codes (and the complement "*"), however, if needed for clarification in the specification or the claims, the above terms are interchangeable with the single letter codes. While the above alternative terms are specifically applied in reference to the embodiments in FIGS. 14A and 31, they can also be appropriately applied/modified for the other embodiments as well (although one of skill in the art will appreciate that the specific reference to the above figures will require that the appropriate functional name be given to the various structures). That is, the functional terms can be used interchangeably with the appropriate single letter terms. In some embodiments, the unprocessed strand can also be configured to result in target silencing.

As used throughout the application, the various domains can be referred to by their one letter codes as a short hand (as used in the figures). Occasionally, quotes or other markings, such as dashes and "" are used around the letters as well. These additional markings are for contextual clarification only and do not change the meaning of the lettered domains. Thus, "a-b-c" and 'a-b-c' and "abc" and abc and a-b-c and 'abc' all denote the same arrangement and structures. The dashes and quotation markers (single and double) do not alter the meaning of the terms. It should be noted that the "*" denotes a sequence that can hybridize to the corresponding domain (and in some embodiments, precisely denotes the complementary strand). As presented herein, the domains are typically listed 5' to 3'. Thus a-b-c can hybridize to c*-b*-a*.

Various embodiments disclosed herein are generally directed towards the conditional formation of shRNA constructs or DsiRNA constructs upon the presence of a target sequence. The resulting shRNA can then be used, in vivo or in vitro, for the formation of various inhibitors (which can be unrelated in sequence to the sequence to be detected). In some embodiments, the shRNA or DsiRNA results in RNA interference (RNAi) mediated by small interfering RNAs (siRNAs) that can allow knockdown of a gene of choice. Unlike traditional applications of inhibitor RNA molecules, such as siRNA which can be constitutively active making it difficult to confine knockdown to a specific locus and time, the present molecules and methods allow for this to become conditional.

To achieve spatiotemporal control over silencing, small conditional RNAs (scRNAs) can be configured so that they can mediate 'conditional RNAi' corresponding to a logical operation in which if gene X is transcribed, independent gene Y can be silenced. By appropriately selecting gene X, knockdown of gene Y can be restricted in a tissue- and time-specific manner. To implement the logic of conditional RNAi, scRNAs can be configured such that upon binding to mRNA 'detection target' X, they can perform shape and sequence transduction to form a Dicer substrate that can target independent mRNA 'silencing target' Y, with subsequent Dicer processing yielding an siRNA targeting mRNA Y for destruction.

Various embodiments are provided herein for the use of scRNAs. In some embodiments, the approaches outlined in FIGS. 14A and 31A are employed. Discussed immediately below are the details of "mechanism 3" for conditional shRNA formation as provided herein. Following this section is a discussion of various embodiments and variations for the various mechanisms provided herein. The remaining mechanisms are discussed in order following this discussion. The disclosure then concludes with additional variations and the examples. Any of the various embodiments can be combined together and/or with any of the alternatives or variations provided herein.

FIG. 14A, Mechanism 3, depicts conditional shRNA formation using a single stable scRNA, which shows a duplex scRNA A·B detecting a target strand, mRNA detection target X (containing subsequence a-b-c), leading to the production of shRNA Dicer substrate B targeting mRNA silencing target Y (containing independent subsequence y-z). scRNA A·B is stable in the absence of X. In the presence of detection target X, detection target X partially displaces strand A from strand B via toehold-mediated 3-way branch migration, exposing a previously sequestered internal toehold, c, within B, mediating a further 3-way branch migration that disassembles B from X·A to yield shRNA Dicer substrate B, which folds into a hairpin via binding of its complementary sequences. Chemical modifications 2'OMe-RNA (optional), are in strand A and are indicated with a dashed backbone. Mechanism 3 need only involve a single duplex scRNA A·B, and in a single step produces a Dicer substrate that is an shRNA monomer (FIG. 14a). The detection target X mediates displacement of A from B to yield a hairpin B with a 2-nt 3'-overhang. The number of reactants and the number of assembly steps are both one. In functional terms, A·B detects X, leading to production of shRNA B targeting Y. The internal toehold is a relevant feature of Mechanism 3. In reference to FIG. 14a, the second strand (in this case, strand B) has the ability to self-nucleate due to the internal toehold (in this case, domain c). In the presence of the mRNA detection target X, the internal toehold is exposed, allowing the second strand or the B strand to change conformation to become an shRNA through complementary binding sequences within itself. Additionally, the scRNA can be used for delivery into humans or other organisms.

A variation of Mechanism 3 can also include a duplex single stable scRNA comprising strands A, B and C in which strands A and C are complementary to adjacent domains of strand B, thereby forming a duplex. Reference is made to FIG. 31a, which shows mRNA detection target X, and scRNA strands A, B, and C. As shown, strand A comprises domains 'c*-b*-a*' and strand C comprises domains 'y-z'. This variation of mechanism 3 introduces a nick between the c* and z domains of FIG. 14a so that there are three strands in the scRNA. This allows B·C to dissociate from X·A before B uses the newly exposed internal toehold "c" to nucleate with "c*" intramolecularly and complete a branch migration leading to formation of shRNA B. In reference to FIG. 31a, the second strand, or the B strand has the ability to talk or signal to itself due to the internal toehold (in this case domain "c"). In the presence of the mRNA detection target X, the internal toehold is exposed, allowing the second strand or the B strand to change conformation to become an shRNA through complementary binding sequences within itself. However in this 3-stranded variation, the difference is that this step can occur away from the mRNA. In some embodiments, the nick that is used to divide the strand A of FIG. 14a into strands A and C of FIG. 31a may be placed one or more nucleotides to either side of the junction between the c* and z domains, or there may be a gap between the A and C strands when bound to the B strand.

The scRNA can be used for delivery into humans. The scRNA can also be engineered to be "stable" rather than "metastable". In some embodiments, when using a stable scRNA, there is not a ticking clock where the scRNA is gradually converting into the shRNA product independent of the presence of detection target X. Instead, the scRNA is stable at equilibrium (the equilibrium partitioning of the scRNA strands is heavily in favor of the scRNA reactant, with only a slight amount of shRNA product forming at equilibrium). This is a desirable feature for the scRNA because it means that the formation of the product is conditional upon the presence of the detection target X even if the scRNA must wait a long time to encounter mRNA detection target X. In some embodiments, the first strand further comprises domain y, wherein the 3'-terminus of domain y is adjacent to the 5' terminus of domain "z".

In some embodiments, the above method or system can be characterized as a complex arrangement (rather than duplex arrangement) in which there are three strands (instead of two strands). The method/arrangement can be described as a method of conditional Dicer substrate formation comprising providing a complex that comprises a first strand (A), a second strand (B), and a third strand (C). The first strand is hybridized to the second strand and the third strand is also hybridized to the second strand when the first strand is hybridized to the second strand (as shown in the lower left of FIG. 31A). One takes the complex and combines the complex with a mixture for detection of a target strand. A presence of the target strand results in a displacement of the first strand from the second strand. The displacement of the first strand from the second strand allows for the second strand to form an shRNA (through the newly exposed domain "c" internal toehold). The third strand is displaced from the second strand by the second strand self-hybridizing to form an shRNA.

In some embodiments, a method of conditional Dicer substrate formation is provided. The method comprises providing a duplex that comprises a first strand hybridized to a second strand and combining the duplex to a mixture for detection of a target strand, wherein a presence of a target strand results in a displacement of the first strand from the second strand. The displacement of the first strand from the second strand allows for the second strand to form an shRNA. The shRNA is formed in a conditional manner. In some embodiments, the target strand comprises a domain "a", a domain "b" and a domain "c". Each of the domain "a", the domain "b" and the domain "c" have a 5' terminus and a 3' terminus, and the 3' terminus of domain "a" is adjacent to the 5' terminus of domain "b", and the 3' terminus of domain "b" is adjacent to the 5' terminus of domain "c". In some embodiment, the term adjacent denotes that the structure is immediately adjacent to the next structure. Furthermore, as shown in the figures, the continuous lines of the various domains denote that the various domains are connected to one another (so a* and b* on A are connected to one another in FIG. 14A).

In some embodiments, the domain "a" comprises a nucleotide length of 8-18 nucleotides. In some embodiments, the domain "a" comprises a nucleotide length of 4-30 nucleotides. In some embodiments, the domain "b" comprises a nucleotide length of 10-16 nucleotides. In some embodiments, the domain "b" comprises a nucleotide length of 6-22 nucleotides. In some embodiments, the domain "c" comprises a nucleotide length of 2-6 nucleotides. In some embodiments, the domain "c" comprises a nucleotide length of 0-12 nucleotides. In some embodiments, the domain "y" comprises a nucleotide length of 2-3 nucleotides. In some embodiments, the domain "y" comprises a nucleotide length of 0-6 nucleotides. In some embodiments, the domain "z" comprises a nucleotide length of 19-22 nucleotides. In some embodiments, the domain "z" comprises a nucleotide length of 12-30 nucleotides.

In some embodiments, the first strand comprises a domain "a*", a domain "b", a domain "c*" and a domain "z", wherein each of the domain "a*", the domain "b*", the domain "c*" and the domain "z" each have a 5' terminus and a 3' terminus, and the 3' terminus of domain "z" is adjacent to the 5' terminus of the domain "c*", the 3' terminus of the domain "c*" is adjacent to the 5' terminus of the domain "b*" and the 3' terminus of the domain "b*" is adjacent to the 5' terminus of domain "a*". In some embodiments, A is y-z-c*-b*-a*.

In some embodiments, the domain "a*", the domain "b*" and the domain "c*" are complimentary to the domain "a", the domain "b", and the domain "c" of the target strand, respectively. As used in the present specification and figures, the "*" symbol indicates that the sequence will hybridize to the corresponding sequence, for example, A will hybridize to "A*". The hybridization is through traditional base pairing. In some embodiments, the bases between the two domains are completely complementary, and thus the sequences between the two sequences are the reverse complement of each other. In embodiments where there is not 100% complementarity, it will be appreciated that the sequences can vary appropriately though the different domains in the process, in some of the embodiments. That is, for example, a variation in a sequence at a first step in domain "a" could further have a different variation in a later step of the process. In some embodiments, the sequences are identical throughout the process. Thus, for FIG. 14a for example, y-z in the final bottom left can be the exact same y-z in the lower right, as in the middle, as in the upper right.

In some embodiments, the complementary section (domain or strand) can be any of the lengths provided herein for the initial strand. In some embodiments, the domain "a*" comprises a nucleotide length of 8-18 nucleotides. In some embodiments, the domain "a*" comprises a nucleotide length of 4-30 nucleotides. In some embodiments, the domain "b*" comprises a nucleotide length of 10-16 nucleotides. In some embodiments, the domain "b*" comprises a nucleotide length of 6-22 nucleotides. In some embodiments, the domain "c*" comprises a nucleotide length of 2-6 nucleotides. In some embodiments, the domain "c*" comprises a nucleotide length of 0-12 nucleotides. In some embodiments, the domain "y*" comprises a nucleotide length of 2-3 nucleotides. In some embodiments, the domain "y*" comprises a nucleotide length of 0-6 nucleotides. In some embodiments, the domain "z*" comprises a nucleotide length of 19-22 nucleotides. In some embodiments, the domain "z*" comprises a nucleotide length of 12-30 nucleotides. In some embodiments, the second strand comprises a domain "z", a domain "c*", a domain "b", a domain "c", a domain "z", and a "y*" domain, wherein each of the domain "z", the domain "c*", the domain "b", the domain "c", the domain "z*", and the domain "y*" each have a 5' terminus and a 3' terminus, and the 3' terminus of domain "z" is adjacent to the 5' terminus of domain "c*", the 3' terminus of domain "c*" is adjacent to the 5' terminus of domain "b", the 3' terminus of domain "b" is adjacent to the 5' terminus of domain "c", the 3' terminus of domain "c" is adjacent to the 5' terminus of domain "z*" and the 3' terminus of the domain "z*" is adjacent to the 5' terminus of the "y*" domain. In some embodiments, the shRNA comprises a Dicer substrate sequence. In some embodiments, the shRNA comprises a sequence that allows for a targeting of a first gene. In some embodiments, the targeting of the first gene is via Dicer processing of the shRNA. In some embodiments, the conditional manner is at least one order of magnitude greater for shRNA formation in a presence of the target strand than in an absence of the target strand. In some embodiments, the conditional manner is at least two orders of magnitude greater for shRNA formation in a presence of the target strand than in an absence of the target strand. In some embodiments, the method further comprises running a detection assay for a presence or an absence of the target strand. In some embodiments, the detection assay for a presence or an absence of the target strand is a qPCR assay. In some embodiments, the shRNA comprises a stem region, wherein the stem region comprises a Dicer substrate and a loop region that is connected to the stem region. In some embodiments, the Dicer substrate comprises the second strand comprising a domain "z", a domain "c*", a domain "b", a domain "c", a domain "z", and a domain "y*" wherein each of the domain "z", the domain "c*", the domain "b", the domain "c", the domain "z*", and the domain "y*" each have a 5' terminus and a 3' terminus, and the 3' terminus of domain "z" is adjacent to the 5' terminus of domain "c*", the 3' terminus of domain "c*" is adjacent to the 5' terminus of domain "b", the 3' terminus of domain "b" is adjacent to the 5' terminus of domain "c", the 3' terminus of domain "c" is adjacent to the 5' terminus of domain "z*", and the 3' terminus of domain "z*" is adjacent to the 5' terminus of domain "y*" and wherein the domain "z" is bound to the domain "z*" and the domain "c" is bound to the domain "c*" forming the stem region, and domain "b" comprises the loop region that is connected to the stem region. In some embodiments, the shRNA is processed by Dicer to form an siRNA. In some embodiments, the first strand further comprises domain y, wherein the 3' terminus of domain y is adjacent to the 5' terminus of domain "z". In some embodiments, the target strand is in a lysate. In some embodiments, the target strand is in a human lysate.

In some embodiments, a method of conditional shRNA formation is provided. In some embodiments, the method comprises providing a duplexed scRNA to a sample comprising a target sequence, wherein the duplexed scRNA comprises a first strand and a second strand, and wherein the first strand hybridizes to the target sequence and partially dissociates from the second strand, and wherein upon partial dissociation of the first strand from the second strand, the second strand self-hybridizes into an shRNA. In some embodiments, the formation of the shRNA occurs as a single step. In some embodiments, the shRNA is configured for silencing a target gene upon being processed by Dicer to form an siRNA. In some embodiments, the shRNA is configured by the second strand comprising a domain "z", a domain "c*", a domain "b", a domain "c", a domain "z*", and a domain "y*" wherein each of the domain "z", the domain "c*", the domain "b", the domain "c", the domain "z*" and the domain "y*" each have a 5' terminus and a 3' terminus, and the 3' terminus of domain "z" is adjacent to the 5' terminus of domain "c*", the 3' terminus of domain "c*" is adjacent to the 5' terminus of domain "b", the 3' terminus of domain "b" is adjacent to the 5' terminus of domain "c", the 3' terminus of domain "c" is adjacent to the 5' terminus of domain "z*", and the 3' terminus of domain "z*" is adjacent to the 5' terminus of domain "y*" and wherein the domain "z" is bound to the domain "z*" and the domain "c"

is bound to the domain "c*" forming a stem region, and domain "b" comprises a loop region that is connected to the stem region. In some embodiments, the domain "y*" is not used. In some embodiments, the shRNA is configured for Dicer-independent silencing. In some embodiments, the shRNA is configured by the partial displacement of the first strand and the complementary binding of domain "z" to the domain "z*" and binding of the domain "c" to the domain "c*" forming the stem region, and the domain "b" forming the loop region that is connected to the stem region. In some embodiments, the shRNA product is configured for RISC-independent silencing. In some embodiments, the shRNA is configured binding of the by domain "z" to the domain "z*" and binding of the domain "c" to the domain "c*" forming the stem region, and domain "b" forming the loop region that is connected to the stem region. In some embodiments, the first strand further comprises domain y, wherein the 3' terminus of domain y is adjacent to the 5' terminus of domain "z".

In some embodiments, a method of conditional Dicer substrate formation is provided. In some embodiments, the method comprises providing a duplex that comprises a first strand hybridized to a second strand, and combining the duplex with a mixture for detection of a target strand, wherein a presence of a target strand results in a displacement of the first strand from the second strand, and wherein the full or partial displacement of the first strand from the second strand allows for the second strand to form an shRNA, and wherein the shRNA is formed in a conditional manner.

In some embodiments, a detection target (the target sequence to be detected) comprises two domains. In some embodiments, the mRNA detection target strand comprises three domains.

In some embodiments, a method for conditional Dicer substrate formation is provided. In some embodiments, the method comprises providing a duplex that comprises a first strand hybridized to a second strand. The first strand comprises four domains. The second strand comprises six domains. In some embodiments, the method comprises providing a first duplex that comprises a first strand hybridized to a second strand and a second duplex that comprises a first strand hybridized to a second strand. The first duplex further comprises a first strand comprising four domains and a second strand comprising four domains. The second duplex further comprises a first strand comprising four domains and the second duplex further comprises a second strand comprising six domains. In some embodiments, a hairpin monomer comprises a toehold region. In some embodiments, domains are targeted for complementary binding.

In some embodiments, a method of conditional Dicer substrate formation is provided. In some embodiments, a small conditional RNA for conditional substrate formation is provided. In some embodiments, the small conditional RNA comprises a duplex comprising a first strand hybridized to a second strand.

In some embodiments, a method of conditional Dicer substrate formation is provided. The method can comprise providing a duplex that comprises a first strand hybridized to a second strand and combining the duplex with a mixture for detection of a target strand, wherein the presence of a target strand results in a full or partial displacement of the first strand from the second strand, and wherein the displacement of the first strand from the second strand allows for the second strand to form an shRNA, and wherein the shRNA is formed in a conditional manner.

In some embodiments, a method of conditional Dicer substrate formation is provided. The method comprises providing a duplex that comprises a first strand hybridized to a second strand and combining the duplex to a mixture for detection of a target strand, wherein the presence of a target strand results in a full or partial displacement of the first strand from the second strand, wherein the displacement of the first strand from the second strand allows for the second strand to form an shRNA, and wherein the shRNA is formed in a conditional manner. In some embodiments, the shRNA comprises a sequence that allows for a targeting of a first gene. In some embodiments, the targeting of the first gene is via Dicer processing of the shRNA. In some embodiments, the conditional manner is at least one order of magnitude greater for shRNA formation in a presence of the target strand than in an absence of the target strand. In some embodiments, the conditional manner is at least two orders of magnitude greater for shRNA formation in a presence of the target strand than in an absence of the target strand. In some embodiments, the method further comprises running a detection assay for a presence or an absence of the silencing target. In some embodiments, the shRNA comprises a stem region, wherein the stem region comprises a Dicer substrate and a loop region that to connected to the stem region. In some embodiments, the shRNA is processed by Dicer to form an siRNA.

In some embodiments, a method of conditional Dicer substrate formation is provided. In some embodiments, the method comprises providing scRNA. In some embodiments, the scRNA are metastable. In some embodiments, the scRNA are stable. In some embodiments, the method comprises non-catalytic production. In some embodiments, the method comprises toehold or toehold nucleation. In some embodiments, the method comprises 3-way branch migration. In some embodiments, the method comprises duplex dimer reactants. In some embodiments, the method comprises Dicer substrate hybridization. In some embodiments, the method comprises shRNA Dicer substrate.

In some embodiments, a method of conditional Dicer substrate formation is provided. In some embodiments, the method comprises providing a first duplex that comprises a first strand hybridized to a second strand, providing a second duplex that comprises a first strand hybridized to a second strand, and combining the first and second duplexes to a mixture for detection of a target strand, wherein a presence of a target strand results in a displacement of the first strand from the second strand. The displacement of the first strand from the second strand allows for the second strand to form a Dicer substrate, and the Dicer substrate is formed in a conditional manner. In some embodiments, the method comprises scDNA reactants. In some embodiments, the method comprises metastable reactants. In some embodiments, the method comprises catalytic production. In some embodiments, the method comprises toehold/toehold nucleation. In some embodiments, the method comprises 3-way branch migration. In some embodiments, the method comprises 4-way branch migration. In some embodiments, the method comprises 2 or 3 hairpin monomer reactants. In some embodiments, the method comprises Dicer substrate transcription.

In some embodiments, a Dicer substrate forming kit is provided. In some embodiments, the kit comprises a duplex that comprises a first strand hybridized to a second strand and reagents for Dicer processing. In some embodiments, the kit can include any and/or all of the components for any of the mechanisms provided herein (1-5) or variations thereof. In some embodiments, the first strand comprises a domain "a*", a domain "b*", a domain "c*" and a domain "z". Each of the domain "a*", the domain "b*", the domain "c*" and the domain "z" have a 5' terminus and a 3' terminus. The 3' terminus of domain "z" is adjacent to the 5' terminus of the domain "c*", the 3' terminus of the domain "c*" is adjacent to the 5' terminus of the domain "b*" and the 3' terminus of the domain "b*" is adjacent to the 5' terminus of domain "a*". In some embodiments, the domain "a*", the domain "b*" and the domain "c*" are complementary to a target strand. In some embodiments, the domain "a*", the domain "b*" and the domain "c*" are complementary to the domain "a", the domain "b", and the domain "c" of the target strand, respectively. In some embodiments, the second strand comprises a domain "z", a domain "c*", a domain "b", a domain "c", a domain "z", and a "y" domain, wherein each of the domain "z", the domain "c*", the domain "b", the domain "c", the domain "z", and the domain "y*" each have a 5' terminus and a 3' terminus, and the 3' terminus of domain "z" is adjacent to the 5' terminus of domain "c*", the 3' terminus of domain "c*" is adjacent to the 5' terminus of domain "b", the 3' terminus of domain "b" is adjacent to the 5' terminus of domain "c", the 3' terminus of domain "c" is adjacent to the 5' terminus of domain "z*" and the 3' terminus of the domain "z" is adjacent to the 5' terminus of the "y*" domain. In some embodiments, the kit includes at least one or more of: additional oligonucleotide strands, a fluorophore labeled oligonucleotide or other molecule, an initiator for HCR, a strand to detect "z", a RT primer, qPCR probes specific to mRNA silencing target, qPCR probes for siRNA, qPCR probes for loop, and/or an adapter for high-throughput sequencing.

In some embodiments, the first strand of FIG. 14a (strand A in this case) is nicked to create the first and third strands of FIG. 31a (strands A and C in this case). In some embodiments, the nick lies between the domain "c*" and the domain "z" of the first strand of FIG. 14a (strand A in this case). In some embodiments, the nick lies within two nucleotides of the domain "c" and the domain "z" junction. In some embodiments, the nick lies within 6 nucleotides of the domain "c" and the domain "z" junction. In some embodiments, there is a gap of one or more nucleotides between the first and the third strands where they hybridize to the second strand. In some embodiments, the first strand further comprises domain y, wherein the 3' terminus of domain "y" is adjacent to the 5' terminus of domain "z". In some embodiments, the third strand further comprises domain y, wherein the 3' terminus of domain "y" is adjacent to the 5' terminus of domain "z".

In some embodiments, a method of forming a Dicer substrate is provided. In some embodiments, the method comprises providing a duplex that comprises a first strand hybridized to a second strand and contacting the duplex to a sample. The sample comprises a target strand. The presence of a target strand in the sample results in a partial or full displacement of the first strand from the second strand, and the partial or full displacement of the first strand from the second strand allows for the second strand to form an shRNA. The shRNA is formed in a conditional manner forming a Dicer substrate. In some embodiments, the target strand comprises a domain "a", a domain "b" and a domain "c", wherein each of the domain "a", the domain "b" and the domain "c" have a 5' terminus and a 3' terminus, and the 3' terminus of domain "a" is adjacent to the 5' terminus of domain "b", and the 3' terminus of domain "b" is adjacent to the 5' terminus of domain "c". In some embodiments, the first strand comprises a domain "a*", a domain "b*", a domain "c*" and a domain "z", wherein each of the domain "a*", the domain "b*", the domain "c*" and the domain "z" each have a 5' terminus and a 3' terminus, and the 3' terminus of domain "z" is adjacent to the 5' terminus of the domain "c", the 3' terminus of the domain "c*" is adjacent to the 5' terminus of the domain "b*" and the 3' terminus of the domain "b*" is adjacent to the 5' terminus of domain "a*". In some embodiments, the domain "a*", the domain "b*" and the domain "c*" are complementary to the domain "a", the domain "b", and the domain "c" of the target strand, respectively. In some embodiments, the second strand comprises a domain "z", a domain "c*", a domain "b", a domain "c", a domain "z", and a "y*" domain, wherein each of the domain "z", the domain "c*", the domain "b", the domain "c", the domain "z*", and the domain "y*" each have a 5' terminus and a 3' terminus, and the 3' terminus of domain "z" is adjacent to the 5' terminus of domain "c*", the 3' terminus of domain "c*" is adjacent to the 5' terminus of domain "b", the 3' terminus of domain "b" is adjacent to the 5' terminus of domain "c", the 3' terminus of domain "c" is adjacent to the 5' terminus of domain "z*" and the 3' terminus of the domain "z" is adjacent to the 5' terminus of the "y*" domain. In some embodiments, the first strand further comprises domain "y", wherein the 3' terminus of domain "y" is adjacent to the 5' terminus of domain "z". In some embodiments, the target strand is in a lysate. In some embodiments, the lysate is human cell lysate. In some embodiments, the target strand is inside a cell. Thus, in some embodiments, any of the methods or compositions provided herein can be used inside a cell and/or in vivo. In some embodiments, the methods or compositions provided herein are used in vitro or ex vivo.

In some embodiments, a method of conditional Dicer substrate formation is provided. In some embodiments, the method comprises providing a duplex that comprises a first strand hybridized to a second strand, and combining the duplex to a mixture for detection of a target strand, wherein a presence of a target strand results in a displacement of the first strand from the second strand, and wherein the displacement of the first strand from the second strand allows for the second strand to form a shRNA, and wherein the shRNA is formed in a conditional manner. In some embodiments, the target strand comprises a domain "a", a domain "b" and a domain "c", wherein each of the domain "a", the domain "b" and the domain "c" have a 5' terminus and a 3' terminus, and the 3' terminus of domain "a" is adjacent to the 5' terminus of domain "b", and the 3' terminus of domain "b" is adjacent to the 5' terminus of domain "c". In some embodiments, the domain "b*" is adjacent to the 5' terminus of domain "a*". In some embodiments, there are three strands, with a nick between the first and the third strand when hybridized to the second strand. In some embodiments, the nick lies between the domain "c*" and the domain "z". In some embodiments, the nick lies within two nucleotides of the domain "c*" and the domain "z" junction. In some embodiments, the nick lies within 6 nucleotides of the domain "c*" and the domain "z" junction. In some embodiments, the domain "a", the domain "b*" and the domain "c*" are complementary to the domain "a", the domain "b", and the domain "c" of the target strand, respectively. In some embodiments, the second strand comprises a domain "z", a domain "c*", a domain "b", a domain "c", a domain "z*", and a domain "y*", wherein each of the domain "z", the domain "c*", the domain "b", the domain "c", the domain "z*", and the domain "y*" each have a 5' terminus and a 3' terminus, and the 3' terminus of domain "z" is adjacent to the 5' terminus of domain "c*", the 3' terminus of domain "c*" is adjacent to the 5' terminus of domain "b", the 3' terminus of domain "b" is adjacent to the 5' terminus of domain "c", the 3' terminus of domain "c" is adjacent to the 5' terminus of domain "z*" and the 3' terminus of the domain "z*" is adjacent to the 5' terminus of the "y*" domain. In some embodiments, the shRNA comprises a Dicer substrate sequence. In some embodiments, the shRNA comprises a sequence that allows for a targeting of a gene. In some embodiments, the targeting of the gene is via Dicer processing of the shRNA. In some embodiments, the conditional manner is at least one order of magnitude greater for shRNA formation in a presence of the target strand than in an absence of the target strand. In some embodiments, the conditional manner is at least two orders of magnitude greater for shRNA formation in a presence of the target strand than in an absence of the target strand. In some embodiments, the method further comprises running a detection assay for a presence or an absence of the target strand. In some embodiments, the detection assay for a presence or an absence of the target strand is a qPCR assay. In some embodiments, the shRNA comprises a stem region, wherein the stem region comprises a Dicer substrate and a loop region that is connected to the stem region. In some embodiments, the Dicer substrate comprises the second strand comprising a domain "z", a domain "c*", a domain "b", a domain "c", and a domain "z*", wherein each of the domain "z", the domain "c", the domain "b", the domain "c*", and the domain "z", each have a 5' terminus and a 3' terminus, and the 3' terminus of domain "z" is adjacent to the 5' terminus of domain "c*", the 3' terminus of domain "c*" is adjacent to the 5' terminus of domain "b", the 3' terminus of domain "b" is adjacent to the 5' terminus of domain "c", and the 3' terminus of domain "c" is adjacent to the 5' terminus of domain "z*" and wherein the domain "z" is bound to the domain "z*" and the domain "c" is bound to the domain "c*" forming the stem region, and domain "b" comprises the loop region that is connected to the stem region. In some embodiments, the second strand comprises a domain "z", a domain "c", a domain "b", a domain "c", a domain "z", and a "y*" domain, wherein each of the domain "z", the domain "c", the domain "b", the domain "c*", the domain "z", and the domain "y*" each have a 5' terminus and a 3' terminus, and the 3' terminus of domain "z" is adjacent to the 5' terminus of domain "c*", the 3' terminus of domain "c*" is adjacent to the 5' terminus of domain "b", the 3' terminus of domain "b" is adjacent to the 5' terminus of domain "c", the 3' terminus of domain "c" is adjacent to the 5' terminus of domain "z*" and the 3' terminus of the domain "z*" is adjacent to the 5' terminus of the "y*" domain and wherein the domain "z" is complementary to the domain "z*", and the domain "c" is complementary to the domain "c". In some embodiments, shRNA formation is achieved by hybridization of the domain "z" to the domain "z*" and the hybridization of domain "c" to the domain "c*". In some embodiments, the shRNA is processed by Dicer to form an siRNA. In some embodiments, the siRNA silences genes for host receptors and coreceptors for HIV, N-myc, Ras, p24, Gag, CCR5, Fas, Nucleocapsid RNA transcriptase, VEGF and kinesin spindle. In some embodiments, the detection target mRNA X is a diagnosis target and the independent silencing target mRNA Y is a treatment target. For example, the diagnosis target X can be a disease marker within a cell such as an mRNA cancer marker, an HIV mRNA, a viral mRNA, or an mRNA marker for an autoimmune disease. For example, the treatment target mRNA Y can be an essential gene or housekeeping gene.

Hence, upon detection of disease marker X within a cell, the scRNAs will mediate knockdown of the essential gene Y, killing the diseased cell while leaving normal cells untouched. In some embodiments, the first strand further comprises domain y, wherein the 3' terminus of domain y is adjacent to the 5' terminus of domain "z".

In some embodiments, a method of conditional Dicer substrate formation is provided. The method comprises providing a duplex that comprises a first strand hybridized to a second strand and combining the duplex to a mixture for detection of a target strand. The presence of a target strand results in a displacement of the first strand from the second strand, and the displacement of the first strand from the second strand allows for the second strand to form an shRNA (or other conditional hairpin structure). The shRNA (or other conditional hairpin structure) is formed in a conditional manner. In some embodiments, the target strand comprises a domain "a", a domain "b" and a domain "c", wherein each of the domain "a", the domain "b" and the domain "c" have a 5' terminus and a 3' terminus, and the 3' terminus of domain "a" is adjacent to the 5' terminus of domain "b", and the 3' terminus of domain "b" is adjacent to the 5' terminus of domain "c", as shown in FIG. 14A or 31. In some embodiments, the second strand comprises a domain "z", a domain "c*", a domain "b", a domain "c", a domain "z", and a domain "y", wherein each of the domain "z", the domain "c*", the domain "b", the domain "c", the domain "z*", and the domain "y*" each have a 5' terminus and a 3' terminus, and the 3' terminus of domain "z" is adjacent to the 5' terminus of domain "c*", the 3' terminus of domain "c*" is adjacent to the 5' terminus of domain "b", the 3' terminus of domain "b" is adjacent to the 5' terminus of domain "c", the 3' terminus of domain "c" is adjacent to the 5' terminus of domain "z" and the 3' terminus of the domain "z" is adjacent to the 5' terminus of the domain "y". In some embodiments, the shRNA comprises a sequence that is configured for targeting of a first gene, and can be via Dicer processing of the shRNA. In some embodiments, the conditional manner is at least one order of magnitude greater for shRNA formation in a presence of the target strand than in an absence of the target strand. In some embodiments, the shRNA comprises a stem region, wherein the stem region comprises a Dicer substrate and a loop region that to connected to the stem region. In some embodiments, the Dicer substrate comprises the second strand comprising a domain "z" linked to a domain "c*" linked to a domain "b" linked to a domain "c" linked to a domain "z*" linked to a domain "y". In some embodiments, shRNA formation is achieved by hybridization of a domain "c" to a domain "c*" and hybridization of a domain "z*" to a domain "z". In some embodiments, the domain "c" comprises an internal toehold that is exposed in the second strand when the target strand at least partially displaces the first strand from the second strand, allowing the second strand to self-hybridize via self-nucleation of the "c*" and "c" domains, leading to full displacement of the first strand from the second strand, with the second strand forming an shRNA. In some embodiments, the shRNA is processed by Dicer to form an siRNA. In some embodiments, the siRNA silences at least one of a housekeeping gene, an essential gene, an overexpressed gene, a gene coding for an autoreactive protein, or a viral gene. In some embodiments, the target strand is a disease marker, such as an mRNA cancer marker, an mRNA coding for the complementarity determining region 3 (CDR3) of an autoreactive T-cell, an HIV mRNA, or a viral mRNA.

In some embodiments, a method of conditional hairpin formation is provided (and can be a variation of any of the shRNA options provided herein, but simply not limited to shRNA characteristics. The method can include providing a duplexed scRNA to a sample comprising a target sequence. The duplexed scRNA comprises a first strand and a second strand, and wherein first strand hybridizes to the target sequence to at least partially dehybridize the second strand from the first strand. Upon partial dehybridization of the second strand from the first strand, the second strand self-hybridizes into a conditional hairpin formation. In some embodiments, the formation of the conditional hairpin formation occurs via a single step in which the first strand of the scRNA swaps its hybridization partner from being the second strand of the scRNA to being the target strand, allowing the second strand of the scRNA to form a conditional hairpin formation. In some embodiments, the conditional hairpin formation comprises a shRNA. In some embodiments, the conditional hairpin formation is configured for silencing a gene. In some embodiments, the conditional hairpin formation is configured for silencing a gene via a non-Dicer pathway. In some embodiments, the conditional hairpin formation is configured for silencing a gene via a Dicer pathway.

In some embodiments, a method of forming a Dicer substrate is provided. The method comprises providing a duplex that comprises a first strand hybridized to a second strand, contacting the duplex with a sample. If and when the sample comprises a target strand and the presence of the target strand results in a partial displacement of the first strand from the second strand. The partial displacement of the first strand from the second strand allows for the second strand to form an shRNA. The shRNA is formed in a conditional manner and forms a Dicer substrate (in some embodiments). In some embodiments a method of conditional Dicer substrate formation is provided that includes providing a duplex that comprises a first strand hybridized to a second strand and combining the duplex with a mixture for detection of a target strand. A presence of a target strand results in a partial displacement of the first strand from the second strand, and the partial displacement of the first strand from the second strand allows for the second strand to form an shRNA. The shRNA is formed in a conditional manner based upon a presence or absence of the target strand.

In some embodiments, a method of conditional Dicer substrate formation is provided. The method comprises providing a complex that comprises: a first strand, a second strand, and a third strand. The first strand is hybridized to the second strand and the third strand is also hybridized to the second strand when the first strand is hybridized to the second strand. The method further includes adding the complex to a mixture for detection of a target strand. A presence of the target strand results in a displacement of the first strand from the second strand, and the displacement of the first strand from the second strand allows for the second strand to self-hybridize and displace the third strand from the second strand to form an shRNA. In some embodiments, the second strand contains an internal toehold that is exposed when the first strand is displaced from the second strand. Upon expose of the internal toehold in the second strand, the second strand self-hybridizes to displace the third strand from the second strand to form an shRNA.

In some embodiments, a method of conditional Dicer substrate formation is provided. The method comprises providing a first duplex comprising: a first strand and a second strand, wherein the first strand is hybridized to the second strand. The method further comprises providing a second duplex comprising: a third strand and a fourth strand, wherein the third strand is hybridized to the fourth strand. The method further comprises combining the first and second duplex with a sample, wherein the presence of a target sequence in the sample results in the first duplex and the second duplex nucleating with the target strand via hybridization of the second strand with the target and hybridization of the fourth strand with the target, mediating hybridization of the first strand to the third strand to yield a duplex Dicer substrate. In some embodiments, the first strand comprises a domain that is not hybridized to the second strand when in the first duplex, and the fourth strand comprises a domain that is not hybridized to the third strand when in the second duplex. In some embodiments, the target sequence is hybridized to both the second strand and the fourth strand, and wherein the second strand is also hybridized to the fourth strand.

In some embodiments, a method of conditional Dicer substrate formation is provided. The method comprises providing a duplexed scRNA to a sample that may or may not contain a target polynucleotide. The duplexed scRNA comprises a first strand and a second strand. The first strand is configured to hybridize to a target sequence and expose an internal toehold in the second strand upon the hybridization, and wherein upon exposing the internal toehold in the second strand, the second strand self-hybridizes into an shRNA.

In some embodiments, a duplexed scRNA is provided. The duplexed scRNA comprises a first strand and a second strand. The first strand is hybridized to the second strand. The first strand is configured to hybridize to a target sequence and upon hybridization expose an internal toehold in the second strand upon the hybridization. Upon exposing the internal toehold in the second strand, the second strand self-hybridizes into a hairpin formation. As will be appreciated by one of skill in the art given the present disclosure, any of the strands or duplexes provided herein can be configured for their appropriate functionality via appropriate sequence selection so that the various hybridization related events occur (partial displacement, full displacement, hybridization, etc.) In some embodiments, the duplexed scRNA is adequately stable such that it predominantly does not convert into the hairpin formation in an absence of the target sequence. This can be applied for all embodiments provided herein. In some embodiments, the hairpin formation comprises a shRNA.

Conditional Dicer Substrate Formation

RNAi can allow one to knock down expression of a gene of choice in eukaryotes, and can provide a powerful tool for probing gene function within endogenous biological circuits. RNAi can be activated by exogenous double-stranded RNAs that are cleaved by the enzyme Dicer to produce siRNAs. One strand of the siRNA duplex (the guide strand) is loaded into the RNA-induced silencing complex (RISC), where it can serve as a recognition domain for recruitment of target mRNAs containing the complementary sequence. RISC can then cleave and release mRNA for subsequent degradation, and can enable a single guide strand to mediate destruction of multiple copies of the mRNA silencing target. The power of RNAi can thus be programmed or configured, whereby changing the sequence of the siRNA, one can change the identity of the gene that is targeted for knockdown. In some embodiments, small conditional RNAs (scRNAs) are provided to mediate knockdown of a specific gene.

In some embodiments, scRNA methods for conditional Dicer substrate formation are provided. In some embodiments, methods for dimensioning and/or chemically modifying the scRNAs for processing products of signal transduction by Dicer are provided.

Figure 2:
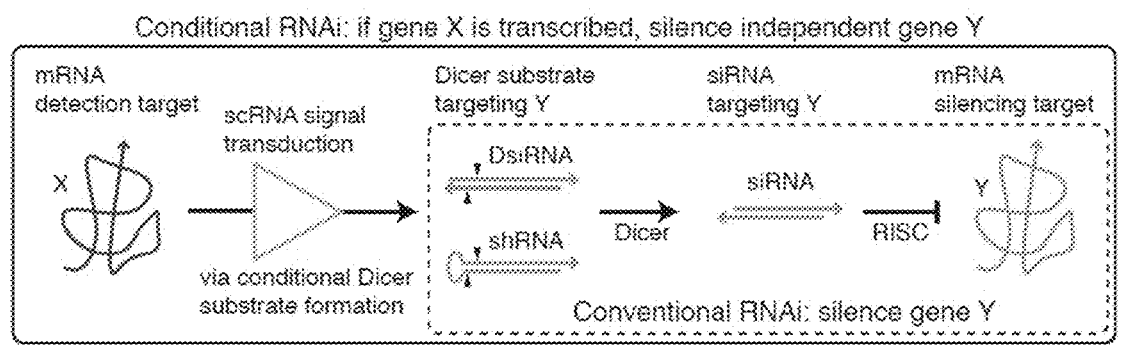
FIG. 2 illustrates the molecular logic of conditional and conventional RNA interference (RNAi). Conditional RNAi implements: if gene X is transcribed, silence independent gene Y. Toward this end, scRNAs interact and change conformation to transduce between binding of mRNA 'detection target' X and production of a Dicer substrate (either a DsiRNA dimer or an shRNA monomer) targeting independent mRNA 'silencing target' Y. Conventional RNAi (inset) implements: silence gene Y.

With reference to FIG. 2, siRNA can be configured to silence gene Y, where the conventional RNAi implements the unconditional molecular logic of silencing gene Y (the inset of FIG. 2). As shown in FIG. 2, to exert control over the strength and/or timing of gene knockdown, numerous methods have been developed to implement drug-inducible RNAi, where the activation or inhibition of knockdown is made dependent on the presence of a small molecule, using either pre-transcriptional protein machinery or post-transcriptional RNA machinery. In order to have spatiotemporal control over gene knockdown, scRNAs can be engineered that can mediate the logic that if gene X is transcribed, independent gene Y can be silenced. This logic can be configured at two levels, where input sequence X can control the scope of silencing and output sequence Y can control the target of silencing (See FIG. 2). In some embodiments, methods for silencing a target gene are provided. In some embodiments, an independent gene is silenced.

FIG. 2 shows the molecular logic of conditional and conventional RNAi. Conditional RNAi (if gene X is transcribed, silence independent gene Y) provides a conceptual framework for exerting spatiotemporal control over gene knockdown. Small conditional RNAs (scRNAs) can interact and change conformation to transduce between binding of mRNA 'detection target' X and production of a Dicer substrate targeting independent mRNA 'silencing target' Y. As shown in the inset of FIG. 2 the conventional RNAi (silence gene Y) employs constitutively active Dicer substrates (DsiRNA or shRNA), making it difficult to control the locus and time of gene knockdown. In some embodiments, a method of conditional Dicer substrate formation is provided. In some embodiments, the method comprises shRNA, wherein the shRNA comprises a sequence that allows for a targeting of a gene.

As noted above, to implement the logic of conditional RNAi, scRNA signal transduction cascades can be engineered, in which hybridization of an scRNA to an mRNA 'detection target' X can initiate downstream conformational changes of one or more scRNAs leading to formation of a Dicer substrate targeting independent mRNA 'silencing target' Y. Dicer processing of this substrate can yield an siRNA targeting mRNA Y for destruction. Two types of signal transduction can be performed simultaneously to achieve this goal: conditional shape change can be performed to produce a molecular geometry that is recognized and processed by Dicer, and conditional sequence change can shift from input sequence X to output sequence Y.

Dicer substrates can include short hairpin RDDs (shRNAs; 19-29-bp stem with a 2-nt 3' overhang) and so-called Dicer-substrate RNAs (DsiRNAs; ~25-bp duplex with a 2-nt 3' overhang at one end). Dicer can function as a molecular ruler, measuring from the 2-nt 3' overhang to cleave ~19-21-bp siRNA strands that form a duplex with 2-nt 3' overhangs at both ends. In several embodiments, engineered scRNA transducers that conditionally assemble shRNA or DsiRNA Dicer substrates with a 2-nt 3' overhang at one end of a minimum 19-bp duplex are provided.

To mediate conditional RNAi via Dicer substrate formation, several design aspects for scRNA function are to be weighed: First, the sequence of the detection target X cannot place a restriction on the sequence of the independent silencing target Y. Second, in the absence of detection target X, the scRNAs cannot interact to form the Dicer substrate targeting Y. Third, the scRNAs must be capable of detecting a subsequence of a full-length endogenous mRNA detection target X. Fourth, in response to detection of X, the scRNAs must undergo an isothermal hybridization cascade mediating formation of a Dicer substrate targeting Y. Fifth, the Dicer substrate should be efficiently processed by Dicer to produce an siRNA targeting Y. Sixth, the scRNAs should be dimensioned and/or chemically modified appropriately so that only the final Dicer substrate is amenable to Dicer processing. Furthermore, it is likely that other unanticipated design requirements will emerge during the engineering and validation process.

Several groups have achieved subsets of these goals. Masu et al. engineered scRNAs that when annealed in a test tube with a short RNA detection target Xs (high temperature followed by slow cooling to room temperature), yielded a Dicer substrate that mediated knockdown of independent silencing target Y upon transfection into mammalian cells. Xie et al. engineered scRNAs that detect a 140-nt RNA target X and produces an siRNA that mediates knockdown of a closely related silencing target X' in *Drosophila* lysate. Kumar et al. express an scRNA in mammalian cells and transfect a short modified-RNA detection target Xs, leading to production of an siRNA that mediates knockdown of independent silencing target Y. However, previous work did not meet all six of the scRNA design requirements.

Previous research in the field of DNA nanotechnology demonstrates that the configurable chemistry of base pairing can provide a versatile medium for engineering diverse dynamic functions including catalysis, amplification, logic, and locomotion. To exploit mechanism and sequence design principles, scRNAs (or scDNAs) can be engineered to be suitable for interfacing with Dicer and RISC to mediate conditional RNAi in vivo by addressing mechanism design, such that the scRNA molecules intended to interact and change conformation can effect signal transduction.

Additional Mechanisms

In order to have conditional Dicer substrate formation, five different mechanisms have been designed where the six design requirements are satisfied and are illustrated below on Table 1 (the broad concept of mechanism 3 was already discussed, in part, above).

TABLE 1

Mechanisms and design alternatives for conditional Dicer substrate formation.

| Design alternatives | Mechanism | | | | |
| --- | --- | --- | --- | --- | --- |
|  | 1 | 2 | 3 | 4 | 5 |
| scRNA reactants | ✓ | ✓ | ✓ | ✓ |  |
| scDNA reactants |  |  |  |  | ✓ |
| metastable reactants | ✓ |  |  | ✓ | ✓ |
| stable reactants |  | ✓ | ✓ |  |  |
| catalytic production | ✓ |  |  |  | ✓ |
| non-catalytic production |  | ✓ | ✓ | ✓ |  |
| toehold/toehold nucleation | ✓ | ✓ | ✓ | ✓ | ✓ |
| loop/toehold nucleation |  |  | ✓ |  |  |
| template/toehold nucleation |  |  |  | ✓ |  |
| 3-way branch migration | ✓ | ✓ | ✓ | ✓ | ✓ |
| 4-way branch migration |  |  |  | ✓ | ✓ |
| spontaneous dissociation |  | ✓ |  | ✓ |  |
| hairpin monomer reactants | 3 | 1 | 0 | 0 | 2 |
| duplex dimer reactants | 0 | 1 | 1 | 2 | 0 |
| Dicer substrate hybridization | ✓ | ✓ | ✓ | ✓ |  |
| Dicer substrate transcription |  |  |  |  | ✓ |
| DsiRNA Dicer substrate | ✓ | ✓ |  | ✓ |  |
| shRNA Dicer substrate |  |  | ✓ |  | ✓ |

To explore the mechanism and sequence design challenges for conditional knock down, five different mechanisms are engineered to satisfy the six noted design requirements, while examining diverse design alternatives spanning (Table 1): reactant material (scRNA vs scDNA), initial reactant state (metastable vs stable), reactant role (catalytic vs non-catalytic), nucleation mechanism (toehold/toehold vs loop/toehold vs template/toehold), strand displacement mechanism (3-way branch migration vs 4-way branch migration vs spontaneous dissociation), reactant type (hairpin monomer vs duplex dimer), Dicer substrate assembly method (hybridization vs transcription), and Dicer substrate type (DsiRNA vs shRNA). As shown in the Examples, performance can be optimized in satisfying the six design requirements, and to achieve simplicity.

For a given scRNA (or scDNA) transduction mechanism, sequence design can be performed subject to the constraints imposed by a given pair of mRNA detection and silencing targets, X and Y. These sequence constraints can dramatically reduce the size of the design space, increasing the challenge of designing well-behaved sequences. NUPACK, a nucleic acid software package for analysis and design of nucleic acid molecules, devices, and systems, can be used to solve a sequence design problem based on a set of target secondary structures representing key states in the intended conditional hybridization cascade. Sequences can be optimized with the goal of reducing the ensemble defect for each target structure below a user-specified stop condition. For a given target secondary structure and candidate sequence, the ensemble defect is the average number of incorrectly paired nucleotides at equilibrium evaluated over the ensemble of (unpseudoknotted) secondary structures. Optimization of the sequences can be performed by computational methods that are known to those skilled in the art. Optimization programs for nucleic acid analysis and design are known to those skilled in the art. Optimization of the ensemble defect encompasses both a positive design paradigm (optimize affinity for the target structure) and a negative design paradigm (optimize selectivity against all other structures in the ensemble). Ensemble defect optimization can provide a framework for designing sequences that execute signal transduction via a prescribed hybridization cascade punctuated by desired secondary structures. In some embodiments, optimization of scRNA sequences are performed. In some embodiments, optimization of scRNA sequences are performed by computational methods.

Following mechanism and sequence design, the OFF/ON response of conditional Dicer substrate formation in test tube studies can be quantified by introducing either a short RNA or a full-length mRNA detection target, and monitoring production of Dicer substrates targeting an independent mRNA silencing target. Recombinant Dicer can be used in studies to verify that only the final product of signal transduction, and not the reactants or intermediates, are efficiently processed by Dicer, yielding siRNAs.

For the engineering studies to test for the six criteria, detection of target DsRed2 (mRNA X) and silencing target d2EGFP (mRNA Y) were considered. In order to meet the 6 design criteria scRNA mechanisms and sequences were designed so that, upon exposure to DsRed2 mRNA (mRNA detection target X), the scRNAs interact and change conformation to form a Dicer substrate targeting d2EGFP mRNA (mRNA silencing target Y) (Examples 1-5). To focus on scRNA signal transduction and eliminate the confounding effects of native mRNA secondary structure, short detection targets (Xs) were synthesized, corresponding to the DsRed2 subsequence that is recognized by a given scRNA mechanism. As shown in the Examples, the relative OFF/ON response of conditional Dicer substrate formation in the absence/presence of the detection target (Xs or X) were quantified. As a test for off-target effects, the response to the silencing target Y and to GAPDH (mRNA Z) were measured, neither of which should initiate signal transduction. To confirm that scRNA transducers interact with Dicer as intended, recombinant Dicer was used to test for undesired processing of the scRNA reactants and transduction intermediates as well as for efficient processing of the final product, for example, the cognate Dicer substrate. Experimental characterizations of conditional OFF/ON response are augmented by computational and experimental stepping analyses that characterize the reactants, intermediates, and products for each mechanism (shown in Examples 1-5).

Figure 3A:
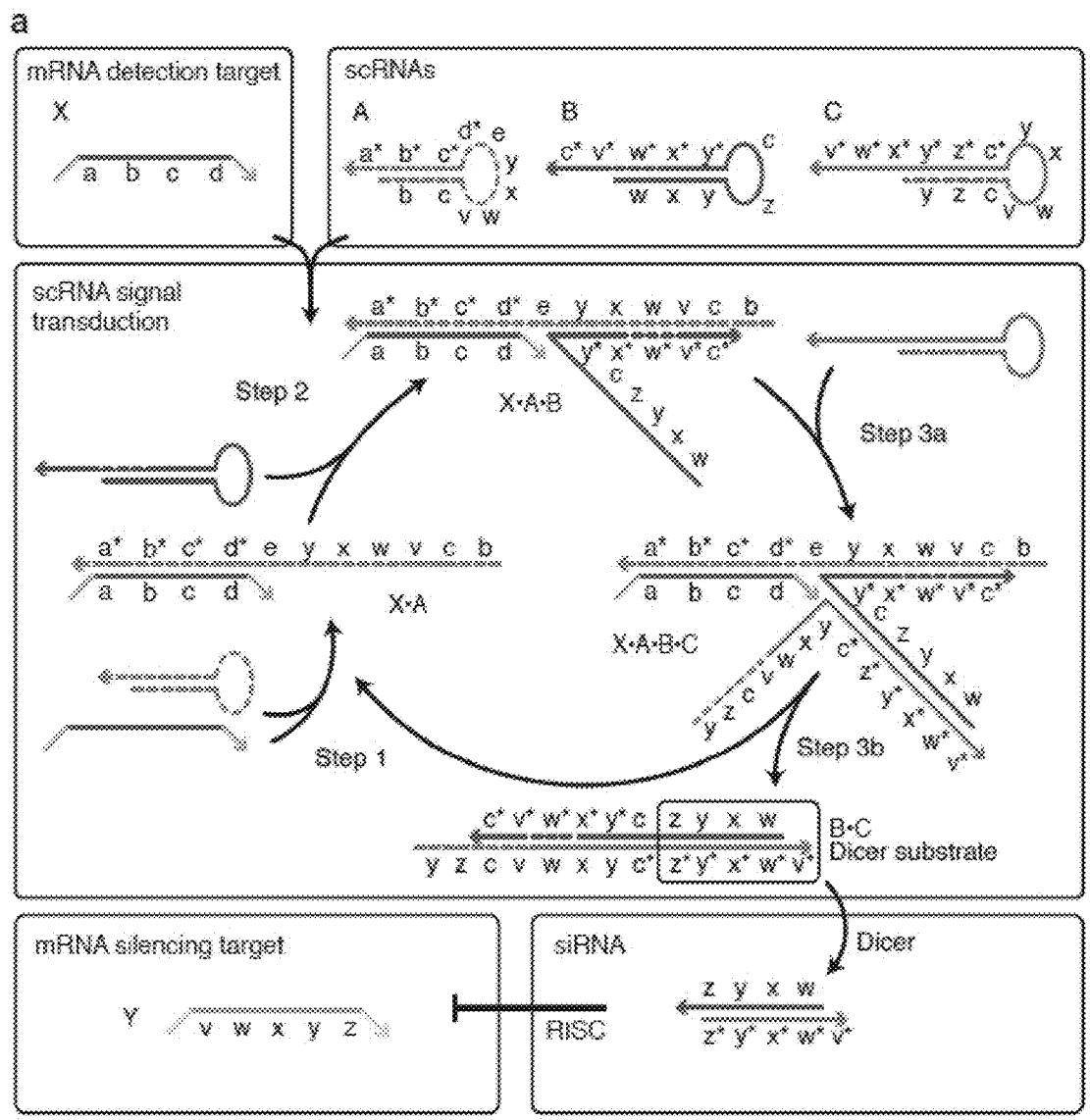
FIG. 3a-d illustrates the conditional catalytic DsiRNA formation using metastable scRNAs for Mechanism 1. a) Mechanism 1. scRNA strand A detects mRNA detection target X (containing subsequence a-b-c-d) to form catalyst X·A, which mediates production of DsiRNA Dicer substrate B·C targeting mRNA silencing target Y (containing independent subsequence v-w-x-y-z). b) Conditional catalytic Dicer substrate formation. c) Quantification of the Dicer substrate band (B·C) in panel (b). d) Conditional Dicer processing.

With reference to FIG. 3a, a schematic of Mechanism 1 is illustrated which is a conditional catalytic DsiRNA formation using metastable scRNAs. As shown, scRNA A detects mRNA detection target X (containing subsequence a-b-c-d) to form catalyst X·A in which A hybridizes to domains a-b-c-d of detection target X, mediating production of DsiRNA Dicer substrate B·C targeting mRNA silencing target Y (containing independent subsequence v-w-x-y-z). As shown in FIG. 3a, only a portion of strand A binds to the mRNA detection target X, and the subsequence b-c-v-w-x-y-e are then bound by scRNA strand B. scRNAs A, B, and C can coexist metastably in the absence of X. Successive toehold-mediated 3-way branch migrations enable assembly of X with A (step 1), X·A with B (step 2), X·A·B with C (step 3a), and disassembly of DsiRNA Dicer substrate B·C from catalyst X·A (step 3b). The preferred domain lengths for Mechanism 1 are as follows: |a|=10, |b|=10, |c|=5, |d|=2, |e|=2, |v|=2, |w|=5, |x|=2, |y|=6, |z|=5. The transduction mechanism of FIG. 3a employs three hairpins (A, B, and C) that co-exist metastably in the absence of detection target X, such that they are kinetically impeded from assembling into an equilibrium distribution of products. The detection target X opens the hairpin of strand A, which in turn opens the hairpin of strand B, which in turn opens the hairpin of strand C, leading to formation of the duplex B·C and regeneration of catalyst X·A. Duplex B·C has a 2-nt 3'-overhang, forming the Dicer substrate, and targets silencing target Y. Chemical modifications (2'OMe-RNA) of A and portions of B and C are employed to prevent Dicer cleavage of scRNA reactants and transduction intermediates, while preserving efficient Dicer processing of the transduction product B·C. In functional teems, strand A detects mRNA detection target X and catalyzes production of the DsiRNA B·C, Dicer substrate, targeting mRNA silencing target Y.

Figure 9A:
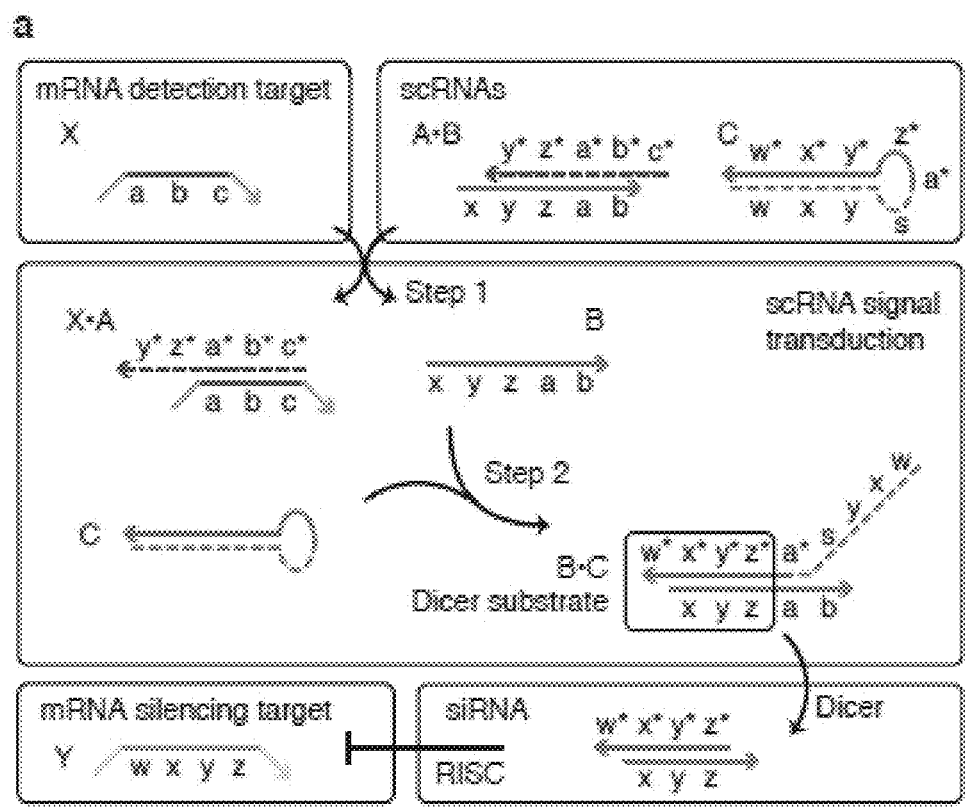
FIGS. 9a-d illustrate conditional DsiRNA formation using stable scRNAs for Mechanism 2. a) Mechanism 2. scRNA duplex A·B detects mRNA detection target X (containing subsequence a-b-c), leading to production of DsiRNA Dicer substrate B·C targeting mRNA silencing target Y (containing independent subsequence w-x-y-z). b) Conditional Dicer substrate formation. c) Quantification of the Dicer substrate band (B·C) in panel (b). d) Conditional Dicer processing.

The second mechanism of conditional Dicer substrate formation (Mechanism 2) is illustrated in FIG. 9a, is a conditional DsiRNA formation using stable scRNAs. As shown, FIG. 9a demonstrates how scRNA A·B detects mRNA detection target X, containing the subsequence a-b-c, leading to the production of DsiRNA Dicer substrate B·C targeting mRNA silencing target Y (containing independent subsequence 'w-x-y-z). For the mechanism, scRNAs A·B and C are stable in the absence of X. When exposed to mRNA detection target X, "c*-b*-a*" of the A strand hybridizes to "a-b-c" of the mRNA detection target X (step 1) via a toehold-mediated 3-way branch migration and the B strand dissociates via spontaneous dissociation. Stand B assembles with C (step 2) via loop/toehold nucleation and 3-way branch migration to form DsiRNA Dicer substrate B·C. The preferred domain lengths are as follows: |a|=6, |b|=4, |c|=8, |s|=5, |w|=2, |x|=12, |y|=4, |z|=3. Chemical modifications (2'OMe-RNA) are in strands A and part of C and are indicated by a dashed backbone, to prevent Dicer cleavage of scRNA reactants and transduction intermediates, while preserving efficient Dicer processing of the transduction product B·C. The signal transduction mechanism was simplified relative to Mechanism 1 by exploiting alternative design principles. In particular, it is desirable to reduce the number of scRNA reactants, the number of assembly steps in the transduction cascade, and the complexity of the reaction intermediates. These goals are achieved by replacing the A and B hairpins of Mechanism 1 with the A·B duplex of Mechanism 2 (FIG. 9a). The detection target X mediates displacement of B from A, which opens C to produce duplex B·C with a 2-nt 3'-overhang, producing a Dicer substrate for silencing mRNA silencing target Y. The number of reactants and the number of assembly steps are both reduced from three to two and the largest intermediate is reduced from a tetramer (resulting from three sequential assembly steps) to a trimer (resulting from one assembly step). This simplified signal transduction mechanism dispenses with catalytic turnover, producing one DsiRNA per detected molecule of X. In functional terms, A·B detects X, leading to production of DsiRNA B·C targeting mRNA silencing target Y.

The details of mechanism 3 were discussed above and elsewhere.

Figure 19A:
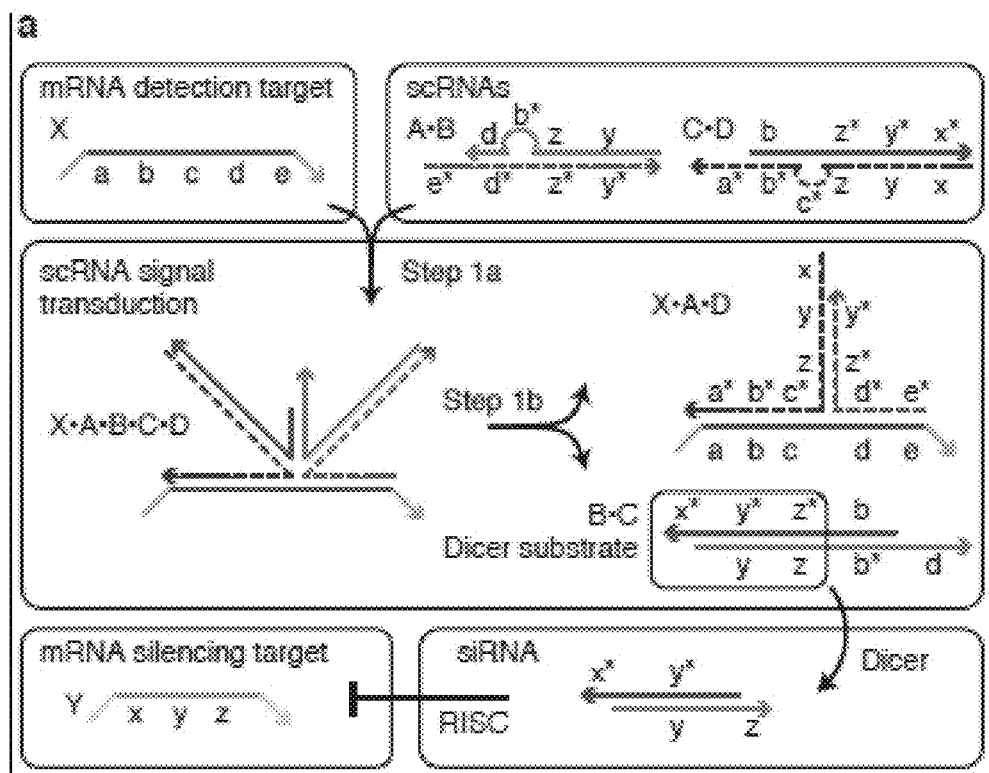
FIGS. 19a-d illustrate conditional DsiRNA formation via template-mediated 4-way branch migration for Mechanism 4. a) Mechanism 4. scRNAs A·B and C·D detect mRNA detection target X (containing subsequence a-b-c-d-e), leading to production of DsiRNA Dicer substrate B·C targeting mRNA silencing target Y (containing independent subsequence x-y-z). b) Conditional Dicer substrate formation. c) Quantification of the Dicer substrate band (B·C) in panel (b). d) Conditional Dicer processing.

FIG. 19a provides a schematic of mechanism 4, which involves a conditional DsiRNA formation via template-mediated 4-way branch migration. FIG. 19a shows scRNAs A·B and C·D detecting mRNA detection target X (containing subsequence 'a-b-c-d-e'), leading to production of DsiRNA Dicer substrate B·C targeting mRNA silencing target Y (containing independent subsequence x-y-z). scRNAs A·B and C·D can coexist metastably in the absence of X. X templates conucleation of A·B and C·D, mediating a short 3-way branch migration that enables toehold/toehold nucleation between B and C to create a 5-way junction (step 1a). Subsequent 4-way branch migration and spontaneous dissociation disassemble DsiRNA Dicer substrate B·C from X·A·D (step 1b). Preferred domain lengths are as follows: |a|=8, |b|=6, |c|=6, |d|=7, |e|=11, |x|=2, |y|=19, |z|=2. Chemical modifications (2'OMe-RNA) are on strands A and D and are indicated by a dashed backbone in FIG. 19a. To date, efforts to engineer conditional hybridization cascades within the field of DNA nanotechnology have focused almost exclusively on strand displacement reactions based on 3-way branch migration, in which an invading strand displaces one strand from a duplex. By comparison, there has been very little study of strand displacement reactions based on 4-way branch migration, in which two duplexes exchange partner strands. In the present setting, a DsiRNA signal transduction product is a duplex, so it was examined if 4-way branch migration might prove especially suitable for conditional Dicer substrate formation (Example 4). Mechanism 4 employs two duplex scRNAs (duplex A·B and duplex C·D of FIG. 19a). The detection target X mediates swapping of partner strands, producing duplex B·C with a 2-nt 3'-overhang, a Dicer substrate. Chemical modifications to A and D prevent Dicer cleavage of the reactants and intermediates, while preserving efficient Dicer processing of transduction product B·C. In functional terms, scRNAs A·B and C·D detect X, leading to production of DsiRNA B·C targeting mRNA silencing target Y.

In some embodiments, a method of conditional Dicer substrate formation is provided. In some embodiments, the method comprises providing a first duplex that comprises a first strand hybridized to a second strand, providing a second duplex that comprises a third strand hybridized to a fourth strand, and combining the first and second duplexes for detection of a target strand. The presence of a target strand results in the two duplexes nucleating with the target via hybridization to the second strand and the fourth strand, mediating a branch migration in which the first strand hybridizes to the third strand to yield a DsiRNA Dicer substrate. The DsiRNA is formed in a conditional manner.

In some embodiments, a method of conditional Dicer substrate formation is provided. The method comprises providing a first duplex comprising: a first strand and a second strand. The first strand is hybridized to the second strand. The method further comprises providing a second duplex comprising: a third strand and a fourth strand. The third strand is hybridized to the fourth strand. The method further comprises combining the first and second duplex with a sample. The presence of a target sequence in the sample results in the two duplexes swapping hybridization partners such that the first strand and the third strand form a Dicer substrate.

In some embodiments, the second strand comprises a domain that is not hybridized to the first strand when in the first duplex and the fourth strand comprises a domain that is not hybridized to the third strand when in the second duplex. In some embodiments, the target sequence is hybridized to both the second strand and the fourth strand, and wherein the second strand is also hybridized to the fourth strand.

Figure 24A:
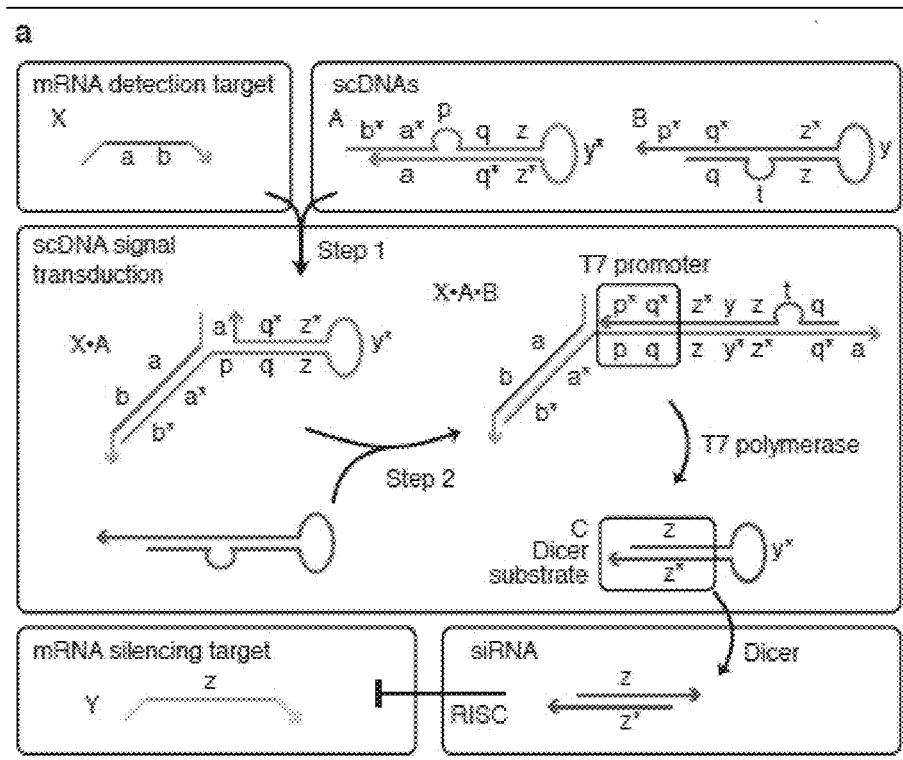
FIGS. 24a-d illustrate the conditional shRNA transcription using scDNAs for Mechanism 5. a) Mechanism 5. scDNA A detects mRNA detection target X (containing subsequence a-b) and assembles with B to form a transcription template (containing promoter, coding, and termination sequences), leading to transcription of the shRNA Dicer substrate C targeting mRNA silencing target Y (containing independent subsequence z). b) Conditional transcription template formation. c) Conditional Dicer substrate transcription and processing. d) Quantification of the Dicer substrate band (C) in lanes 1 and 3 of panel (c).

With reference to FIG. 24a, Mechanism 5, conditional shRNA transcription using scDNAs is illustrated, which shows that scDNA first strand, A, detects mRNA detection target X (containing subsequence a-b) and assembles with B to form a transcription template (containing promoter, coding, and termination sequences), leading to transcription of the shRNA Dicer substrate C targeting mRNA silencing target Y (containing independent subsequence z). scDNAs A and B can coexist metastably in the absence of mRNA detection target strand X. mRNA detection target strand X assembles with A via toehold-mediated 3-way branch migration (step 1). Subsequently, X·A assembles with B via toehold mediated 4-way branch migration to produce a dsDNA transcription template (step 2), mediating transcription of shRNA Dicer substrate C with catalytic turnover. The preferred domain lengths are as follows: |a|=10, |b|=8, |p|8, |q|9, |t|7, |y|=6, |z|=19. The previous mechanisms explored design alternatives for conditional Dicer substrate hybridization using scRNAs. In Mechanism 5 the alternative strategy of conditional Dicer substrate transcription is based on signal transduction with scDNAs. Kim et al. have previously demonstrated conditional in vitro transcription mediated by conditional hybridization of a double-stranded DNA promoter sequence. However, mechanism 5 combines conditional promoter assembly with sequence transduction to implement conditional Dicer substrate transcription. For this design study (Example 5), T7 RNA polymerase is employed for in vitro transcription, taking advantage of well-characterized promoter and termination sequences. Mechanism 5 employs two metastable DNA hairpins (A and B of FIG. 24a). The detection target X opens hairpin A, which in turn opens hairpin B via a 4-way branch migration to assemble a dsDNA template (including promoter sequence, coding sequence, and termination sequence) for transcription of RNA hairpin C. This signal transduction approach incorporates the catalytic turnover inherent in repeated transcription of the template. In functional terms, A detects X leading to transcription of shRNA C targeting Y.

For each of the five mechanisms (Examples 1-5), test tube experiments demonstrated a strong OFF/ON conditional response, with at least an order of magnitude increase in Dicer substrate formation in the presence of the cognate full-length mRNA detection target X (for the scDNAs of Mechanism 5, the detection target was not constrained to be an mRNA sequence, so only the designed short DNA detection target Xs was tested experimentally). Reactant structural domains were dimensioned and/or chemically modified to ensure that only the cognate Dicer substrates that were the final products of signal transduction were efficiently processed by Dicer.

These mechanism studies explored diverse design principles for shape and sequence transduction via conditional assembly and disassembly of scRNA and scDNA complexes (summarized in Table 1). In broad terms, it appears that varied design concepts that have paced progress in the field of dynamic DNA nanotechnology (including mechanisms for strand nucleation, strand displacement, catalytic hybridization, and motif metastability) are equally applicable to dynamic RNA nanotechnology, which is relatively unexplored, yet holds great potential for synthetic regulation in the context of biology; biological RNAs interface with diverse endogenous pathways, and hence synthetic RNA signal transducers that accept RNA inputs and produce RNA outputs represent a particularly appealing framework for engineering conditional regulation in vivo.

Programmable signal transduction with small conditional RNAs offers an enticing framework for implementing diverse modes of conditional regulation.

EXAMPLES

The following examples are offered for illustrative purposes only, and are not intended to limit the scope of the present invention in any way. Indeed, various modifications of the invention in addition to those shown and described herein will become apparent to those skilled in the art from the foregoing description and fall within the scope of the appended claims.

Methods

Oligonucleotide Synthesis Preparation:

RNA oligonucleotides were synthesized by Integrated DNA Technologies (IDT) and either HPLC purified by IDT or purified in the lab by denaturing PAGE followed by ethanol precipitation. To establish correct stoichiometry for duplex scRNA reactants, the two strands were annealed (heating to 90° C. for 3 minutes followed by controlled cooling to 23° C. at 1° C. per minute in a PCR block) and the duplex was isolated via native PAGE. Duplexes were then eluted in 1× duplex buffer (100 mM potassium acetate, 20 mM HEPES, pH 7.5) overnight, filtered, and frozen (Mechanisms 2 and 4) or stored at 4° C (Mechanism 3). scDNAs for Mechanism 5 were synthesized and PAGE purified in two pieces by IDT, then ligated to produce the full hairpin using T4 DNA ligase (New England Biolabs), followed by denaturing PAGE purification and ethanol precipitation. Prior to each reaction, all monomers were snap cooled (95° C. for 90 seconds, 30 second incubation on ice, and room temperature incubation of at least 30 minutes) and duplex dimers were either annealed (Mechanisms 2 and 4) or used without annealing after storage at 4° C. (Mechanism 3). For each mechanism, concentrations were estimated by measuring UV absorbance on a NANODROP-8000 spectrophotometer (Thermo Scientific) using extinction coefficients provided by IDT, and then scRNA or scDNA concentrations were corrected relative to the concentration of short target Xs by performing titration experiments (2 hour reaction at 37° C. followed by native PAGE).

Polyacrylamide Gel Electrophoresis:

scRNA reactions were performed in 1× duplex buffer (100 mM potassium acetate, 20 mM HEPES, pH 7.5) and scDNA reactions were performed in 1× SPSC buffer (50 mM Na2HPO4, 0.5 M NaCl, pH 7.5). Reactants were incubated at 0.5 μm each for two hours at 37° C. For stepping studies, annealed reactions were run on a gel upon completion of the cooling protocol without further incubation. Gels were cast and run in 1× TBE (Tris-Borate-EDTA). Native polyacrylamide gel electrophoresis (PAGE) was performed using 20% native polyacrylamide gels run at 200 V for 8-10.5 hours unless otherwise specified. Denaturing PAGE was performed using 15% denaturing polyacrylamide gels run at 500 V for 1.5 hours unless otherwise specified. Each lane was loaded with a reaction volume corresponding to 2 pmol of the specified strands (4 pmol for mRNAs) in 1× loading buffer. Gels were post-stained in 1× SYBR GOLD nucleic acid gel stain (Life Technologies) for 10 minutes at room temperature and imaged using an FLA-5100 imaging system (Fuji Photo Film). For Dicer processing gels, 45 ng of siRNA markers (New England Biolabs, N2101S) were used for native PAGE, or 60 ng of miRNA markers (New England Biolabs, N2102S) were used for denaturing PAGE.

Conditional Radioactive shRNA Transcription:

For Mechanism 5, radioactive in vitro transcription was performed simultaneously with scDNA transduction using the T7-Scribe standard RNA IVT kit (CELLSCRIPT). 2 pmol of each scDNA were used for each 20μL reaction. Transcription reactions were carried out as directed by the manufacturer with the following modification: 50 nmol of UTP and 3- 4 μL of [α-$^{32}$P] UTP (10 mCi/mL, MP Biomedicals). Reactions were incubated for 3 hours at 37° C. followed by 20 minutes of DNaseI treatment at 37° C. The reaction volume was adjusted to 200 μL using RNase-free water and extracted using 1:1 (v/v) TE-saturated phenol/chloroform. Unincorporated NTPs were removed from the aqueous phase by NUCAWAY spin columns (Life Technologies) as directed by the manufacturer. Ethanol precipitation was done by incubation on ice for 15 minutes in 1:10 (v/v) of 3M sodium acetate and 2.5×(v/v) 95% EtOH. The RNA was pelleted and then washed with 70% EtOH. The pellet was dried and resuspended in 1× duplex buffer. Counts were measured on an LS-5000TD Liquid Scintillation Counter (Beckman). siRNA markers (New England Biolabs, N2101S) and miRNA markers (New England Biolabs, N2102S) were 5'-end labeled with [γ-$^{32}$P] ATP (10mCi/ml, MP Biomedicals) using T4 polynucleotide kinase (New England Biolabs) to serve as size markers in radioactive gels. Unincorporated [γ-$^{32}$P ] ATP was removed by spin column chromatography using ILLUSTRA MICROSPIN G-25 columns (GE Healthcare) as directed by the manufacturer.

Gel Quantification:

To characterize variability in scRNA and scDNA signal transduction performance for each mechanism, gels used for quantification of ON and OFF states were run on three separate days, preparing reactants each day as described above. Multi Gauge software (Fuji Photo Film) was used to calculate the SYBR GOLD nucleic acid gel stain intensity profile surrounding the band corresponding to the transduction product. Each intensity profile is displayed for ±4mm of gel migration distance with the peak value centered at 0 (a smaller window than ±4 mm was used for Mechanism 1 to avoid a nearby band). The intensity values are normalized so that the highest peak value for each gel is set to 1. The quantification percentages were calculated either using Multi Gauge (with auto-detection of signal and background) or using a MATLAB script that subtracted the background, which was approximated by fitting a straight line to the intensity values in the last 0.5 mm at either end of the quantified window. The calculated values for ON and OFF states were normalized to the ON state for the short detection target Xs. After quantifying the gels shown in the main text six times each, the uncertainty in quantifying any given gel is estimated to be less than 0.5%. This gel quantification uncertainty is significantly smaller than the variability observed between the three independent reaction replicates for a given mechanism.

In Vitro Dicer Processing:

Dicer reactions were performed using the Recombinant Human Turbo Dicer Enzyme kit (Genlantis, catalog number T520002). For Mechanisms 1-4, the reactions were performed at 0.5 µM in 10 µL using enough Turbo Dicer to process approximately all of the final substrate after 2 hours at 37° C. (0.5 units for Mechanisms 1-3 and 1 unit for Mechanism 4). Dicer, target and scRNAs were mixed simultaneously (i.e., the reactants were not pre-incubated with the target prior to addition of Dicer). siRNA production was verified by native PAGE. For Mechanism 5, the cognate shRNA Dicer substrate is a radio-labeled transcription product. Dicer reactions were performed following in vitro transcription. For a given Dicer processing gel, the same volume of transcription product was used for each reaction, determined so as to correspond to 20,000 cpm for the reaction containing short detection target Xs. Likewise, the same amount of Turbo Dicer was used for each reaction (1 unit of Dicer per 20,000 cpm in the Xs reaction). Radioactive gels were exposed overnight on an image plate (Fujifilm Type BAS-MS) and scanned using an FLA-5100 imaging system (Fuji Photo Film).

mRNA In Vitro Transcription and Preparation:

The DsRed2, d2EGFP, and GAPDH mRNAs were generated by in vitro transcription. Plasmids were constructed, linearized, and transcribed as follows:

DsRed2.

The mRNA coding sequence was amplified from pDsRed2-C1 (Clontech, #632407) and directionally cloned into the PTNT Vector plasmid (Promega, catalog #L5610) to construct plasmid pTnT-DsRed2. The plasmid was linearized using NotI (New England Biolabs) and in vitro transcribed for 2 to 4 hours using the T7-Scribe Standard RNA IVT kit (CELL SCRIPT).

d2EGFP.

The d2EGFP mRNA coding sequence was cloned from cells expressing d2EGFP (gift from Dr. C. Beisel; based on the pd2EGFP-1 (Clontech, catalog #6008-1) sequence) and cloned into the PGEM-T Easy Vector plasmid (Promega, catalog #A1360) to construct plasmid pGEM-T-Easy-d2EGFP. The plasmid was linearized using AatII (New England Biolabs) and in vitro transcribed for 2 to 4 hours using the SP6-Scribe Standard RNA IVT kit (CELLSCRIPT).

GAPDH.

The GAPDH mRNA coding sequence was cloned from HEK 293 cells and cloned into the PGEM-T Easy Vector plasmid (Promega, catalog #A1360) to construct plasmid pGEM-T-Easy-GAPDH. The plasmid was linearized using SPHI-HF enzyme (New England Biolabs) and in vitro transcribed for 2 to 4 hours using the SP6-Scribe Standard RNA IVT kit (CELLSCRIPT). Transcribed mRNA was purified using the RNeasy Protect Mini Kit (Qiagen). Transcripts are expected to be slightly longer than the coding sequences listed below due to additional transcription at the start and termination sites. mRNA concentrations were estimated based on UV absorbance on a NANODROP-8000 spectrophotometer (Thermo Scientific). Prior to each reaction, mRNAs were heated to 65° C. for 5 minutes and cooled at room temperature for a minimum of 30 minutes. mRNA targets (X, Y, or Z) were used at twice the estimated concentration of the short target Xs to account for uncertainties in concentration determination.

```
DsRed2 mRNA sequence
                                            (SEQ ID NO: 1)
AUGGCCUCCU CCGAGAACGU CAUCACCGAG UUCAUGCGCU

UCAAGGUGCG CAUGGAGGGC ACCGUGAACG GCCACGAGUU

CGAGAUCGAG GGCGAGGGCG AGGGCCGCCC CUACGAGGGC

CACAACACCG UGAAGCUGAA GGUGACCAAG GGCGGCCCCC

UGCCCUUCGC CUGGGACAUC CUGUCCCCCC AGUUCCAGUA

CGGCUCCAAG GUGUACGUGA AGCACCCCGC CGACAUCCCC

GACUACAAGA AGCUGUCCUU CCCCGAGGGC UUCAAGUGGG

AGCGCGUGAU GAACUUCGAG GACGGCGGCG UGGCGACCGU

GACCCAGGAC UCCUCCCUGC AGGACGGCUG CUUCAUCUAC

AAGGUGAAGU UCAUCGGCGU GAACUUCCCC UCCGACGGCC

CCGUGAUGCA GAAGAAGACC AUGGGCUGGG AGGCCUCCAC

CGAGCGCCUG UACCCCCGCG ACGGCGUGCU GAAGGGCGAG

ACCCACAAGG CCCUGAAGCU GAAGGACGGC GGCCACUACC

UGGUGGAGUU CAAGUCCAUC UACAUGGCCA AGAAGCCCGU

GCAGCUGCCC GGCUACUACU ACGUGGACGC CAAGCUGGAC

AUCACCUCCC ACAACGAGGA CUACACCAUC GUGGAGCAGU

ACGAGCGCAC CGAGGGCCGC CACCACCUGU UCCUGAGAUC

UCGAGCUCAA GCUUCGAAUU CUGCAGUCGA CGGUACCGCG

GGCCCGGGAU CCACCGGAUC UAGAUAA d2EGFP mRNA sequence
                                            (SEQ ID NO: 2)
AUGGUGAGCA AGGGCGAGGA GCUGUUCACC GGGGUGGUGC

CCAUCCUGGU CGAGCUGGAC GGCGACGUAA ACGGCCACAA

GUUCAGCGUG UCCGGCGAGG GCGAGGGCGA UGCCACCUAC

GGCAAGCUGA CCCUGAAGUU CAUCUGCACC ACCGGCAAGC

UGCCCGUGCC CUGGCCCACC CUCGUGACCA CCCUGACCUA

CGGCGUGCAG UGCUUCAGCC GCUACCCCGA CCACAUGAAG

CAGCACGACU UCUUCAAGUC CGCCAUGCCC GAAGGCUACG

UCCAGGAGCG CACCAUCUUC UUCAAGGACG ACGGCAACUA

CAAGACCCGC GCCGAGGUGA AGUUCGAGGG CGACACCCUG

GUGAACCGCA UCGAGCUGAA GGGCAUCGAC UUCAAGGAGG

ACGGCAACAU CCUGGGGCAC AAGCUGGAGU ACAACUACAA

CAGCCACAAC GUCUAUAUCA UGGCCGACAA GCAGAAGAAU

GGCAUCAAGG UGAACUUCAA GAUCCGCCAC AACAUCGAGG

ACGGCAGCGU GCAGCUCGCC GACCACUACC AGCAGAACAC

CCCCAUCGGC GACGGCCCCG UGCUGCUGCC CGACAACCAC

UACCUGAGCA CCCAGUCCGC CCUGAGCAAA GACCCCAACG

AGAAGCGCGA UCACAUGGUC CUGCUGGAGU UCGUGACCGC
```

```
CGCCGGGAUC ACUCUCGGCA UGGACGAGCU GUACAAGAAG

CUUAGCCAUG GCUUCCCGCC GGAGGUGGAG GAGCAGGAUG

AUGGCACGCU GCCCAUGUCU UGUGCCCAGG AGAGCGGGAU

GGACCGUCAC CCUGCAGCCU GUGCUUCUGC UAGGAUCAAU

GUGUAG

GAPDH mRNA sequence
                                    (SEQ ID NO: 3)
AUGGGGAAGG UGAAGGUCGG AGUCAACGGA UUUGGUCGUA

UUGGGCGCCU GGUCACCAGG GCUGCUUUUA ACUCUGGUAA

AGUGGAUAUU GUUGCCAUCA AUGACCCCUU CAUUGACCUC

AACUACAUGG UUUACAUGUU CCAAUAUGAU UCCACCCAUG

GCAAAUUCCA UGGCACCGUC AAGGCUGAGA ACGGGAAGCU

UGUCAUCAAU GGAAAUCCCA UCACCAUCUU CCAGGAGCGA

GAUCCCUCCA AAAUCAAGUG GGGCGAUGCU GGCGCUGAGU

ACGUCGUGGA GUCCACUGGC GUCUUCACCA CCAUGGAGAA

GGCUGGGGCU CAUUUGCAGG GGGGAGCCAA AAGGGUCAUC

AUCUCUGCCC CCUCUGCUGA UGCCCCCAUG UUCGUCAUGG

GUGUGAACCA UGAGAAGUAU GACAACAGCC UCAAGAUCAU

CAGCAAUGCC UCCUGCACCA CCAACUGCUU AGCACCCCUG

GCCAAGGUCA UCCAUGACAA CUUUGGUAUC GUGGAAGGAC

UCAUGACCAC AGUCCAUGCC AUCACUGCCA CCCAGAAGAC

UGUGGAUGGC CCCUCCGGGA AACUGUGGCG UGAUGGCCGC

GGGGCUCUCC AGAACAUCAU CCCUGCCUCU ACUGGCGCUG

CCAAGGCUGU GGGCAAGGUC AUCCCUGAGC UGAACGGGAA

GCUCACUGGC AUGGCCUUCC GUGUCCCCAC UGCCAACGUG

UCAGUGGUGG ACCUGACCUG CCGUCUAGAA AAACCUGCCA

AAUAUGAUGA CAUCAAGAAG GUGGUGAAGC AGGCGUCGGA

GGGCCCCCUC AAGGGCAUCC UGGGCUACAC UGAGCACCAG

GUGGUCUCCU CUGACUUCAA CAGCGACACC CACUCCUCCA

CCUUUGACGC UGGGGCUGGC AUUGCCCUCA ACGACCACUU

UGUCAAGCUC AUUUCCUGGU AUGACAACGA AUUUGGCUAC

AGCAACAGGG UGGUGGACCU CAUGGCCCAC AUGGCCUCCA

AGGAGUAA
```

Computational Sequence Design:

scRNA and scDNA sequences were designed using the NUPACK web application. Sequences of the mRNA detection target X (DsRed2) and the mRNA silencing target Y (d2EGFP) were specified as external sequence constraints. For each reaction, the design problem was formulated in terms of a set of target secondary structures corresponding to key states in the reaction pathway (Table 2). Sequences were optimized to reduce the ensemble defect for each target secondary structure. Based on additional computational stepping analyses performed using the Analysis page of the NUPACK web application (see Section Computational and experimental stepping analyses), final sequence designs (see EXAMPLES 1-5) were selected from a list of promising candidate sequences returned by the designer. The subsequences of mRNA X and mRNA Y that were selected for each mechanism are shown in Table 2. Design calculations were performed using nearest-neighbor free energy parameters for RNA (Mechanisms 1-4) or DNA (Mechanism 5) at 37° C. in 1M Na+. Chemical modifications (2'OMe-RNA) were not accounted for in the physical model.

TABLE 2

| Mechanism | Target structures | mRNA detection target X dsRed2 subsequence | mRNA silencing target Y d2EGFP subsequence |
| --- | --- | --- | --- |
| 1 | $X_S$, A, B, C, $X_S \cdot A$, $X_S \cdot A \cdot B$ | 592-618 | 252-271 |
| 2 | $X_S$, A, B, C, $A \cdot B$, $A \cdot B \cdot C$, $X_S \cdot A$, $B \cdot C$ | 598-615 | 542-562 |
| 3 | $X_S$, A, B, $A \cdot B$, $X_S \cdot A$ | 277-305 | 137-157 |
| 4 | XS, $A \cdot B$, $C \cdot D$, $B \cdot C$ | 9-46 | 70-92 |
| 5 | $X_S$, A, B | — | 240-258 |

For each mechanism, the objective function was formulated in terms of multiple target secondary structures with base-pairing states depicted in the mechanism schematics of FIGS. 3A, 9A, 14A, 19A, 24A. For Mechanism 2, the target secondary structure for A was single-stranded, and the target secondary structure for 'trimer' A·B·C was comprised of duplex A·B and hairpin C. For Mechanism 3, the target secondary structure for A was single-stranded. Subsequences of mRNA detection target X and mRNA silencing target Y selected during the design process (for Mechanism 5, the sequence of the detection target was not constrained).

Computational And Experimental Stepping Analyses:

Equilibrium test tube calculations (see EXAMPLES 1-5) were performed using the analysis feature of the NUPACK web application to step through the molecular assembly and disassembly operations for each mechanism. These calculations were used to check that the desired reactants, intermediates, and products were predicted to form with high yield in test tubes containing different subsets of strands. Typically, it is observed that sequence domains that were intended to be completely unstructured were predicted to have some degree of base pairing at equilibrium. These imperfections reflect the challenge of designing scRNA and scDNA hybridization cascades using sequences that are predominantly constrained to be drawn from mRNAs X and Y. Analysis calculations were performed using nearest-neighbor free energy parameters for RNA (Mechanisms 1-4) or DNA (Mechanism 5) at 37° C. in 1M Na+. Chemical modifications (2'OMe-RNA) were not accounted for in the physical model. Similar mechanism stepping analyses were then performed experimentally to verify that the desired assembly and disassembly operations occurred with high yield (see EXAMPLES 1-5). Finally, these stepping analyses were repeated in the context of Dicer to verify that only the final product of signal transduction, and not the reactants or intermediates, were efficiently processed by Dicer (see EXAMPLES 1-5).

Interpretation of Annealed Reactions:

In the stepping experiments, both isothermal and annealed reactions for each step were included (see EXAMPLES 1-5). In structural nucleic acid nanotechnology, annealing (heating followed by slow cooling) is often relied on to relax systems to equilibrium. However, for nucleic acid self-assembly systems that involve metastable hairpin monomers, annealing can dramatically fail to relax systems to equilibrium. During the cooling phase of the anneal, intramolecular base pairs become favorable at higher temperatures than intermolecular base pairs, allowing hairpins to close before it becomes energetically favorable to interact with other molecules. If the hairpin is designed to be metastable, closure of the hairpin resets the kinetic trap and inhibits relaxation to equilibrium. Hence, care should be used in interpreting annealed reactions involving hairpins or other strands with strong internal secondary structure.

Example 1

Mechanism 1, Conditional Catalytic DsiRNA Formation Using Metastable scRNAs

The hairpin motif of Yin et al. was employed, which has previously been used to program diverse self-assembly and disassembly hybridization cascades, including catalytic duplex formation. In the present circumstances, the duplex to be formed must have the canonical 2-nt 3'-overhang of a DsiRNA, and the catalysis process must also achieve sequence transduction between detection target X and silencing target Y. The transduction mechanism of FIG. 9*a* employs three hairpins (A (UCACCUCCCACAACGCUU-CAAGUCCGCCAUCUCUCGUUGUGGGAGGUGAU-GUCCAGCUU; SEQ ID NO: 5), B (UCAAGUCCGC-CAUGCCCGCAACGAUGGCGGACUUGAAGCGUUG; SEQ ID NO: 6), and C (CGCCAUGCCCGCAACGCUU-CAAGUCCGCCAUCGUUGCGGGCAUGGCGGAC-UUGAAG); SEQ ID NO: 7) that co-exist metastably in the absence of detection target X (i.e., they are kinetically impeded from assembling into an equilibrium distribution of products). The detection target X opens hairpin A, which in turn opens hairpin B, which in turn opens hairpin C, leading to formation of duplex B·C and regeneration of catalyst X·A. Duplex B·C has a 2-nt 3'-overhang and targets silencing target Y. Chemical modifications (2'OMe-RNA) of A and portions of B and C are employed to prevent Dicer cleavage of scRNA reactants and transduction intermediates, while preserving efficient Dicer processing of the transduction product B·C. In functional terms, A detects X and catalyzes production of DsiRNA B·C targeting Y.

FIGS. 3*b* and 3*c* examine the conditional OFF/ON response of the transduction mechanism. In the absence of the detection target X, there is minimal production of DsiRNA B·C, corresponding to minimal 'leakage' of the kinetically trapped hairpins out of their metastable states. Neither the mRNA silencing target Y (which is necessarily related in sequence to the hairpins) nor the unrelated mRNA off-target Z, causes measurable production of B·C above the background leakage. Stoichiometric introduction of the short detection target Xs leads to strong production of B·C, and substoichiometric introduction of Xs demonstrates catalytic turnover in producing B·C. Strong production of B·C is also observed using full-length mRNA detection target X. The OFF/ON conditional response of the transduction mechanism yields more than an order of magnitude increase in production of Dicer substrate above background (FIG. 3*c*).

FIG. 3*d* demonstrates signal transduction in the presence of recombinant Dicer. Only the DsiRNA B·C that is the final product of transduction is recognized and efficiently processed by Dicer, yielding canonical 21- and 23-nt siRNAs (FIG. 6). In assessing the advantages and disadvantages of this scRNA transduction mechanism, it is helpful to classify the design features that contribute to conditional shape change and conditional sequence change (Table 1). The hairpin reactants are metastable, and could potentially leak into the DsiRNA product on a biologically relevant time scale, even in the absence of detection target X. Three hairpins are required to effect the necessary shape and sequence transduction: hairpin A achieves partial sequence independence via the loop, hairpin B moves the independent sequence to the end of the strand for presentation to Dicer, and hairpin C contributes the additional independent sequence of the 2-nt 3'-overhang and liberates the fully-formed DsiRNA B·C from catalyst X·A. This process requires transient formation of a relatively complex intermediate (tetramer X·A·B·C including mRNA X). Use of monomer hairpins simplifies preparation of purified reactants, but eventual delivery of three scRNA species to cells could prove burdensome. On the other hand, each self-assembly operation (opening of a new A, B, or C hairpin) and disassembly operation (liberation of a new B·C duplex) occurs via toehold-mediated 3-way branch migration, providing a robust framework for engineering fast reaction kinetics. The mechanism has the potentially useful property that a single detection target X can catalyze production of multiple DsiRNAs targeting silencing target Y, augmenting the catalytic turnover that is already present in the RNAi pathway (via RISC-mediated cleavage of multiple silencing targets using a single guide strand).

Oligonucleotide synthesis and preparation were performed as described herein. Sequences used for Mechanism 1 and are indicated below in Table 3.

TABLE 3

Sequences for Mechanism 1

| Strand | Domains | Sequence (5'-3') | SEQ ID NO |
|---|---|---|---|
| Strand $X_s$ | s1-a-b-c-d-s2 | GGCAAGCUGGACAUCACCUCCCACAACGAGGAC | 4 |
| Strand A | b-c-v-w-x-y-e-d*-c*-b*-a* | UCACCUCCCACAACG(CUUCAAGUCCGCCAU)CUCUCGUUGUGGGAGGUGAUGUCCAGCUU | 5 |
| Strand B | w-x-y-z-c-y*-x*-w*-v*-c* | (UCAAGUCCGCCAUGCCCG)CAACG(AUGGCGGACUUGAAG)CGUUG | 6 |
| Strand C | y-z-c-v-w-x-y-c*-z*-y*-x*-w*-v* | (CGCCAUGCCCG)CAACG(CUUCAAGUCCGCCAU)CGUUG(CGGGCAUGGCGGACUUGAAG) | 7 |

Sequences constrained by DsRed2 (mRNA detection target X) are shown in bold. Sequences constrained by d2EGFP (mRNA silencing target Y) are shown in parentheses. Underlined nucleotides are 2'OMe-RNA; all other nucleotides are RNA. Domain lengths: |a|=10, |b|=10, |c|=5, |d|=2, |e|=2, |s1|=3, |s2|=3, |v|=2, |w|=5, |x|=2, |y|=6, |z|=5. To allow for better gel separation of the various reactants, intermediates, and products using native PAGE, the length of Xs was increased (by adding 3 nt to the 3' end and 3 nt to the 5' end). As an unintended consequence of shortening a sequence domain in hairpin C, the 5'-most nucleotide of the cognate siRNA guide strand is not complementary to the d2EGFP silencing target. Mutations at the 5' end of the guide strand are well-tolerated and for human Agog, similar silencing activities are observed with either the correct or mutated base at the 5' end. This mismatch was therefore allowed to remain in the design. However, in future designs, the length of the "z*" domain should be increased by 1 nt to avoid introducing a mismatch between the guide strand and its silencing target.

Figure 4A:
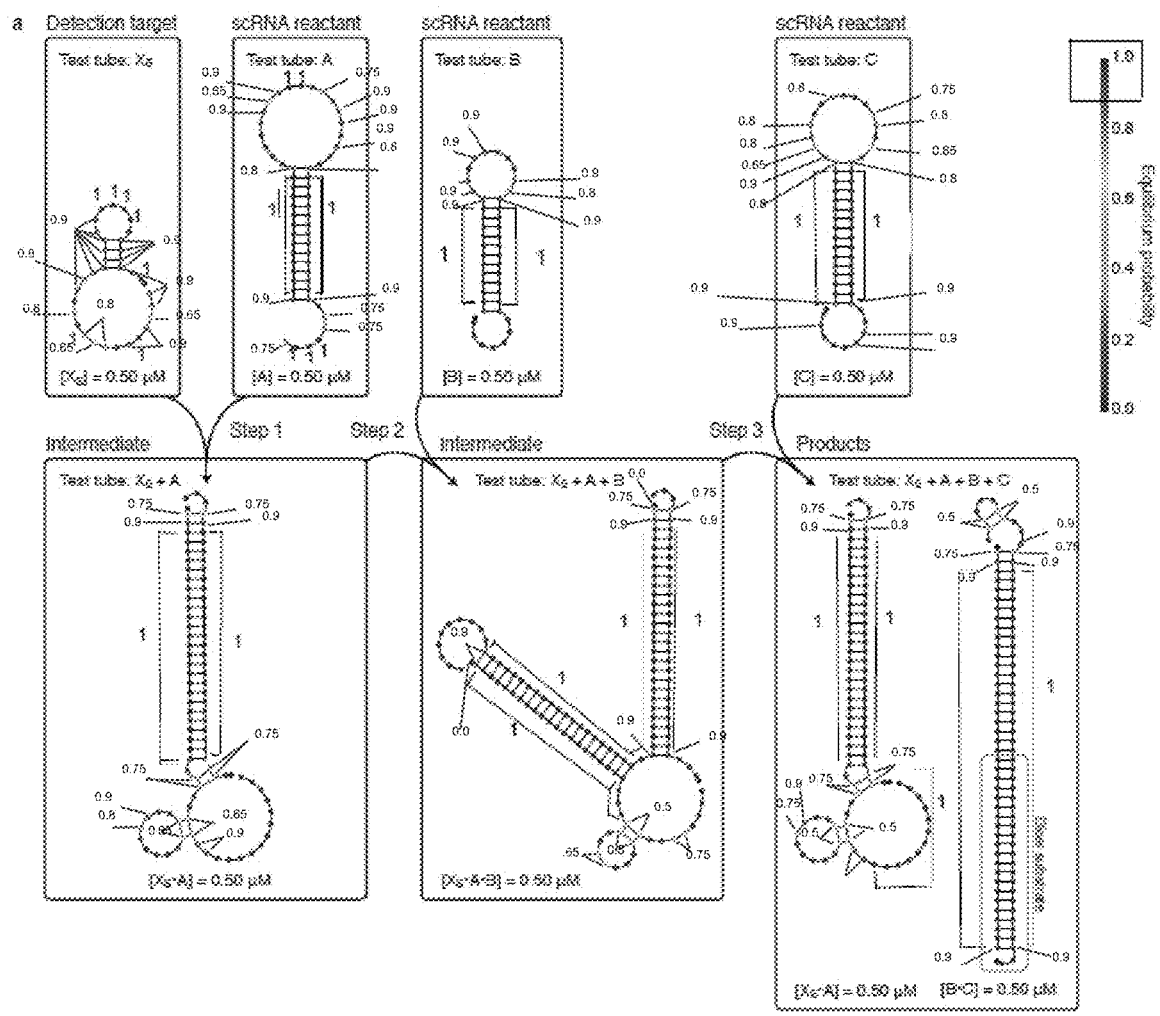
FIG. 4a-b illustrates a computational stepping analysis for Mechanism 1. a) Equilibrium test tube calculations showing the predicted concentrations and base-pairing properties of reactants, intermediates, and products. b) Equilibrium test tube calculation predicting that scRNAs B and C are metastable, not stable.
Figure 4B:
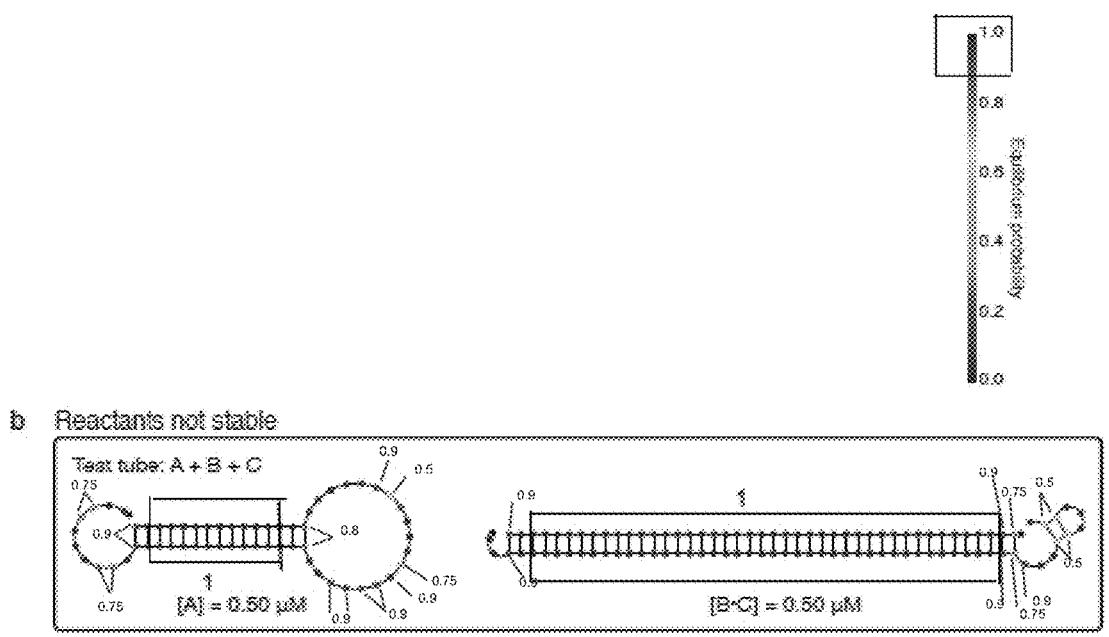

Using the methods for computational and experimental stepping analyses described above, a computational stepping analysis was performed for this mechanism. The mechanism stepping analyses were also performed experimentally to verify that the desired assembly and disassembly operations occurred with high yield. Reference is made to FIGS. 4a and 4b, which show the steps of the computational stepping analysis. As shown in FIG. 4a, equilibrium test tube calculations are indicated which show the predicted concentrations and base-pairing properties of reactants, intermediates, and products. The short RNA detection target $X_s$ is predicted to have some internal base pairing on average at equilibrium. The reactants, intermediates, and products are predicted to form with quantitative yield. In the intermediates, domains that are intended to be single-stranded are predicted to contain some weak base-pairing on average at equilibrium. With reference to FIG. 4b, equilibrium test tube calculation predicted that scRNAs B and C are metastable, not stable. Placing A, B, and C together in a test tube led predominantly to monomer hairpin A and duplex dimer B·C at equilibrium, demonstrating that B and C are not stable. In FIGS. 4a and 4b, each box represents a test tube containing the strands listed at the top at 0.5 µM each. For each test tube, thermodynamic analysis at 37° C. yields the equilibrium concentrations and base-pairing ensemble properties for all complexes containing up to four strands. Each complex predicted to form with appreciable concentration at equilibrium is depicted by its minimum free energy structure, with each nucleotide shaded by the probability that it adopts the depicted base pairing state at equilibrium. The predicted equilibrium concentration is noted next to each complex.

Figure 5:
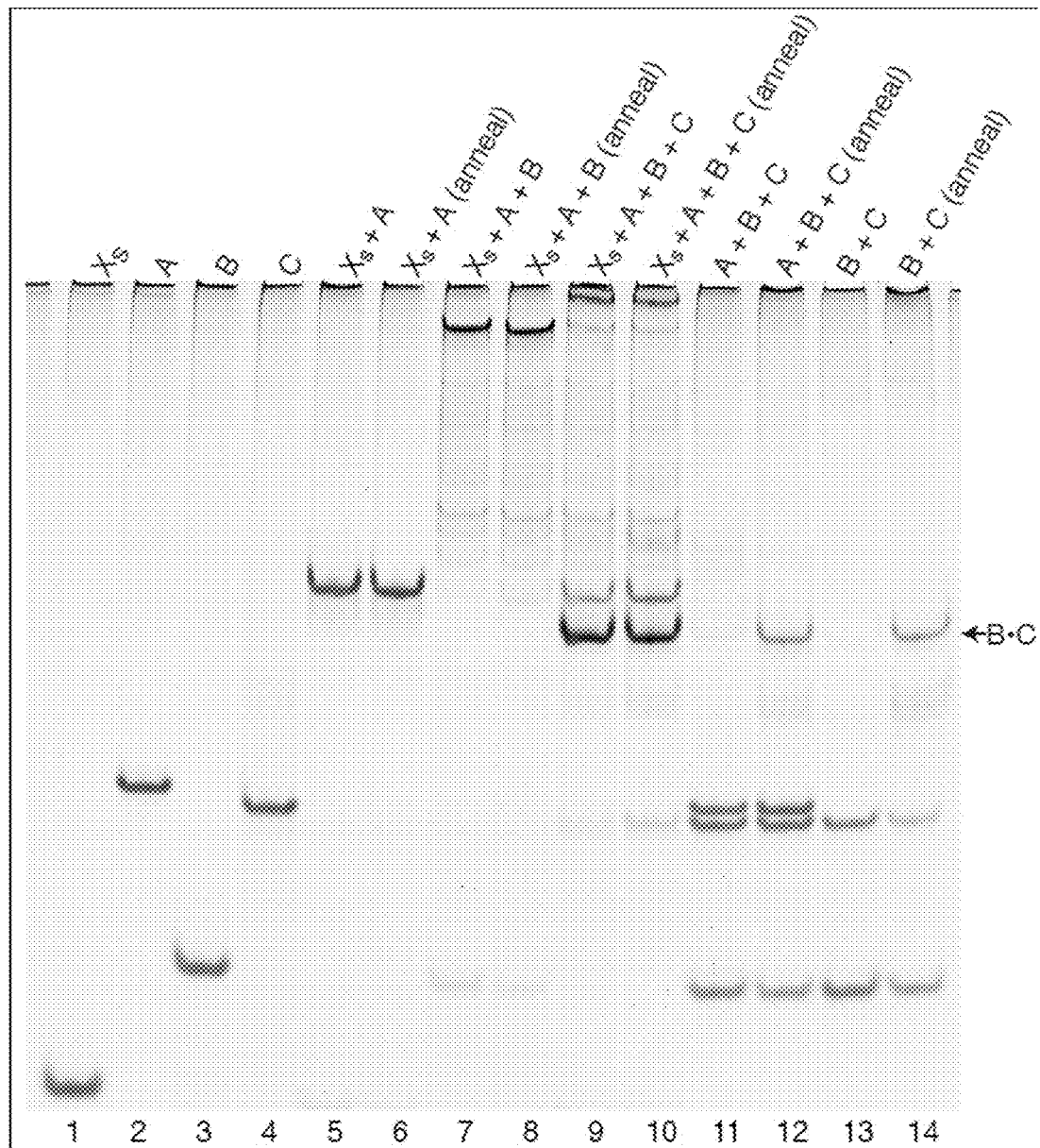

With reference to FIG. 5, the results of the assembly and the disassembly operations in FIG. 3a are illustrated, as the mechanism stepping analyses were performed experimentally to verify that the desired assembly and disassembly operations occurred with high yield. Native PAGE was then performed as described in the methods above. As shown in the following lanes are: Short RNA detection target: Xs (lane 1), scRNA reactants: A, B and C (lanes 2-4), Step 1: Xs and A interact to form intermediate Xs·A (lane 5), Step 1+Step 2: Xs, A and B interact to form intermediate Xs·A·B (lane 7), Step 1+Step 2+Step 3 (ON state): Xs, A, B and C interact to form intermediate Xs·A, intermediate Xs·A·B·C, and Dicer substrate B·C (lane 9), OFF state: A, B and C co-exist metastably, yielding minimal production of B·C (lane 11), annealing A, B and C leads to increased production of B·C (lane 12), hairpins B and C co-exist metastably, yielding minimal production of B·C (lane 13), and annealing B and C leads to increased production of B·C (lane 14).

Figure 6:
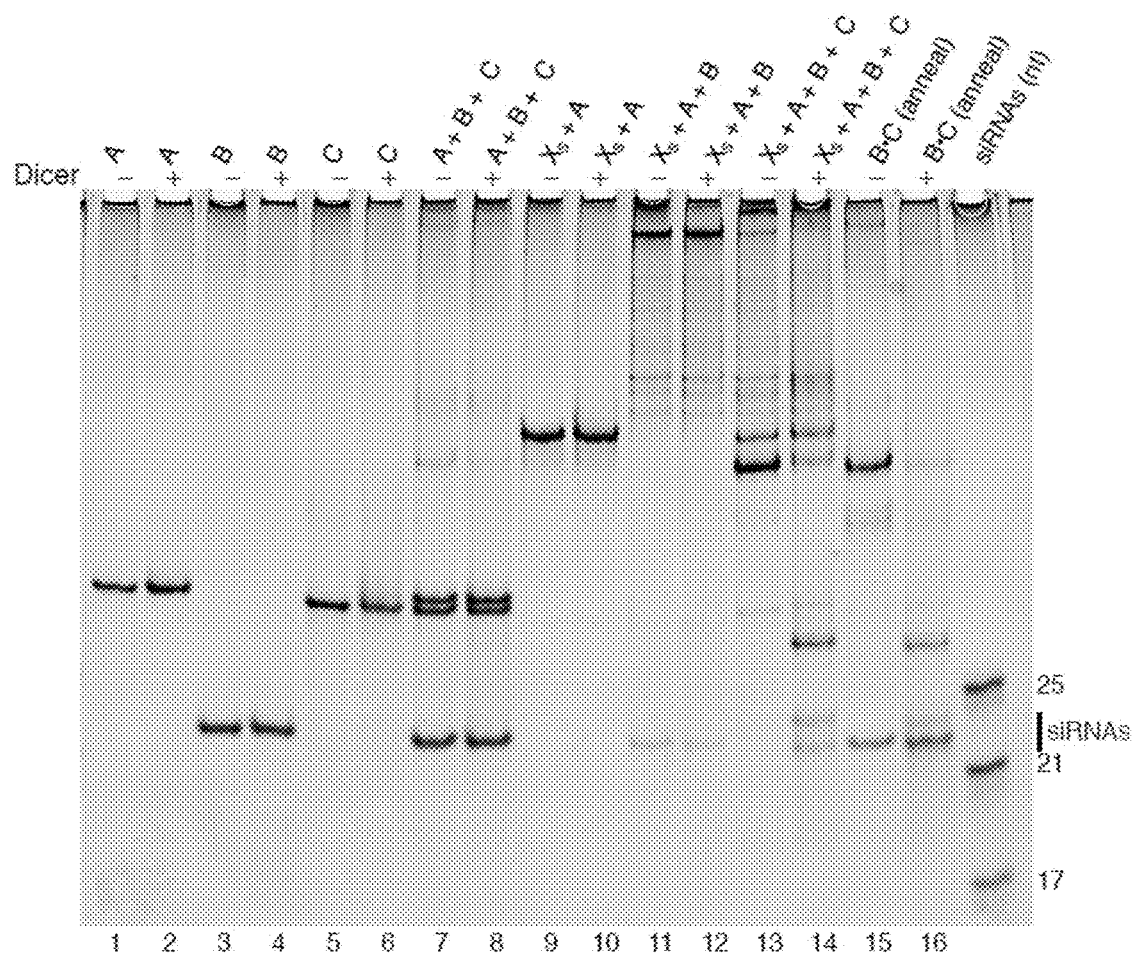
FIG. 6 illustrates a Dicer processing stepping gel for Mechanism 1 in which native PAGE demonstrates each signal transduction step in Dicer reaction conditions in the absence/presence of Dicer (−/+ lanes).

With reference to FIG. 6, the stepping analyses were repeated in the context of Dicer to verify that only the final product of signal transduction, and not the reactants or intermediates, were efficiently processed by Dicer. As shown in FIG. 6, native PAGE demonstrates each signal transduction step in Dicer reaction conditions in the absence/presence of Dicer (−/+ lanes). As shown, only the final product B·C is efficiently processed by Dicer to produce siRNAs (compare lanes 13 and 14).

Figure 7A:
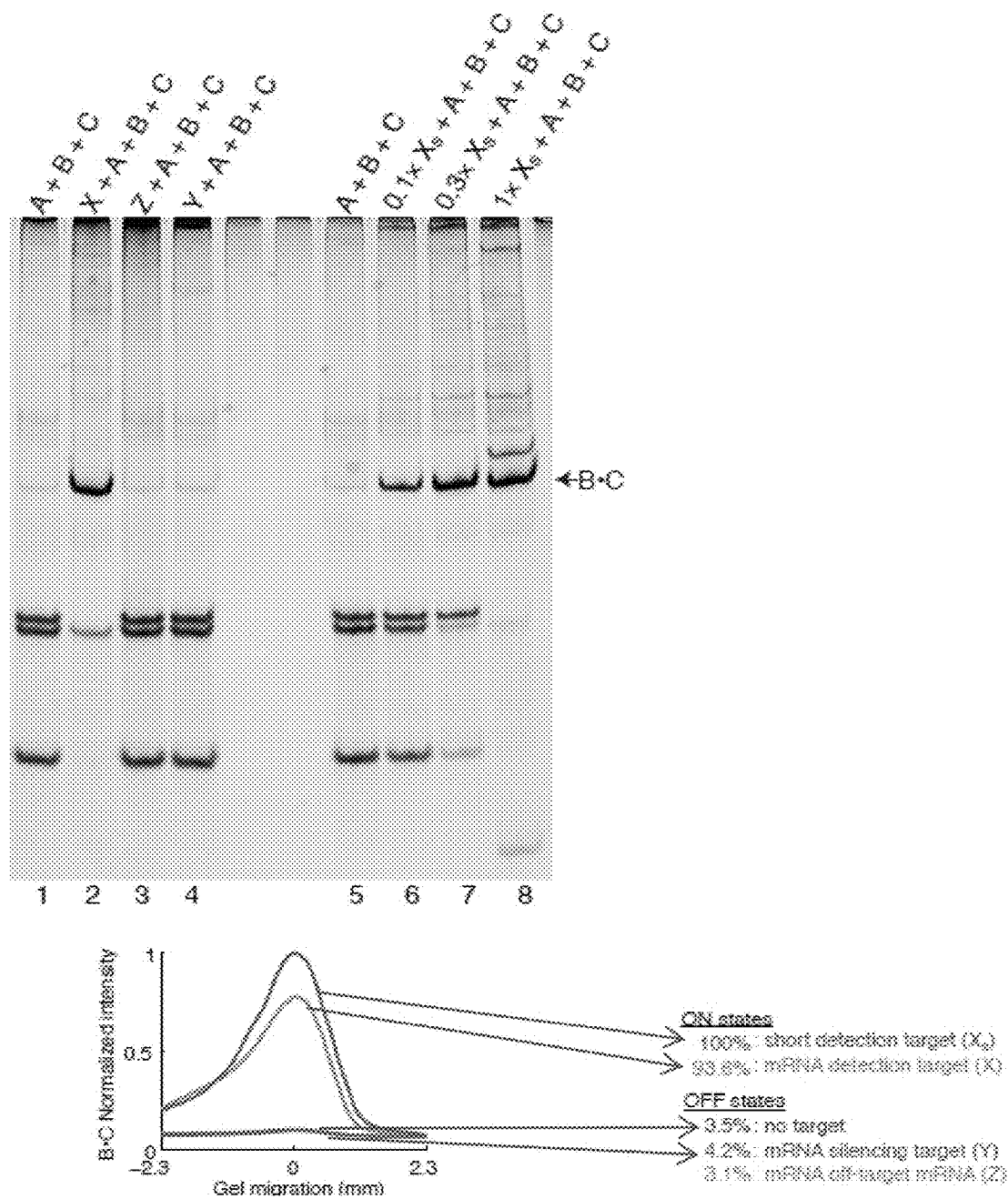
FIG. 7a-c is a series of gels and graphs that illustrate the quantification of conditional Dicer substrate formation for Mechanism 1. As illustrated, three independent experiments were used to characterize the variability in the OFF/ON conditional response in production of Dicer substrate.
Figure 7B:
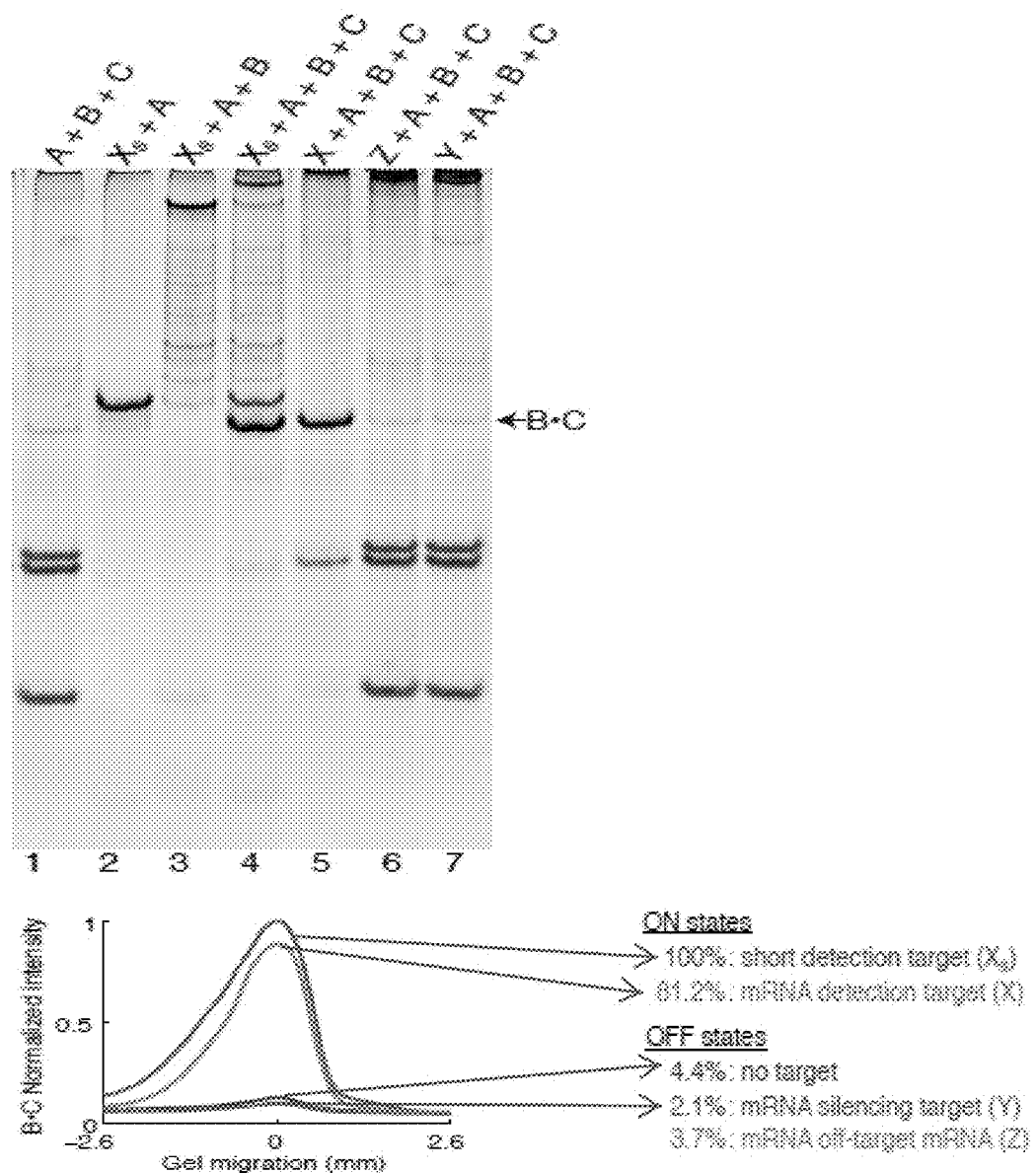
Figure 7C:
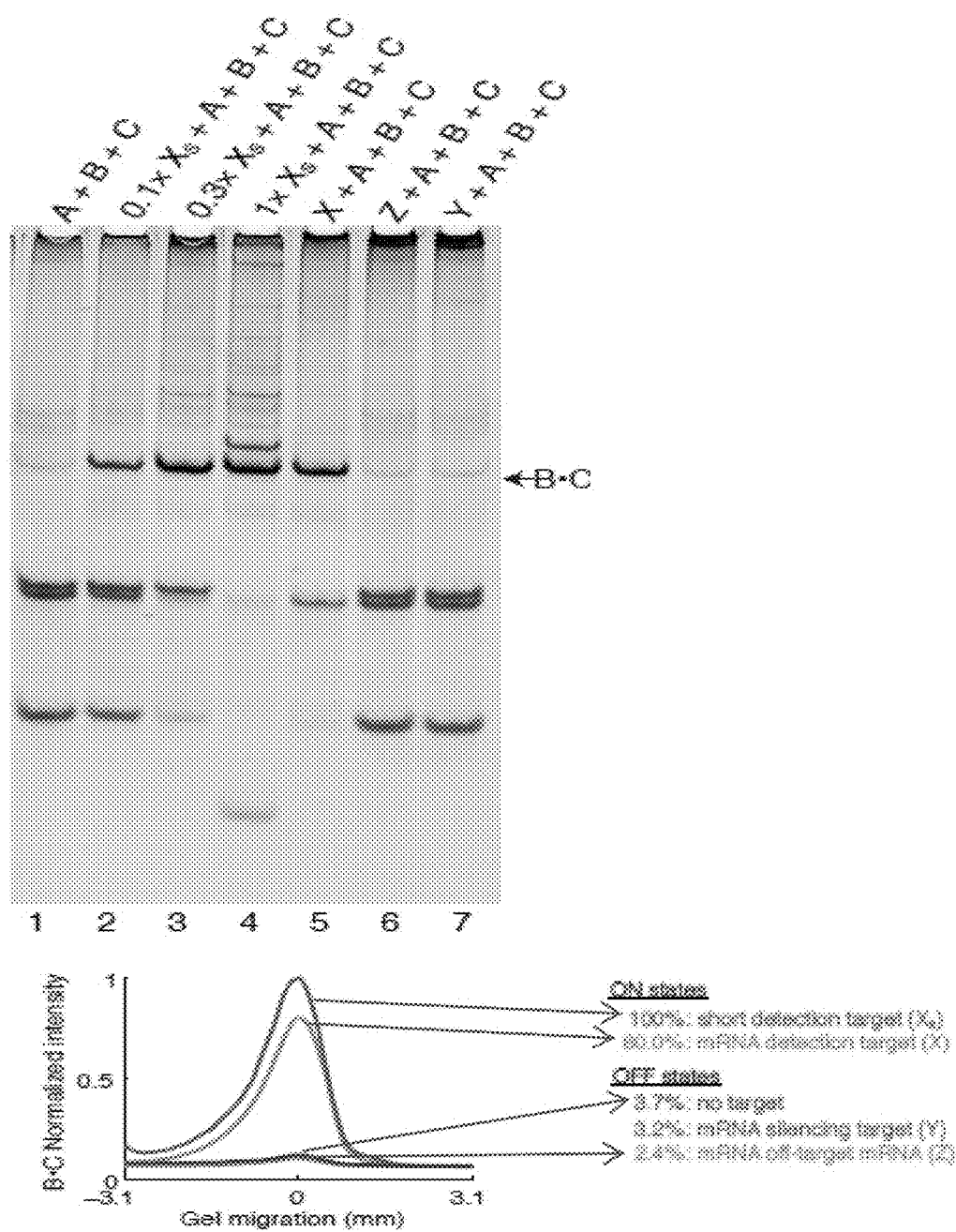

As shown in FIG. 7, is the quantification of conditional Dicer substrate formation for Mechanism 1. Three independent experiments were used to characterize the variability in the OFF/ON conditional response in production of Dicer substrate. OFF states: no target, mRNA silencing target Y, mRNA off-target Z. ON states: short RNA detection target Xs, mRNA detection target X. All values are normalized relative to the amount of Dicer substrate produced using Xs.

Figure 8A:
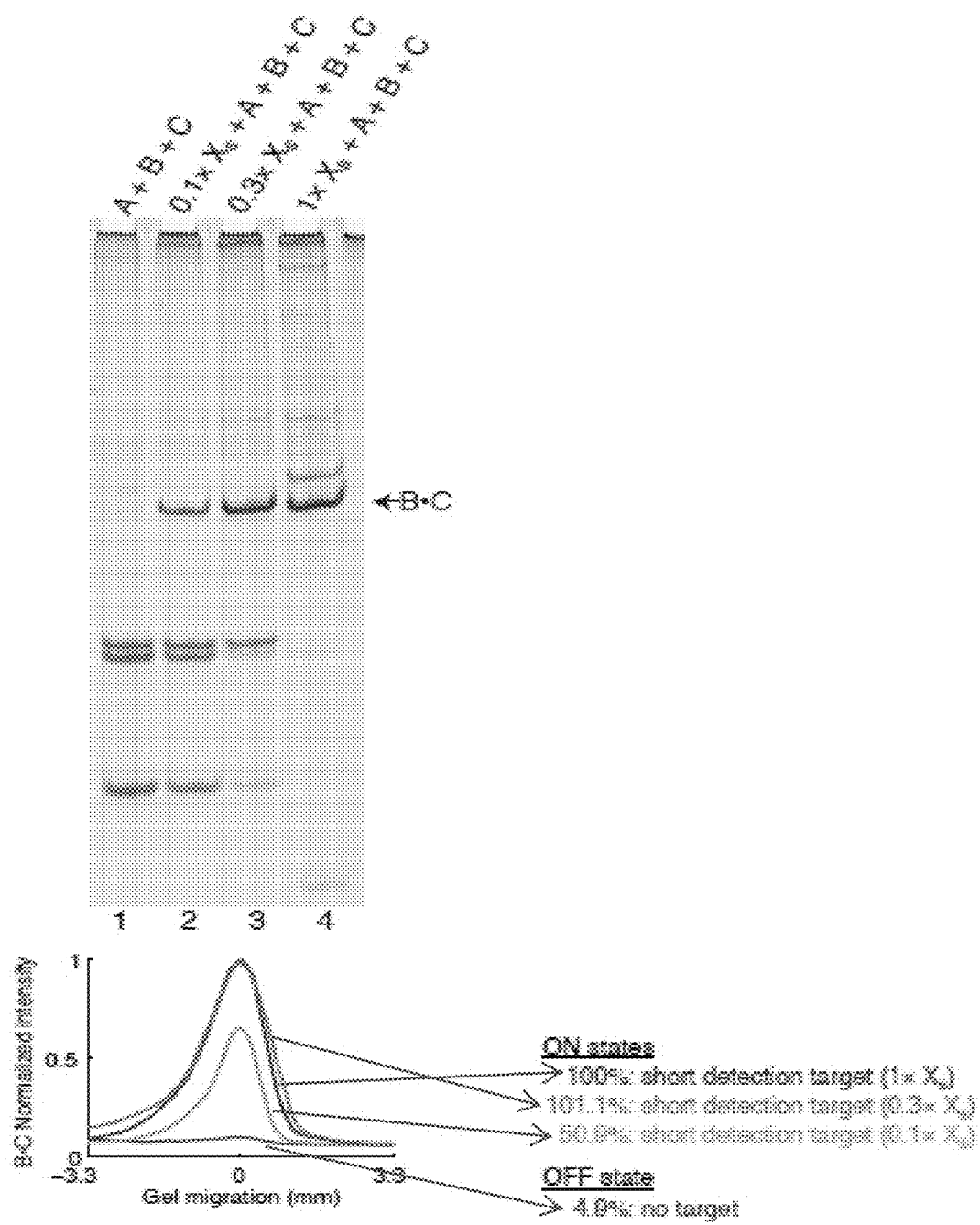
FIGS. 8a-c are a series of gels and graphs that illustrate quantification of catalytic Dicer substrate formation for Mechanism 1. As illustrated, three independent experiments were used to characterize the variability in the catalytic production of Dicer substrate.
Figure 8B:
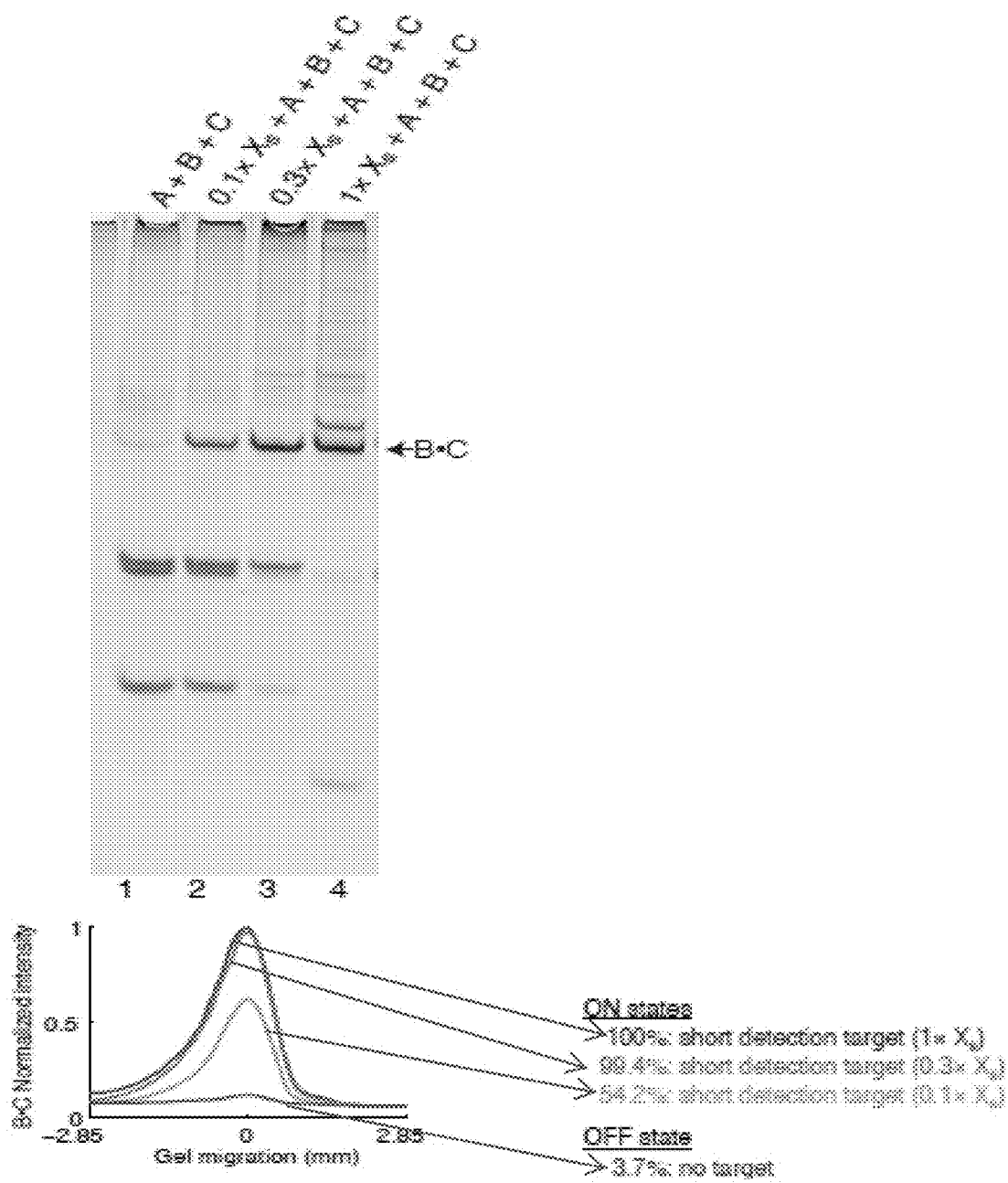
Figure 8C:
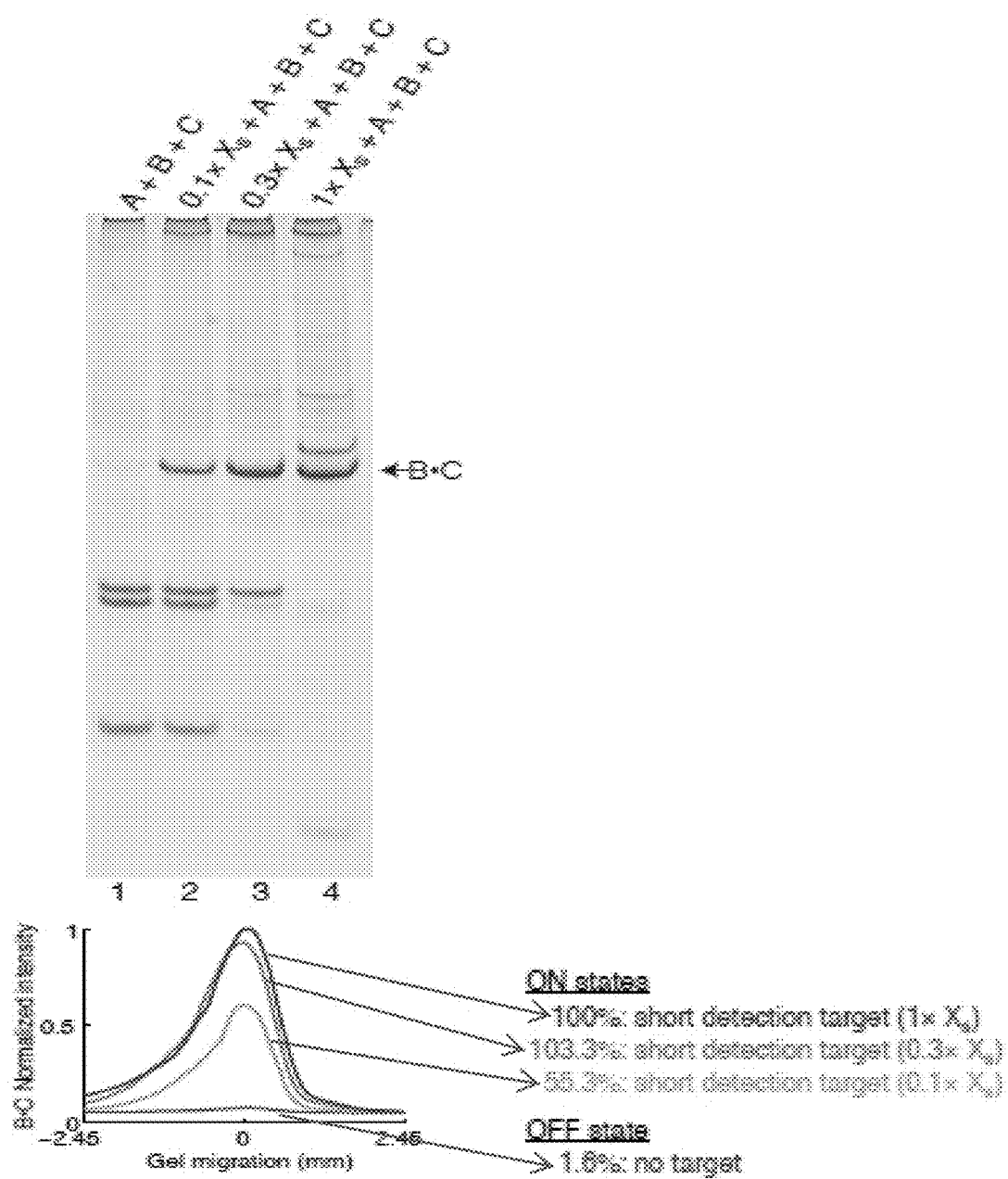

FIG. 8 shows the quantification of catalytic Dicer substrate formation for Mechanism 1. Three independent experiments were used to characterize the variability in the catalytic production of Dicer substrate. OFF state: no target. ON states: short RNA detection target Xs at three concentrations (0.1×, 0.3×, 1×) relative to the scRNA reactants. All values are normalized relative to the amount of Dicer substrate produced using 1× Xs.

Example 2

Mechanism 2, Conditional DsiRNA Formation Using Stable scRNAs

Figure 9B:
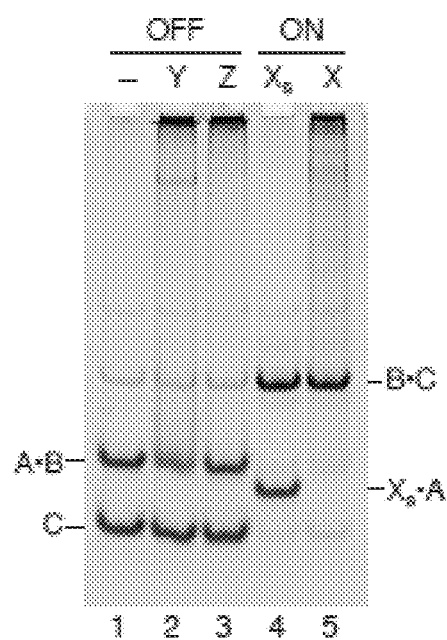
Figure 9C:
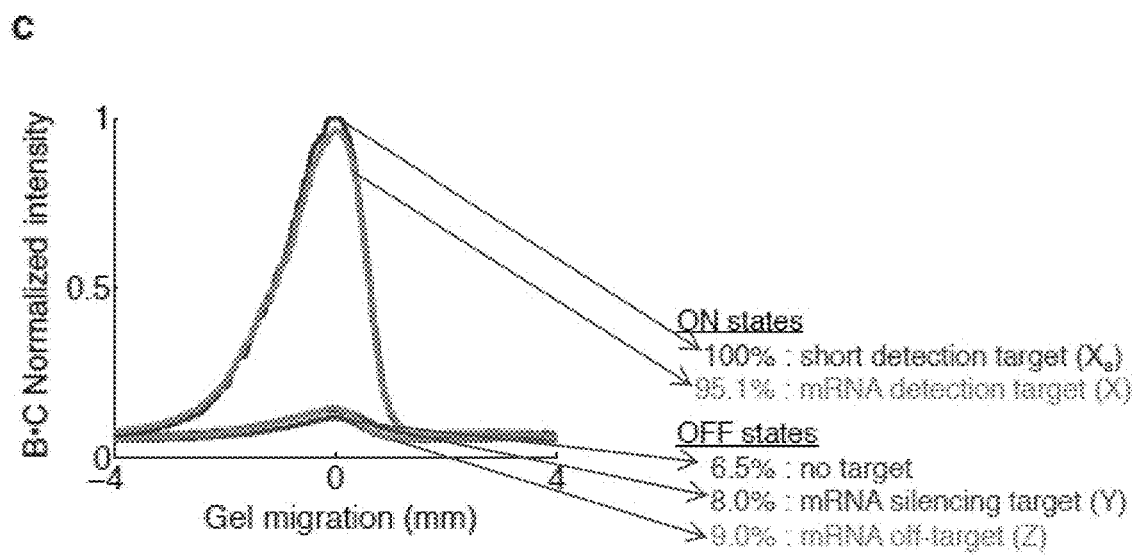
Figure 9D:
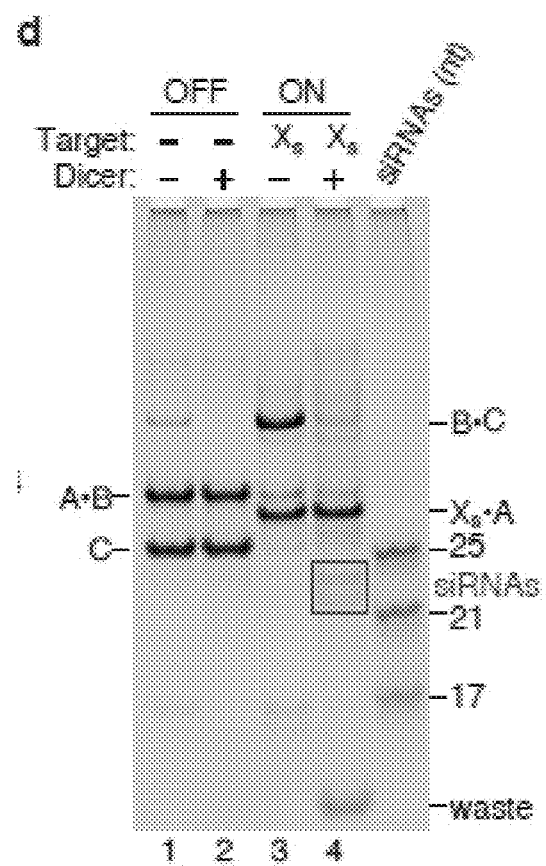
Figure 12:
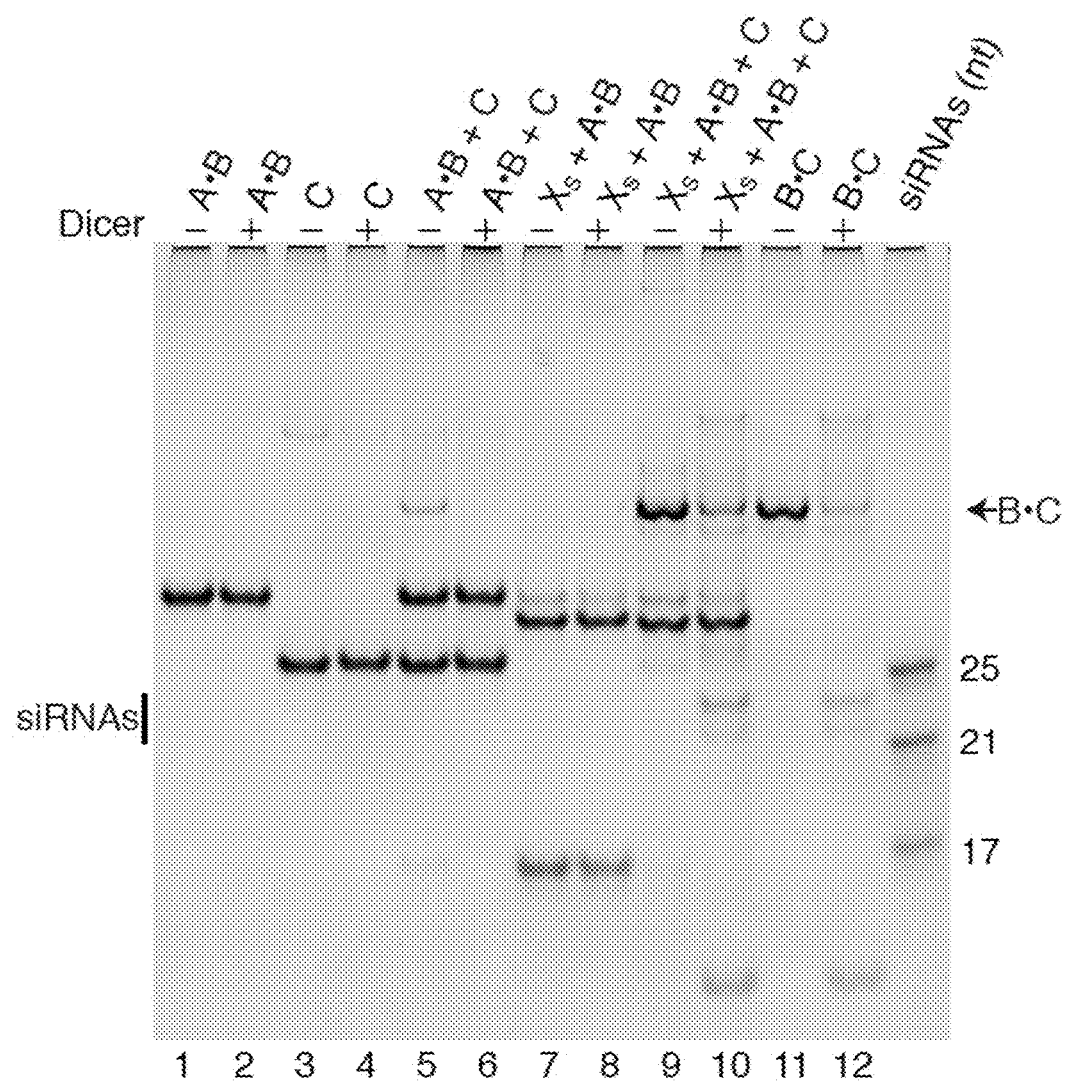
FIG. 12 illustrates a Dicer processing stepping gel for Mechanism 2. As shown, native PAGE demonstrates each signal transduction step in Dicer reaction conditions in the absence/presence of Dicer (−/+ lanes).
Figure 13A:
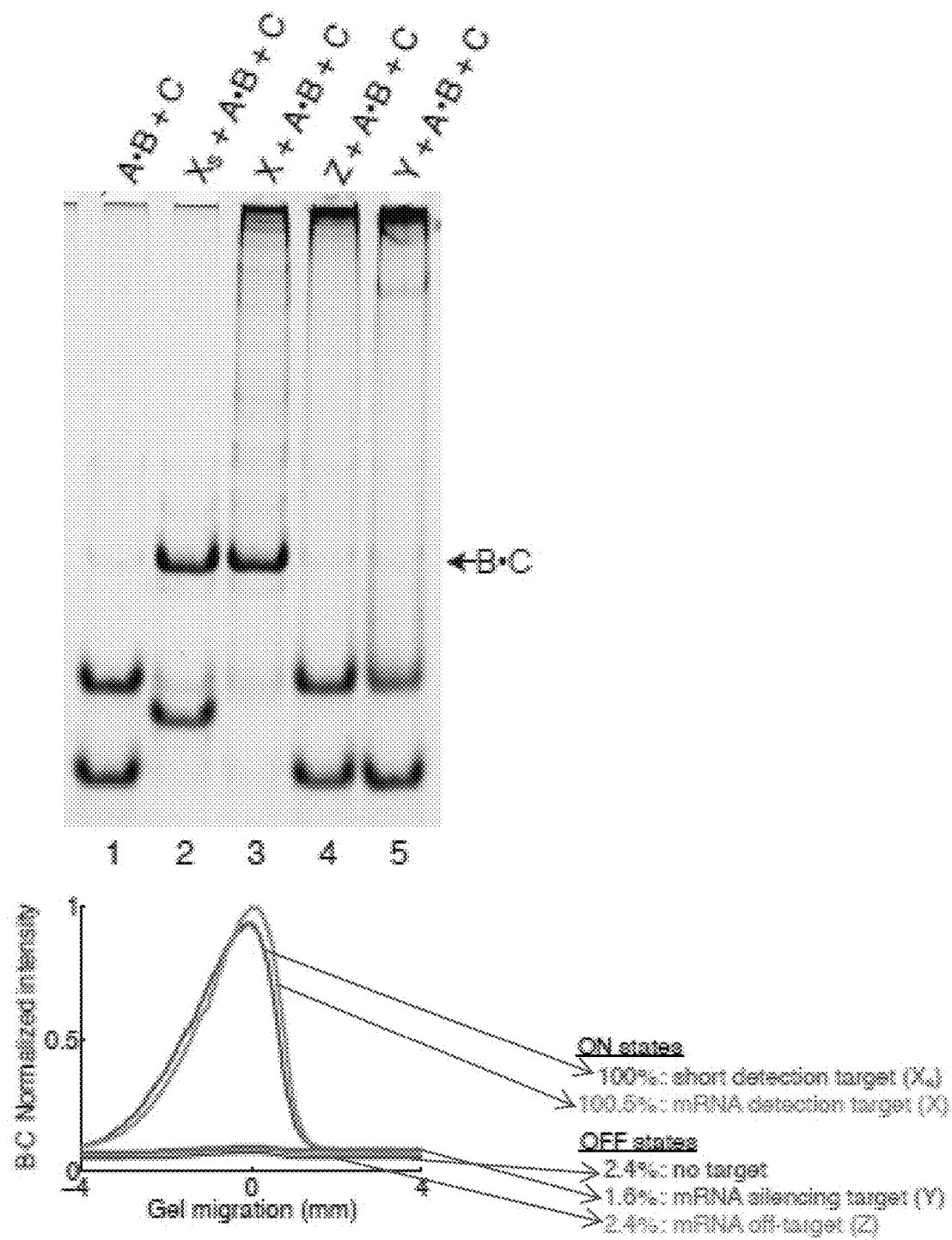
FIGS. 13a-c are a series of gels and graphs that illustrate the quantification of conditional Dicer substrate formation for Mechanism 2. As shown, three independent experiments were used to characterize the variability in the OFF/ON conditional response in production of Dicer substrate.
Figure 13B:
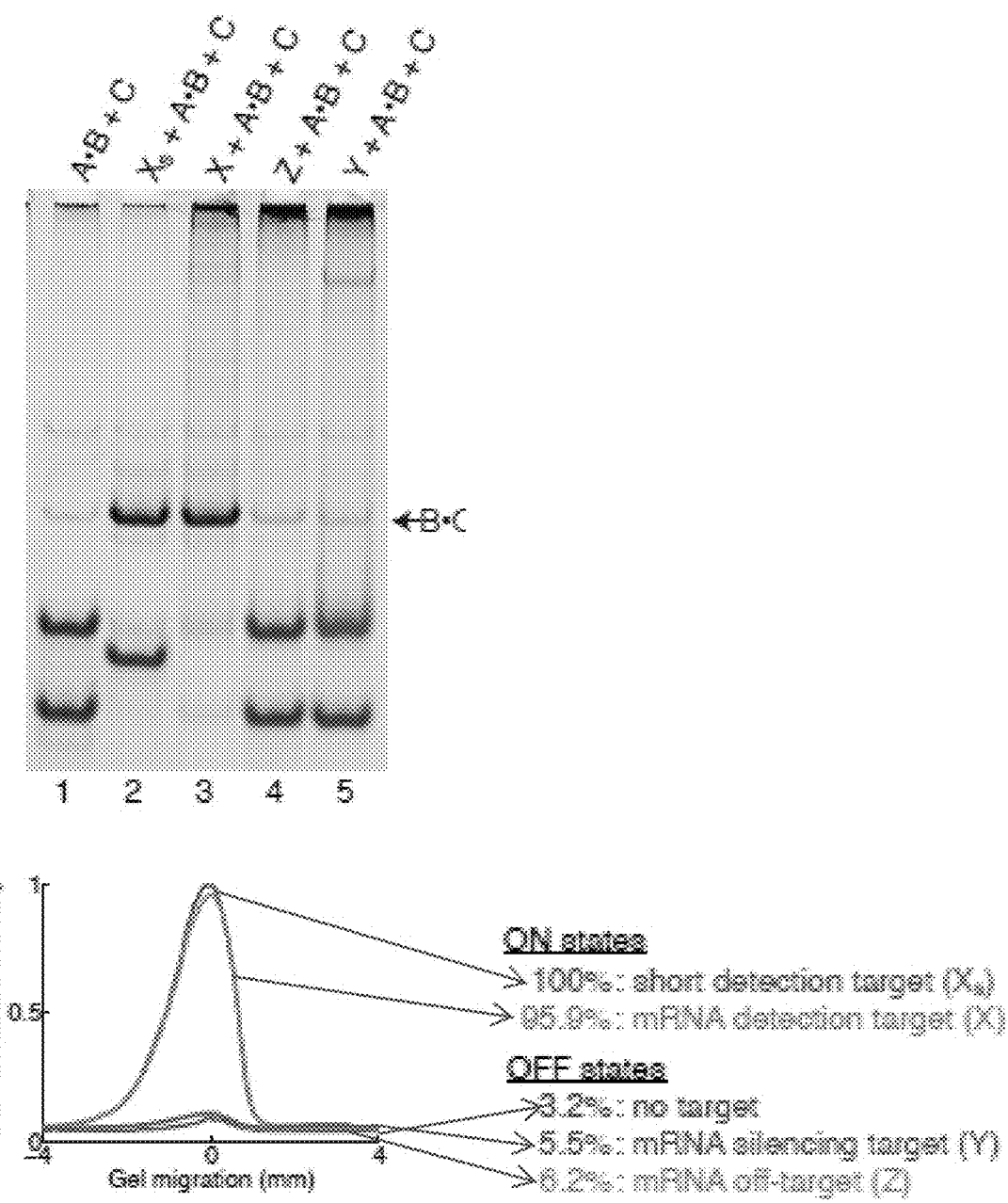
Figure 13C:
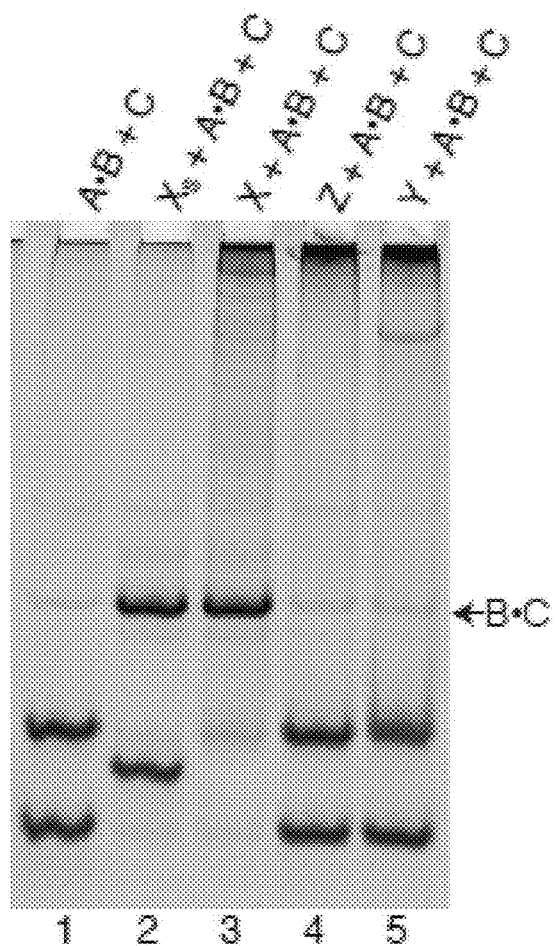
Figure 13C:
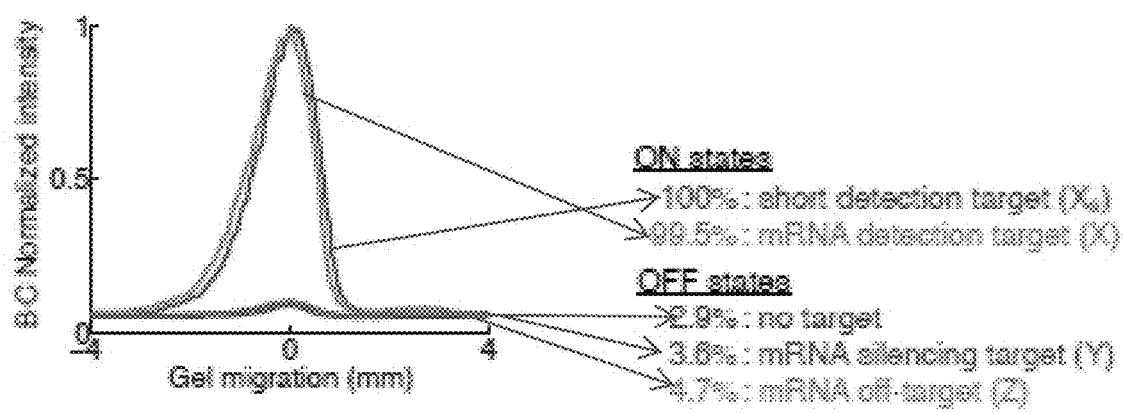

It was speculated whether the signal transduction mechanism could be simplified by exploiting alternative design principles. In particular, it seems intuitively desirable to reduce the number of scRNA reactants, the number of assembly steps in the transduction cascade, and the complexity of the reaction intermediates. These goals are achieved by replacing the A and B hairpins of Mechanism 1 with the A·B duplex of Mechanism 2 (FIG. 9a). The detection target X mediates displacement of B (CACUAC-CAGCAGAACACCCGACAUCACCU; SEQ ID NO: 10) from A (GUUGUGGGAGGUGAUGUCGGGUGUU; SEQ ID NO: 9), which opens C (ACCACUACCAGCA-GAACAAGGUAGAUGUCGGGUGUUCUGCUG-GUAGUGGU; SEQ ID NO: 11) to produce duplex B·C with a 2-nt 3'-overhang. The number of reactants and the number of assembly steps are both reduced from three to two and the largest intermediate is reduced from a tetramer (resulting from three sequential assembly steps) to a trimer (resulting from one assembly step). This simplified signal transduction mechanism dispenses with catalytic turnover, producing one DsiRNA per detected molecule of X. In functional terms, A·B detects X, leading to production of DsiRNA B. C targeting Y. The mechanism exhibits strong OFF/ON conditional Dicer substrate formation, achieving an order of magnitude increase in DsiRNA production in the presence of either the short detection target Xs (CUGGACAUCAC-CUCCCACAACGAGGACUA; SEQ ID NO: 8) or the full-length mRNA detection target X (FIGS. 9b and 9c). Chemical modifications of A and portions of C are employed to prevent Dicer processing of the reactants and intermediates. Only the DsiRNA B·C is efficiently processed by Dicer (FIG. 9d; see also FIG. 12).

Compared to Mechanism 1, shape and sequence transduction are achieved based on dramatically altered design principles (Table 1). Mechanism 1 repeatedly exploits toehold/toehold hybridization for nucleation and 3-way branch migration for strand displacement, while Mechanism 2 simplifies the transduction pathway by also exploiting spontaneous dissociation to achieve strand displacement (of B from X·A and loop/toehold hybridization to nucleate interactions (between B and C). Strikingly, the scRNAs for Mechanism 2 are stable rather than metastable (i.e., if the scRNAs are allowed to equilibrate in the absence of X, they will predominantly remain in the reactant state rather than converting to the product state). This is a major conceptual advantage because it places a thermodynamic rather than a kinetic limit on the amount of spurious DsiRNA that can form in the absence of X. With Mechanism 2, strong production of DsiRNA is only thermodynamically favorable if X is present, whereas with the metastable reactants of Mechanism 1, X catalyzes a reaction that is kinetically impeded but thermodynamically favorable in the absence of X. In our studies, the metastable scRNAs of Mechanism 1 and the stable scRNAs of Mechanism 2 happen to produce comparable amounts of background DsiRNA in the absence of X (both yielding an OFF state that is approximately 5% of the ON state achieved using Xs). Nonetheless, stable reactants offer a conceptually appealing framework for engineering robust OFF/ON signal transduction in vivo; if the thermodynamic driving force for spontaneous DsiRNA formation can be further reduced, stable reactants promise a clean and reliable OFF state.

Figure 10A:
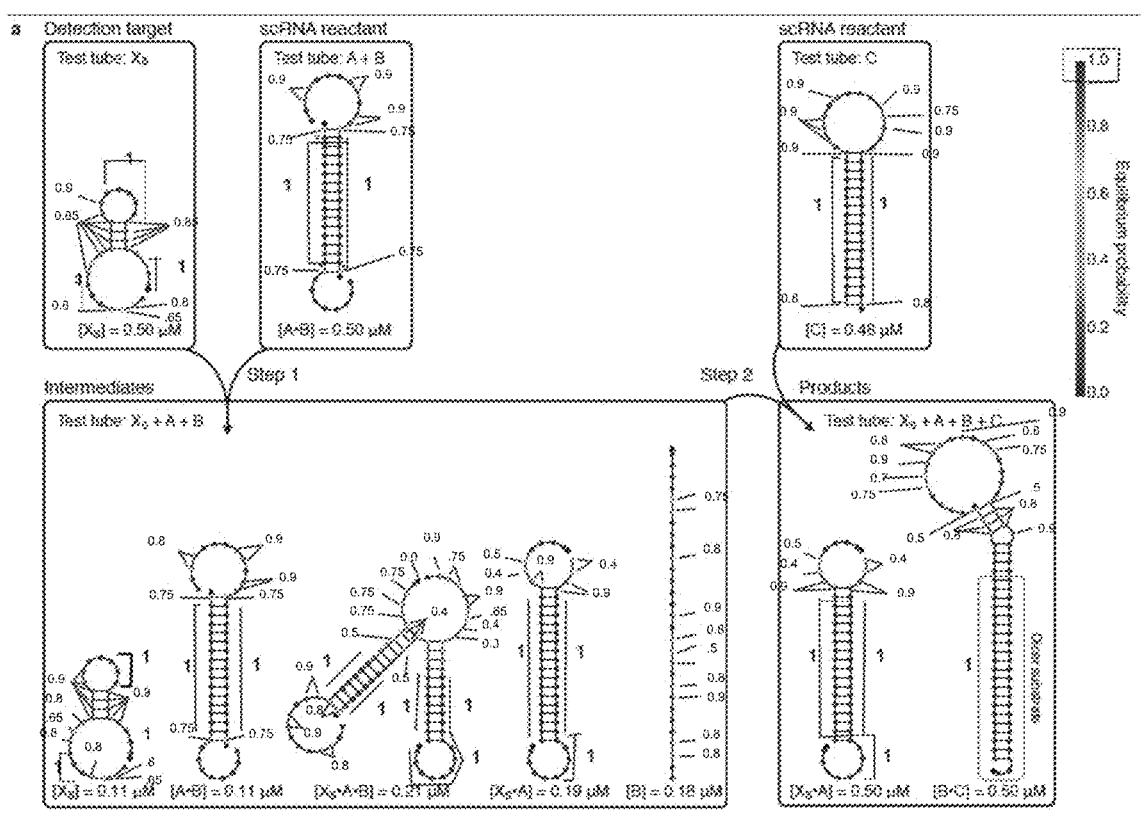
FIGS. 10a-b illustrate a computational stepping analysis for Mechanism 2. a) Equilibrium test tube calculations showing the predicted concentrations and base-pairing properties of reactants, intermediates, and products. b) Equilibrium test tube calculation predicting that scRNAs A·B and C are stable, rather than metastable.
Figure 10B:
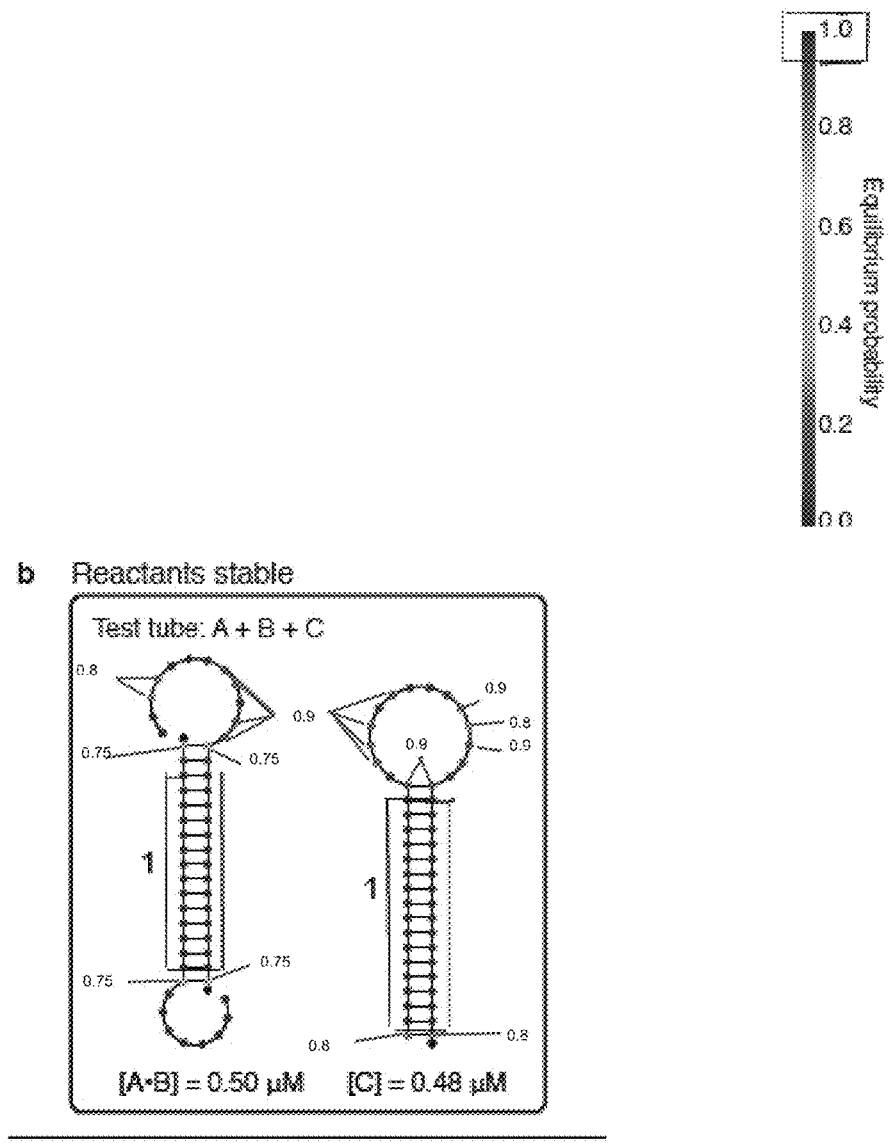

Oligonucleotide synthesis and preparation were performed as described above for Mechanism 2. Sequences used for Mechanism 2 are indicated below in Table 4.

near-quantitative yield. Step 1 yielded several complexes with appreciable yield at equilibrium. The desired intermediates are Xs·A and B. As expected, these exist in equilibrium with the intermediate Xs·A·B since this mechanism relies on spontaneous dissociation of B from Xs·A. Finally, some of the target Xs and scRNA A·B are unreacted, in part due to the internal secondary structure in Xs. After Step 2, the products form with quantitative yield, with C driving the reaction to completion. In panel (b), equilibrium test tube calculation predicting that scRNAs A·B and C are stable, not metastable. Placing A, B, and C together in a test tube led predominantly to duplex dimer A·B and hairpin monomer C at equilibrium, demonstrating that reactants A·B and C are stable. As shown, each box in FIG. 10 represents a test tube containing the strands listed at the top at 0.5 µM each. For each test tube, thermodynamic analysis at 37° C. yields the equilibrium concentrations and base-pairing ensemble properties for all complexes containing up to four strands. Each complex predicted to form with appreciable concentration at equilibrium is depicted by its minimum free energy structure, with each nucleotide shaded (and some labeled) by the approximate probability that it adopts the depicted base pairing state at equilibrium. The predicted equilibrium concentration is noted next to each complex.

Figure 11:
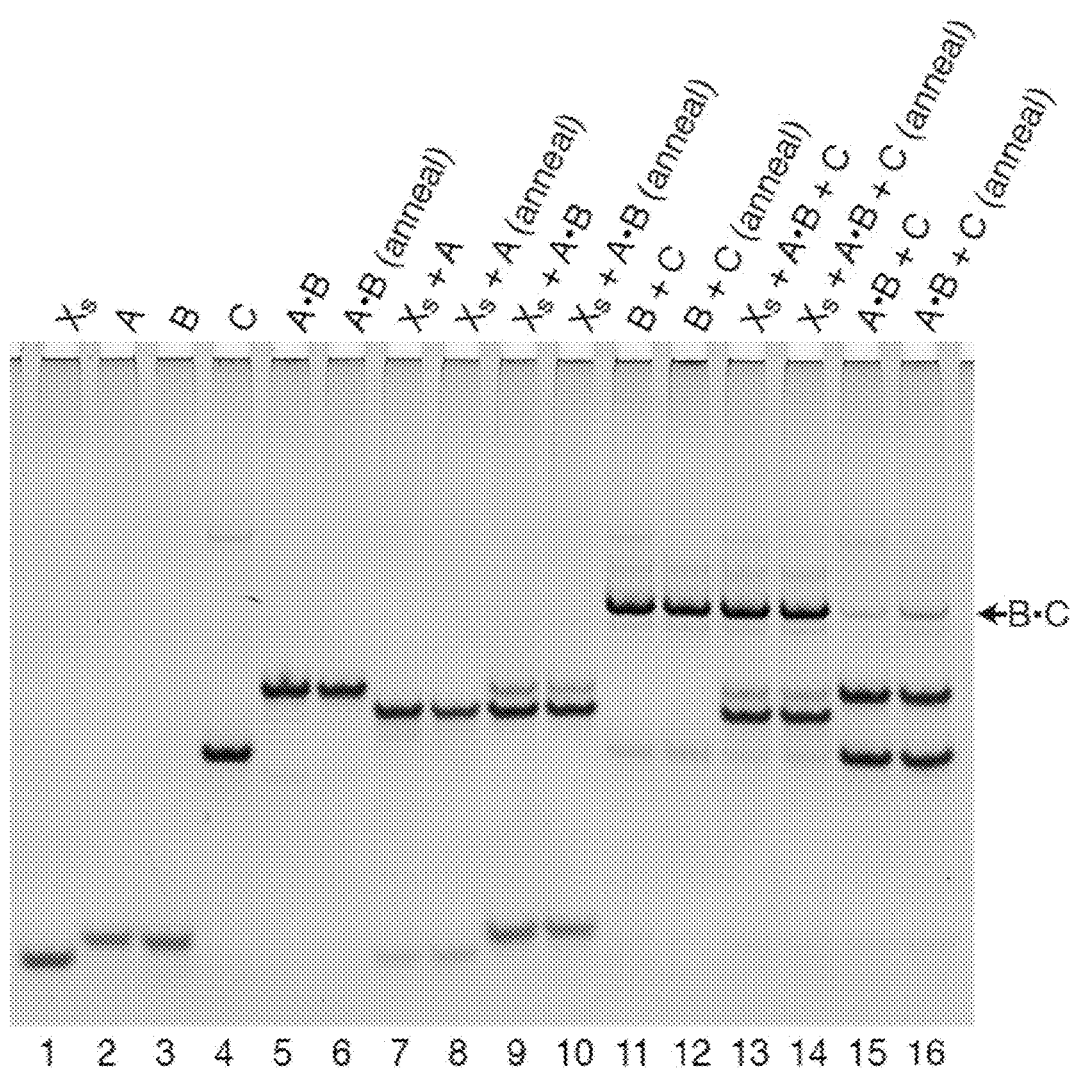

With reference to FIG. 11, native PAGE demonstrating the assembly and disassembly operations in FIG. 9a are shown. In the gel are short RNA detection target: Xs (lane 1), scRNA reactants: C and A·B (lanes 4 and 5), Step 1: Xs and A·B interact to form intermediates Xs·A and B (lane 9), Step 2: B and C interact to form product B·C (lane 11), Step 1+Step 2 (ON state), Xs, A·B, and C interact to form

TABLE 4

| Sequences for Mechanism 2 | | | |
|---|---|---|---|
| Strand | Domains | Sequence (5'-3') | SEQ ID NO |
| Strand X$_s$ | s1-a-b-c-s2 | CUGGACAUCACCUCCCACA ACGAGGACUA | 8 |
| Strand A | c*-b*-a*-z*-y* | GUUGUGGGAGGUGAUGUC (GGGUGUU) | 9 |
| Strand B | x-y-z-a-b | (CACUACCAGCAGAACACCC) GACAUCACCU | 10 |
| Strand C | w-x-y-s-a*-z*-y*-x*-w* | (ACCACUACCAGCAGAACA)A GGUAGAUGUC(GGGUGUUCU GCUGGUAGUGGU) | 11 |

Sequences constrained by DsRed2 (mRNA detection target X) are shown in bold. Sequences constrained by d2EGFP (mRNA silencing target Y) are shown within parentheses. Underlined nucleotides are 2'OMe-RNA; all other nucleotides are RNA. Domain lengths: |a|=6, |b|=4, |c|=8, |s|=5, |s1|=3, |s2|=8, |w|=2, |x|=12, |y|=4, |z|=3. To allow for better gel separation of the various reactants, intermediates, and products using native PAGE, the length of Xs was increased (by adding 3 nt to the 3' end and 8 nt to the 5' end) and 5 nt were inserted in the loop of C.

With reference to FIG. 10, a computational stepping analysis for Mechanism 2 was performed using the methods previously described herein. In panel (a) equilibrium test tube calculations were performed showing the predicted concentrations and base-pairing properties of reactants, intermediates, and products. The short RNA detection target Xs is predicted to have some internal base pairing on average at equilibrium. Reactants are predicted to form with products Xs·A and B·C (lane 13), OFF state: A·B and C co-exist stably, yielding minimal production of A and B·C (lane 15), and annealing A·B and C yields slightly higher production of A and B·C (lane 16).

With reference to FIG. 12, Dicer processing stepping gel for Mechanism 2 are shown. As illustrated, native PAGE demonstrates each signal transduction step in Dicer reaction conditions in the absence or presence of Dicer (−/+ lanes). Only the final product B·C is efficiently processed by Dicer to produce siRNAs (compare lanes 9 and 10). As such the product indicates the functions of Dicer to produce siRNA from the provided scRNA.

With reference to FIG. 13, three independent experiments were used to characterize the variability in the OFF/ON conditional response in production of Dicer substrate. OFF states: no target, mRNA silencing target Y, mRNA off-target Z. ON states: short RNA detection target Xs, mRNA detection target X. All values are normalized relative to the amount of Dicer substrate produced using Xs.

Example 3

Mechanism 3, Conditional shRNA Formation Using a Single Stable scRNA

Figure 14B:
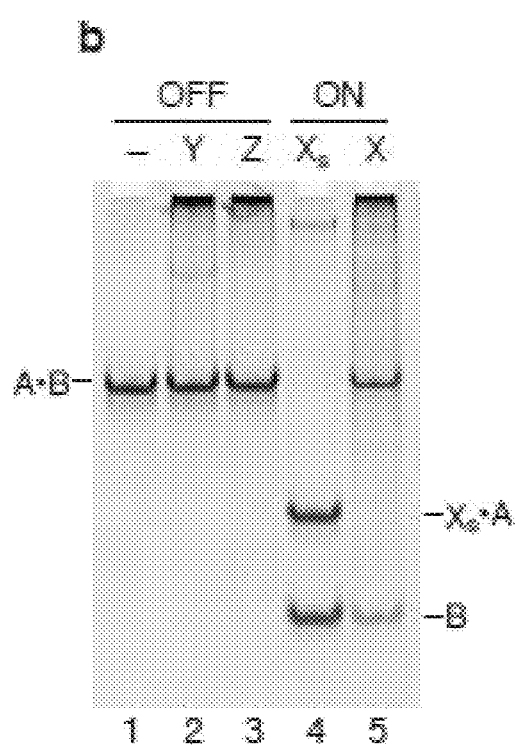
Figure 14C:
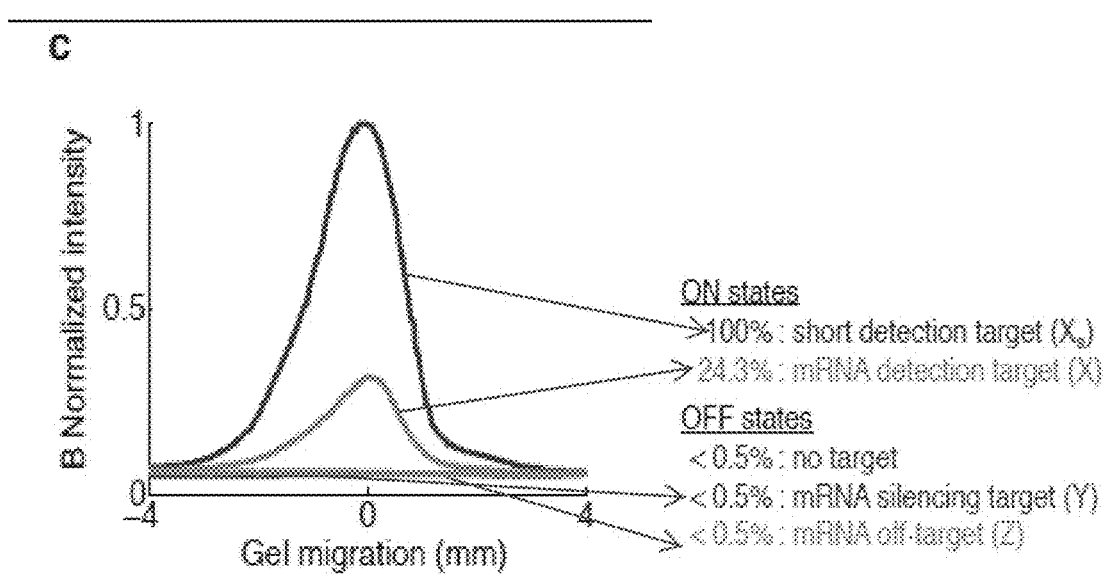

Motivated by the simplifications of Mechanism 2, it was speculated whether the shape and sequence transduction could be simplified. Mechanism 3 requires only a single duplex scRNA A·B, and in a single step produces a Dicer substrate that is an shRNA monomer instead of a DsiRNA duplex (FIG. 14a). The detection target X mediates displacement of strand A from strand B to yield a hairpin B with a 2-nt 3'-overhang. The number of reactants and the number of assembly steps are both reduced from two to one. This is the simplest known mechanism for conditional Dicer substrate formation. In functional terms, the duplex A·B detects X, leading to production of a duplex strand shRNA B targeting Y. The mechanism exhibits strong OFF/ON conditional Dicer substrate formation, achieving two orders of magnitude increase in shRNA production in the presence of the short detection target Xs and one order of magnitude increase for the full-length mRNA target X (FIGS. 14b and 4c). It is unclear why the performance is diminished for the full-length target; however, it is expected that this behavior is specific to this test case and not general to the mechanism. The most striking feature of these data is that the OFF state is undetectable (i.e., smaller than our estimated gel quantification uncertainty).

FIG. 14 a shows the conditional DsiRNA formation using stable scRNAs. As shown in panel a) scRNA A·B detects mRNA detection target X (containing subsequence a-b-c), leading to production of shRNA Dicer substrate B targeting mRNA silencing target Y (containing independent subsequence y-z). scRNA A·B is stable in the absence of X. X partially displaces A from B via toehold-mediated 3-way branch migration, exposing a previously sequestered internal toehold, 'c', within B, mediating a further 3-way branch migration that disassembles B from X·A to yield shRNA Dicer substrate B. Domain lengths: |a|=12, |b|=14, |c|=3, |y|=2, |z|=19. Chemical modifications (2'OMe-RNA): A (dashed backbone). Panel b shows the conditional Dicer substrate formation. OFF state: minimal production of Dicer substrate B in the absence of detection target X, the presence of mRNA silencing target Y, or the presence of mRNA off-target Z. ON state: strong production of B in the presence of short RNA detection target Xs (a-b-c) (UGGGAGCGCGUGAUGAACUUCGAGGACGG; SEQ ID NO: 12) or full-length mRNA detection target X. Panel c indicates the quantification of the Dicer substrate band (B) in panel (b). In panel d, conditional Dicer processing is illustrated. As shown is the OFF state: minimal Dicer processing of the reactants (lane 2), ON state: efficient Dicer processing of shRNA Dicer substrate B (lane 4), yielding canonical 21- and 22-nt siRNAs.

The clean OFF state follows from the fact that the siRNA reactant, A·B, is highly stable, with very little thermodynamic driving force for production of shRNA B in the absence of X. Hence, this mechanism compellingly exhibits the benefit of using stable rather than metastable reactants.

Figure 14D:
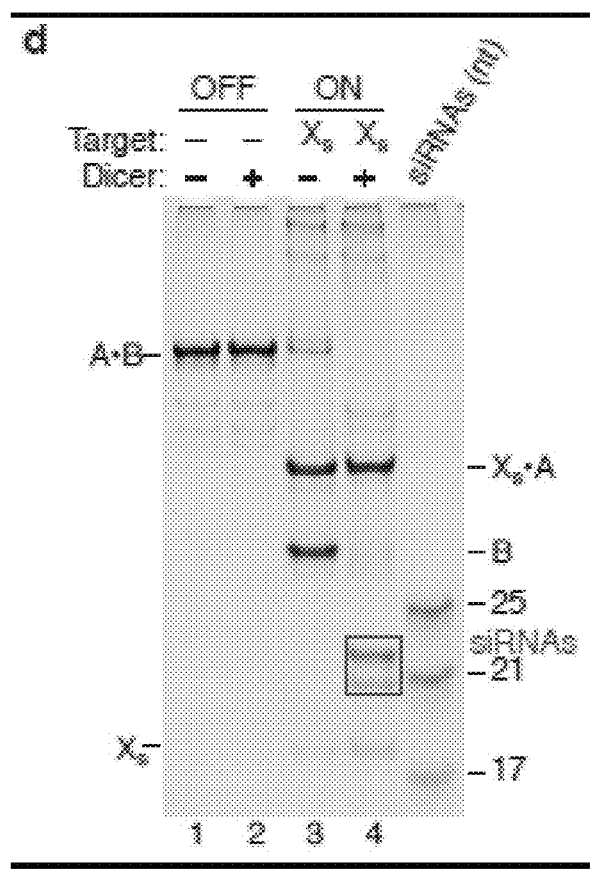
Figure 17:
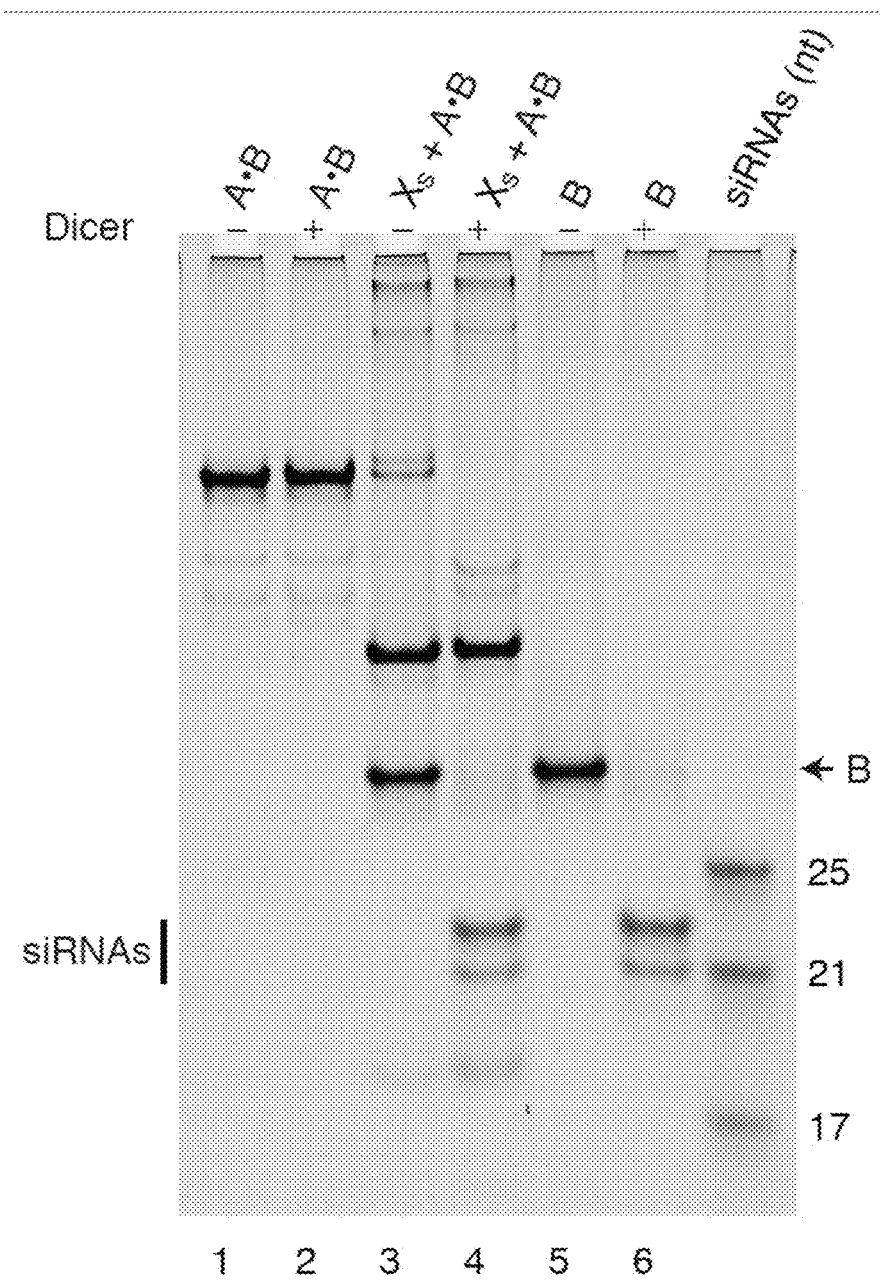
FIG. 17 illustrates a Dicer processing stepping gel for Mechanism 3. As shown, native PAGE demonstrates each signal transduction step in Dicer reaction conditions in the absence/presence of Dicer (−/+ lanes).

For Mechanism 3, the design elements underlying sequence and shape transduction are simple. mRNA detection strand X partially displaces A (UUCAUCUGCACCAC-CGGCACCGUCCUCGAAGUUCAUCACGCGCUCCCA; SEQ ID NO: 13) from B (UUCAUCUGCACCACCG-GCACCGAUGAACUUCGAGGACGGUGCCGGUG-GUGCAGAUGAACU; SEQ ID NO: 14) via toehold-mediated 3-way branch migration, exposing a previously sequestered internal toehold, which B then uses to nucleate a 3-way branch migration with itself, completing displacement of A. Chemical modifications of A are employed to ensure that only shRNA B is efficiently processed by Dicer (FIG. 14d; see also FIG. 17)

The internal toehold is a novel feature of this mechanism. The B strand has the ability to conditionally self-nucleate due to this internal toehold. In the presence of the target X, the internal toehold is exposed, allowing the B strand to change conformation to become an scRNA. This is true in either the 2-stranded scRNA variant (FIG. 14a) or the 3-stranded scRNA variant (FIG. 31a). The only difference for the 3-stranded variant is that this self-nucleation step can occur away from the mRNA X.

Additionally, for mechanism 3, there is only one duplex scRNA, so it is not necessary to try to get multiple complexes to colocalize in order for the mechanism to work. With either the 2-stranded scRNA variant (FIG. 14a) or the 3-stranded scRNA variant (FIG. 31a), there is a "single scRNA".

This single scRNA can be engineered to be "stable" not "metastable". For a stable scRNA, there is not a ticking clock where the scRNA is gradually converting into the shRNA product independent of the presence of detection target X. Instead, the scRNA is stable at equilibrium (i.e., the equilibrium partitioning of the scRNA strands is heavily in favor of the scRNA reactant, with only a slight amount of shRNA product forming at equilibrium). It has been appreciated that this is a very desirable feature for the scRNA because it means that the formation of the product is conditional upon the presence of the detection target X even if the scRNA must wait a long time to encounter X.

Oligonucleotide synthesis and preparation were performed as described above for Mechanism 3. Sequences used for Mechanism 3 are indicated below in Table 5.

TABLE 5

Sequences for Mechanism 3

| Strand | Domains | Sequence (5'-3') | SEQ ID NO |
|---|---|---|---|
| Strand $X_s$ | a-b-c | UGGGAGCGCGUGAUGAACUUCGA GGACGG | 12 |
| Strand A | z-c*-b*-a* | (UUCAUCUGCACCACCGGCA)CCGU CCUCGAAGUUCAUCACGCGCUCCCA | 13 |
| Strand B | z-c*-b-c-z*-y* | (UUCAUCUGCACCACCGGCA)CCGA UGAACUUCGAGGACGG(UGCCGGU GGUGCAGAUGAACU) | 14 |

Sequences for Mechanism 3. Sequences constrained by DsRed2 (mRNA detection target X) are shown in bold. Sequences constrained by d2EGFP (mRNA silencing target Y) are shown within parentheses. Underlined nucleotides are 2'OMe-RNA; all other nucleotides are RNA. Domain lengths: |a|=12, |b|=14, |c|3, |y|=2, |z|=19.

Figure 15A:
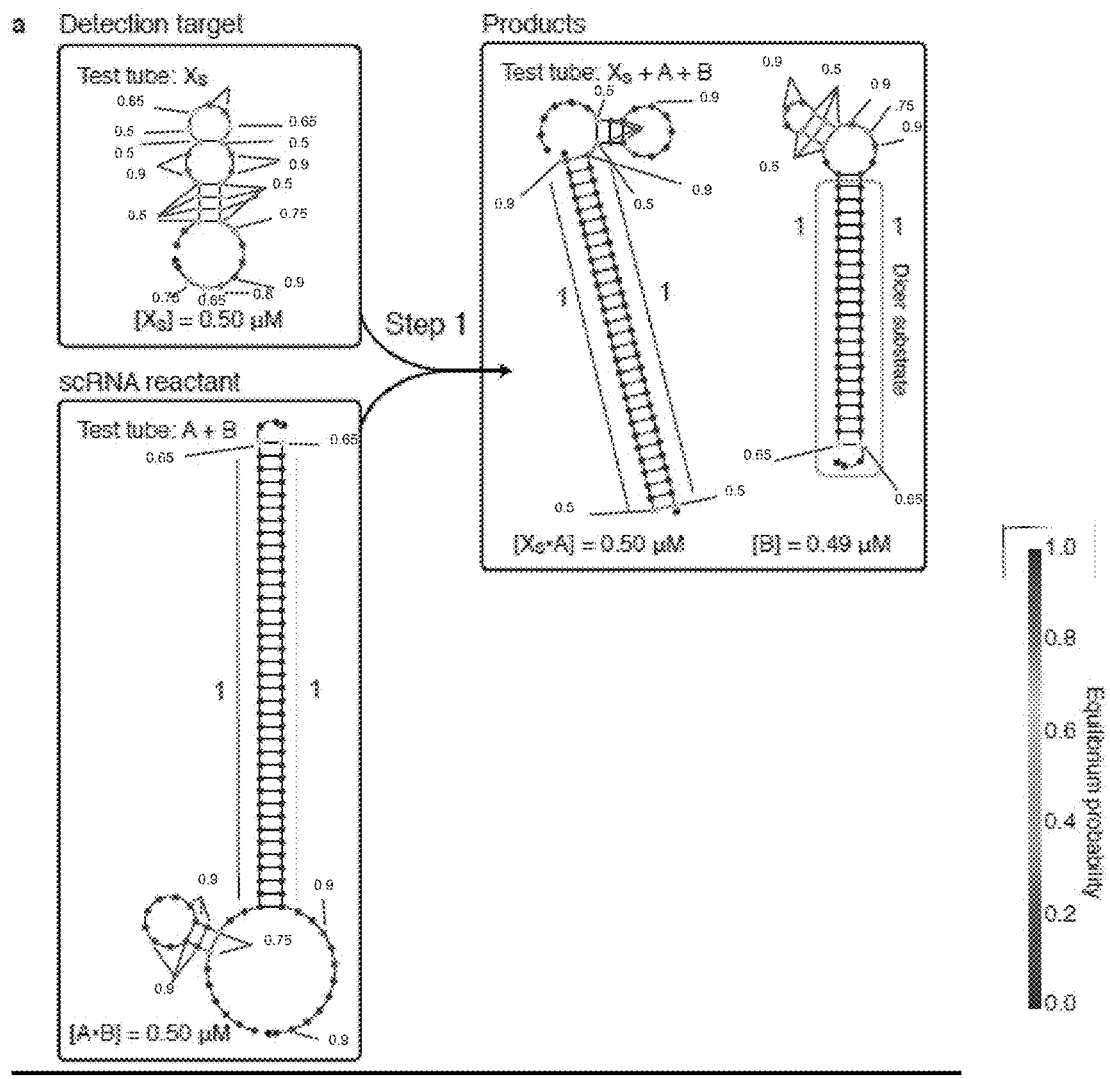
FIGS. 15a-b illustrate a computational stepping analysis for Mechanism 3. a) Equilibrium test tube calculations showing the predicted concentrations and base-pairing properties of reactants and products. b) Equilibrium test tube calculation predicting that scRNA A·B is stable, not metastable. Placing A and B together in a test tube leads predominantly to duplex dimer A·B at equilibrium, demonstrating that reactant A·B is stable.
Figure 15B:
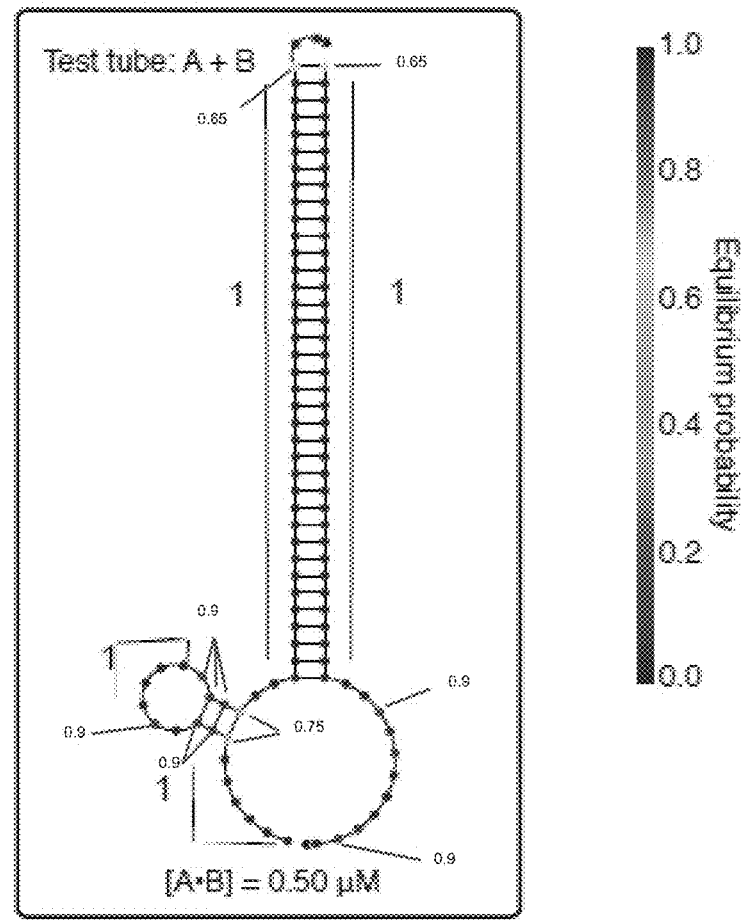

Reference is made to FIG. 15, which illustrates a computational stepping analysis for Mechanism 3. As indicated, equilibrium test tube calculations showing the predicted concentrations and base-pairing properties of reactants and products are shown. The short RNA detection target Xs is predicted to have some internal base pairing on average at equilibrium. The scRNA A·B is predicted to have some internal base pairing in a domain that is intended to be single-stranded. The reactant and products are predicted to form with near-quantitative yield. In panel (b), equilibrium test tube calculation predicting that scRNA A·B is stable, not metastable. Placing A and B together in a test tube leads predominantly to duplex dimer A·B at equilibrium, demonstrating that reactant A·B is stable. In FIG. 15, each box represents a test tube containing the strands listed at the top at 0.5 µM each. For each test tube, thermodynamic analysis at 37° C. yields the equilibrium concentrations and base-pairing ensemble properties for all complexes containing up to three strands. Each complex predicted to form with appreciable concentration at equilibrium is depicted by its minimum free energy structure, with each nucleotide shaded (with some nucloetides labeled with the approximate probability) by the probability that it adopts the depicted base pairing state at equilibrium. The predicted equilibrium concentration is noted next to each complex.

Figure 16:
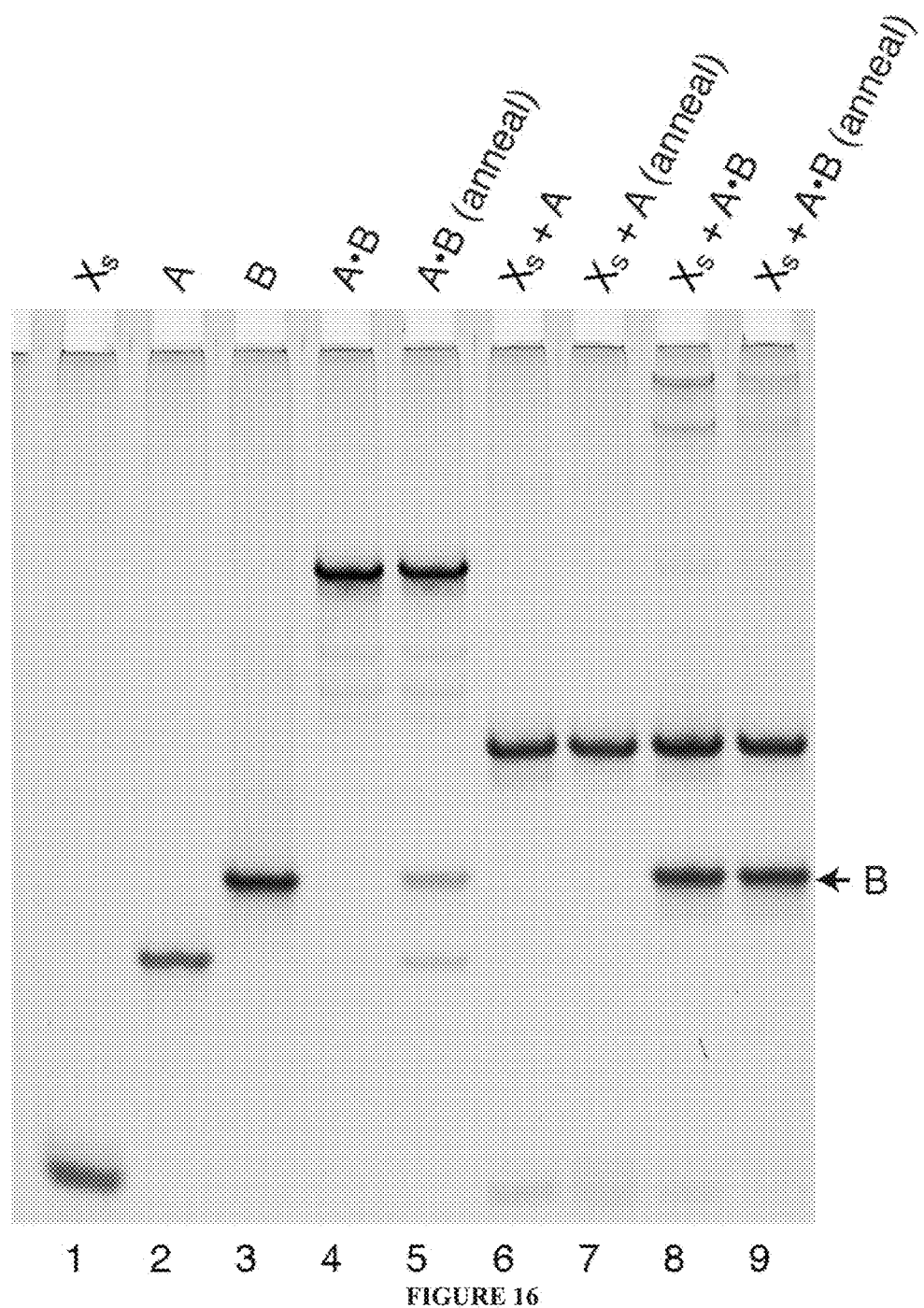

Reference is made to FIG. 16, illustrating a stepping gel for Mechanism 3. Native PAGE is shown demonstrating the assembly and disassembly operations in FIG. 14*a*. Shown on the gel are short RNA detection target: Xs (lane 1), scRNA reactant: A·B (lane 4), ON state: Xs and A·B interact to form products Xs·A and B (lane 8), OFF state: A·B yields minimal production of A and B (lane 4), and annealing A·B yields predominantly A·B, as well as some A and B (lane 5).

Reference is made to FIG. 17, illustrating a Dicer processing stepping gel for Mechanism 3. As shown, native PAGE demonstrates each signal transduction step in Dicer reaction conditions in the absence or presence of Dicer (−/+ lanes). Only the final product B is efficiently processed by Dicer to produce siRNAs (compare lanes 3 and 4), indicating that the provided scRNA can change confirmation to produce an shRNA that acts as a Dicer substrate.

Figure 18A:
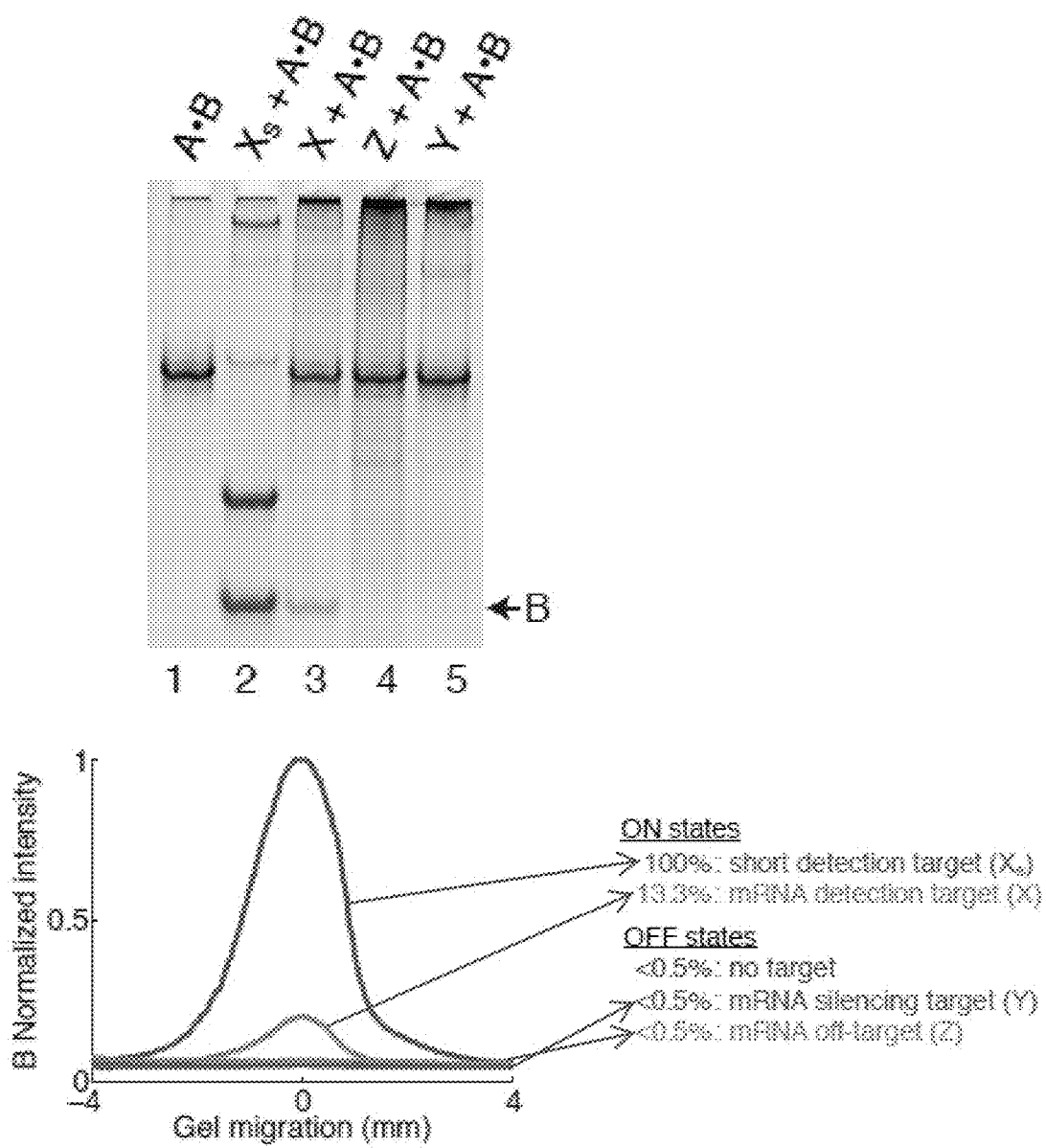
FIGS. 18a-c are a series of gels and graphs that illustrate quantification of conditional Dicer substrate formation for Mechanism 3. As shown, three independent experiments were used to characterize the variability in the OFF/ON conditional response in production of Dicer substrate.
Figure 18B:
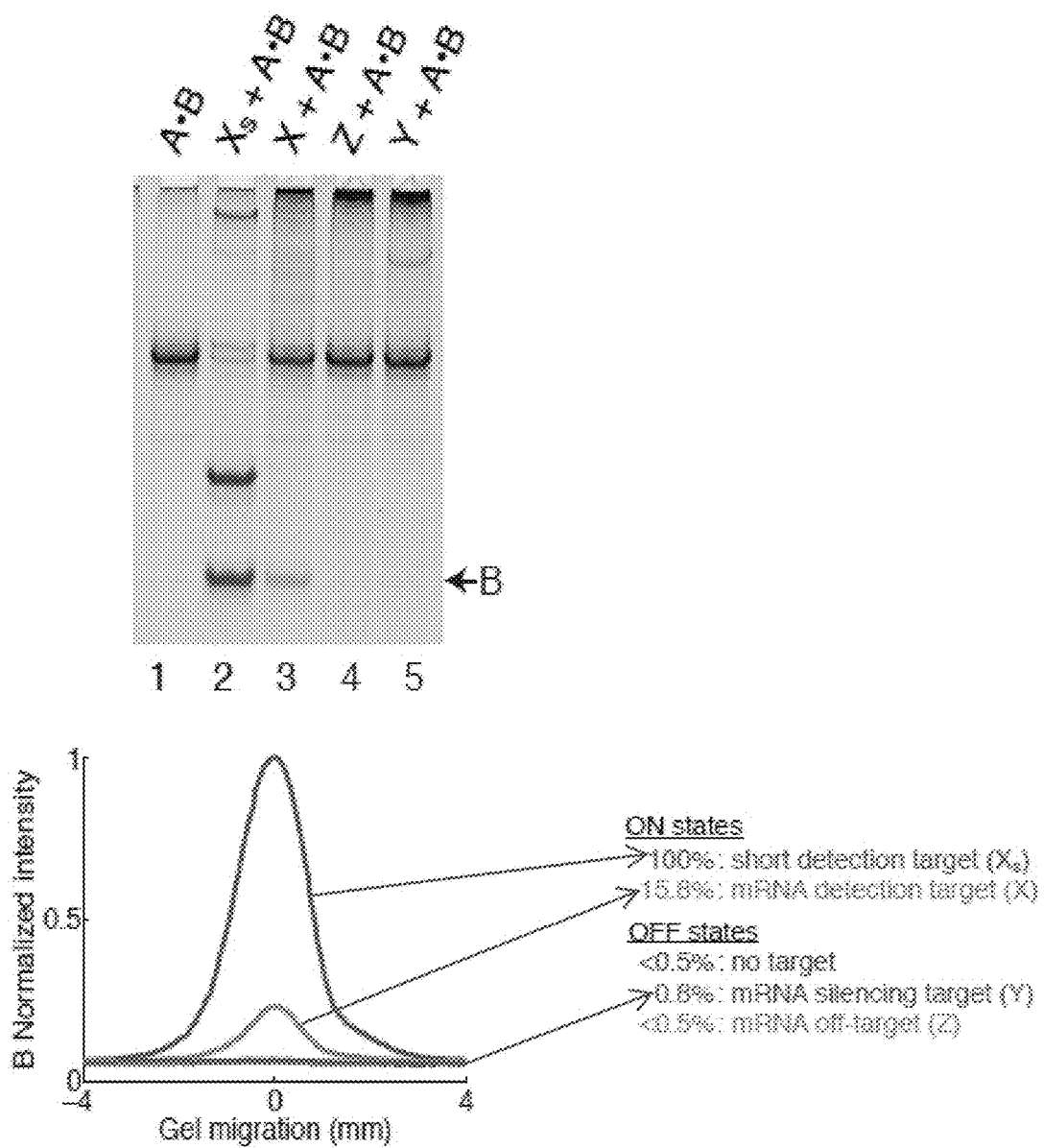
Figure 18C:
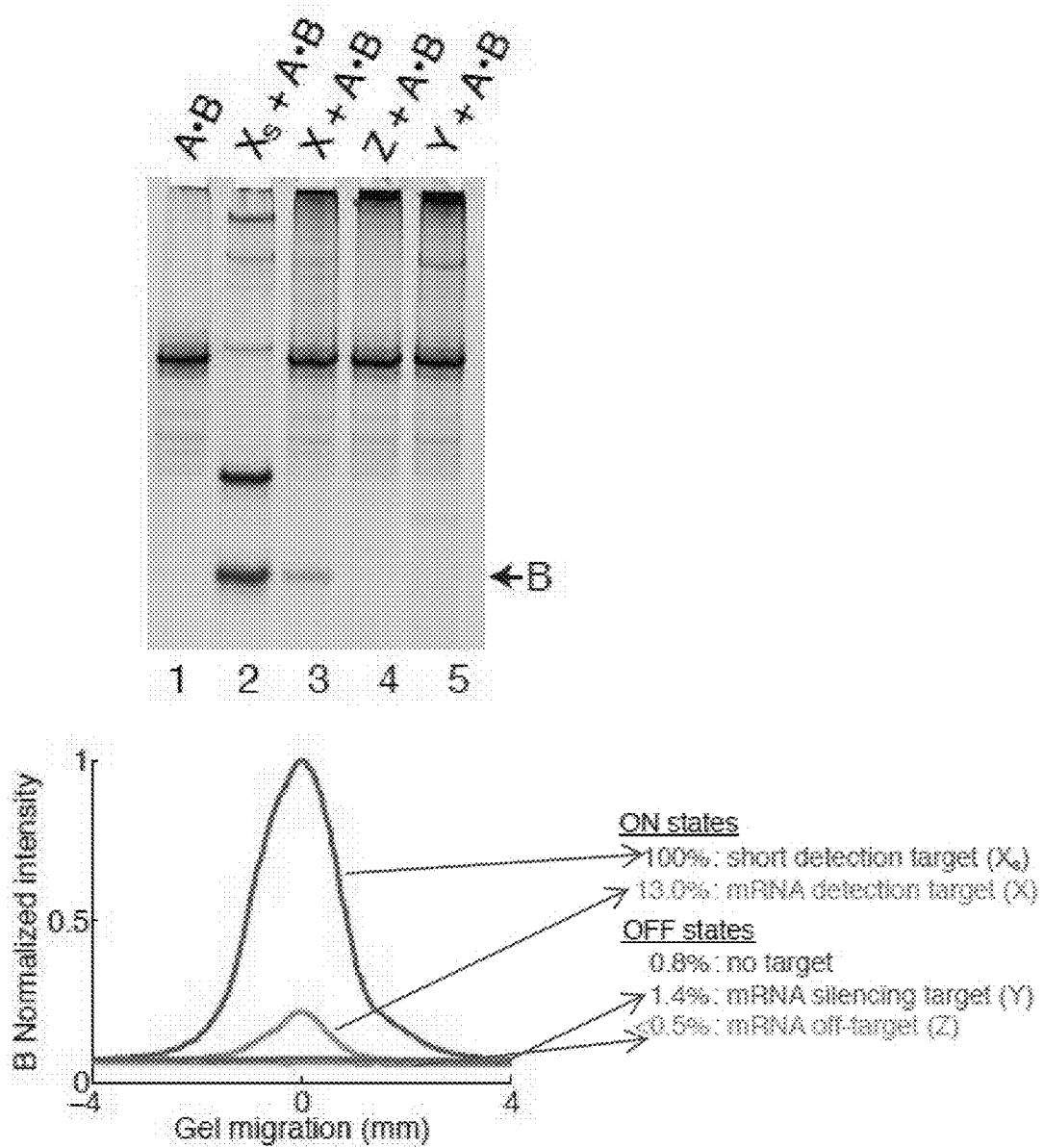

Reference is made to FIG. 18, which illustrates quantification of conditional Dicer substrate formation for Mechanism 3. Three independent experiments were used to characterize the variability in the OFF/ON conditional response in production of Dicer substrate. For the OFF states three conditions were tested: no target, mRNA silencing target Y, mRNA off-target Z. ON states: short RNA detection target Xs, mRNA detection target X. All values were normalized relative to the amount of Dicer substrate produced using Xs. A number of the OFF states had undetectable production of shRNA B, and are denoted as <0.5% corresponding to the estimated uncertainty in gel quantification. Reference is also made to FIG. 31, which indicates functional Mechanism 3 in human cell lysate, as indicated in panel 31(b). As shown, this variant of mechanism 3 introduces a nick between the c* and z domains so that there are three strands in the scRNA. This allows B·C to dissociate from X·A before B uses the newly exposed internal toehold "c" to nucleate with "c*" intramo-lecularly and complete a branch migration leading to formation of shRNA B. This is in interesting variation on Mechanism 3

Example 4

Mechanism 4, Conditional DsiRNA Formation Via Template-mediated 4-Way Branch Migration To date, efforts to engineer conditional hybridization cascades within the field of DNA nanotechnology have focused almost exclusively on strand displacement reactions based on 3-way branch migration, in which an invading strand displaces one strand from a duplex. By comparison, there has been very little study of strand displacement reactions based on 4-way branch migration, in which two duplexes exchange partner strands. In the present setting, a DsiRNA signal transduction product is a duplex, so it was speculated whether a 4-way branch migration might prove especially suitable for conditional Dicer substrate formation. Mechanism 4 employs two duplex scRNAs (A·B and C·D of FIG. 19*a*). The detection target X mediates swapping of partner strands, producing duplex B·C with a 2-nt 3'-overhang. Chemical modifications to A and D prevent Dicer cleavage of the reactants and intermediates, while preserving efficient Dicer processing of transduction product B·C. In functional terms, A·B and C·D detect X, leading to production of DsiRNA B·C targeting Y.

Figure 19B:
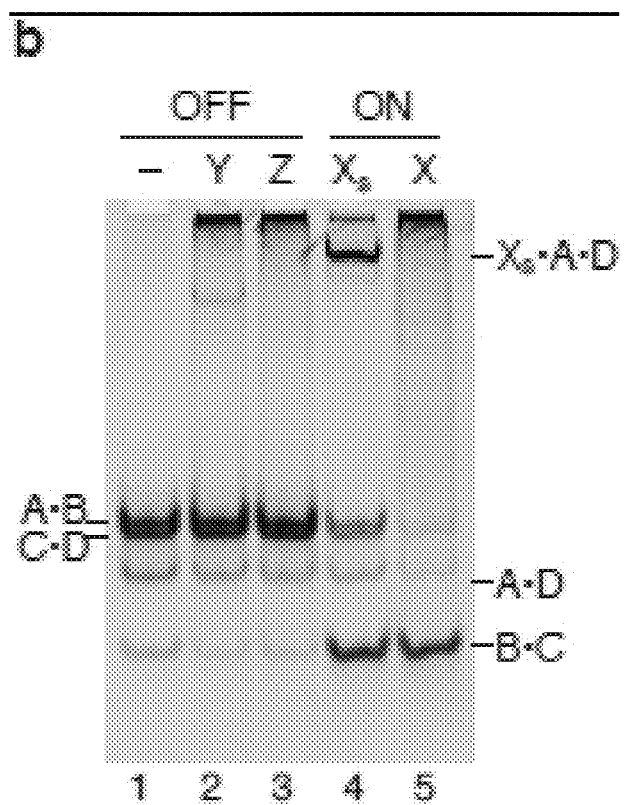
Figure 19C:
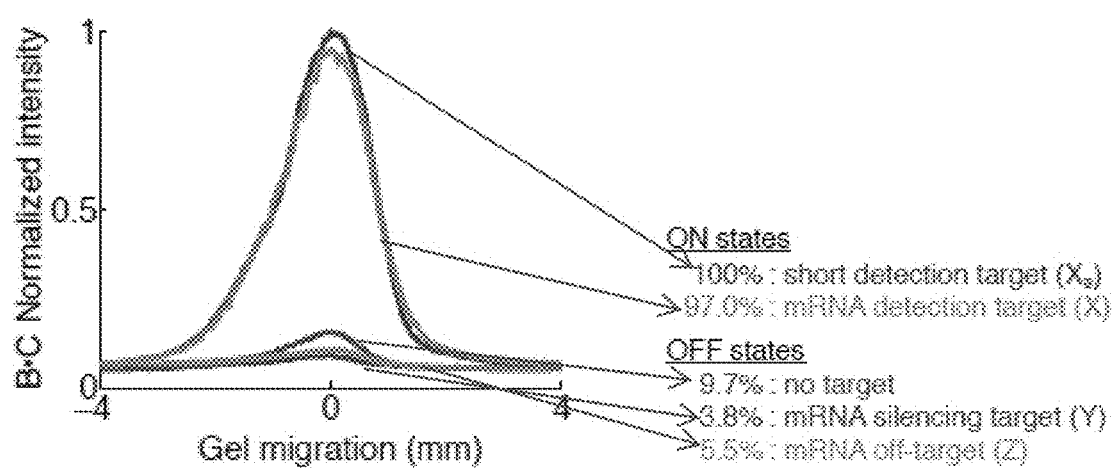
Figure 19D:
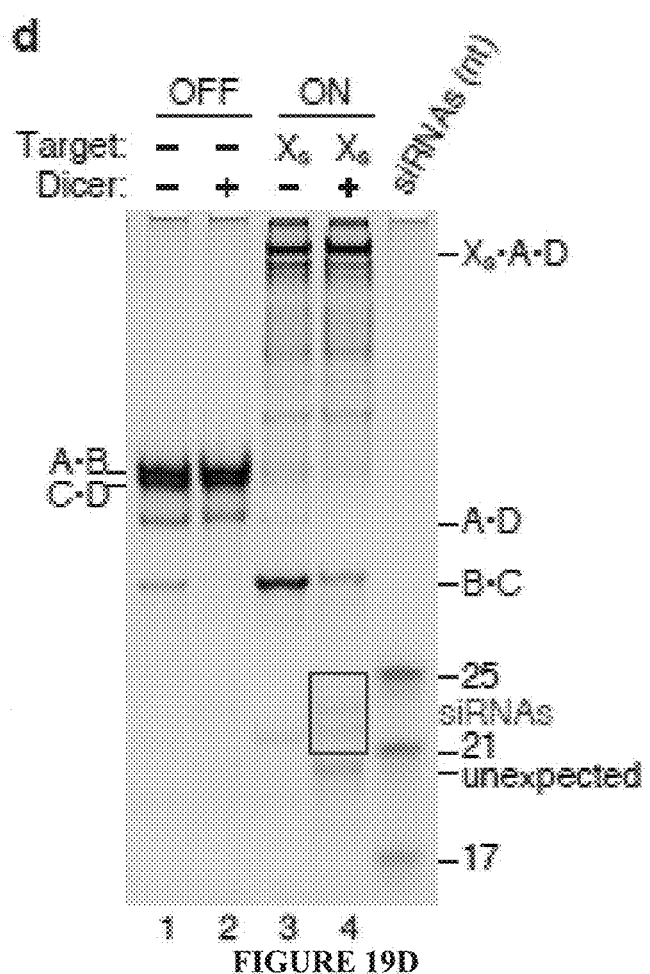
Figure 22:
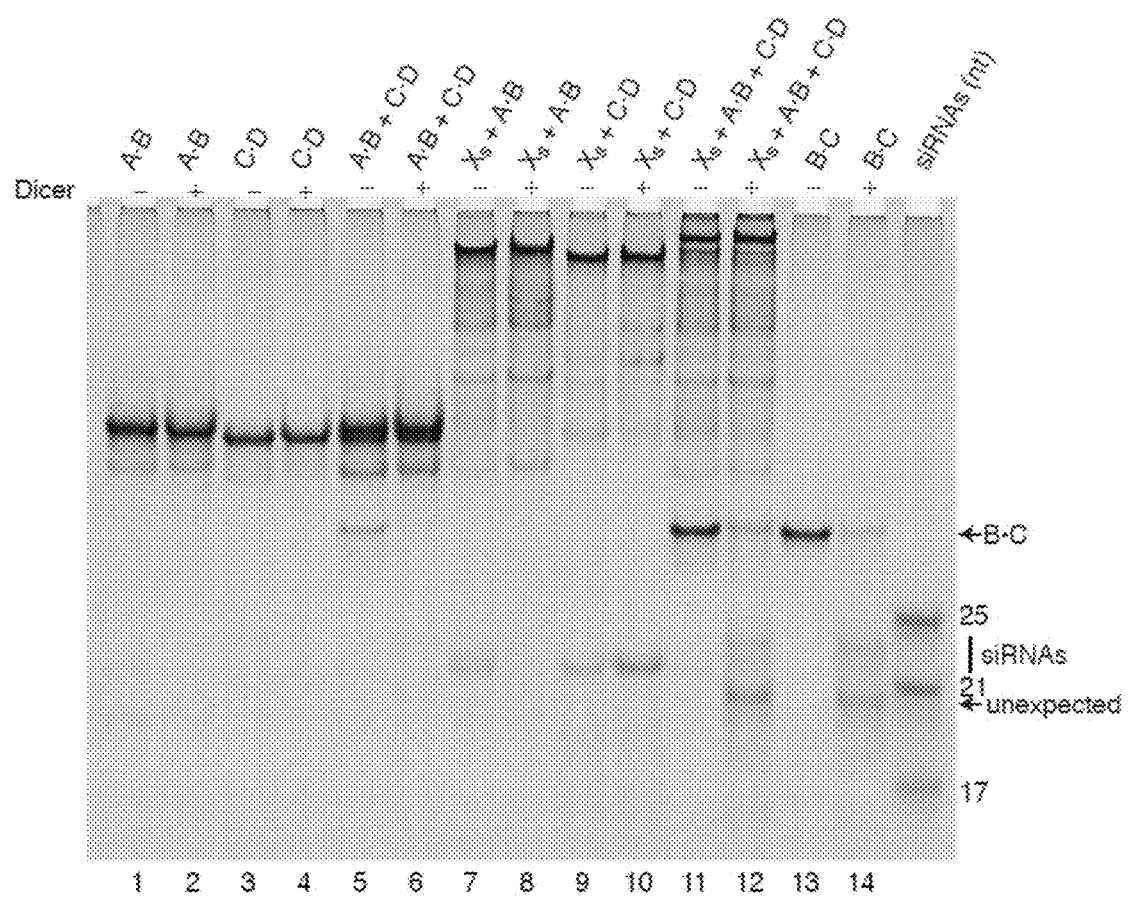
FIG. 22 illustrates a Dicer processing stepping gel for Mechanism 4. As shown, native PAGE demonstrates each signal transduction step in Dicer reaction conditions in the absence/presence of Dicer (−/+ lanes).
Figure 23A:
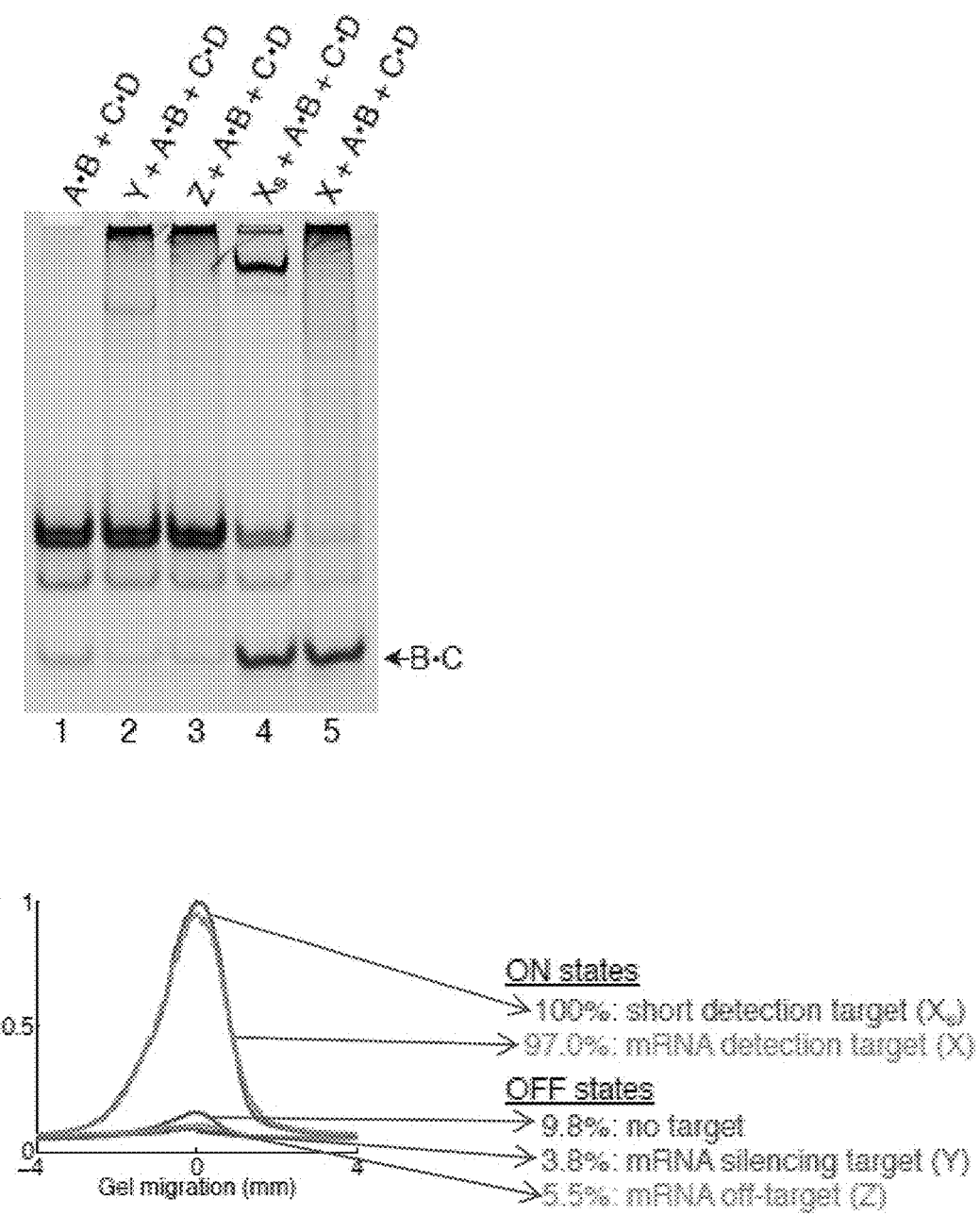
FIGS. 23a-c are a series of gels and graphs that illustrate quantification of conditional Dicer substrate formation for Mechanism 4. As shown, three independent experiments were used to characterize the variability in the OFF/ON conditional response in production of Dicer substrate.
Figure 23B:
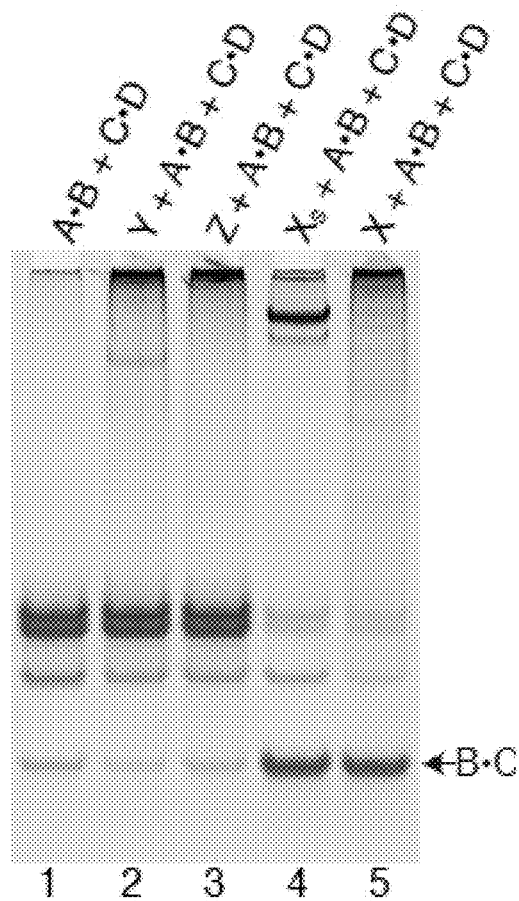
Figure 23B:
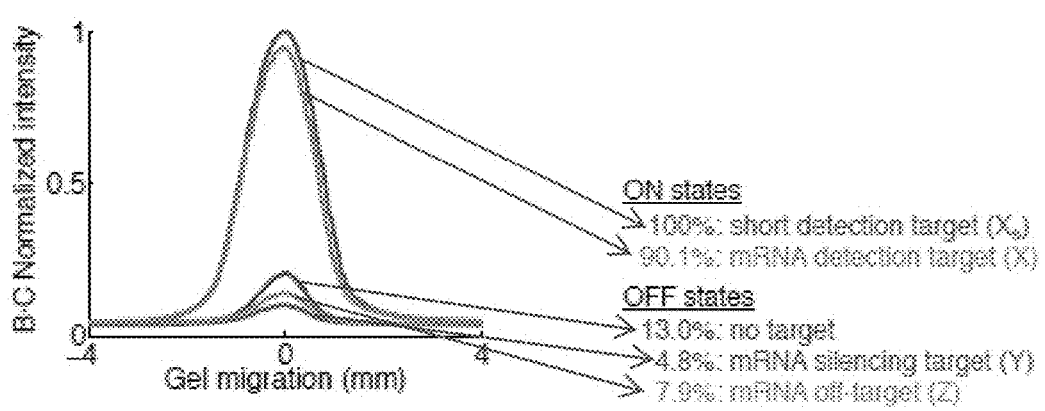
Figure 23C:
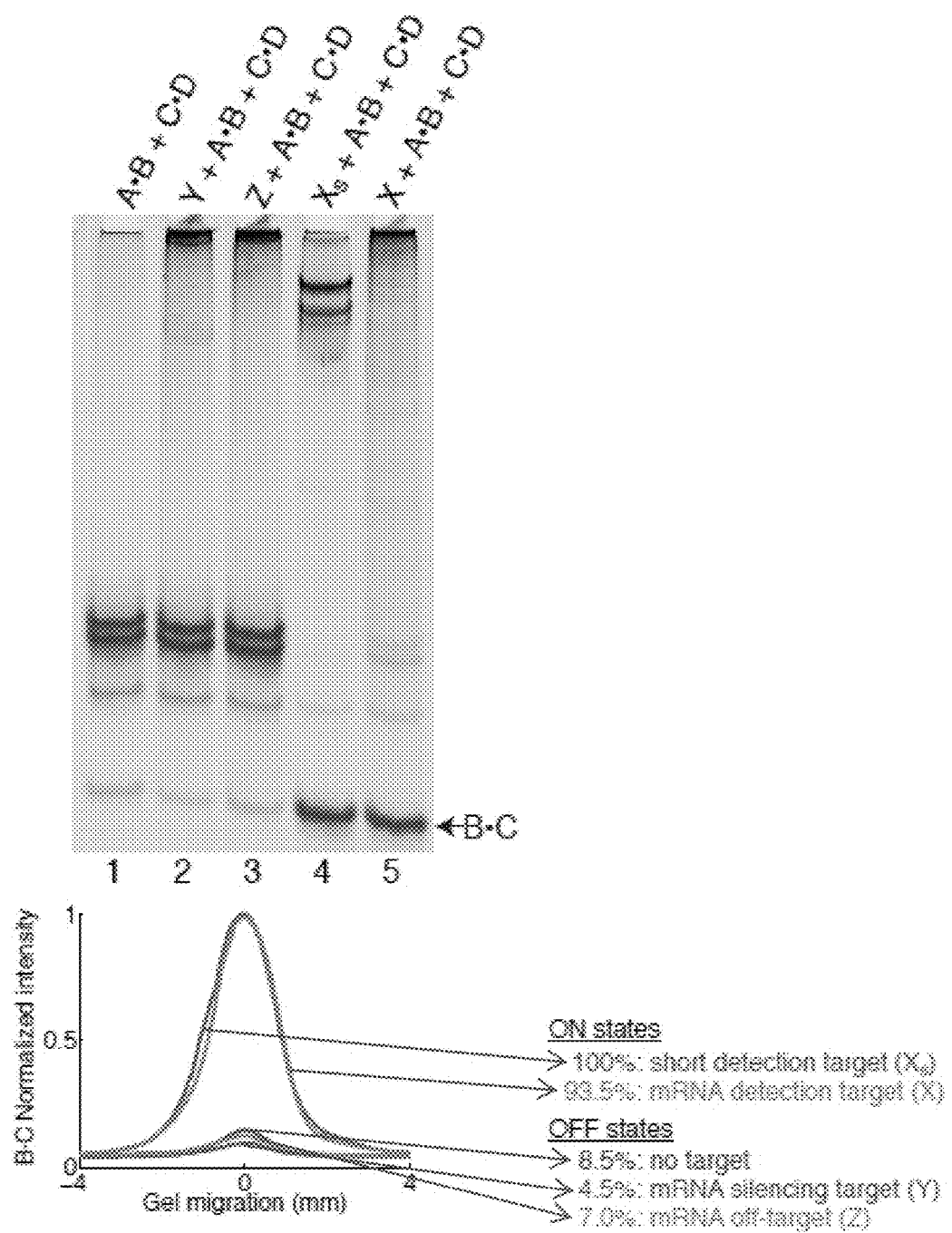

The mechanism exhibits strong OFF/ON conditional Dicer substrate formation, achieving an order of magnitude increase in DsiRNA production in the presence of either the short detection target Xs (CUCCGAGAACGUCAUCAC-CGAGUUCAUGCGCUUCAAGG; SEQ ID NO: 15) or the full-length mRNA target X (FIGS. 19*b* and 19*c*). Only the transduction product B·C is efficiently processed by Dicer (FIG. 19*d*; see also FIG. 22).

This mechanism achieves sequence and shape transduction using markedly different design elements than Mechanisms 1-3 (Table 1). Sequence transduction is achieved via the novel approach of template nucleation, with the two scRNAs A·B and C·D being brought into proximity not via mutual complementarity to each other (as with conventional toehold/toehold or toehold/loop nucleation), but due to complementarity to adjacent segments of another strand, the detection target X, which serves as a template for their nucleation. Templated nucleation provides a simple approach to sequence transduction because by construction, the template sequence (the input) is independent from the sequences of the nucleated duplexes (the output). After the two scRNAs are co-localized via template nucleation, shape transduction is completed via 4-way branch migration in which the two scRNA duplexes swap base-pairing partners. Initially the scRNAs each undergo short 3-way branch migrations with the template to liberate short mutually complementary toeholds, creating a 5-way junction with the template which resolves into a 4-way branch migration as strand swapping commences. Previous studies demonstrated that 4-way branch migrations are dramatically faster when they are mediated by two toehold/toehold nucleations to create an initial 4-way junction. This principle was adapted to the templated scenario, where each duplex experiences first template/toehold nucleation with X and then toehold/toehold nucleation with each other. By including this auxiliary toehold/toehold nucleation step to enhance branch migration kinetics, some sequence dependence of duplex B·C on X was introduced, which is then removed by Dicer to produce a completely independent siRNA targeting Y.

Template mediated 4-way branch migration provides a simple one-step approach to conditional Dicer substrate formation that provides an intriguing alternative to the more familiar concepts of toehold/toehold nucleation and 3-way branch migration.

Oligonucleotide synthesis and preparation were performed as described above for Mechanism 4. Sequences used for Mechanism 4 are indicated below in Table 6.

TABLE 6

Sequences for Mechanism 4.

| Strand | Domains | Sequence (5'-3') | SEQ ID NO |
|---|---|---|---|
| Strand $X_s$ | a-b-c-d-e | CUCCGAGAACGUCAUCACCGAGUUCA UGCGCUUCAAGG | 15 |
| Strand A | e*-d*-z*-y* | CCUUGAAGCGCAUGAACU(GACACGCU GAACUUGUGGCCG) | 16 |
| Strand B | y-z-b*-d | (CGGCCACAAGUUCAGCGUGUC)UGACG UAGUUCAU | 17 |
| Strand C | b-z*-y*-x* | ACGUCA(GACACGCUGAACUUGUGGCCG UU) | 18 |
| Strand D | x-y-z-c*-b*-a* | (AACGGCCACAAGUUCAGCGUGUC)CGG UGAUGACGUUCUCGGAG | 19 |

Sequences constrained by DsRed2 (mRNA detection target X) are shown in bold. Sequences constrained by d2EGFP (mRNA silencing target Y) are shown within parentheses. Underlined nucleotides are 2'OMe-RNA; all other nucleotides are RNA. Domain lengths: $|a|=8$, $|b|=6$, $|c|=6$, $|d|=7$, $|e|=11$, $|x|=2$, $|y|=19$, $|z|=2$.

Figure 20A:
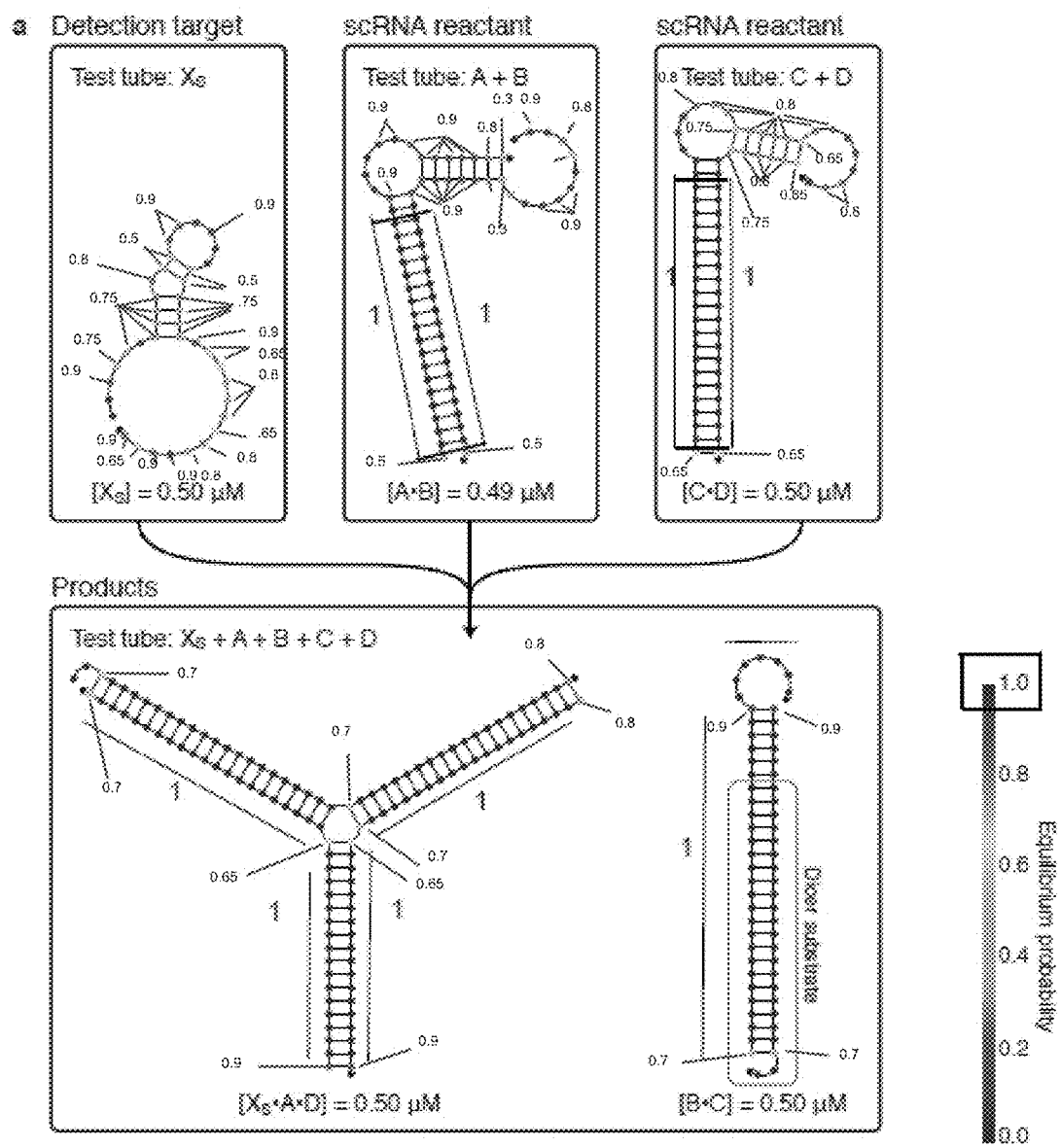
FIGS. 20a-b illustrate a computational stepping analysis for Mechanism 4. a) Equilibrium test tube calculations showing the predicted concentrations and base-pairing properties of reactants and products. b) Equilibrium test tube calculation predicting that scRNAs A·B and C·D are metastable, not stable.
Figure 20B:
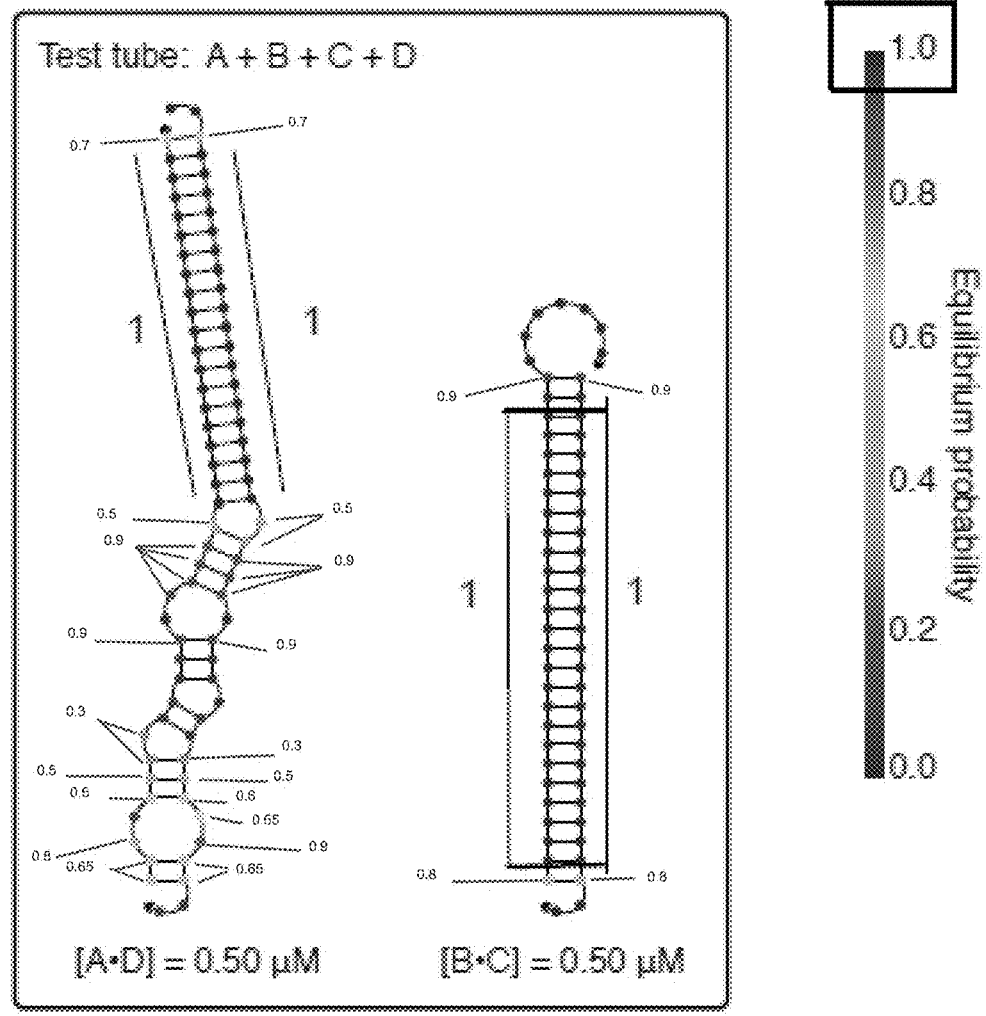

Reference is made to FIGS. 20A and 20B, which shows a computational stepping analysis for Mechanism 4. In panel a, equilibrium test tube calculations showing the predicted concentrations and base-pairing properties of reactants and products are shown. The short RNA detection target Xs is predicted to have some internal base-pairing on average at equilibrium. The reactant and products are predicted to form with near-quantitative yield. In panel b, equilibrium test tube calculations are shown predicting that scRNAs A·B and C·D are metastable, and not stable. Placing A (CCUUGAAGCG-CAUGAACUGACACGCUGAACUUGUGGCCG; SEQ ID NO: 16), B (CGGCCACAAGUUCAGCGUGU-CUGACGUAGUUCAU; SEQ ID NO: 17), C (ACGUCA-GACACGCUGAACUUGUGGCCGUU; SEQ ID NO: 18), and D (AACGGCCACAAGUUCAGCGUGUCCG-GUGAUGACGUUCUCGGAG; SEQ ID NO: 19) together in a test tube leads predominantly to duplex dimers A·D and B·C at equilibrium, demonstrating that the reactants are not stable. In FIGS. 20A and 20B, each box represents a test tube containing the strands listed at the top at 0.5 µM each. For each test tube, thermodynamic analysis at 37° C. yields the equilibrium concentrations and base-pairing ensemble properties for all complexes containing up to five strands. Each complex predicted to form with appreciable concentration at equilibrium is depicted by its minimum free energy structure, with each nucleotide shaded (and some labeled with approximate probability) by the probability that it adopts the depicted base pairing state at equilibrium. The predicted equilibrium concentration is noted next to each complex.

Figure 21:
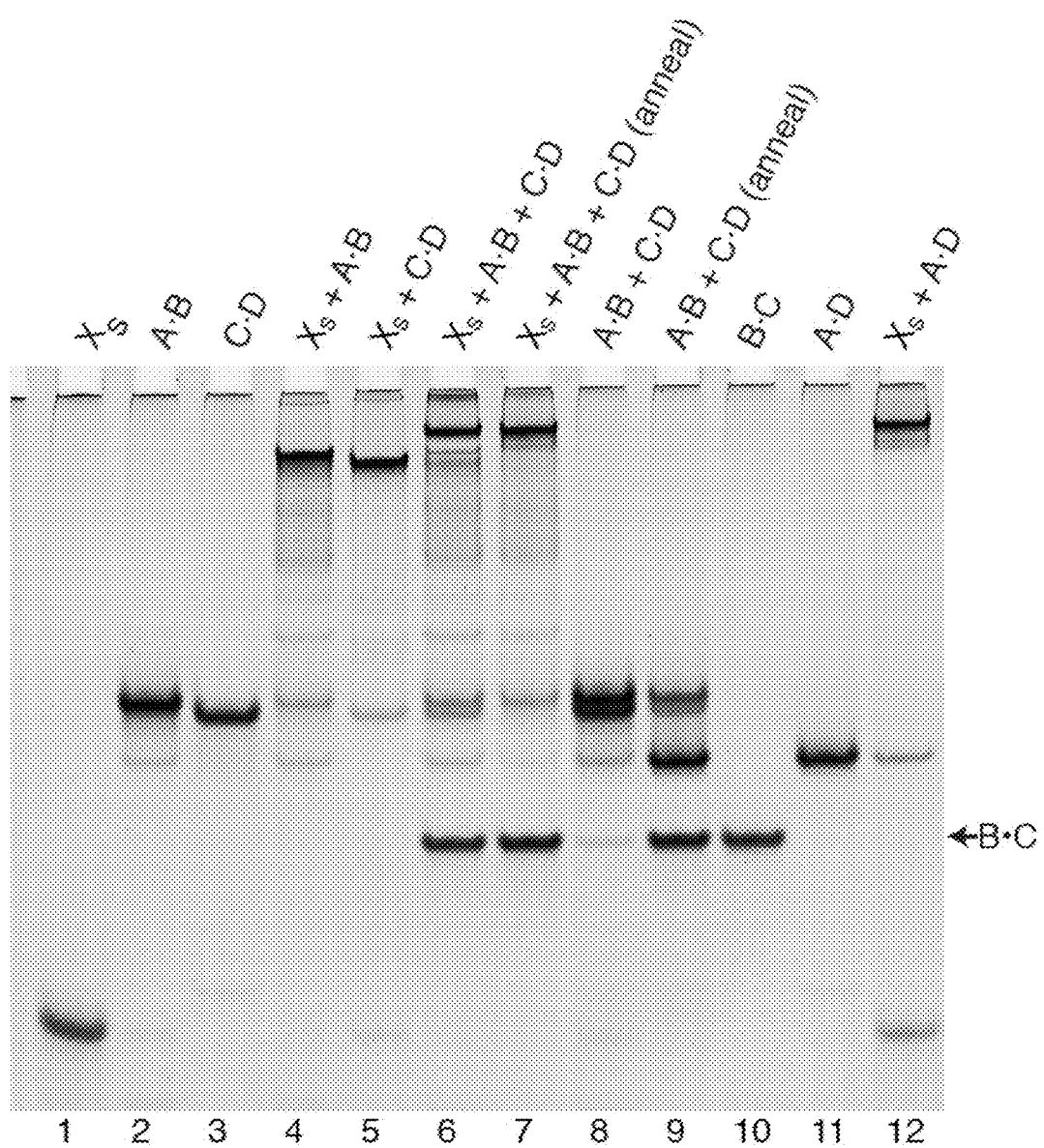

Reference is made to FIG. 21, which illustrates a stepping gel for Mechanism 4. Native PAGE demonstrating the assembly and disassembly operations in FIG. 19a are shown. In the lanes are short RNA detection target: Xs (lane 1), scRNA reactants: A·B and C·D (lanes 2 and 3), Step 1 (ON state): Xs, A·B and C·D interact to form products Xs·A·D and B·C (lane 6), OFF state: A·B and C·D co-exist metastably, yielding minimal production of B·C (lane 8). Annealing A·B and CAD leads to substantial production of B·C (lane 9).

Reference is made to FIG. 22, Dicer processing stepping gel for Mechanism 4. Native PAGE demonstrating each signal transduction step in Dicer reaction conditions in the absence/presence of Dicer (−/+ lanes). Only the final product B·C is efficiently processed by Dicer to produce siRNAs (compare lanes 11 and 12).

Reference is made to FIG. 23, which shows quantification of conditional Dicer substrate formation for Mechanism 4. Three independent experiments were used to characterize the variability in the OFF/ON conditional response in production of Dicer substrate. As shown are OFF states: no target, mRNA silencing target Y, mRNA off-target Z and ON states: short RNA detection target Xs, mRNA detection target X. All values are normalized relative to the amount of Dicer substrate produced using Xs.

Example 5

Mechanism 5, Conditional shRNA Transcription Using scDNAs

The previous mechanisms explored design alternatives for conditional Dicer substrate hybridization using scRNAs. It was considered that the alternative strategy of conditional Dicer substrate transcription based on signal transduction with scDNAs. Kim et al. have previously demonstrated conditional in vitro transcription mediated by conditional hybridization of a double-stranded DNA promoter sequence. Conditional promoter assembly with sequence transduction was combined to implement conditional Dicer substrate transcription. For this design study, T7 RNA polymerase is employed for in vitro transcription, taking advantage of well-characterized promoter and termination sequences. Mechanism 5 employs two metastable DNA hairpins (A and B of FIG. 24a). The detection target X opens hairpin A, which in turn opens hairpin B via a 4-way branch migration to assemble a dsDNA template for transcription of RNA hairpin C (including promoter sequence, coding sequence, and termination sequence). This signal transduction approach incorporates the catalytic turnover inherent in repeated transcription of the template. In functional terms, A detects X leading to transcription of shRNA C targeting Y.

Figure 27A:
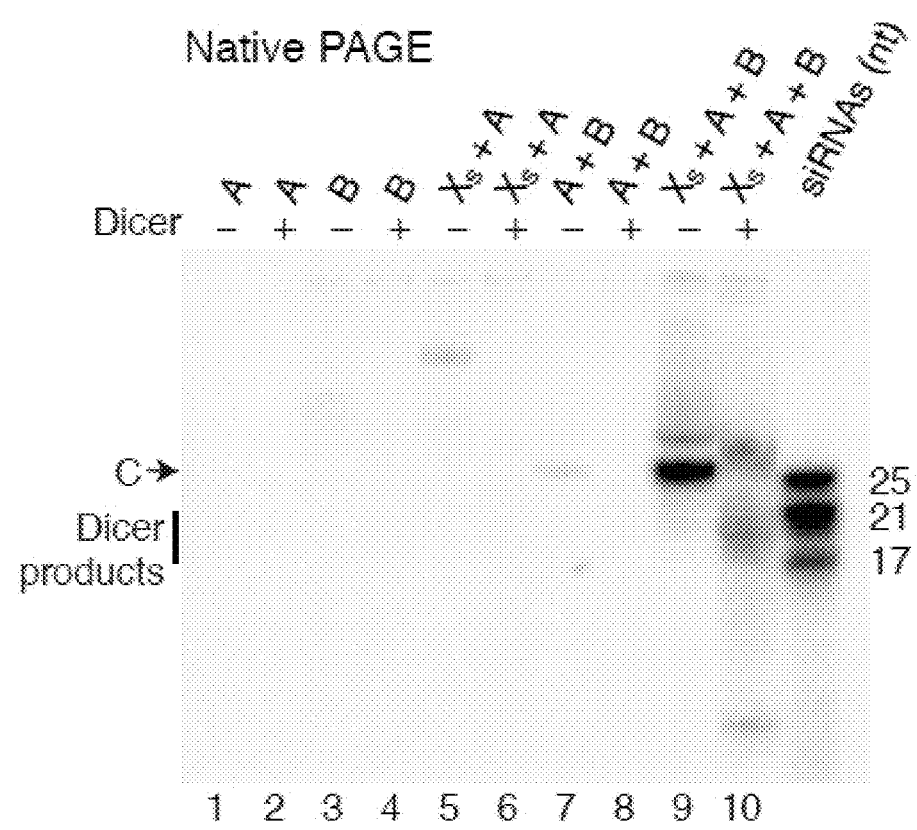
FIGS. 27a-b illustrate a Dicer processing stepping gel for Mechanism 5. As shown, (a) native and (b) denaturing PAGE gels demonstrate each signal transduction step.
Figure 27B:
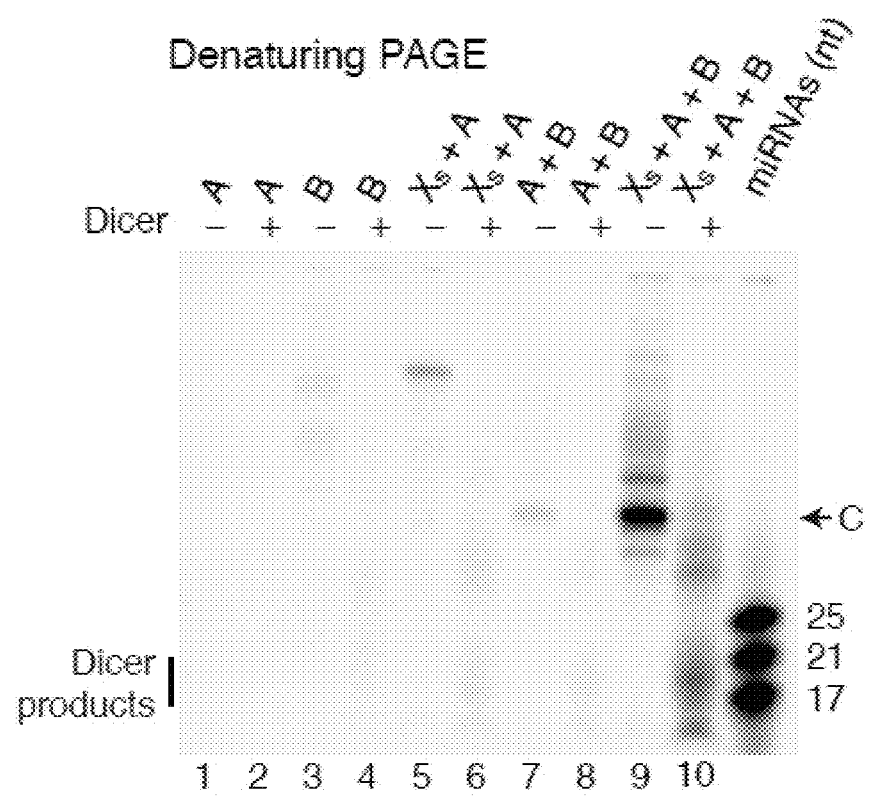

Both the OFF/ON response of conditional transcription template formation and the OFF/ON response of conditional Dicer substrate transcription were characterized. For this mechanism, scDNAs to detect a random short DNA target Xs were engineered. Therefore, the performance for a full-length mRNA detection target X was not characterized. However, spurious transcription template formation using the full-length mRNA silencing target Y and off-target mRNA Z were characterized. In the absence/presence of short DNA detection target Xs, the mechanism demonstrates strong OFF/ON conditional transcription template formation (FIG. 24b) and transcription of shRNA Dicer substrate C (FIG. 24c), yielding more than an order of magnitude increase in shRNA production (FIG. 24d). The transcription product C is efficiently processed by Dicer (FIG. 24c; see also FIG. 27).

Oligonucleotide synthesis and preparation were performed as described above for Mechanism 5. Sequences used for Mechanism 5 are indicated below in Table 7.

TABLE 7

Sequences for Mechanism 5.

| Strand | Domains | Sequence (5'-3') | SEQ ID NO |
|---|---|---|---|
| Strand $X_s$ | a-b | ATAAGCCCTCATCCAACT | 20 |
| Strand A | b*-a*-p-q-z-y*-z*-q*-a | AGTTGGATGAGGGCTTATtaatacgactc actata(gCAGCACGACTTCTTCAAG)A GCTGA(CTTGAAGAA GTCGTGCTGC)tatagtgagATAAGCCCTC | 21 |
| Strand B | q-t-z-y-z*-q*-p* | ctcactataAAAAAAA(GCAGCACGACT TCTTCAAG)TCAGCT(CTTGAAGAAG TCGTGCTGC)tatagtgagtcgtatta | 22 |
| Strand C | z-y*-z*-poly(U) | (gCAGCACGACUUCUUCAAG)AGCU GA(CUUGAAGAAGUCGUGCUGC)poly(U) | 23 |

Sequences constrained by d2EGFP (mRNA silencing target Y) are shown within parentheses. Sequences constrained by the T7 promoter are shown as lower case letters. Sequences constrained by the T7 transcription termination sequence are shown in bold. Xs, A, and B are DNA; C is an shRNA in vitro transcription product. The terminal poly(U) in shRNA C result from the transcription termination sequence. Domain lengths: |a|=10, |b|=8, |p|=8, |q|=9, |t|=7, |y|=6, |z|=19.

Figure 25A:
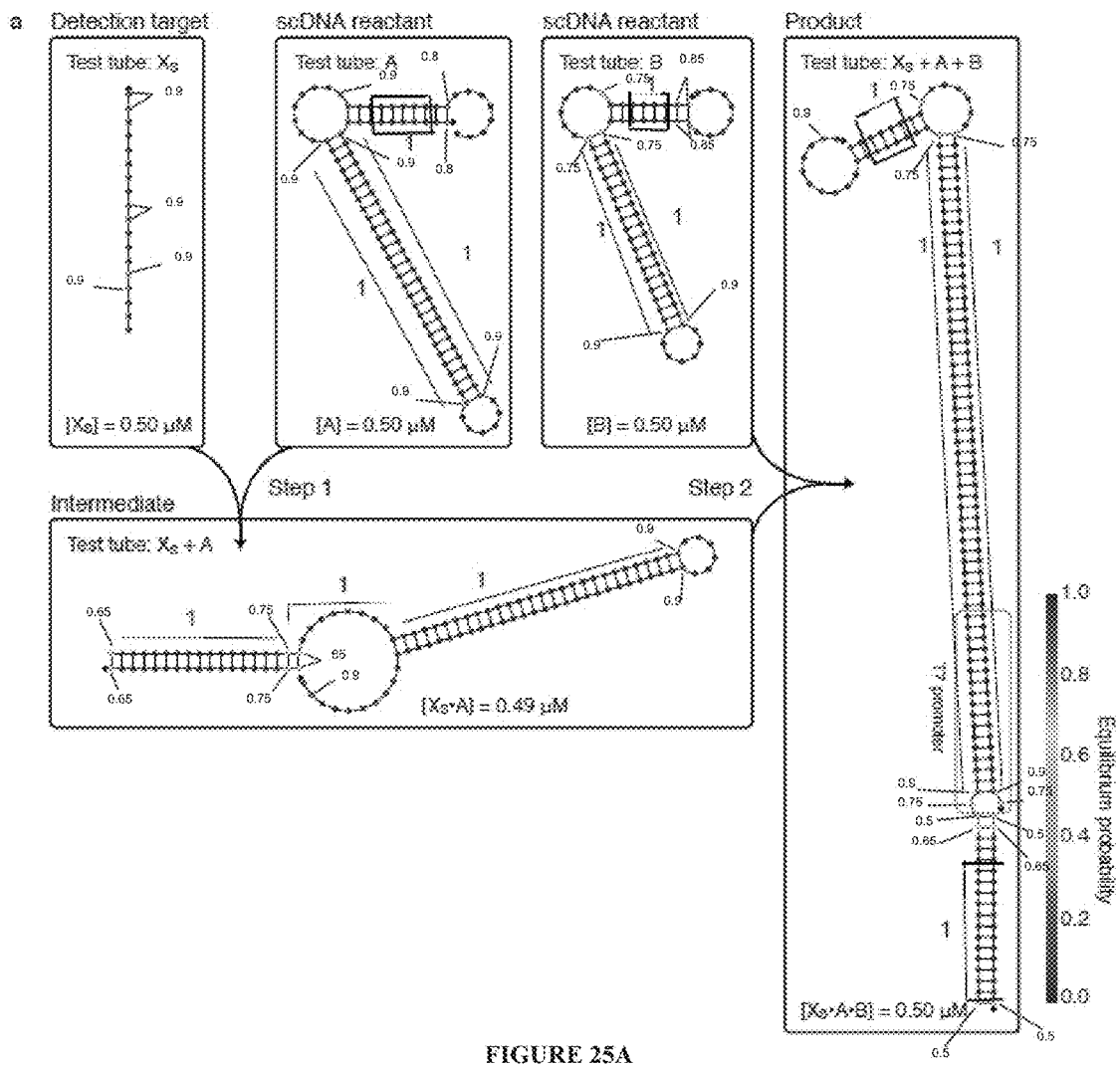
FIGS. 25a-b illustrate a computational stepping analysis for Mechanism 5. a) Equilibrium test tube calculations showing the predicted concentrations and base-pairing properties of reactants, intermediates, and products. b) Equilibrium test tube calculation predicting that scDNAs A and B are metastable, not stable.
Figure 25B:
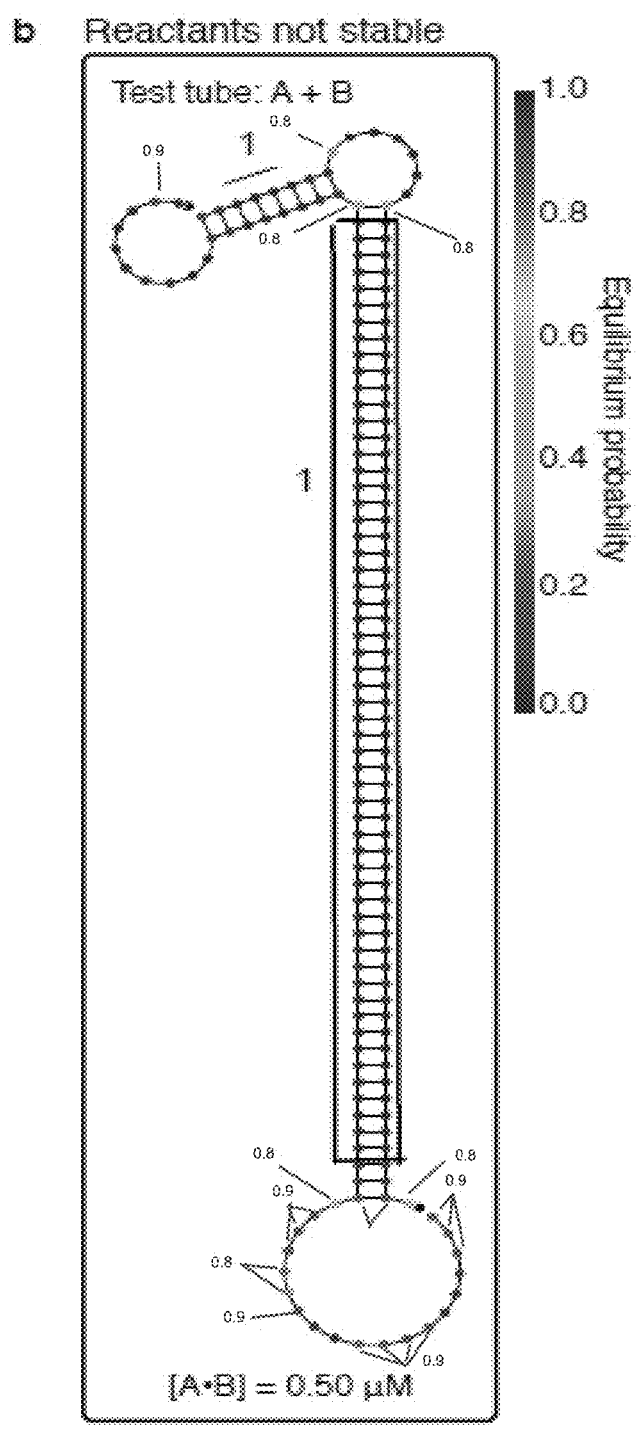

Reference is made to FIG. 25, which illustrates a computational stepping analysis for Mechanism 5. In panel a, equilibrium test tube calculations are shown, showing the predicted concentrations and base-pairing properties of reactants, intermediates, and products. Reactants, intermediates, and products are predicted to form with near-quantitative yield. In panel b, an equilibrium test tube calculation was performed, predicting that scDNAs A and B are metastable, not stable. Placing A and B together in a test tube leads predominantly to duplex dimer A·B at equilibrium, demonstrating that A and B are not stable. In FIG. 25, each box represents a test tube containing the strands listed at the top at 0.5 μM each. For each test tube, thermodynamic analysis at 37° C. yields the equilibrium concentrations and base-pairing ensemble properties for all complexes containing up to three strands. Each complex predicted to form with appreciable concentration at equilibrium is depicted by its minimum free energy structure, with each nucleotide shaded by the probability that it adopts the depicted base pairing state at equilibrium. The predicted equilibrium concentration is noted next to each complex.

Figure 26:
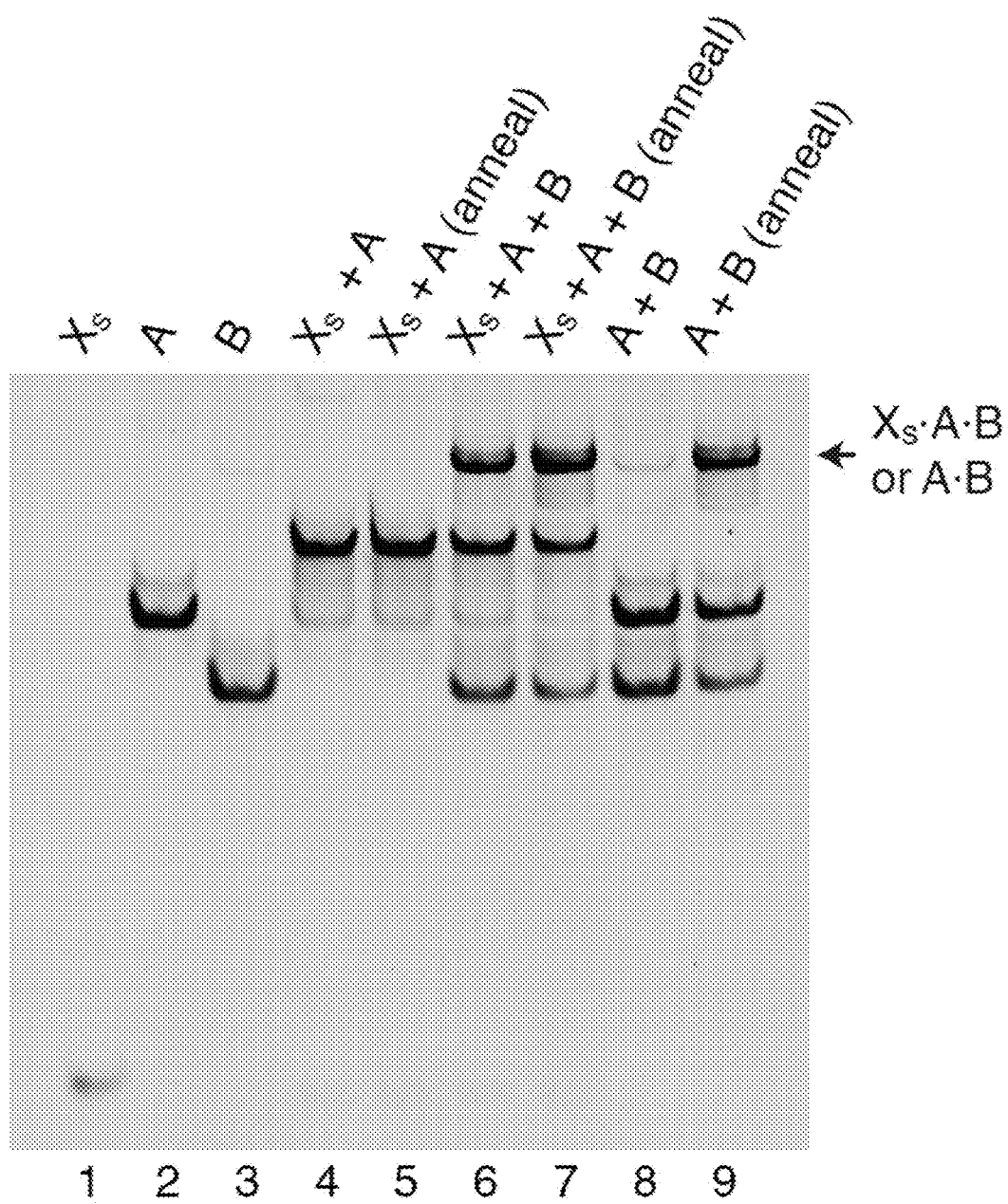

Reference is made to FIG. 26, which illustrates a stepping gel for Mechanism 5. As shown is native PAGE demonstrating the assembly operations in FIG. 24a. In the lanes are short DNA detection target: Xs (lane 1), scDNA reactants: A and B (lanes 2 and 3), Step 1: Xs and A interact to form intermediate Xs·A (lane 4), Step 1+Step 2 (ON state): Xs, A and B interact to form product Xs·A·B (lane 6), OFF state: A and B co-exist metastably, yielding minimal production of A·B (lane 8) and annealing A and B leads to substantial production of A·B (lane 9).

Reference is made to FIG. 27, which shows a transcription and Dicer processing stepping gel for Mechanism 5. As shown are native and denaturing PAGE demonstrating each signal transduction step. In vitro transcription is performed concurrently with scDNA signal transduction. As shown on the gels, optional Dicer processing is performed following in vitro transcription (−/+ lanes). Step 1: Minimal transcription is observed for a product that is longer than the expected shRNA C (lane 5). For the OFF state: Minimal transcription of shRNA C (lane 7). Step 1+Step 2 (ON state): Substantial transcription of shRNA C (lane 9), which is efficiently processed by Dicer (lane 10). Each reaction was split in half and separated by either 20% native PAGE (250 V for 4 hours) or 15% denaturing PAGE (500 V for 1.5 hours).

Figure 28A:
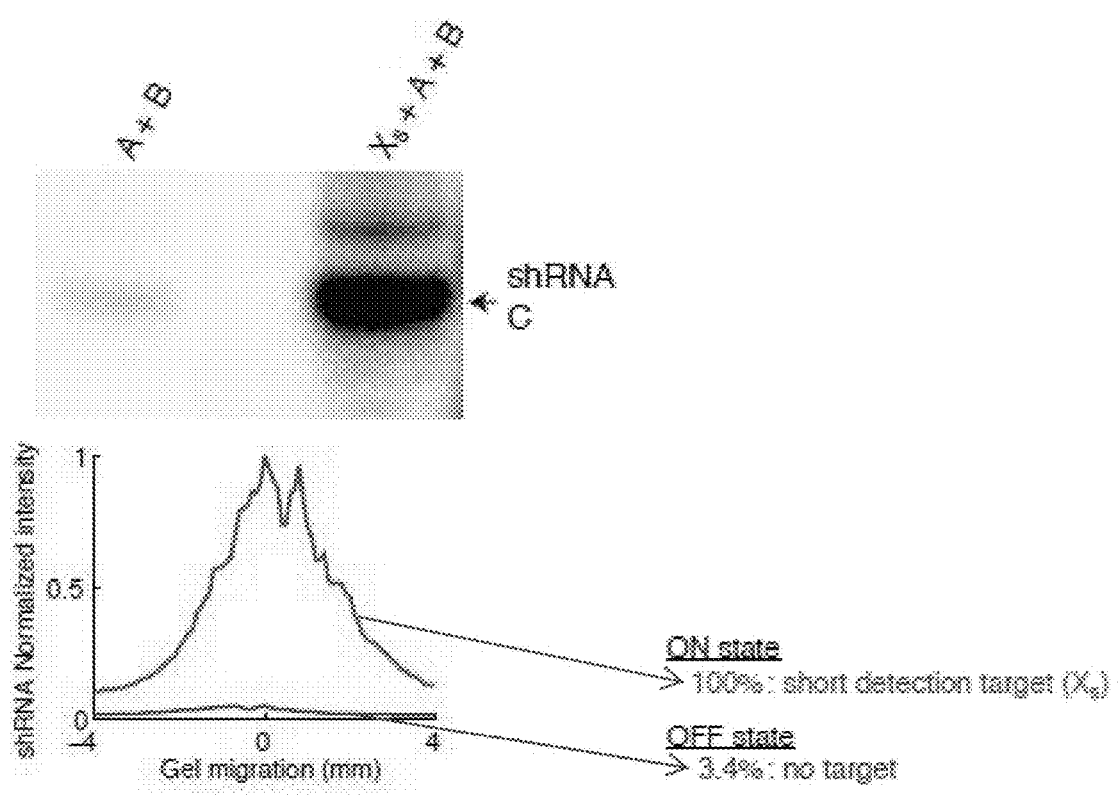
FIGS. 28a-c are a series of gels and graphs that illustrate the quantification of conditional Dicer substrate formation for Mechanism 5. As shown, three independent experiments were used to characterize the variability in the OFF/ON conditional response in production of Dicer substrate.
Figure 28B:
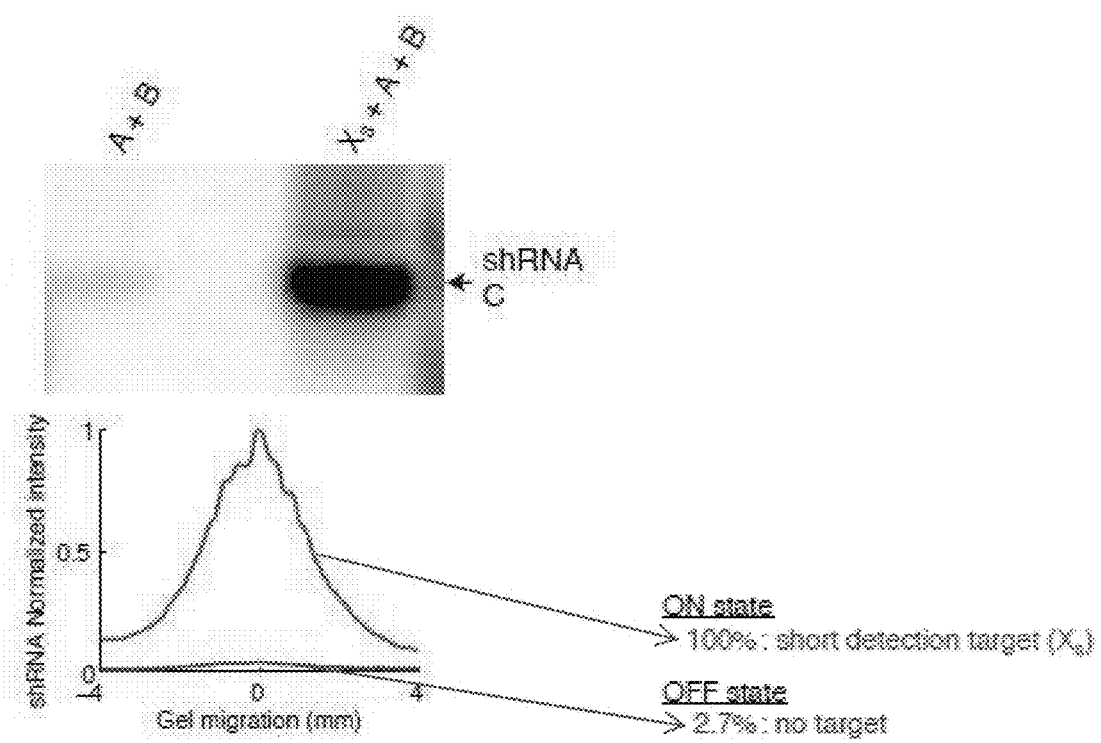
Figure 28C:
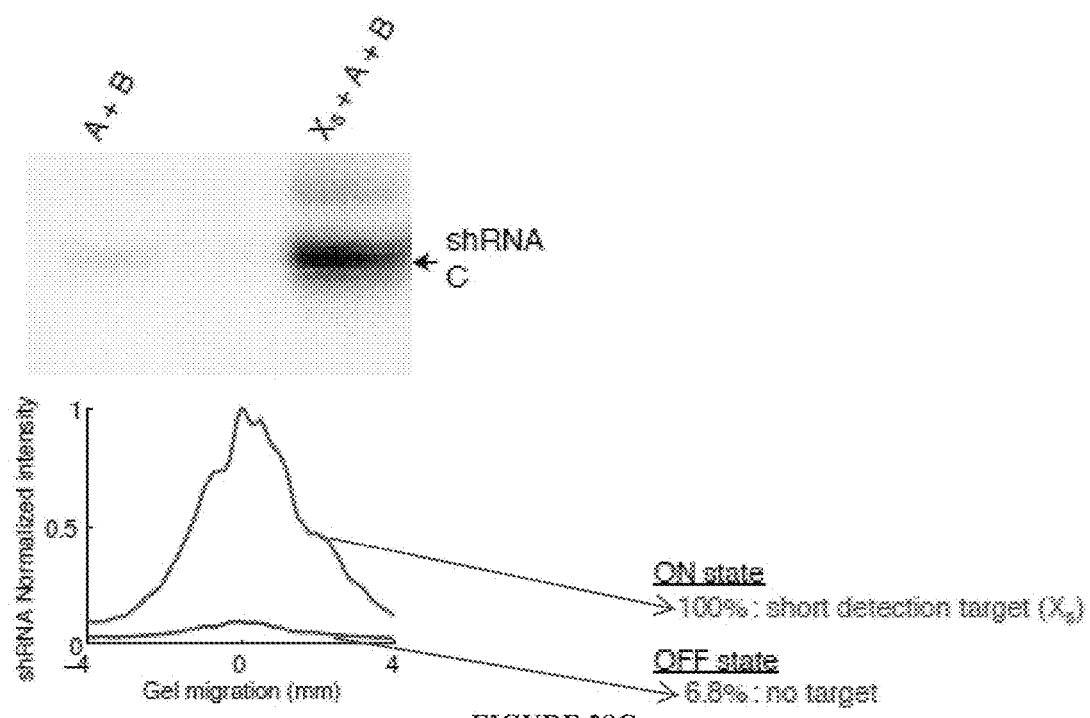

Reference is made to FIG. 28, which illustrates quantification of conditional Dicer substrate transcription for Mechanism 5. As shown, three independent experiments were used to characterize the variability in the OFF/ON conditional response in production of Dicer substrate. As shown, in the OFF state: no target. ON state: short DNA detection target Xs. All values are normalized relative to the amount of Dicer substrate produced using Xs.

In classifying the design principles underlying each mechanism, a major distinguishing feature is reactant metastability vs reactant stability. Metastable reactants are kinetically trapped. If they are allowed to equilibrate in the absence of the detection target, they will form the transduction product even in the absence of the detection target. In order to obtain a clean OFF/ON conditional response using metastable scRNAs or scDNAs, it is important that they 'leak' out of the kinetically trapped state slowly. On the other hand, if stable reactants are allowed to equilibrate in the absence of the detection target, they will predominantly remain in the reactant state rather than converting to the product state. This is a major conceptual advantage because it places a thermodynamic rather than a kinetic limit on the amount of spurious transduction product that can form in the absence of the detection target.

To examine whether scRNA (or scDNA) reactants are predicted to be stable in the absence of the detection target, the Analysis page of the NUPACK web application was used to perform a computational thermodynamic analysis for a test tube containing all the reactants for a given mechanism; the results are summarized in Table 8. For Mechanisms 1, 4, and 5, full conversion to product is observed whether or not short detection target Xs is present, indicating that these reactants are predicted not to be stable. In order to achieve clean OFF/ON signal transduction, these mechanisms must rely on reactant metastability (which cannot be assessed via these equilibrium calculations). For Mechanisms 2 and 3, minimal conversion to product is observed at equilibrium in the absence of Xs, indicating that these reactants are predicted to be stable.

TABLE 8

| | Reactants only | | Reactants + $X_s$ | | Computational | Experimental |
|---|---|---|---|---|---|---|
| Mechanism | Product | Concentration (μM) | Product | Concentration (μM) | classification | classification |
| 1 | B·C | 0.5 | B·C | 0.5 | not stable | metastable |
| 2 | B·C | $1 \times 10^{-3}$ | B·C | 0.5 | stable | stable |
| 3 | B | $2 \times 10^{-7}$ | B | 0.5 | stable | stable |
| 4 | B·C | 0.5 | B·C | 0.5 | not stable | metastable |
| 5 | A·B | 0.5 | $X_s$·A·B | 0.5 | not stable | metastable |

Computational and experimental classification of reactant metastability vs stability. For each mechanism, computational thermodynamic analysis is performed for a test tube at 37° C. containing all scRNA (or scDNA) reactants in the absence or presence of short detection target Xs (each strand at 0.5 μM).

With reference to Table 8, which show computational and experimental classification of reactant metastability vs stability. Experimental studies confirm that the reactants for Mechanisms 1, 4, and 5 are metastable and that the reactants for Mechanisms 2 and 3 are stable.

Figure 3B:
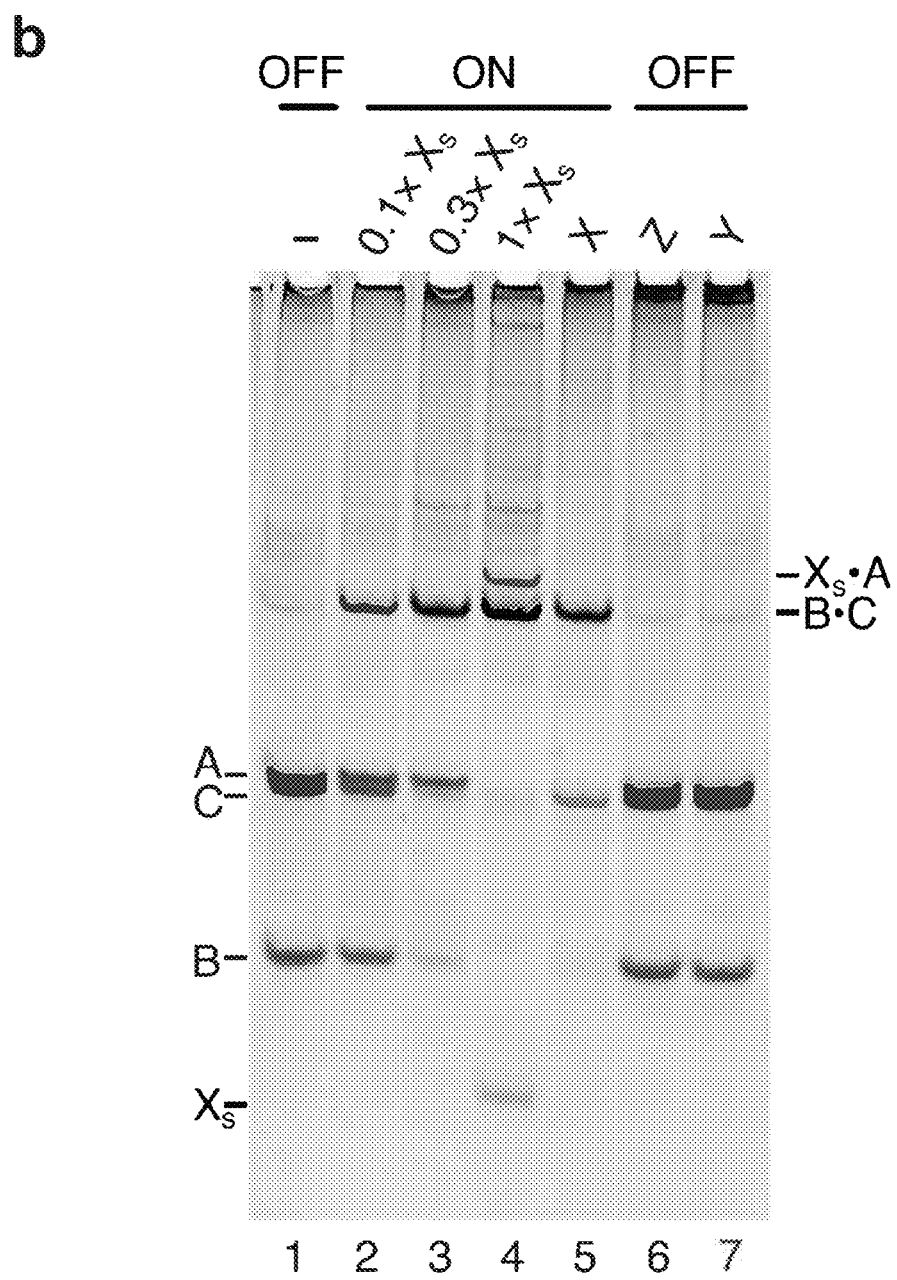
Figure 3C:
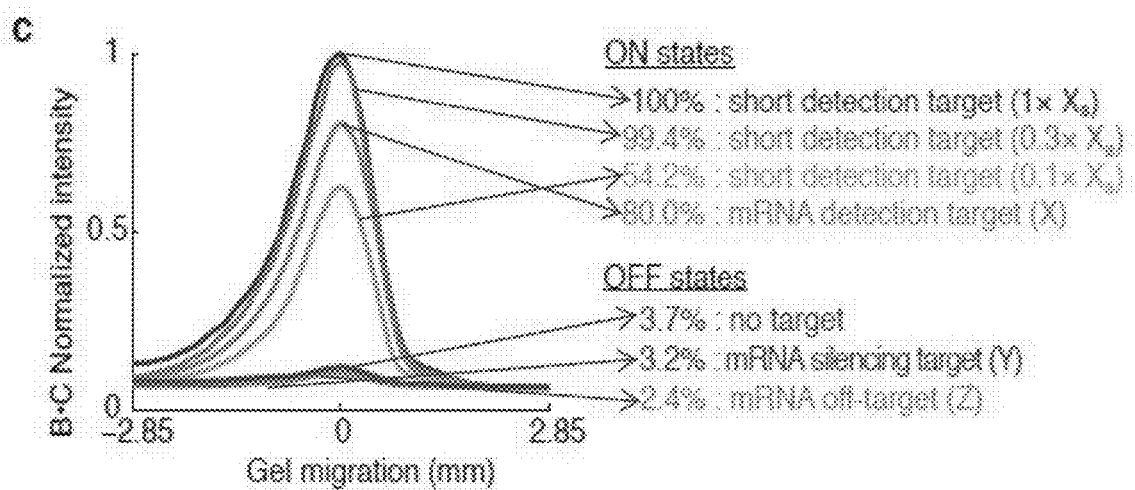
Figure 3D:
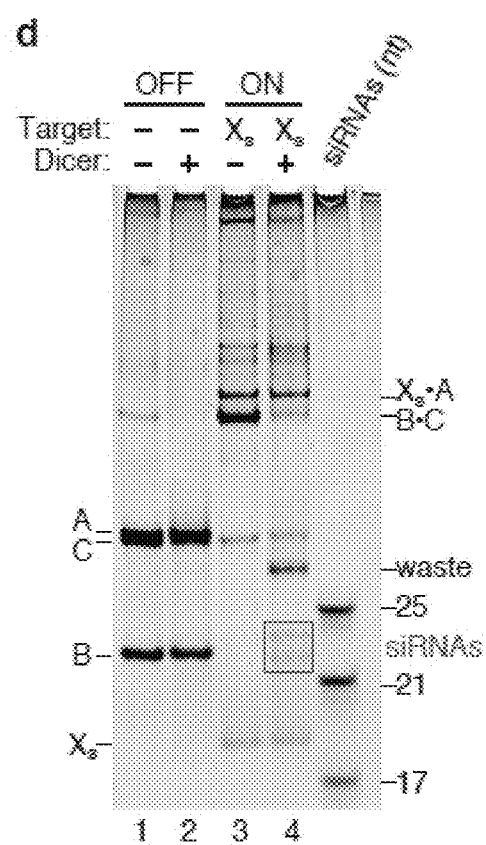

For Mechanism 1 (metastable reactants), catalytic formation of Dicer substrate B·C (FIGS. 3B and 5) demonstrate that equilibrium partitioning between reactants B and C and product B·C strongly favors product formation. Hence, the fact that scRNA reactants A, B and C co-exist for two hours at 37° C. with only minimal production of Dicer substrate B·C demonstrates metastability (FIG. 3B (lane 1) and FIG. 5 (lane 11)). Annealing A, B, C yields increased production of B·C (FIG. 5 (lane 12)), but the reactant state is still favored, consistent with the annealing properties of metastable hairpins.

Figure 29:
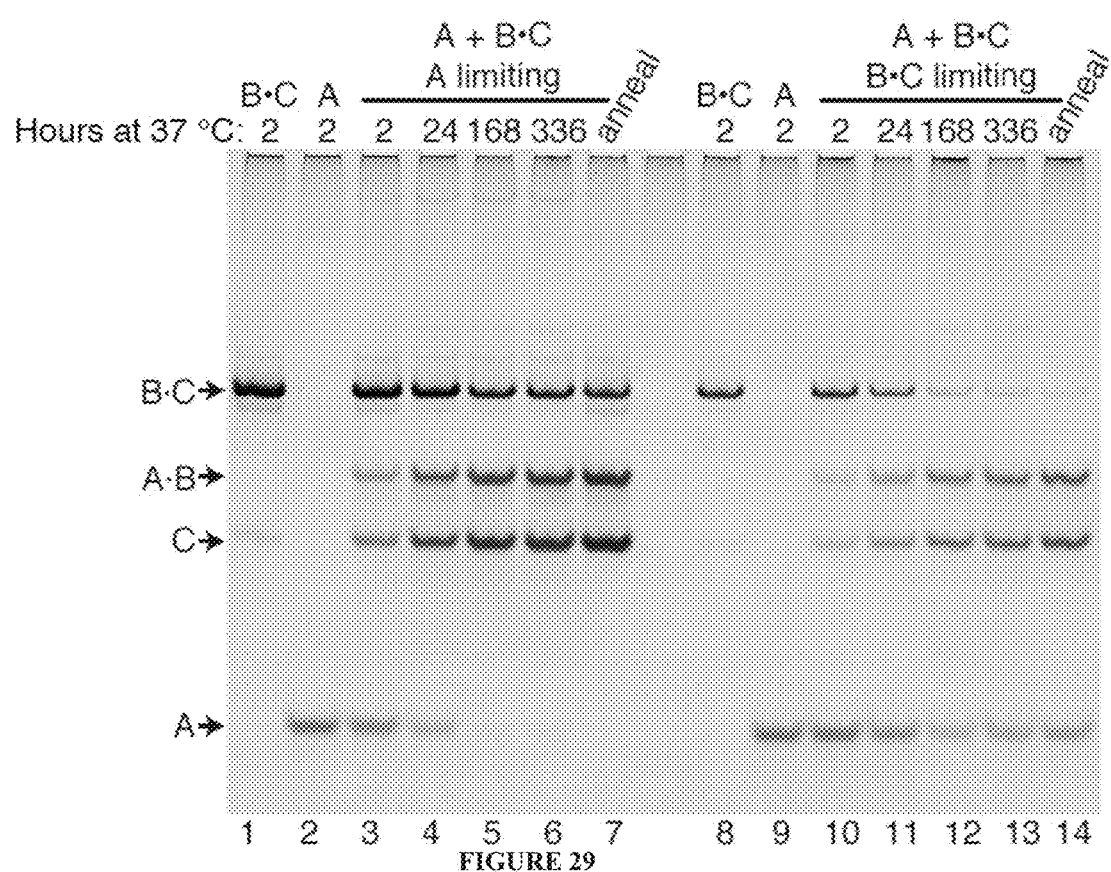
FIG. 29 illustrates a gel that demonstrates the scRNA stability for Mechanism 2. As shown, native PAGE demonstrates that the reverse reaction A+B·C→A·B+C nearly exhausts the limiting reagent with either A or B·C limiting. Incubation at 37° C. for 2, 24, 168 (1 week), or 336 (2 weeks) hours.

As shown in Example 2, Mechanism 2 (stable reactants): scRNA reactants A·B and C co-exist for two hours at 37° C. with only minimal production of A and B·C (FIG. 9B (lane 1) and FIG. 11 (lane 15)). Annealing A·B and C yields only slightly increased production of A and B·C (FIG. 11 (lane 16)). Because of the annealing properties of hairpins the anneal is expected to favor the reactant state of C, so these results do not provide definitive evidence of reactant stability. To establish that the reactants are in fact stable and not metastable, the reverse reaction (A+B·C→A·B+C), was monitored using a time course experiment (FIG. 29). To account for possible stoichiometry mismatches between the initial species, the experiment with either A as the limiting reagent or with B·C as the limiting reagent was performed. In both cases, the reverse reaction proceeded until the limiting reagent was predominantly consumed, demonstrating that the scRNAs A·B and C are stable, not metastable.

Figure 30:
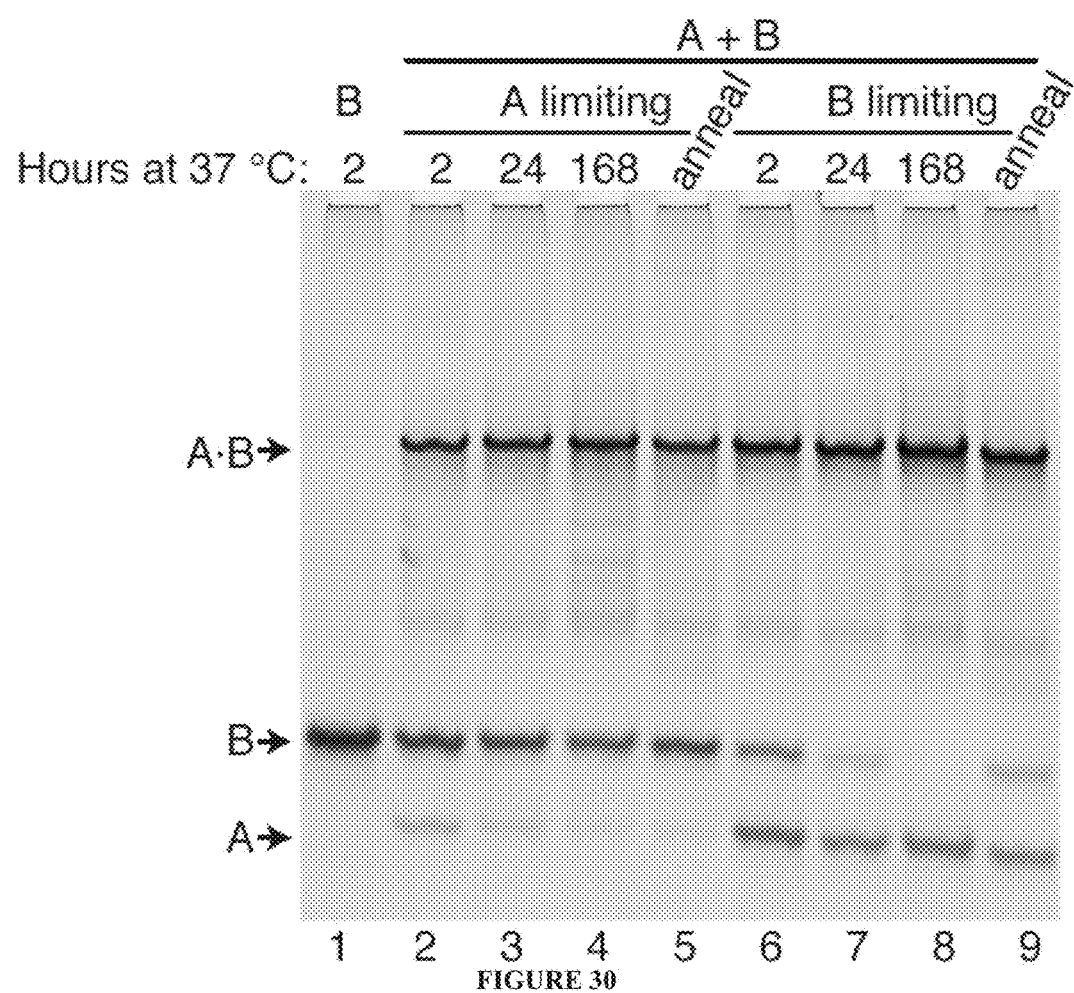
FIG. 30 illustrates a gel that demonstrates the scRNA stability for Mechanism 3. As shown, a native PAGE dem onstrates that the reverse reaction A+B→A·B nearly exhausts the limiting reagent with either A or B limiting. Incubation at 37° C. for 2, 24, or 168 (1 week) hours.

As shown in Example 3, Mechanism 3 (stable reactants): scRNA reactant A·B yields no detectible production of A and B after two hours at 37° C. (FIG. 14B (lane 1) and FIG. 16 (lane 4)). Annealing A·B yields increased but minimal production of A and B (FIG. 16 (lane 5)). Because of the annealing properties of hairpins the annealing is expected to favor the product state of B. Hence, these results are consistent with stability of the scRNA reactants and may actually overestimate the equilibrium concentration of the product state. To confirm that the reactants are stable, the reverse reaction (A+B→A·B) using a time course experiment was monitored (FIG. 30). To account for possible stoichiometry mismatches between the initial species, the experiment with either A as the limiting reagent or with B as the limiting reagent was performed. In both cases, the reverse reaction proceeded until the limiting reagent was predominantly consumed, demonstrating that the scRNA A·B is stable, not metastable.

As shown in Example 4, Mechanism 4 (metastable reactants): scRNA reactants A·B and C·D co-exist for two hours at 37° C. with minimal production of Dicer substrate B·C (FIG. 19B (lane 1) and FIG. 21 (lane 8)). Annealing A·B and C·D yields substantial production of A·D and B·C (FIG. 21 (lane 9)). This anneal is not expected to favor either reactants or products, as none of the strands are expected to have substantial internal secondary structure. Hence, the anneal strongly suggests that the reactants are metastable, not stable.

Figure 24B:
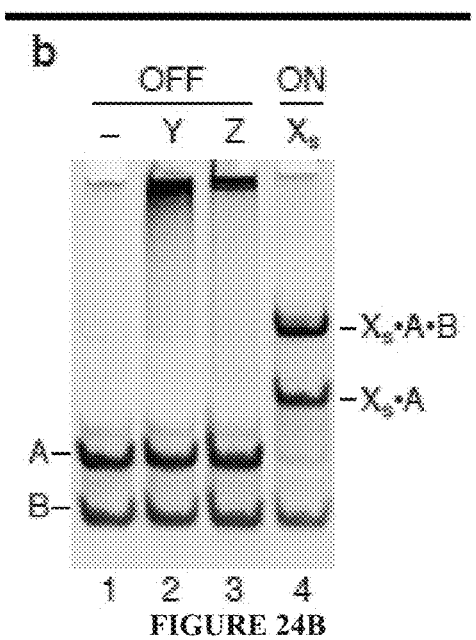
Figure 24C:
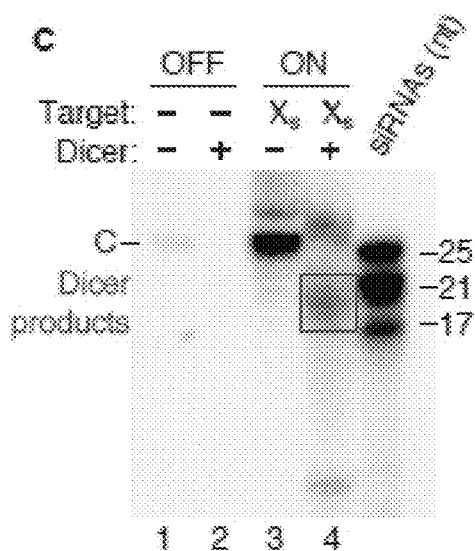
Figure 24D:
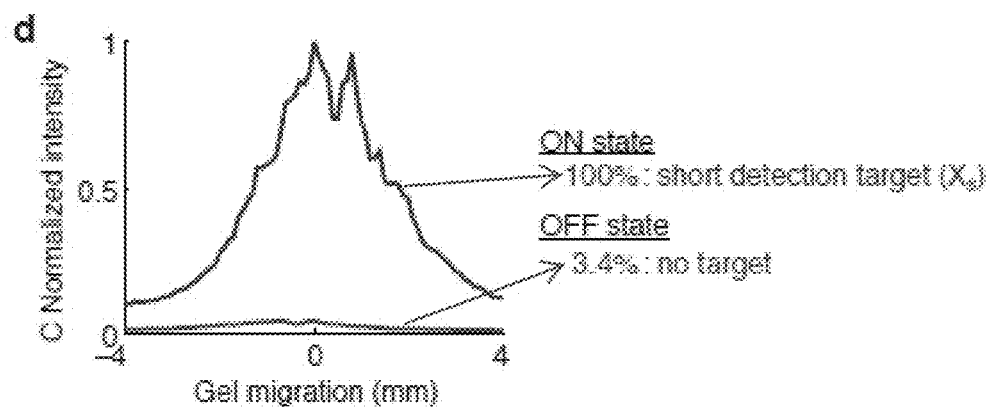

Mechanism 5 (metastable reactants): scRNA reactants A and B co-exist for two hours at 37° C. with minimal production of transcription template A·B (FIG. 24B (lane 1) and FIG. 26 (lane 8)). Annealing A and B yields substantial production of A·B (FIG. 26 (lane 9)). This anneal is expected to favor reactants over products, because A and B are both hairpins. Hence, the fact that the anneal nonetheless produces a substantial quantity of A·B strongly suggests that the reactants are metastable, not stable.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

While the present invention has been described in some detail for purposes of clarity and understanding, one skilled in the art will appreciate that various changes in form and detail can be made without departing from the true scope of the invention.

The term "comprising" as used herein is synonymous with "including," "containing," or "characterized by," and is inclusive or open-ended and does not exclude additional, unrecited elements or method steps.

All numbers expressing quantities of ingredients, reaction conditions, and so forth used in the specification are to be understood as being modified in all instances by the term "about." Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

The above description discloses several methods and materials of the present invention. This invention is susceptible to modifications in the methods and materials, as well as alterations in the fabrication methods and equipment. Such modifications will become apparent to those skilled in the art from a consideration of this disclosure or practice of the invention disclosed herein. Consequently, it is not intended that this invention be limited to the specific embodiments disclosed herein, but that it cover all modifications and alternatives coming within the true scope and spirit of the invention.

The foregoing description and Examples detail certain embodiments. It will be appreciated, however, that no matter how detailed the foregoing may appear in text, the invention may be practiced in many ways and the invention should be construed in accordance with the appended claims and any equivalents thereof.

The section headings used herein are for organizational purposes only and are not to be construed as limiting the described subject matter in any way. All literature and similar materials cited in this application, including but not limited to, patents, patent applications, articles, books, treatises, and interne web pages are expressly incorporated by reference in their entirety for any purpose. When definitions of terms in incorporated references appear to differ from the definitions provided in the present teachings, the definition provided in the present teachings shall control. It will be appreciated that there is an implied "about" prior to the temperatures, concentrations, times, etc discussed in the present teachings, such that slight and insubstantial deviations are within the scope of the present teachings herein. In this application, the use of the singular includes the plural unless specifically stated otherwise. Also, the use of "comprise", "comprises", "comprising", "contain", "contains", "containing", "include", "includes", and "including" are not intended to be limiting. It is to be understood that both the foregoing general description and the following detailed description are exemplary and explanatory only and are not restrictive.

Unless otherwise defined, scientific and technical terms used herein shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well-known and commonly used in the art. Standard techniques are used, for example, for nucleic acid purification and preparation, chemical analysis, recombinant nucleic acid, and oligonucleotide synthesis. Enzymatic reactions and purification techniques are performed according to manufacturer's specifications or as commonly accomplished in the art or as described herein. The techniques and procedures described herein are generally performed according to conventional methods well known in the art and as described in various general and more specific references that are cited and discussed throughout the instant specification. See, e.g., Sambrook et al., *Molecular Cloning: A Laboratory Manual* (Third ed., Cold Spring Harbor Laboratory Press, Cold Spring Harbor, N.Y. 2000). The nomenclatures utilized in connection with, and the laboratory procedures and techniques of described herein are those well-known and commonly used in the art.

It is noted that the exemplary sequences and subsequences shown in the examples in regard to domains a, b, c, d, e, x, z, y, and their corresponding complementary sequences a*, b*, c*, d*, e*, x*, z*, y*, are for purposes of the examples only and are not intended to define the noted domains. Unless stated otherwise, the domains can be any that are configured to function as noted in the application. That is, they will have the appropriate nucleic acid sequences to hybridize in the depicted manner.

What is claimed is:

1. A method of conditional Dicer substrate formation, the method comprising:
providing a duplex that comprises a first strand hybridized to a second strand; and
combining the duplex to a mixture for detection of a target strand, wherein a presence of a target strand results in a displacement of the first strand from the second strand, and wherein the displacement of the first strand from the second strand allows for the second strand to form an shRNA, wherein the shRNA comprises a conditionally-formed Dicer substrate, and wherein the shRNA is formed in a conditional manner, and wherein the shRNA has a stem of not less than 13 base pairs and not more than 29 base pairs with a 3' overhang of not less than 1 nucleotide and not more than 5 nucleotides.

2. The method of claim 1, wherein the target strand comprises a domain "a", a domain "b" and a domain "c", wherein each of the domain "a", the domain "b" and the domain "c" have a 5' terminus and a 3' terminus, and the 3' terminus of domain "a" is adjacent to the 5' terminus of domain "b", and the 3' terminus of domain "b" is adjacent to the 5' terminus of domain "c".

3. The method of claim 2, wherein the domain "a" has a nucleotide length of about 4-30 nucleotides.

4. The method of claim 2, wherein the domain "b" has a nucleotide length of about 10-16 nucleotides.

5. The method of claim 2, wherein the domain "c" has a nucleotide length of not less than 1 nucleotide and not more than 12 nucleotides.

6. The method of claim 1, wherein the first strand comprises a domain "a*", a domain "b*", a domain "c*" and a domain "z", wherein each of the domain "a*", the domain "b*", the domain "c*" and the domain "z" each have a 5' terminus and a 3' terminus, and the 3' terminus of domain "z" is adjacent to the 5' terminus of the domain "c*", the 3' terminus of the domain "c*" is adjacent to the 5' terminus of the domain "b*" and the 3' terminus of the domain "b*" is adjacent to the 5' terminus of domain "a*".

7. The method of claim 6, wherein the domain "a*", the domain "b*", and the domain "c*" are complementary to the domain "a", the domain "b", and the domain "c" of the target strand, respectively.

8. The method of claim 1, wherein the second strand comprises a domain "z", a domain "c*", a domain "b", a domain "c", a domain "z*", and a domain "y*", wherein each of the domain "z", the domain "c*", the domain "b", the domain "c", the domain "z*", and the domain "y*" each have a 5' terminus and a 3' terminus, and the 3' terminus of domain "z" is adjacent to the 5' terminus of domain "c*", the 3' terminus of domain "c*" is adjacent to the 5' terminus of domain "b", the 3' terminus of domain "b" is adjacent to the 5' terminus of domain "c", the 3' terminus of domain "c" is adjacent to the 5' terminus of domain "z*" and the 3' terminus of the domain "z*" is adjacent to the 5' terminus of the domain "y*".

9. The method of claim 1, wherein the shRNA comprises a Dicer substrate sequence.

10. The method of claim 1, wherein the shRNA comprises a sequence that is configured for targeting of a first gene.

11. The method of claim 10, wherein the targeting of the first gene is via Dicer processing of the shRNA.

12. The method of claim 1, wherein the conditional manner is at least one order of magnitude greater for shRNA formation in a presence of the target strand than in an absence of the target strand.

13. The method of claim 1, wherein the shRNA comprises:
a stem region, wherein the stem region comprises a Dicer substrate; and
a loop region that to connected to the stem region.

14. The method of claim 13, wherein the Dicer substrate comprises the second strand comprising a domain "z" linked to a domain "c*" linked to a domain "b" linked to a domain "c" linked to a domain "z*" linked to a domain "y*".

15. The method of claim 1 wherein shRNA formation is achieved by hybridization of a domain "c" to a domain "c*" and hybridization of a domain "z*" to a domain "z".

16. The method of claim 15 where the domain "c" comprises an internal toehold that is exposed in the second strand when the target strand at least partially displaces the first strand from the second strand, allowing the second strand to self-hybridize via self-nucleation of the "c*" and "c" domains, leading to full displacement of the first strand from the second strand, with the second strand forming an shRNA.

17. The method of claim 16, wherein the shRNA is processed by Dicer to form an siRNA, wherein the siRNA contains a duplex region of not less than 13 base pairs and not more than 25 base pairs with a 3' overhang at one end of not less than 1 nucleotide and not more than 5 nucleotides and a 3' overhang at an other end of not less than 1 nucleotide and not more than 5 nucleotides.

18. The method of claim 17, wherein the siRNA silences at least one of a housekeeping gene, an essential gene, an overexpressed gene, a gene coding for an autoreactive protein, or a viral gene.

19. The method of claim 1, wherein the target strand is a disease marker, wherein the disease marker is at least one of an mRNA cancer marker, an mRNA coding for the complementarity determining region 3 of an autoreactive T-cell, an HIV mRNA, or a viral mRNA.

20. A method of conditional hairpin formation, the method comprising:
providing an RNA duplex to a sample comprising a target sequence, wherein the RNA duplex changes conformation to perform signal transduction in response to binding a cognate input, wherein the RNA duplex comprises a first strand and a second strand, and wherein the first strand hybridizes to the target sequence to at least partially dehybridize the second strand from the first strand, and wherein upon partial dehybridization of the second strand from the first strand, the second strand self-hybridizes to form a hairpin, and wherein the hairpin is formed in a conditional manner that is dependent upon the presence of the target strand.

21. The method of claim 20, wherein the conditional manner occurs via a single step in which the first strand of the RNA duplex swaps its hybridization partner from being the second strand of the RNA duplex to being the target strand, allowing the second strand of the RNA duplex to form a hairpin if the target strand is present.

22. The method of claim 20, wherein the hairpin comprises a shRNA, and wherein the shRNA has a stem of not less than 13 base pairs and not more than 29 base pairs with a 3' overhang of not less than 1 nucleotide and not more than 5 nucleotides.

23. The method of claim 20, wherein the conditional hairpin formation is configured for silencing a gene.

24. The method of claim 22, wherein the conditional hairpin formation is configured for silencing a gene via a non-Dicer pathway.

25. The method of claim 22, wherein the conditional hairpin formation is configured for silencing a gene via a Dicer pathway.

26. A method of forming a Dicer substrate, the method comprising:
providing a duplex that comprises a first strand hybridized to a second strand;
contacting the duplex with a sample, wherein the sample comprises a target strand and wherein
the presence of a target strand in the sample results in a partial displacement of the first strand from the second strand, and wherein the partial displacement of the first strand from the second strand allows for the second strand to form an shRNA, and wherein the shRNA is formed in a conditional manner and forms a Dicer substrate, and wherein the shRNA has a stem of not less than 13 base pairs and not more than 29 base pairs with a 3' overhang of not less than 1 nucleotide and not more than 5 nucleotides.

27. A method of conditional Dicer substrate formation, the method comprising:
providing a duplex that comprises a first strand hybridized to a second strand;
combining the duplex with a mixture for detection of a target strand, wherein a presence of a target strand results in a partial displacement of the first strand from the second strand, and wherein the partial displacement of the first strand from the second strand allows for the second strand to form an shRNA, wherein the shRNA comprises a conditionally-formed Dicer substrate, and wherein the shRNA is formed in a conditional manner based upon a presence or absence of the target strand, and wherein the shRNA has a stem of not less than 13 base pairs and not more than 29 base pairs with a 3' overhang of not less than 1 nucleotide and not more than 5 nucleotides.

28. A method of conditional Dicer substrate formation comprising
providing a complex that comprises:
a first strand;
a second strand; and
a third strand, wherein the first strand is hybridized to the second strand and wherein the third strand is also hybridized to the second strand when the first strand is hybridized to the second strand; and
adding the complex to a mixture for detection of a target strand, wherein a presence of the target strand results in a displacement of the first strand from the second strand, and wherein the displacement of the first strand from the second strand allows for the second strand to self-hybridize and displace the third strand from the second strand such that the second strand forms an shRNA, wherein the shRNA comprises a conditionally-formed Dicer substrate, and wherein the shRNA has a stem of not less than 13 base pairs and not more than 29 base pairs with a 3' overhang of not less than 1 nucleotide and not more than 5 nucleotides.

29. The method of claim 28 wherein the second strand contains an internal toehold that is exposed when the first strand is displaced from the second strand, and wherein upon exposing the internal toehold in the second strand, the second strand self-hybridize to displace the third strand from the second strand such that the second strand forms an shRNA.

30. A method of conditional Dicer substrate formation, the method comprising:
providing a first duplex comprising:
a first strand; and
a second strand, wherein the first strand is hybridized to the second strand;
providing a second duplex comprising:
a third strand; and
a fourth strand, wherein the third strand is hybridized to the fourth strand; and
combining the first and second duplex with a sample, wherein the presence of a target sequence in the sample results in:
the first duplex and the second duplex nucleating with the target sequence via hybridization of the second strand with the target sequence and hybridization of the fourth strand with the target sequence, mediating hybridization of the first strand to the third strand to yield a duplex Dicer substrate.

31. The method of claim 30, wherein the first strand comprises a domain that is not hybridized to the second strand when in the first duplex, and wherein the fourth strand comprises a domain that is not hybridized to the third strand when in the second duplex.

32. The method of claim 31, wherein the target sequence is hybridized to both the second strand and the fourth strand, and wherein the second strand is also hybridized to the fourth strand.

33. A method of conditional Dicer substrate formation, the method comprising providing a RNA duplex to a sample that may or may not contain a target polynucleotide, wherein the RNA duplex changes conformation to perform signal transduction in response to binding a cognate input, wherein the RNA duplex comprises a first strand and a second strand, wherein the first strand is configured to hybridize to a target sequence and expose an internal toehold in the second strand upon the hybridization, and wherein upon exposing the internal toehold in the second strand, the second strand self-hybridizes into an shRNA, wherein the shRNA comprises a conditionally-formed Dicer substrate, wherein the first strand has a nucleotide length of not less than 22 nucleotides and not more than 70 nucleotides and the second strand has a nucleotide length of not less than 31 nucleotides and not more than 80 nucleotides, and wherein the shRNA has a stem of not less than 13 base pairs and not more than 29 base pairs and a 3' overhang of not less than 1 nucleotide and not more than 5 nucleotides.

34. The method of claim 1, wherein each strand comprises at least one selected from the group consisting of natural RNA, modified RNA, and artificial RNA analog.

35. The method of claim 20, wherein each strand comprises at least one selected from the group consisting of natural RNA, modified RNA, and artificial RNA analog.

36. The method of claim 26, wherein each strand comprises at least one selected from the group consisting of natural RNA, modified RNA, and artificial RNA analog.

37. The method of claim 27, wherein each strand comprises at least one selected from the group consisting of natural RNA, modified RNA, and artificial RNA analog.

38. The method of claim 28, wherein each strand comprises at least one selected from the group consisting of natural RNA, modified RNA, and artificial RNA analog.

39. The method of claim 30, wherein each strand comprises at least one selected from the group consisting of natural RNA, modified RNA, and artificial RNA analog.

40. The method of claim 33, wherein each strand comprises at least one selected from the group consisting of natural RNA, modified RNA, and artificial RNA analog.

* * * * *

UNITED STATES PATENT AND TRADEMARK OFFICE
CERTIFICATE OF CORRECTION

PATENT NO. : 9,856,472 B2
APPLICATION NO. : 14/320479
DATED : January 2, 2018
INVENTOR(S) : Niles A. Pierce It is certified that error appears in the above-identified patent and that said Letters Patent is hereby corrected as shown below:

On the Title Page

In Column 2 (page 2, item (56)) at Line 28, Under Other Publications, change "blosensor" to --biosensor--.

In the Specification

In Column 4 at Line 49, Change "FIG." to --FIGS.--.

In Column 4 at Line 59, Change "FIG." to --FIGS.--.

In Column 5 at Line 5, Change "FIG." to --FIGS.--.

In Column 7 at Line 51, Change "description" to --description.--.

In Column 8 at Line 19, Change "H+, NH4+," to --$H^+$, $NH_4^+$,--.

In Column 8 at Line 20, Change "$Mg^2$+, Na+" to --$Mg^{2+}$, $Na^+$--.

In Column 9 at Line 42, Change "Y" to --Y.--.

In Column 21 at Line 40, Change ""c"," to --"c*",--.

In Column 22 at Line 34, Change ""z"" to --"z*"--.

In Column 22 at Line 35, Change ""z"" to --"z*"--.

In Column 22 at Line 35, Change ""y"." to --"y*".--.

In Column 25 at Line 48, Change "RDDs" to --RNAs--.

Signed and Sealed this
Eighth Day of May, 2018

Andrei Iancu
*Director of the United States Patent and Trademark Office*

CERTIFICATE OF CORRECTION (continued)
U.S. Pat. No. 9,856,472 B2

In Column 28 at Line 53, Change "'w-x-y-z')." to --'w-x-y-z').--.

In Column 30 at Lines 38-39, Change "|p|8, |q|9, |t|7," to --|p|=8, |q|=9, |t|=7,--.

In Column 32 at Line 25, Change "20μL" to --20 μL--.

In Column 32 at Line 30, Change "DNaseI" to --DNaseI--.

In Column 32 at Line 58, Change "±4mm" to --±4 mm--.

In Column 36 at Line 6, Change "Na+." to --Na$^+$.--.

In Column 36 at Line 52, Change "Na+." to --Na$^+$.--.

In Column 44 at Line 23 (approx.), Change "FIG. 17)" to --FIG. 17).--.

In Column 45 at Line 6, Change "|c|3," to --|c|=3,--.

In Column 45 at Line 29 (approx.), Change "nucloetides" to --nucleotides--.

In Column 46 at Line 3, Change "Mechanism 3" to --Mechanism 3.--.

In Column 48 at Line 5, Change "CAD" to --C·D--.

In Column 49 at Line 46, Change "|y|–6," to --|y|=6,--.

In the Claims

In Column 67 at Line 65, In Claim 29, change "self-hybridize" to --self-hybridizes--.

SEQUENCE LISTING

```
<160> NUMBER OF SEQ ID NOS: 23

<210> SEQ ID NO 1
<211> LENGTH: 747
<212> TYPE: RNA
<213> ORGANISM: Artificial Sequence
<220> FEATURE:
<223> OTHER INFORMATION: Synthetic oligonucleotide

<400> SEQUENCE: 1
auggccuccu  ccgagaacgu  caucaccgag  uucaugcgcu  ucaaggugcg  cauggagggc      60
accgugaacg  gccacgaguu  cgagaucgag  ggcgagggcg  agggccgccc  cuacgagggc     120
cacaacaccg  ugaagcugaa  ggugaccaag  ggcggccccc  ugcccuucgc  cugggacauc     180
cugucccccc  aguuccagua  cggcuccaag  guguacguga  agcaccccgc  cgacaucccc     240
gacuacaaga  agcuguccuu  ccccgagggc  uucaagugggg  agcgcgugau  gaacuucgag     300
gacggcggcg  uggcgaccgu  gacccaggac  uccucccugc  aggacggcug  cuucaucuac     360
aaggugaagu  caucggcgu   gaacuucccc  uccgacggcc  ccgugaugca  gaagaagacc     420
augggcuggg  aggccuccac  cgagcgccug  uaccccgcg   acggcgugcu  gaagggcgag     480
acccacaagg  cccugaagcu  gaaggacggc  ggccacuacc  ugguggaguu  caaguccauc     540
uacauggcca  agaagcccgu  gcagcugccc  ggcuacuacu  acguggacgc  caagcuggac     600
aucaccuccc  acaacgagga  cuacaccauc  guggagcagu  acgagcgcac  cgagggccgc     660
caccaccugu  uccugagauc  ucgagcucaa  gcuucgaauu  cugcagucga  cgguaccgcg     720
ggcccgggau  ccaccggauc  uagauaa                                           747

<210> SEQ ID NO 2
<211> LENGTH: 846
<212> TYPE: RNA
<213> ORGANISM: Artificial Sequence
<220> FEATURE:
<223> OTHER INFORMATION: Synthetic oligonucleotide

<400> SEQUENCE: 2
auggugagca  agggcgagga  gcuguucacc  ggggugguge  ccauccuggu  cgagcuggac      60
ggcgacguaa  acggccacaa  guucagcgug  uccggcgagg  gcgagggcga  ugccaccuac     120
ggcaagcuga  cccugaaguu  caucugcacc  accggcaagc  ugcccgugcc  cugggccacc     180
cucgugacca  cccugaccua  cggcgugcag  ugcuucagcc  gcuaccccga  ccacaugaag     240
cagcacgacu  ucuucaaguc  cgccaugccc  gaaggcuacg  uccaggagcg  caccaucuuc     300
```

| | |
|---|---|
| uucaaggacg acggcaacua caagacccgc gccgagguga aguucgaggg cgacacccug | 360 |
| gugaaccgca ucgagcugaa gggcaucgac uucaaggagg acggcaacau ccugggcac | 420 |
| aagcuggagu acaacuacaa cagccacaac gucuauauca uggccgacaa gcagaagaau | 480 |
| ggcaucaagg ugaacuucaa gauccgccac aacaucgagg acggcagcgu gcagcucgcc | 540 |
| gaccacuacc agcagaacac ccccaucggc gacggccccg ugcugcugcc cgacaaccac | 600 |
| uaccugagca cccagccgc ccugagcaaa gaccccaacg agaagcgcga ucacaugguc | 660 |
| cugcuggagu ucgugaccgc cgccgggauc acucucggca uggacgagcu guacaagaag | 720 |
| cuuagccaug gcuucccgcc ggagguggag gagcaggaug auggcacgcu gcccaugucu | 780 |
| ugugcccagg agagcgggau ggaccgucac ccugcagccu gucuucugc uaggaucaau | 840 |
| guguag | 846 |

<210> SEQ ID NO 3
<211> LENGTH: 1008
<212> TYPE: RNA
<213> ORGANISM: Artificial Sequence
<220> FEATURE:
<223> OTHER INFORMATION: Synthetic oligonucleotide

<400> SEQUENCE: 3

| | |
|---|---|
| auggggaagg ugaaggucgg agucaacgga uuuggucgua uugggcgccu ggucaccagg | 60 |
| gcugcuuuua acucugguaa aguggauauu guugccauca augaccccuu cauugacccu | 120 |
| aacuacaugg uuuacauguu ccaauaugau uccacccaug gcaaauucca uggcaccguc | 180 |
| aaggcugaga acgggaagcu ugucaucaau ggaaauccca ucaccaucuu ccaggagcga | 240 |
| gaucccucca aaaucaagug gggcgaugcu ggcgcugagu acgucgugga guccacuggc | 300 |
| gucuucacca ccauggagaa ggcuggggcu cauuugcagg gggagccaa aagggucauc | 360 |
| aucucugccc ccucugcuga ugcccccaug uucgucaugg gugugaacca ugagaaguau | 420 |
| gacaacagcc ucaagaucau cagcaaugcc uccugcacca caacugcuu agcaccccug | 480 |
| gccaagguca uccaugacaa cuuugguauc gugaaggac ucaugaccac aguccaugcc | 540 |
| aucacugcca cccagaagac uguggauggc cccuccggga acuguggcg ugauggccgc | 600 |
| ggggcucucc agaacaucau cccugccucu acuggcgcug ccaaggcugu gggcaagguc | 660 |
| aucccugagc ugaacgggaa agcuacuggc auggccuucc guguccccac ugccaacgug | 720 |
| ucagugguag accugaccug ccgucuagaa aaaccugcca auaugauga caucaagaag | 780 |
| gugugaagc aggcgucgga gggcccuc aaggcaucc uggcuacac ugagcaccag | 840 |
| guggucuccu cugacuucaa cagcgacacc cacuccucca ccuuugacgc uggggcuggc | 900 |
| auugcccuca cgaccacuu ugucaagcuc auuccuggu augacaacga auuggcuac | 960 |
| agcaacaggg ugguggaccu caugggcccac augggccucca aggaguaa | 1008 |

<210> SEQ ID NO 4
<211> LENGTH: 33
<212> TYPE: RNA
<213> ORGANISM: Artificial Sequence
<220> FEATURE:
<223> OTHER INFORMATION: Synthetic oligonucleotide

<400> SEQUENCE: 4

| | |
|---|---|
| ggcaagcugg acaucaccuc ccacaacgag gac | 33 |

<210> SEQ ID NO 5
<211> LENGTH: 59

```
<212> TYPE: RNA
<213> ORGANISM: Artificial Sequence
<220> FEATURE:
<223> OTHER INFORMATION: Synthetic oligonucleotide

<400> SEQUENCE: 5
ucaccuccca caacgcuuca aguccgccau cucucguugu gggaggugau guccagcuu      59

<210> SEQ ID NO 6
<211> LENGTH: 43
<212> TYPE: RNA
<213> ORGANISM: Artificial Sequence
<220> FEATURE:
<223> OTHER INFORMATION: Synthetic oligonucleotide

<400> SEQUENCE: 6
ucaaguccgc caugcccgca acgauggcgg acuugaagcg uug                      43

<210> SEQ ID NO 7
<211> LENGTH: 56
<212> TYPE: RNA
<213> ORGANISM: Artificial Sequence
<220> FEATURE:
<223> OTHER INFORMATION: Synthetic oligonucleotide

<400> SEQUENCE: 7
cgccaugccc gcaacgcuuc aaguccgcca ucguugcggg cauggcggac uugaag         56

<210> SEQ ID NO 8
<211> LENGTH: 29
<212> TYPE: RNA
<213> ORGANISM: Artificial Sequence
<220> FEATURE:
<223> OTHER INFORMATION: Synthetic oligonucleotide

<400> SEQUENCE: 8
cuggacauca ccucccacaa cgaggacua                                      29

<210> SEQ ID NO 9
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 9
guugugggag gugaugucgg guguu                                          25

<210> SEQ ID NO 10
<211> LENGTH: 29
<212> TYPE: RNA
<213> ORGANISM: Artificial Sequence
<220> FEATURE:
<223> OTHER INFORMATION: Synthetic oligonucleotide

<400> SEQUENCE: 10
cacuaccagc agaacacccg acaucaccu                                      29

<210> SEQ ID NO 11
<211> LENGTH: 50
<212> TYPE: RNA
<213> ORGANISM: Artificial Sequence
<220> FEATURE:
<223> OTHER INFORMATION: Synthetic oligonucleotide

<400> SEQUENCE: 11
```
accacuacca gcagaacaag guagaugucg gguguucugc ugguaguggu            50

<210> SEQ ID NO 12
<211> LENGTH: 29
<212> TYPE: RNA
<213> ORGANISM: Artificial Sequence
<220> FEATURE:
<223> OTHER INFORMATION: Synthetic oligonucleotide

<400> SEQUENCE: 12
ugggagcgcg ugaugaacuu cgaggacgg                                   29

<210> SEQ ID NO 13
<211> LENGTH: 48
<212> TYPE: RNA
<213> ORGANISM: Artificial Sequence
<220> FEATURE:
<223> OTHER INFORMATION: Synthetic oligonucleotide

<400> SEQUENCE: 13
uucaucugca ccaccggcac cguccucgaa guucaucacg cgcuccca              48

<210> SEQ ID NO 14
<211> LENGTH: 60
<212> TYPE: RNA
<213> ORGANISM: Artificial Sequence
<220> FEATURE:
<223> OTHER INFORMATION: Synthetic oligonucleotide

<400> SEQUENCE: 14
uucaucugca ccaccggcac cgaugaacuu cgaggacggu gccgguggug cagaugaacu 60

<210> SEQ ID NO 15
<211> LENGTH: 38
<212> TYPE: RNA
<213> ORGANISM: Artificial Sequence
<220> FEATURE:
<223> OTHER INFORMATION: Synthetic oligonucleotide

<400> SEQUENCE: 15
cuccgagaac gucaucaccg aguucaugcg cuucaagg                         38

<210> SEQ ID NO 16
<211> LENGTH: 39
<212> TYPE: RNA
<213> ORGANISM: Artificial Sequence
<220> FEATURE:
<223> OTHER INFORMATION: Synthetic oligonucleotide

<400> SEQUENCE: 16
ccuugaagcg caugaacuga cacgcugaac uuguggccg                        39

<210> SEQ ID NO 17
<211> LENGTH: 34
<212> TYPE: RNA
<213> ORGANISM: Artificial Sequence
<220> FEATURE:
<223> OTHER INFORMATION: Synthetic oligonucleotide

<400> SEQUENCE: 17
cggccacaag uucagcgugu cugacguagu ucau                             34

<210> SEQ ID NO 18
<211> LENGTH: 29
<212> TYPE: RNA
<213> ORGANISM: Artificial Sequence

```
<220> FEATURE:
<223> OTHER INFORMATION: Synthetic oligonucleotide

<400> SEQUENCE: 18
acgucagaca cgcugaacuu guggccguu                                          29

<210> SEQ ID NO 19
<211> LENGTH: 43
<212> TYPE: RNA
<213> ORGANISM: Artificial Sequence
<220> FEATURE:
<223> OTHER INFORMATION: Synthetic oligonucleotide

<400> SEQUENCE: 19
aacggccaca aguucagcgu guccggugau gacguucucg gag                          43

<210> SEQ ID NO 20
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 20
ataagccctc atccaact                                                      18

<210> SEQ ID NO 21
<211> LENGTH: 98
<212> TYPE: DNA
<213> ORGANISM: Artificial Sequence
<220> FEATURE:
<223> OTHER INFORMATION: Synthetic oligonucleotide

<400> SEQUENCE: 21
agttggatga gggcttatta atacgactca ctatagcagc acgacttctt caagagctga        60
cttgaagaag tcgtgctgct atagtgagat aagccctc                                98

<210> SEQ ID NO 22
<211> LENGTH: 77
<212> TYPE: DNA
<213> ORGANISM: Artificial Sequence
<220> FEATURE:
<223> OTHER INFORMATION: Synthetic oligonucleotide

<400> SEQUENCE: 22
ctcactataa aaaaaagcag cacgacttct tcaagtcagc tcttgaagaa gtcgtgctgc        60
tatagtgagt cgtatta                                                       77

<210> SEQ ID NO 23
<211> LENGTH: 46
<212> TYPE: RNA
<213> ORGANISM: Artificial Sequence
<220> FEATURE:
<223> OTHER INFORMATION: Synthetic oligonucleotide

<400> SEQUENCE: 23
gcagcacgac uucuucaaga gcugacuuga agaagucgug cugcuu                       46
```